United States Patent
Purschke et al.

(10) Patent No.: US 9,822,369 B2
(45) Date of Patent: Nov. 21, 2017

(54) SDF-1 BINDING NUCLEIC ACIDS

(71) Applicant: NOXXON Pharma AG, Berlin (DE)

(72) Inventors: Werner Purschke, Berlin (DE); Florian Jarosch, Berlin (DE); Dirk Eulberg, Berlin (DE); Sven Klussmann, Berlin (DE); Klaus Buchner, Berlin (DE); Christian Maasch, Berlin (DE); Nicole Dinse, Berlin (DE)

(73) Assignee: NOXXON Pharma AG, Berlin (DE)

( * ) Notice: Subject to any disclaimer, the term of this patent is extended or adjusted under 35 U.S.C. 154(b) by 0 days.

(21) Appl. No.: 14/705,809

(22) Filed: May 6, 2015

(65) Prior Publication Data

US 2015/0232853 A1   Aug. 20, 2015

Related U.S. Application Data

(63) Continuation of application No. 13/651,385, filed on Oct. 13, 2012, now Pat. No. 9,035,038, which is a continuation of application No. 12/374,311, filed on Jan. 18, 2009, now Pat. No. 8,314,223, which is a continuation of application No. PCT/EP2007/006387, filed on Jul. 18, 2007.

(30) Foreign Application Priority Data

Jul. 18, 2006 (EP) .................................. 06014957

(51) Int. Cl.
C07H 21/04 (2006.01)
C12N 15/115 (2010.01)

(52) U.S. Cl.
CPC ........ C12N 15/115 (2013.01); *C12N 2310/16* (2013.01); *C12N 2310/351* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 5,567,588 A | 10/1996 | Gold et al. | |
| 5,582,981 A | 12/1996 | Toole et al. | |
| 5,840,867 A | 11/1998 | Toole et al. | |
| 6,011,020 A | 1/2000 | Gold et al. | |
| 6,949,243 B1 | 9/2005 | Mueller et al. | |
| 7,282,338 B2 | 10/2007 | Wei et al. | |
| 7,396,653 B2 | 7/2008 | Wei et al. | |
| 7,468,253 B2 | 12/2008 | Wei | |
| 8,119,126 B2 | 2/2012 | Kishimoto et al. | |
| 8,314,223 B2 | 11/2012 | Purschke et al. | |
| 8,772,257 B2 | 7/2014 | Purschke et al. | |
| 2003/0186906 A1 | 10/2003 | Schlingensiepen et al. | |
| 2005/0186556 A1 | 8/2005 | Wei et al. | |
| 2006/0234926 A1 | 10/2006 | Stockley et al. | |
| 2007/0203089 A1 | 8/2007 | Rodrigues et al. | |
| 2008/0063682 A1 | 3/2008 | Cashman et al. | |
| 2009/0274687 A1 | 11/2009 | Young et al. | |
| 2009/0285817 A1 | 11/2009 | Schlingensiepen et al. | |
| 2010/0074887 A1 | 3/2010 | Mehrad et al. | |
| 2010/0104508 A1 | 4/2010 | Kuhne et al. | |
| 2011/0104295 A1 | 5/2011 | Cashman et al. | |
| 2011/0250275 A1 | 10/2011 | Cashman et al. | |

OTHER PUBLICATIONS

Li et al., "Retina-committed . . . retina," Ann Meeting Assoc Res Vision 46, Supp 8, 3247, 2005.
Luker & Luker, "Functions of . . . cancer," Canc Lett 238, 30-41, 2006.
Smith et al., Porcine EST collection, Genbank, XP002465983, 2004.
Burger & Kipps, "CXCR4: a key . . . microenvironment," Blood 107(5)1761-1767, 2006.
Kucia et al., "CXCR4-SDF-1 . . . adhesion," J Mol Hist 35:233-245, 2004.
Chalasani et al., "A chemokine . . . pathfinding," K Neurosci 23(4)1360-1371, 2003.
Kato et al., Breast Canc Res 5(5)144-150, 2003.
Tang et al., Asian Pac J Canc Prey 13(10)5281-5286, 2012.
Andrews et al., Stem Cells 17:210-216, 1999.
Guleng et al., Canc Res 65:5864-5871, 2005.
Hong et al., Canc Lett 236:39-45, 2006.
Wu et al., J Cell Biochem 103:245-255, 2007.
Flomenburg et al., Blood 106:1867-1874, 2005.
Netelenbos et al., Leukemia 17:175-18/4, 2003.
Sayyed et al., Podocytes . . . diabetes, Diabet 52:2445-2454, 2009.
Rachet-Haas et al., JBC 280(34)23189-23199, 2008.
Otsuka et al., J Thorac Oncol 3:1379-1383, 2008.
Vaday et al., Clin Canc Res 10:5630-5639, 2004.
Curran et al., Drugs 69(7)8669-88, 2009.
Gelboin et al., Chem Res Tox 9:1023-1030, 1996.
Azab et al., "CXCR4 . . . therapy," Blood 113(18)4341-4351, 2009.
Meike Burger et al., "Small . . . cells," Blood 106(5)1824-1830, 2005.
Rajagopalan et al., "Structural . . . selectivity," Biosci Rep 26(5)325-339, 2006.
Crump et al., "Solution . . . HIV-1," EMBO J 16(23)6996-7007, 1997.
Balabanian et al., "The chemokine . . . lymphocytes," JBC 280(42)35760-35766, 2005.

*Primary Examiner* — Celine Qian
(74) *Attorney, Agent, or Firm* — MDIP LLC

(57) ABSTRACT

The present invention is related to an L nucleic acid that binds to an SDF-1.

14 Claims, 48 Drawing Sheets

Type A SDF-1 binding nucleic acids

| Name | nt. | Sequence: 5'-3' | Comp. |
|---|---|---|---|
| 192-A10-001 (SEQ ID NO:5) | 38 | GCUGUG AAAGCAACAUGUCAA-UGAAAGGUAGC CGCAGC | |
| 192-G10 (SEQ ID NO:6) | 38 | GCUGUG AAAGUAACAUGUCAA-UGAAAGGUAAC CACAGC | < |
| 192-F10 (SEQ ID NO:7) | 38 | GCUGUG AAAGUAACACGUCAA-UGAAAGGUAAC CGCAGC | < |
| 192-B11 (SEQ ID NO:8) | 38 | GCUGUG AAAGUAACACGUCAA-UGAAAGGUAAC CACAGC | = |
| 192-C9 (SEQ ID NO:9) | 38 | GCUGUA AAAGUAACAUGUCAA-UGAAAGGUAAC UACAGC | < |
| 192-E10 (SEQ ID NO:10) | 38 | GCUGUA AAAGUAACAAGUCAA-UGAAAGGUAAC UACAGC | < |
| 192-C10 (SEQ ID NO:11) | 38 | GCUGUG AAAGUAACAAGUCAA-UGAAAGGUAAC CACAGC | = |
| 192-D11 (SEQ ID NO:12) | 38 | GCAGUG AAAGUAACAUGUCAA-UGAAAGGUAAC CACAGC | < |
| 192-G11 (SEQ ID NO:13) | 38 | GCUGUG AAAGUAACAUGUCAA-UGAAAGGUAAC CACUGC | < |
| 192-H11 (SEQ ID NO:14) | 38 | GCUAUG AAAGUAACAUGUCAA-UGAAAGGUAAC CAUAGC | < |
| 192-D10 (SEQ ID NO:15) | 38 | GCUGCG AAAGCGACAUGUCAA-UGAAAGGUAGC CGCAGC | << |
| 192-E9 (SEQ ID NO:16) | 38 | GCUGUG AAAGCAACAUGUCAA-UGAAAGGUAGC CACAGC | << |
| 192-H9 (SEQ ID NO:17) | 38 | GCUGUG AAAGUAACAUGUCAA-UGAAAGGUAGC CGCAGC | << |

Fig. 1

| | | | | |
|---|---|---|---|---|
| 191-A6 (SEQ ID NO:18) | 39 | AGCGUGAAAGUAACACGUAAAAUGAAAGGUAACCACGCU | | < |
| | | | | |
| Type A Formula-1 (SEQ ID NO:19) | 26 | AAAGYRACAHGUMAAXUGAAAGGUARC | | |
| Type A Formula-2 (SEQ ID NO:20) | 26 | AAAGYRACAHGUMAA-UGAAAGGUARC | | |
| Type A Formula-3 (SEQ ID NO:21) | 27 | AAAGYRACAHGUMAAAUGAAAGGUARC | | |
| Type A Formula-4 (SEQ ID NO:22) | 26 | AAAGYAACAHGUCAA-UGAAAGGUARC | | |
| Type A Formula-5-5' (SEQ ID NO:23) | | RSHRYR | | |
| Type A Formula-5-3' (SEQ ID NO:24) | | | YRYDSY | | terminal nucleotides that may hybridize to each other (bold)

nucleotides which may mainly comprise a SDF-binding motif nt.:= nucleotides      variable position^

Comp.:= Clones were tested as aptamers in a competition binding assay vs. 192-A10-001

=:= equal binding affinity as 192-A10-001;    <:= weaker binding affinity than 192-A1-001

<<:= much weaker binding affinity than 192-A10-001

Fig. 1 continued

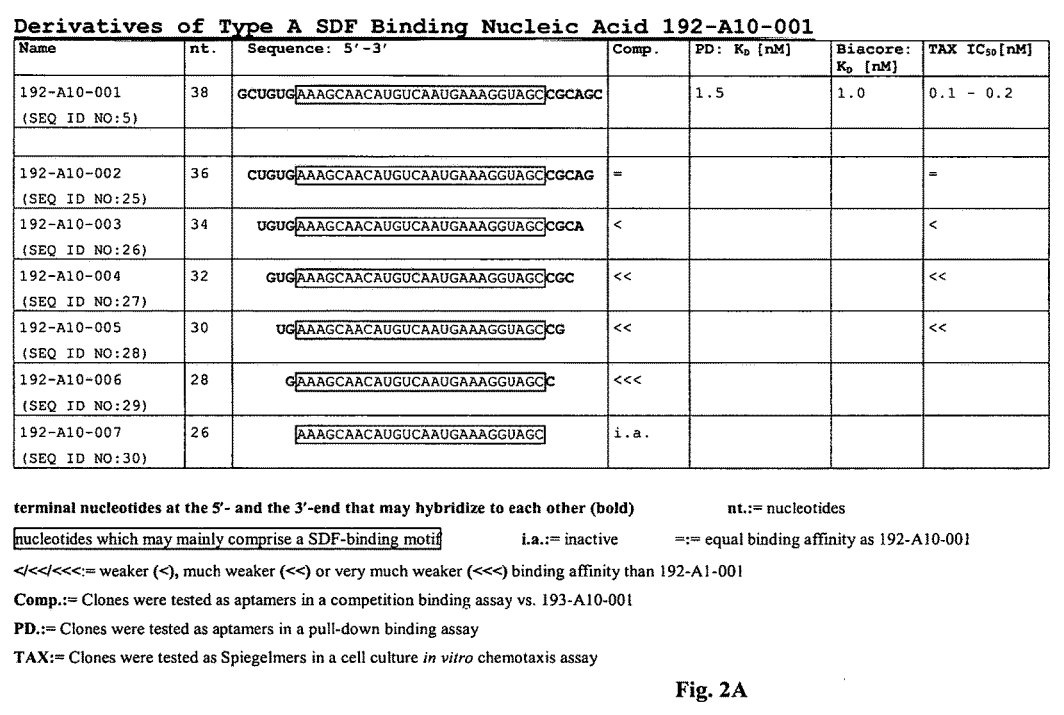

Derivatives of Type A SDF Binding Nucleic Acid 192-A10-001

| Name | nt. | Sequence: 5'-3' | Comp. | PD: $K_D$ [nM] | Bi

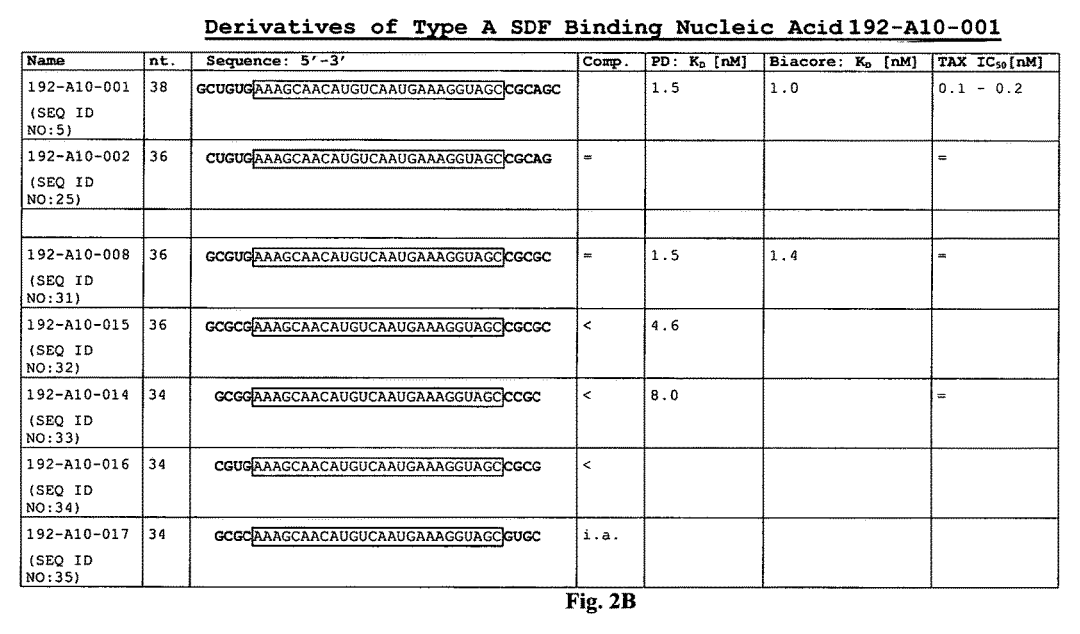

Derivatives of Type A SDF Binding Nucleic Acid 192-A10-001

| Name | nt. | Sequence: 5'-3' | Comp. | P

| | | | | | | |
|---|---|---|---|---|---|---|
| 192-A10-018 (SEQ ID NO:36) | 34 | GUGC AAAGCAACAUGUCAAUGAAAGGUAGC GCGC | <<< | | | |
| 192-A10-019 (SEQ ID NO:37) | 34 | CGCG AAAGCAACAUGUCAAUGAAAGGUAGC CGUG | << | | | |
| 192-A10-020 (SEQ ID NO:38) | 34 | GGGC AAAGCAACAUGUCAAUGAAAGGUAGC GCCC | <<* | | | |
| 192-A10-021 (SEQ ID NO:39) | 34 | GGCC AAAGCAACAUGUCAAUGAAAGGUAGC GGCC | <<* | | | |
| 192-A10-022 (SEQ ID NO:40) | 34 | GCCC AAAGCAACAUGUCAAUGAAAGGUAGC GGGC | <<* | | | |
| 192-A10-023 (SEQ ID NO:41) | 34 | CCCC AAAGCAACAUGUCAAUGAAAGGUAGC GGGG | <<* | | | | terminal nucleotides at the 5'- and the 3'-end that may hybridize to each other (bold)   nt.:= nucleotides nucleotides which may mainly comprise a SDF-binding motif   i.a.:= inactive   =:= equal binding affinity as 192-A10-001/ -008

</<<<<<:= weaker (<), much weaker (<<) or very much weaker (<<<) binding affinity than 192-A1-001/ -008

Comp.:= Clones were tested as aptamers in a competition binding assay vs. 192-A10-001 (* = except from 192-A10-020, -021, -022, and –023 which were tested vs. 193-A10-008 that has the identical binding affinity to SDF-1 as 192-A10-001)

PD.:= Clones were tested as aptamers in a pull-down binding assay

TAX:= Clones were tested as Spiegelmers in a cell culture *in vitro* chemotaxis assay

Fig. 2B continued

Type B SDF-1 binding nucleic acids

| Name | nt. | Sequence: 5'-3' | Comp. |
|---|---|---|---|
| 193-C2-001 (SEQ ID NO:46) | 47 | AGCGUG GUGUGAUCUAGAUGUAGUGGCUGAUCCUAGUCAGG UACGCU | + |
| 193-G2-001 (SEQ ID NO:47) | 47 | AGCGUG GUGUGAUCUAGAUGUAUUGGCUGAUCCUAGUCAGG UACGCU | + |
| 193-F2-001 (SEQ ID NO:48) | 47 | AGCGUG GUGUGAUCUAGAUGUAAUGGCUGAUCCUAGUCAGG UGCGCU | + |
| | | | |
| 193-G1-002 (SEQ ID NO:49) | 45 | GCGAG GUGUGAUCUAGAUGUAGUGGCUGAUCCUAGUCAGG UGCGC | << |
| 193-D2-002 (SEQ ID NO:50) | 45 | GCGUG GUGUGAUCUAGAUGUAGUGGCUGAUCCUAGUCAGG UGCGC | < |
| 193-A1-002 (SEQ ID NO:51) | 45 | GCAUG GUGUGAUCUAGAUGUAGUGGCUGAUCCUAGUCAGG UGCCC | <<< |
| 193-D3-002 (SEQ ID NO:52) | 45 | GCGUG GUGUGAUCUAGAUGUAAUGGCUGAUCCUAGUCAGG GACGC | < |
| 193-B3-002 (SEQ ID NO:53) | 45 | GCGUG GUGUGAUCUAGAUGUAGAGGCUGAUCCUAGUCAGG UACGC | << |
| 193-H3-002 (SEQ ID NO:54) | 45 | GCGUG GUGUGAUCUAGAUGUAAAGGCUGAUCCUAGUCAGG UACGC | < |
| 193-E3-002 (SEQ ID NO:55) | 45 | GCGUG GUGUGAUCUAGAUGUAGUGGCUGUUCCUAGUCAGG UAUGC | << |

Fig. 3

| 193-D1-002 (SEQ ID NO:56) | 45 | GCGUG GUGUGAUCUAGAUGUAGUGGCUGAUCCUAGUUAGG UACGC | <<< |
|---|---|---|---|
| | | | |
| Type B Formula-1 (SEQ ID NO:57) | 35 | GUGUGAUCUAGAUGUADWGGCUGWUCCUAGUYAGG | |
| Type B Formula-2 (SEQ ID NO:58) | 35 | GUGUGAUCUAGAUGUADUGGCUGAUCCUAGUCAGG | |
| Type B Formula-3-5' (SEQ ID NO:59) | | $X_1$GCRWG | |
| Type B Formula-3-3' (SEQ ID NO:60) | | KRYSC$X_4$ | | terminal nucleotides that may hybridize to each other (bold)

nucleotides which may mainly comprise a SDF-binding motif nt.:= nucleotides  variable position

Comp.:= Clones C2, G2, and F2 were tested as aptamers in a competition binding assay vs. 192-A10-001; all other clones were tested as aptamers in a competition binding assay vs. 193-G2-012 that has the identical binding affinity to SDF-1 as 193-G2-001 (see Fig. 4B)

+:= better binding affinity than 192-A10-001

</<</<<<:= weaker (<), much weaker (<<) or very much weaker (<<<) binding affinity than 193-G2-001/ -012

$X_1$ = 'A' or absent     $X_4$ = 'U' or absent     Fig. 3 continued

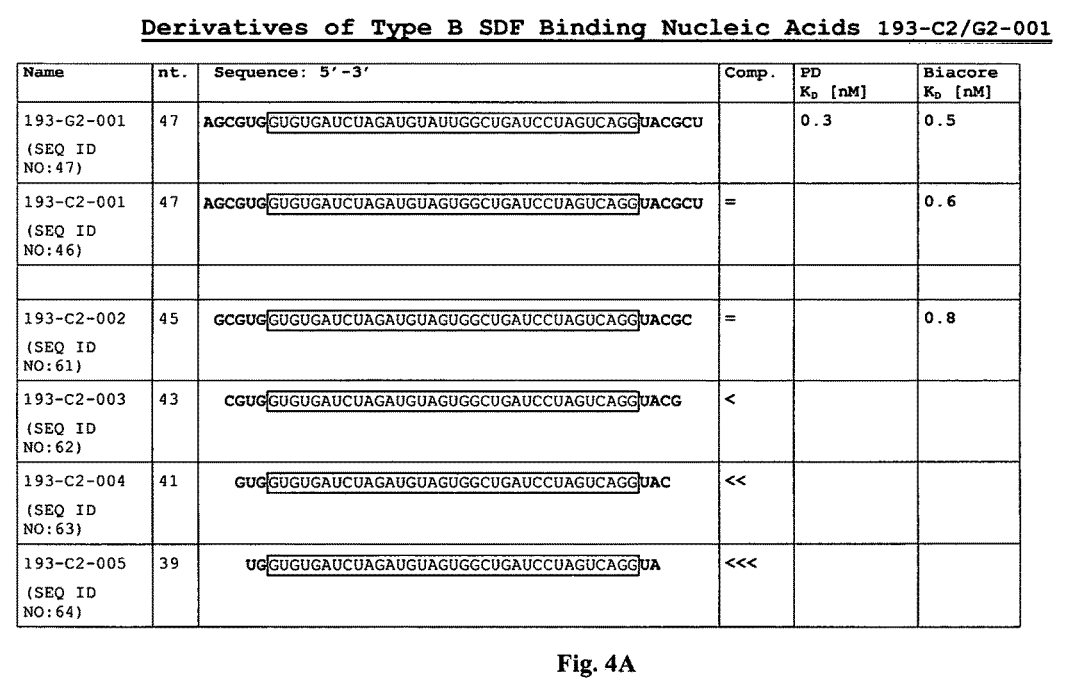

Derivatives of Type B SDF Binding Nucleic Acids 193-C2/G2-001

| Name | nt. | Sequence: 5'-3' | Comp. | PD K$

| | | | | | | |
|---|---|---|---|---|---|---|
| 193-C2-006 (SEQ ID NO:65) | 37 | G<u>GUGUGAUCUAGAUGUAGUGGCUGAUCCUAGUCAGG</u>U | <<< | | | |
| 193-C2-007 (SEQ ID NO:66) | 35 | <u>GUGUGAUCUAGAUGUAGUGGCUGAUCCUAGUCAGG</u> | i.a. | | | | terminal nucleotides at the 5'- and the 3'-end that may hybridize to each other (bold)   nt.:= nucleotides nucleotides which may mainly comprise a SDF-binding motif   i.a.:= inactive   =:= equal binding affinity as 193-G2-001

</</<<<:= weaker (<), much weaker (<<) or very much weaker (<<<) binding affinity than 193-G2-001

Comp.:= Clones were tested as aptamers in a competition binding assay vs. 193-G2-001

PD.:= Clones were tested as aptamers in a pull-down binding assay

Fig. 4A continued

Derivatives of Type B SDF Binding Nucleic Acid 193-C2/G2-001

| Name | nt. | Sequence: 5'-3' | Comp. | PD $K_D$ [nM] | Biacore $K_D$ [nM] |
|---|---|---|---|---|---|
| 193-G2-001 (SEQ ID NO:47) | 47 | AGCGUG\|GUGUGAUCUAGAUGUAUUGGCUGAUCCUAGUCAGG\|UACGCU | | 0.3 | 0.5 |
| 193-G2-012 (SEQ ID NO:67) | 45 | GCGUG\|GUGUGAUCUAGAUGUAUUGGCUGAUCCUAGUCAGG\|UACGC | = | 0.3 | |
| 193-G2-013 (SEQ ID NO:68) | 45 | GCGCG\|GUGUGAUCUAGAUGUAUUGGCUGAUCCUAGUCAGG\|CGCGC | << | 5.3 | |
| 193-G2-014 (SEQ ID NO:69) | 43 | GCGC\|GUGUGAUCUAGAUGUAUUGGCUGAUCCUAGUCAGG\|GCGC | << | 4.7 | |
| 193-G2-015 (SEQ ID NO:70) | 43 | GGGC\|GUGUGAUCUAGAUGUAUUGGCUGAUCCUAGUCAGG\|GCCC | <<* | 4.5 | |

Fig. 4B

| 193 G2-016 (SEQ ID NO:71) | 43 | GGCC GUGUGAUCUAGAUGUAUUGGCUGAUCCUAGUCAGG GGCC | <<* | 4.2 | |
|---|---|---|---|---|---|
| 193-G2-017 (SEQ ID NO:72) | 43 | GCCC GUGUGAUCUAGAUGUAUUGGCUGAUCCUAGUCAGG GGGC | <<* | 4.2 | | terminal nucleotides at the 5'- and the 3'-end that may hybridize to each other (bold)  nt.:= nucleotides nucleotides which may mainly comprise a SDF-binding motif    i.a.:= inactive    =:= equal binding affinity as 193-G2-001/ -012

</<</<<<:= weaker (<), much weaker (<<) or very much weaker (<<<) binding affinity than 193-G2-001 and 193-G2-012, respectively Comp.:= Clones were tested as aptamers in a competition binding assay vs. 193-G2-001 (* = except from 193-G2-015, -016, -017 which were tested in a competition binding assay vs. 193-G2-012 that has the identical binding affinity to SDF-1 as 193-G2-001)

PD.:= Clones were tested as aptamers in a pull-down binding assay

Fig. 4B continued

Type C SDF-1 binding nucleic acids

| Name | nt. | Sequence: 5'-3' | Comp. |
|---|---|---|---|
| 197-B2 (SEQ ID NO:79) | 39 | GUGCUGCGGG`GGUUAGGGCUAGAAGUCGG`CCUGCAGCAC | < |
| 191-D5-001 (SEQ ID NO:80) | 39 | AGCGUGGCGA`GGUUAGGGCUAGAAGUCGG`UCGACACGCU | < |
| 197-H1 (SEQ ID NO:81) | 39 | GUGUUGCGGA`GGUUAGGGCUAGAAGUCGG`UCAGCAGCAC | < |
| 190-D3 | 48 | CGUGCGGCCUAAGA`GGUUAGGGCUUAAAGUCGG`UCUUUGGCCAACACG | << |
| 190-A3-001 (SEQ ID NO:82) | 48 | CGUGCGCUUGAGAUAGG`GGUUAGGGCUUAAAGUCGG`CUGAUUCUCACG | < |
| 190-A3-001* (SEQ ID NO:82) | 48 | CGUGCGCUUGAGAUAGG`GGUUAGGGCUUAAAGUCGG`CUGAUUCUCACG | < |
| 190-A2 | 48 | CGUGAUUGGUGAGG`GGUUAGGGCUUGAAGUCGG`CCUUGUCCAGUCACG | << |
| 191-A5 (SEQ ID NO:83) | 39 | AGCGUGAAGG`GGUUAGGGCUCGAAGUCGG`CUGACACGCU | << |
| 197-H3 (SEQ ID NO:84) | 39 | GUGCUGCGGG`GGUUAGGGCUCGAAGUCGG`CCCGCAGCAC | < |
| 197-B1 (SEQ ID NO:85) | 39 | GUGUUCCCGG`GGUUAGGGCUUGAAGUCGG`CCGGCAGCAC | << |
| 197-E3 (SEQ ID NO:86) | 39 | GUGUUGCAGG`GGUUAGGGCUUGAAGUCGG`CCUGCAGCAC | < |
| 197-H2 (SEQ ID NO:87) | 39 | GUGCUGCGGG`GGUUAGGGCUCAAAGUCGG`CCUGCAGCAC | << |

Fig. 5

| 197-D1 (SEQ ID NO:88) | 38 | GUGCUGCCGG GGUUAGGGCUAA-AGUCGG CCGACAGCAC | << |
|---|---|---|---|
| 197-D2 (SEQ ID NO:89) | 39 | GUGCUGUGGG GGUCAGGGCUAGAAGUCGG CCUGCAGCAC | << |
| Type C Formula-1 (SEQ ID NO:90) | 19 | GGUYAGGGCUHRXAGUCGG | |
| Type C Formula-2 (SEQ ID NO:91) | 18 | GGUYAGGGCUHRAAGUCGG | |
| Type C Formula-3 (SEQ ID NO:92) | 19 | GGUYAGGGCUHR-AGUCGG | |
| Type C Formula-4 (SEQ ID NO:93) | 19 | GGUUAGGGCUHGAAGUCGG | | terminal nucleotides that may hybridize to each other (bold)   nucleotides which may mainly comprise a SDF-binding motif
nt.:= nucleotides   variable position   Comp.:= Clones were tested as aptamers in a competition binding assay vs. 192-A10-001
=:= equal binding affinity as 192-A10;   <:= weaker binding affinity than 192-A10     <<:= much weaker binding affinity than 192-A10
*:= alternative hybridization

Fig. 5 continued

Derivatives of Type C SDF Binding Nucleic Acid 190-A3-001

| Name | nt. | Sequence: 5'-3' | Comp. |
|---|---|---|---|
| 190-A3-001 (SEQ ID NO:82) | 48 | CGUGCGCUUGAGAUAGG GGUUAGGGCUUAAAGUCGG CUGAUUCUCACG | |
| 190-A3-001* (SEQ ID NO:82) | 48 | CGUGCGCUUGAGAUAGG GGUUAGGGCUUAAAGUCGG CUGAUUCUCACG | |
| | | | |
| 190-A3-003 (SEQ ID NO:94) | 38 | UGAGAUAGG GGUUAGGGCUUAAAGUCGG CUGAUUCUCA | = |
| 190-A3-004 (SEQ ID NO:95) | 36 | GAGAUAGG GGUUAGGGCUUAAAGUCGG CUGAUUCUC | = |
| 190-A3-007 (SEQ ID NO:96) | 29 | GG GGUUAGGGCUUAAAGUCGG CUGAUUCU | <<< | terminal nucleotides at the 5'- and the 3'-end that may hybridize to each other (bold)       nt.:= nucleotides nucleotides which may mainly comprise a SDF-binding motif       i.a.:= inactive       =:= equal binding affinity as 190-A3-001

</<</<<<:= weaker (<), much weaker (<<) or very much weaker (<<<) binding affinity than 190-A3-001

Comp.:= Clones were tested as aptamers in a competition binding assay vs. 190-A3-001

*:= alternative hybridization of the terminal nucleotides

Fig. 6

Derivatives of Type C SDF Binding Nucleic Acid 191-D5-001

| Name | nt. | Sequence: 5'-3' | Comp. vs. 191-D5-001 | Comp. vs. 191-D5-007 | Biacore K_D [nM] |
|---|---|---|---|---|---|
| 191-D5-001 (SEQ ID NO:80) | 39 | AGCGUGGCGA GGUUAGGGCUAGAAGUCGG UCGACACGCU | | < | 0.73 |
| 191-D5-002 (SEQ ID NO:97) | 37 | GCGUGGCGA GGUUAGGGCUAGAAGUCGG UCGACACGC | = | | |
| 191-D5-003 (SEQ ID NO:98) | 35 | CGUGGCGA GGUUAGGGCUAGAAGUCGG UCGACACG | = | | |
| 191-D5-004 (SEQ ID NO:99) | 33 | CG-GGCGA GGUUAGGGCUAGAAGUCGG UCGAC-CG | < | | |
| 191-D5-005 (SEQ ID NO:100) | 33 | CG-GGCGA GGUUAGGGCUAGAAGUCGG UCGCC-CG | = | | |
| 191-D5-006 (SEQ ID NO:101) | 31 | CG--GCGA GGUUAGGGCUAGAAGUCGG UCGC--CG | = | | |
| 191-D5-007 (SEQ ID NO:102) | 29 | CG---G-GA GGUUAGGGCUAGAAGUCGG UC-C--CG | + | | 0.75 |
| 191-D5-010 (SEQ ID NO:103) | 27 | G--G-GA GGUUAGGGCUAGAAGUCGG UC-C---C | | < | |

Fig. 7A terminal nucleotides at the 5'- and the 3'-end that may hybridize to each other (bold)    nt.:= nucleotides nucleotides which may mainly comprise a SDF-binding motif    i.a.:= inactive    =:= equal binding affinity as 191-D5-001/ -007

</<</<<<:= weaker (<), much weaker (<<) or very much weaker (<<<) binding affinity than 191-D5-001/ -007

Comp.:= Clones were tested as aptamers in a competition binding assay vs. 191-D5-001 or 191-D5-007 whereas both clones have the identical binding affinity to SDF-1 as 191-D5-001

Fig. 7A continued

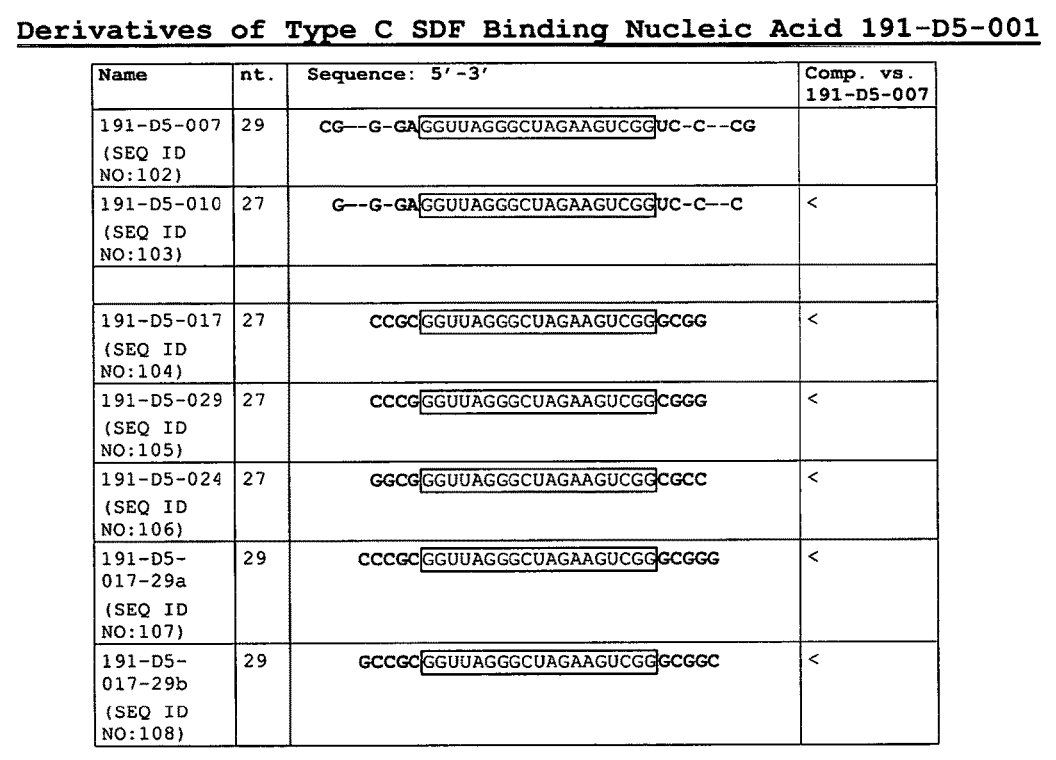

Derivatives of Type C SDF Binding Nucleic Acid 191-D5-001

| Name | nt. | Sequence: 5'-3' | Comp. vs. 191-D5-007 |
|---|---|---|---|

| | | | |
|---|---|---|---|
| 191-D5-019-29a (SEQ ID NO:109) | 29 | CCCCG GGUUAGGGCUAGAAGUCGG CGGGG | < |
| 191-D5-024-29a (SEQ ID NO:110) | 29 | CGGCG GGUUAGGGCUAGAAGUCGG CGCCG | = |
| 191-D5-024-29b (SEQ ID NO:111) | 29 | GGGCG GGUUAGGGCUAGAAGUCGG CGCCC | = | terminal nucleotides at the 5'- and the 3'-end that may hybridize to each other (bold)     nt.:= nucleotides nucleotides which may mainly comprise a SDF-binding motif    i.a.:= inactive    =:= equal binding affinity as 191-D5-007

</</<<<:= weaker (<), much weaker (<<) or very much weaker (<<<) binding affinity than 191-D5-007

Comp.:= Clones were tested as aptamers in a competition binding assay vs. 191-D5-007

Fig. 7B continued

Derivatives of Type C SDF Binding Nucleic Acid 197-B2

| Name | nt. | Sequence: 5'-3' | Comp.vs. 197-B2 | Comp. vs. 191-D5-007 | Biacore $K_D$ [nM] | TAX $IC_{50}$ [nM] |
|---|---|---|---|---|---|---|
| 197-B2 | 39 | GUGCUGCGGG GGUUAGGGCUAGAAGUCGG CCUGCAGCAC | | = | 0.9 | 0.1-0.2 |
| 197-B2-001 (SEQ ID NO:112) | 37 | UGCUGCGGG GGUUAGGGCUAGAAGUCGG CCUGCAGCA | = | | 1.1 | |
| 197-B2-002 (SEQ ID NO:113) | 35 | GCUGCGGG GGUUAGGGCUAGAAGUCGG CCUGCAGC | = | | | |
| 197-B2-003 (SEQ ID NO:114) | 33 | CUGCGGG GGUUAGGGCUAGAAGUCGG CCUGCAG | = | | | |
| 197-B2-004 (SEQ ID NO:115) | 31 | UGCGGG GGUUAGGGCUAGAAGUCGG CCUGCA | = | | | |
| 197-B2-005 (SEQ ID NO:116) | 29 | GCGGG GGUUAGGGCUAGAAGUCGG CCUGC | = | | | |
| 197-B2-006 (SEQ ID NO:117) | 29 | GCCGG GGUUAGGGCUAGAAGUCGG CCGGC | = | = | | 0.1-0.2 |
| 197-B2-006-31a (SEQ ID NO:118) | 31 | GGCCGG GGUUAGGGCUAGAAGUCGG CCGGCC | | = | | |
| 197-B2-006-31b (SEQ ID NO:119) | 31 | CGCCGG GGUUAGGGCUAGAAGUCGG CCGGCG | | = | | |

Fig. 8 terminal nucleotides at the 5'- and the 3'-end that may hybridize to each other (bold)  nt.:= nucleotides
nucleotides which may mainly comprise a SDF-binding motif    i.a.:= inactive    =:= equal binding affinity as 197-B2 or 191-D5-007
</<</<<<:= weaker (<), much weaker (<<) or very much weaker (<<<) binding affinity than as 197-B2 or 191-D5-007
Comp.:= Clones were tested as aptamers in a competition binding assay vs. 197-B2 or 191-D5-007 whereas both clones have the identical binding affinity to SDF-1
TAX:= Clones were tested as Spiegelmers in a cell culture *in vitro* chemotaxis assay

Fig. 8 continued

Further SDF-1 Binding Nucleic Acids

| Name | nt. | Sequence: 5'-3' | PD K_D [nM] |
|---|---|---|---|
| 194-A2-001 (SEQ ID NO:142) | 48 | CGUGGUCCGUUGUGUCAGGUCUAUUCGCCCCGGUGCAGGGCAUCCGCG | 12.0 |
| 196-B12-003 (SEQ ID NO:143) | 49 | GCAGUGUGACGCGGACGUGAUAGGACAGAGCUGAUCCCGCUCAGGUGAG | 7.6 |
| 196-B12-004 (SEQ ID NO:144) | 49 | CAACAGCAGUGUGACGCGGACGUGAUAGGACAGAGCUGAUCCCGCUCAG | 5.3 | terminal nucleotides at the 5'- and the 3'-end that may hybridize to each other (bold)    nt.:= nucleotides PD.:= Clones were tested as aptamers in a pull-down binding assay

Fig. 9

SDF-1 BINDING NUCLEIC ACIDS

The instant application is a continuation application of PCT Ser. No. EP07/006387 filed 18 Jul. 2007, which claims benefit to EP Ser. No. 06014957.2 filed 18 Jul. 2006, the contents of which are incorporated herein by reference in entirety.

FIELD OF THE INVENTION

The present invention is related to nucleic acids binding to the CXC chemokine stromal cell-derived factor-1 (SDF-1), and their use in the manufacture of a medicament, and their use in the manufacture of a diagnostic agent.

BACKGROUND OF THE INVENTION

The chemokines are a family of structurally related, heparin-binding basic small proteins of 8-14 kDa. Functionally, they can be classified as proinflammatory, homeostatic, or dual function (Moser, Wolf et al. 2004). Inflammatory chemokines are induced by pathogens, cytokines, or growth factors and recruit effector leukocytes to sites of infection, inflammation, tissue injury, and tumor. Such chemokines regulate the recruitment, activation, and proliferation of white blood cells (leukocytes) (Schall and Bacon 1994; Springer 1995; Baggiolini 1998). Chemokines selectively induce chemotaxis of neutrophils, eosinophils, basophils, monocytes, macrophages, mast cells, T and B cells. In addition to their chemotactic effect, they can selectively exert other effects in responsive cells like changes in cell shape, transient increase in the concentration of free intracellular calcium ions, degranulation, upregulation of integrins, formation of bioactive lipids (leukotrienes, prostaglandins, thromboxane), or respiratory burst (release of reactive oxygen species for destruction of pathogenic organisms or tumor cells). Thus, by provoking the release of further proinflammatory mediators, chemotaxis and extravasation of leukocytes towards sites of infection or inflammation, chemokines trigger escalation of the inflammatory response. Homeostatic chemokines, on the other hand, are expressed predominantly in bone marrow and lymphoid tissues and are involved in hematopoiesis, immune surveillance, and adaptive immune responses (Godessart 2005).

Based on the arrangement of the first two of four conserved cysteine residues, the chemokines are divided into four classes: CC or β-chemokines (e.g.) in which the cysteines are in tandem, CXC or α-chemokines, where they are separated by one additional amino acid residue, XC or γ chemokines (lymphotactin/XCL1 as only representative to date) that possess only one disulfide bridge, and CX3C-chemokines which feature three amino acid residues between the cysteines (membrane-bound fractalkine as only class member; (Bazan, Bacon et al. 1997)).

The CXC chemokines act primarily on neutrophils, in particular those CXC chemokines that carry the amino acid sequence ELR on their amino terminus. Examples of CXC chemokines that are active on neutrophils are IL-8/CXCL8, GROα/CXCL1, GROβ/CXCL2, and GROγ/CXCL3, NAP-2/CXCL7, ENA-78/CXCL5, SDF-1/CXCL12 and GCP-2/CXCL6. The CC chemokines act on a larger variety of leukocytes, such as monocytes, macrophages, eosinophils, basophils, as well as T and B lymphocytes (Oppenheim, Zachariae et al. 1991; Miller and Krangel 1992; Baggiolini, Dewald et al. 1994; Jose, Griffiths-Johnson et al. 1994; Ponath, Qin et al. 1996). Examples of these are I-309/CCL1; MCP-1/CCL2, MCP-2/CCL8, MCP-3/CCL7, MCP-4/CCL13, MIP-1α/CCL3 and MIP-1β/CCL4, RANTES/CCL5, and cotaxin/CCL11.

Chemokines act through receptors that belong to a super-family of seven transmembrane-spanning G protein-coupled receptors (GPCRs; (Murphy, Baggiolini et al. 2000)). Generally speaking, chemokine and chemokine receptor interactions tend to be promiscuous in that one chemokine can bind many chemokine receptors and conversely a single chemokine receptor can interact with several chemokines Some known receptors for the CXC chemokines include CXCR1, which binds GROα, GCP-2, and IL-8; CXCR2, which binds chemokines including GROα, GROβ, GROγ, ENA-78, and IL-8; CXCR3, which binds chemokines including PF4, MIG, IP-10, and I-TAC; CXCR4 which thus far has been found only to signal in response to SDF-1, and CXCR5, which has been shown to signal in response to BCA-1 (Godessart 2005).

SDF-1 (stromal-cell derived factor-1; synonyms, CXCL12; PBSF [pre-B-cell growth-stimulating factor]; TPAR-1 [TPA repressed gene 1]; SCYB12; TLSF [thymic lymphoma cell stimulating factor]; hIRH [human intercrine reduced in hepatomas]) is an angiogenic CXC chemokine that does not contain the ELR motif typical of the IL-8-like chemokines (Salcedo, Wasserman et al. 1999; Salcedo and Oppenheim 2003) that binds and activates the G-protein coupled receptor CXCR4. The chemokine was discovered by three groups independently, either by cloning cDNAs that carry N-terminal signal sequences (Tashiro, Tada et al. 1993), by virtue of its ability to stimulate early B cell progenitors when expressed by the stromal cell line PA6 (Nagasawa, Kikutani et al. 1994), or by isolation from a cDNA library constructed from mouse embryo fibroblasts treated with the protein kinase C-activator tetra dodecanoyl phorbol acetate (TPA) (Jiang, Zhou et al. 1994).

As a result of alternative splicing, there are two forms of SDF-1, SDF-1α (68 AA) and SDF-1β, which carries four additional residues at the C-terminus (Shirozu, Nakano et al. 1995). The biological significance of these two splice variants is not completely understood.

The sequence conservation between SDF-1 from different species is remarkable: human SDF-1α (SEQ ID NO:1) and murine SDF-1α (SEQ ID NO:2) are virtually identical. There is a only a single conservative change of V to I at position 18 (Shirozu, Nakano et al. 1995). Another unusual feature that distinguishes SDF-1 from most other chemokines is its selectivity. In fact, SDF-1 and the receptor CXCR4 seem to comprise a monogamous receptor-ligand pair.

An NMR structure model exists (PDB access, 1SDF) for SDF-1 [8-68]. SDF-1 was found to be a monomer with a disordered N-terminal region. Differences from other chemokines are found mainly in the packing of the hydrophobic core and surface charge distribution (Crump, Gong et al. 1997).

Physiological activities of SDF-1: since the SDF-1 receptor CXCR4 is widely expressed on leukocytes, mature dendritic cells, endothelial cells, brain cells, and megakaryocytes, the activities of SDF-1 are pleiotropic. This chemokine, more than any other identified thus far, exhibits the widest range of biological functions, especially outside of the immune system. The most significant functional effects of SDF-1 are:

Homing and attachment of epithelial cells to neovascular sites in the choroid portion of the retina. SDF-1 has been shown to be involved in homing of epithelial cells to the choroid during neovascularization in eye tissue. The exact role of these cells is still under investigation but the published hypothesis is that epithelial cells are involved in the formation of aberrant blood vessels (Sengupta, Caballero et al. 2005);

Hematopoiesis. SDF-1 is required to maintain hematopoietic progenitor (CD34$^+$) cells in the bone marrow of the adult. AMD3100, a selective CXCR4 antagonist, can be used to mobilize CD34$^+$ cells for hematopoietic stem cell transplantation. CD34$^+$ cells migrate in vitro and in vivo towards a gradient of SDF-1 produced by stromal cells (Aiuti, Webb et al. 1997);

B cell development and chemotaxis. SDF-1 supports proliferation of pre-B-cells and augments the growth of bone marrow B cell progenitors (Nagasawa, Kikutani et al. 1994); it induces specific migration of pre-B cells and pro-B cells, while not acting as a significant chemoattractant for mature B cells (D'Apuzzo, Rolink et al. 1997; Bleul, Schultze et al. 1998). Presumably, SDF-1 is important for the positioning of B cells within secondary lymphoid tissue;

T cell chemotaxis. SDF-1 is one of the most efficacious T cell chemoattractants; CXCR4 is present on many T cell subsets (Bleul, Farzan et al. 1996);

Embryonic development. SDF-1 and its receptor CXCR4 are essential for embryonic development. SDF-1 and CXCR4 knockout mice die perinatally; they exhibit cardiac ventricular septal defects or abnormal cerebellar development in addition to reduced numbers of B cell and myeloid progenitors (Nagasawa, Hirota et al. 1996; Ma, Jones et al. 1998; Zou, Kottmann et al. 1998). SDF-1 is also required for normal ontogeny of blood development during embryogenesis (Juarez and Bendall 2004); and HIV infection. SDF-1 is able to inhibit T-tropic HIV-1 entry into CXCR4-bearing cell lines, and SDF-1 expression may have an important bearing on AIDS pathogenesis, since a polymorphism in the human SDF-1 gene affects the onset of AIDS (Bleul, Farzan et al. 1996).

Altered expression levels of SDF-1 or its receptor CXCR4 or altered responses towards those molecules are associated with many human diseases, such as retinopathy (Brooks, Caballero et al. 2004; Butler, Guthrie et al. 2005; Meleth, Agron et al. 2005); cancer of breast (Muller, Homey et al. 2001; Cabioglu, Sahin et al. 2005), ovary (Scotton, Wilson et al. 2002), pancreas (Koshiba, Hosotani et al. 2000), thyroid (Hwang, Chung et al. 2003), nasopharynx (Wang, Wu et al. 2005); glioma (Zhou, Larsen et al. 2002); neuroblastoma (Geminder, Sagi-Assif et al. 2001); B cell chronic lymphocytic leukemia (Burger, Tsukada et al. 2000); WHIM syndrome (warts, hypogammaglobulinemia, infections, myelokathexis) (Gulino, Moratto et al. 2004; Balabanian, Lagane et al. 2005; Kawai, Choi et al. 2005); immunologic deficiency syndromes (Arya, Ginsberg et al. 1999; Marechal, Arenzana-Seisdedos et al. 1999; Soriano, Martinez et al. 2002); pathologic neovascularization (Salvucci, Yao et al. 2002; Yamaguchi, Kusano et al. 2003; Grunewald, Avraham et al. 2006); inflammation (Murdoch 2000; Fedyk, Jones et al. 2001; Wang, Guan et al. 2001); multiple sclerosis (Krumbholz, Theil et al. 2006); rheumatoid arthritis/osteoarthritis (Buckley, Amft et al. 2000; Kanbe, Takagishi et al. 2002; Grassi, Cristino et al. 2004).

In experimental animal settings, antagonists of SDF-1 or its receptor have proved efficient for blocking growth and/or metastatic spreading of human cancer cells of different origin, such as pancreas (Guleng, Tateishi et al. 2005; Saur, Seidler et al. 2005), colon (Zeelenberg, Ruuls-Van Stalle et al. 2003; Guleng, Tateishi et al. 2005), breast (Muller, Homey et al. 2001; Lapteva, Yang et al. 2005), lung (Phillips, Burdick et al. 2003), glioblastoma/medulloblastoma (Rubin, Kung et al. 2003), prostate (Sun, Schneider et al. 2005), osteosarcoma (Perissinotto, Cavalloni et al. 2005), melanoma (Takenaga, Tamamura et al. 2004), stomach (Yasumoto, Koizumi et al. 2006) and multiple myeloma (Menu, Asosingh et al. 2006).

In addition, anti-SDF-1 therapy was beneficial in animal models in preventing retinal neovascularization (Butler, Guthrie et al. 2005), nephritis (Balabanian, Couderc et al. 2003) and arthritis (Matthys, Hatse et al. 2001; Tamamura, Fujisawa et al. 2004; De Klerck, Geboes et al. 2005).

SDF-1 is a player in the pathology of diseases of the back of the eye such as diabetic retinopathy (DR) (Fong, Aiello et al. 2004) and age-related macular degeneration (AMD) (Ambati, Anand et al. 2003). Both of these diseases damage the eye and lead to gradual loss of vision culminating in blindness. The damage occurs due to the inappropriate growth of blood vessels in the back of the eye, a process known as choroidal neovascularization (CNV). During CNV, new blood vessels that originate from the choroid migrate through a break in the Bruch membrane into the sub-retinal pigment epithelium (sub-RPE) or subretinal space. The abnormal vessels can bleed (intraretinal hemorrhage) or leak fluid under the retina. This can leave scars and can elevate the macula, which distorts vision.

SDF-1 is thought to play a role in CNV via recruitment of endothelial precursor cells (EPCs) to the eye. These precursor cells then become key structural components in the aberrant blood vessels.

Diabetic retinopathy is a major sequel to diabetes, occurring frequently in patients with both type 1 and type 2 diabetes. There are approximately 16 million diabetics in the U.S., with nearly 8 million having some form of diabetic retinopathy. When proliferative diabetic retinopathy (PDR) is left untreated, about 60% of patients become blind in one or both eyes within 5 years. With the alarming rise in the prevalence of diabetes in North America, Europe and many emerging countries, the patient population is growing quickly. For instance, the incidence of blindness is 25 times higher in patients with diabetes than in the general population. Furthermore, diabetic retinopathy (DR) is the most common cause of blindness in middle-aged subjects, accounting for at least 12 percent of all new cases in the United States each year. Screening programs are in place so that the vision of diabetes patients can be monitored and treatment, such as is available, can be delivered in time.

The direct causes of diabetic retinopathy are poorly understood, but the disease is thought to have its origins in a combination of sources: impaired auto-regulation of retinal blood flow; accumulation of sorbitol inside retinal cells; and accumulation of advanced glycosylation end products in the extracellular fluid. All of these factors are related directly or indirectly to hyperglycemia, the abundance of sugar in the bloodstream.

The symptoms of DR are similar to those of AMD. Patients lose cells in the retina and microaneurysms (blood flows) occur in the basement membrane of the retina. In addition, VEGF, IGF-1 and other blood-borne factors, possibly including SDF-1, attract new vascular cells and encourage the formation of damaging blood vessels.

Age-related macular degeneration (AMD) destroys a person's central vision. The early stages of the disease may not even be noticeable, because symptoms vary among patients. Sometimes a patient is affected only in one eye, or vision may be impaired in both eyes but not significantly. The disease causes distortion or faulty color perception. There is often a dark spot in the center of the visual field.

The etiology (course) of the disease is poorly understood. AMD is often thought of as the aging of the outermost layer of the retina. The physical alterations occur in the center of the retina, also known as the macula, which is the part of the retina relied upon for the most acute vision.

Wet AMD begins as a sequel to the dry form of the disease. Some 90% of patients suffer from the dry form of AMD, which results in the thinning of macular tissues and disturbances in its pigmentation. The rest have the wet form, which involves the bleeding described above.

The wet form of AMD represents an ideal market for a novel therapeutic: already the most common cause of blindness in people over the age of 55, AMD afflicts an estimated 4% to 5% of the United States population aged 65-74 and nearly 10% of those 75 years of age or older. There are already 5 million people in the United States alone over the age of 80 who have this disease and another 5 million people are expected to be affected by 2020.

Tumors are not just masses of cancer cells: infiltration of tumors with immune cells is a characteristic of cancer. Many human cancers have a complex chemokine network that influences the extent and phenotype of this infiltrate, as well as tumor growth, survival and migration, and angiogenesis. Most solid tumors contain many non-malignant stromal cells. Indeed, stromal cells sometimes outnumber cancer cells. The predominant stromal cells that are found in cancers are macrophages, lymphocytes, endothelial cells and fibroblasts.

Malignant cells from different cancer types have different profiles of chemokine-receptor expression, but the SDF-1 receptor CXCR4 is most commonly found in mouse and man. Tumor cells from at least 23 different types of human cancers of epithelial, mesenchymal, and haematopoietic origin express CXCR4 (Balkwill 2004). SDF-1 is the only known ligand for CXCR4. Apart from the bone marrow and secondary lymphoid tissue, where it is constitutively expressed, SDF-1 is found in primary tumor sites in lymphoma (Corcione, Ottonello et al. 2000) and brain tumors of both neuronal and astrocytic lineage. Furthermore, it is present at high levels in ovarian (Scotton, Wilson et al. 2002) and pancreatic cancer (Koshiba, Hosotani et al. 2000) as well as at sites of metastasis in breast (Muller, Homey et al. 2001) and thyroid cancer (Hwang, Chung et al. 2003), neuroblastoma and haematological malignancies (Geminder, Sagi-Assif et al. 2001). In contrast, CXCR4 expression is low or absent on normal breast (Muller, Homey et al. 2001), ovarian (Scotton, Wilson et al. 2002) and prostate epithelia (Sun, Schneider et al. 2005). CXCR4 expression thus seems to be a general characteristic of the malignant epithelial cell and not its normal counterpart.

Inhibiting chemokine-receptor signalling on tumor cells has the potential to induce growth arrest or apoptosis, and prevent invasion and metastasis in vivo.

CXCR4 knockdown by siRNA abrogated breast tumor growth (Lapteva, Yang et al. 2005); T-hybridoma cells which were transfected with a construct that prevents surface expression of CXCR4 could no longer metastasize to distant organs when injected intravenously into mice (Zeelenberg, Ruuls-Van Stalle et al. 2001); in similar experiments with colorectal cancer cells, lung and liver metastases were greatly reduced (Zeelenberg, Ruuls-Van Stalle et al. 2003); anti-CXCR4 antibodies inhibited the spread of breast cancer xenografts to the lymph nodes (Muller, Homey et al. 2001); treatment of lymphoblastoid cells with anti-CXCR4 or anti-SDF-1 antibodies delayed tumor growth in (NOD)/SCID mice (Bertolini, Dell'Agnola et al. 2002); anti-SDF-1 antibodies inhibited development of organ metastases of non-small-cell lung cancer (NSCLC) cells (Phillips, Burdick et al. 2003); systemic administration of the CXCR4 antagonist AMD3100 (AnorMED) inhibited the growth of intracranial glioblastoma and medulloblastoma xenografts, and increased tumor cell apoptosis within 24 hours (Rubin, Kung et al. 2003); anti-SDF-1 antibodies inhibited growth of MCF-7 breast cancer cells admixed with carcinoma-associated fibroblasts (Orimo, Gupta et al. 2005); neutralization of CXCR4 with antibodies blocked prostate cancer metastasis and growth in osseous sites (Sun, Schneider et al. 2005); and development of lung metastasis after injection of osteosarcoma cells was prevented by administration of the peptidic CXCR4 antagonist T134 (Perissinotto, Cavalloni et al. 2005).

Different authors come to the conclusion that targeting the SDF-1/CXCR4 axis may provide new therapeutic options for cancer patients:

Human ovarian tumors strongly express SDF-1 plus, on a lower level, VEGF. Both proteins are triggered by hypoxia in the tumor. Pathologic concentrations of any of the proteins alone were not sufficient to induce in vivo angiogenesis, but together, SDF-1 and VEGF in pathologic concentrations efficiently and synergistically induced neovascularization. Thus, interrupting this synergistic axis, rather than VEGF alone, can be a novel efficient antiangiogenesis strategy to treat cancer (Kryczek, Lange et al. 2005);

Breast cancer cell lines, when equipped with the autocrine SDF-1/CXCR4 signalling pathway, display aggressive behavior. This includes an increase in invasiveness and migration together with faster growth. The SDF-1/CXCR4 axis may thus provide important information for predicting the aggressive nature and constitute important therapeutic targets in human breast cancer (Kang, Watkins et al. 2005);

Migration and metastasis of small cell lung cancer (SCLC) cells—which express high levels of CXCR4—are regulated by SDF-1. Activation of CXCR4 promotes adhesion to accessory cells (such as stromal cells) and extracellular matrix molecules within the tumor microenvironment. These adhesive interactions result in an increased resistance of SCLC cells to chemotherapy. As such, inhibitors of the SDF-1/CXCR4 axis may increase the chemosensitivity of SCLC cells and lead to new therapeutic avenues for patients with SCLC (Hartmann, Burger et al. 2004); and The SDF-1/CXCR4 axis emerges as a pivotal regulator of trafficking of various types of stem cells in the body. Since most if not all malignancies originate in the stem/progenitor cell compartment, cancer stem cells also express CXCR4 on their surface and, as a result, the SDF-1/CXCR4 axis is involved in directing their trafficking/metastasis to organs that express SDF-1 (e.g. lymph nodes, lungs, liver and bone). In consequence, strategies aimed at modulating the SDF-1/CXCR4 axis could have important clinical applications both in regenerative medicine to deliver normal stem cells to the tissues and in clinical oncology to inhibit metastasis of cancer stem cells (Kucia, Reca et al. 2005).

SUMMARY OF THE INVENTION

The problem underlying the present invention is to provide a specific antagonist of SDF-1. A further aspect of the problem underlying the present invention is to provide a compound for the treatment of diseases and disorders involving SDF-1 and the CXCR4 receptor, respectively.

Another problem underlying the present invention is to provide methods for the specific detection of SDF-1.

The problem underlying the present invention is solved by the subject matter of the independent claims. Preferred embodiments may be taken from the dependent claims.

In a first aspect, the problem underlying the present invention is solved by a nucleic acid molecule, preferably binding to SDF-1, selected from the group comprising type A nucleic acid molecules, type B nucleic acid molecules, type C nucleic acid molecules and nucleic acid molecules having a nucleic acid sequence according to any of SEQ ID NO:142, SEQ ID NO:143 and SEQ ID NO:144.

In an embodiment the type A nucleic acid molecules comprise the following core nucleotide sequence: 5' AAAGYRACAHGUMAAX$_4$UGAAAGGUARC 3' (SEQ ID NO:19) whereby X$_4$ is either absent or is A.

In a preferred embodiment the type A nucleic acid molecules comprise a core nucleotide sequence selected from the group comprising:

```
5' AAAGYRACAHGUMAAUGAAAGGUARC 3', (SEQ ID NO: 20)

5' AAAGYRACAHGUMAAAUGAAAGGUARC 3', (SEQ ID NO: 21)
and

5' AAAGYAACAHGUCAAUGAAAGGUARC 3', (SEQ ID NO: 22)
``` preferably the core nucleotide sequence comprises:

```
5' AAAGYAACAHGUCAAUGAAAGGUARC 3'. (SEQ ID NO: 22)
```

In an embodiment, the nucleic acid molecule comprises in the 5'→3' direction a first stretch of nucleotides, the core nucleotide sequence, and a second stretch of nucleotides.

In an embodiment, the nucleic acid molecule comprises in 5'→3' direction a second stretch of nucleotides, the core nucleotide sequence, and a first stretch of nucleotides.

In a preferred embodiment the nucleic acid molecule comprises the first and the second stretch of nucleotides and said first and said second stretch of nucleotides optionally hybridize with each other, whereby upon hybridization a double-stranded structure is formed.

In a further preferred embodiment, the double-stranded structure consists of four to six base pairs, preferably five base pairs.

In an embodiment, the first stretch of nucleotides comprise a nucleotide sequence of 5' X$_1$X$_2$NNBV 3' (SEQ ID NO:44) and the second stretch of nucleotides comprises a nucleotide sequence of 5' BNBNX$_3$X$_4$ 3' (SEQ ID NO:45), wherein X$_1$ is either absent or R, X$_2$ is S, X$_3$ is S and X$_4$ is either absent or Y; or X$_1$ is absent, X$_2$ is either absent or S, X$_3$ is either absent or S and X$_4$ is absent.

In an embodiment, the first stretch of nucleotides comprises a nucleotide sequence of 5' RSHRYR 3' (SEQ ID NO:23) and the second stretch of nucleotides comprises a nucleotide sequence of 5' YRYDSY 3'(SEQ ID NO:24), preferably the first stretch of nucleotides comprises a nucleotide sequence of 5' GCUGUG 3' and the second stretch of nucleotides comprises a nucleotide sequence of 5' CGCAGC 3'.

In an embodiment, the first stretch of nucleotides comprises a nucleotide sequence of 5' X$_2$BBBS 3' (SEQ ID NO:42) and the second stretch of nucleotides comprises a nucleotide sequence of 5' SBBVX$_3$ 3' (SEQ ID NO:43), wherein X$_2$ is either absent or is S and X$_3$ is either absent or is S; preferably the first stretch of nucleotides comprises a nucleotide sequence of 5' CUGUG 3' and the second stretch of nucleotides comprises a nucleotide sequence of 5' CGCAG 3'; or the first stretch of nucleotides comprises a nucleotide sequence of 5' GCGUG 3' and the second stretch of nucleotides comprises a nucleotide sequence of 5' CGCGC 3'.

In an embodiment the nucleic acid molecule has a nucleic acid sequence according to any of SEQ ID NOs:5 to 18, 25 to 41, 133, 137 or 139 to 141.

In an embodiment the type B nucleic acid molecules comprise the following core nucleotide sequence: 5' GUGUGAUCUAGAUGUADWGGCUGWUCCUAGUY-AGG 3' (SEQ ID NO:57).

In a preferred embodiment, the type B nucleic acid molecules comprise a core nucleotide sequence of GUGUGAUCUAGAUGUADUGGCUGAUCCUAGU-CAGG (SEQ ID NO:58).

In an embodiment, the nucleic acid molecule comprises in the 5'→3' direction a first stretch of nucleotides, the core nucleotide sequence, and a second stretch of nucleotides.

In an embodiment, the nucleic acid molecule comprises in the 5'→3' direction a second stretch of nucleotides, the core nucleotide sequence, and a first stretch of nucleotides.

In a preferred embodiment, the nucleic acid molecule comprises the first and the second stretch of nucleotides and said first and said second stretch of nucleotides optionally hybridize with each other, whereby upon hybridization a double-stranded structure is formed.

In an embodiment, the double-stranded structure consists of four to six base pairs, preferably five base pairs.

In an embodiment, the first stretch of nucleotides comprises a nucleotide sequence of 5' X$_1$X$_2$SVNS 3' (SEQ ID NO:77) and the second stretch of nucleotides comprises a nucleotide sequence of 5' BVBSX$_3$X$_4$ 3' (SEQ ID NO:78), wherein X$_1$ is either absent or is A, X$_2$ is G, X$_3$ is C and X$_4$ is either absent or is U; or X$_1$ is absent, X$_2$ is either absent or is G, X$_3$ is either absent or is C and X$_4$ is absent.

In an embodiment, the first stretch of nucleotides comprises a nucleotide sequence of 5' X$_1$GCRWG 3' (SEQ ID NO:59) and the second stretch of nucleotides comprises a nucleotide sequence of 5' KRYSCX$_4$ 3'(SEQ ID NO:60), wherein X$_1$ is either absent or A, and X$_4$ is either absent or U.

In an embodiment the first stretch of nucleotides comprises a nucleotide sequence of 5' X$_1$GCGUG 3' (SEQ ID N0:75) and the second stretch of nucleotides comprises a nucleotide sequence of 5' UACGCX$_4$ 3' (SEQ ID N0:76), wherein X$_1$ is either absent or A, and X$_4$ is either absent or U, preferably the first stretch of nucleotides comprises a nucleotide sequence of 5' AGCGUG 3' and the second stretch of nucleotides comprises a nucleotide sequence of 5' UACGCU 3'.

In an embodiment, the first stretch of nucleotides comprises a nucleotide sequence of 5' X$_2$SSBS 3' (SEQ ID NO:73) and the second stretch of nucleotides comprises a nucleotide sequence of 5' BVSSX$_3$ 3' (SEQ ID N0:74), wherein X$_2$ is either absent or G, and X$_3$ is either absent or C, preferably the first stretch of nucleotides comprises a nucleotide sequence of 5' GCGUG 3' and the second stretch of nucleotides comprises a nucleotide sequence of 5' UACGC 3'.

In an embodiment, the nucleic acid molecule has a nucleic acid sequence according to any of SEQ ID NOs:46 to 56, 61 to 72 or 132.

In an embodiment, the type C nucleic acid molecules comprise a core nucleotide sequence of GGUY-AGGGCUHRX$_4$AGUCGG (SEQ ID N0:90), wherein X$_4$ is either absent or is A.

In a preferred embodiment, the type C nucleic acid molecules comprise a core nucleotide sequence selected from the group comprising:

```
5' GGUYAGGGCUHRAAGUCGG 3', (SEQ ID NO: 91)

5' GGUYAGGGCUHRAGUCGG 3', (SEQ ID NO: 92)
and

5' GGUUAGGGCUHGAAGUCGG 3', (SEQ ID NO: 93)
``` preferably the core nucleotide sequence comprises 5' GGUUAGGGCUHGAAGUCGG 3' (SEQ ID NO:93).

In an embodiment, the nucleic acid molecule comprises in the 5'→3' direction, a first stretch of nucleotides, the core nucleotide sequence, and a second stretch of nucleotides.

In an embodiment, the nucleic acid molecule comprises in the 5'→3' direction, a second stretch of nucleotides, the core nucleotide sequence, and a first stretch of nucleotides.

In a preferred embodiment, the nucleic acid molecule comprises the first and the second stretch of nucleotides and whereby at least a part of said first stretch and at least a part of said second stretch of nucleotides optionally hybridize with each other, whereby upon hybridization a double-stranded structure is formed.

In an embodiment, the length of the first stretch and the length of the second stretch is individually and independently 0 to 17 nucleotides, preferably 4 to 10 nucleotides and more preferably 4 to 6 nucleotides.

In an embodiment, the double-stranded structure comprises 4 to 10 base pairs, preferably 4 to 6 base pairs, more preferably 5 base pairs.

In a preferred embodiment, the double-stranded structure comprises 4 to 10 consecutive base pairs, preferably 4 to 6 consecutive base pairs, more preferably 5 consecutive base pairs.

In an embodiment, the first stretch of nucleotides comprises a nucleotide sequence of 5' RKSBUSNVGR 3' (SEQ ID NO:120) and the second stretch of nucleotides comprises a nucleotide sequence of 5' YYNRCASSMY 3' (SEQ ID NO:121), preferably the first stretch of nucleotides comprises a nucleotide sequence of 5' RKSBUGSVGR 3' (SEQ ID NO:122) and the second stretch of nucleotides comprises a nucleotide sequence of 5' YCNRCASSMY 3' (SEQ ID NO:123).

In an embodiment, the first stretch of nucleotides comprises a nucleotide sequence of 5' X$_S$SSSV 3' (SEQ ID NO:124) and the second stretch of nucleotides comprises a nucleotide sequence of 5' BSSSX$_S$ 3' (SEQ ID NO:125), whereby X$_S$ is either absent or is S.

In an embodiment, the first stretch of nucleotides comprises a nucleotide sequence of 5' SSSSR 3' (SEQ ID NO:130) and the second stretch of nucleotides comprise a nucleotide sequence of 5' YSBSS 3' (SEQ ID NO:131), preferably the first stretch of nucleotides comprises a nucleotide sequence of 5' SGGSR 3' (SEQ ID NO:126) and the second stretch of nucleotides comprises a nucleotide sequence of 5' YSCCS 3' (SEQ ID NO:127).

In an embodiment, the first stretch of nucleotides comprises a nucleotide sequence of 5' GCSGG 3' (SEQ ID NO:128) and the second stretch of nucleotides comprises a nucleotide sequence of 5' CCKGC 3' (SEQ ID NO:129), preferably the first stretch of nucleotides comprises a nucleotide sequence of 5' GCCGG 3' and the second stretch of nucleotides comprises a nucleotide sequence of 5' CCGGC 3'.

In an embodiment, the first stretch of nucleotides comprises a nucleotide sequence of 5' CGUGCGCUUGA-GAUAGG 3' (SEQ ID NO:82) and the second stretch of nucleotides comprises a nucleotide sequence of 5' CUGAUUCUCACG 3' (SEQ ID NO:82).

In an embodiment, the first stretch of nucleotides comprises a nucleotide sequence of 5' UGAGAUAGG 3' and the second stretch of nucleotides comprises a nucleotide sequence of 5' CUGAUUCUCA 3' (SEQ ID NO:82).

In an embodiment, the first stretch of nucleotides comprises a nucleotide sequence of 5' GAGAUAGG 3' and the second stretch of nucleotides comprises a nucleotide sequence of 5' CUGAUUCUC 3'.

In an embodiment the nucleic acid molecule has a nucleic acid sequence according to any of SEQ ID NOs:79 to 89, 94 to 119 or 134 to 136.

In an embodiment, the nucleic acid molecule has a nucleic acid sequence according to any of SEQ ID NOs:142 to 144.

In an embodiment, the nucleic acid molecule is an antagonist to SDF-1.

In an embodiment, the nucleic acid molecule is an antagonist of the SDF-1 receptor system, preferably the SDF-1 receptor of the SDF-1 receptor system is the CXCR4 receptor.

In an embodiment, the SDF-1 is a human SDF-1 and/or the SDF-1 receptor is a human SDF-1 receptor.

In an embodiment, SDF-1 comprises an amino acid sequence according to SEQ ID NO:1.

In an embodiment, the nucleic acid comprises a modification.

In a preferred embodiment, the modification is selected from the group comprising a HES moiety and a PEG moiety.

In a further preferred embodiment, the modification is a PEG moiety consisting of a straight or branched PEG, whereby the molecular weight of the PEG moiety is preferably from about 2 to 180 kD, more preferably from about 60 to 140 kD and most preferably about 40 kD.

In an embodiment, the modification is a HES moiety, whereby preferably the molecular weight of the HES moiety is from about 10 to 130 kD, more preferably from about 30 to 130 kD and most preferably about 100 kD.

In an embodiment, the nucleotides of the nucleic acid are L-nucleotides, preferably the nucleotides of the sequences according to any of SEQ ID NOs:19, 20, 21, 22, 57, 58, 90, 91, 92, and 93.

In a second aspect, the problem underlying the present invention is solved by a pharmaceutical composition comprising a nucleic acid according to the first aspect and optionally a further constituent, whereby the further constituent is selected from the group comprising pharmaceutically acceptable excipients and pharmaceutically active agents.

In a third aspect, the problem underlying the present invention is solved by the use of a nucleic acid according to the first aspect for the manufacture of a medicament.

In an embodiment of the third aspect, the medicament is for the treatment and/or prevention of a disease or disorder, whereby such disease or disorder is mediated by SDF-1, preferably such disease or disorder is selected from the group comprising back-of-the-eye diseases like diabetic retinopathy and age-related macular degeneration; cancer of breast, ovary, prostate, pancreas, thyroid, nasopharynx, colon, lung, and stomach; osteosarcoma; melanoma; glioma; medullo- and neuroblastoma; leukemia; WHIM syndrome; immunologic deficiency syndromes; pathologic neovascularization; inflammation; multiple sclerosis; rheumatoid arthritis/osteoarthritis and nephritis.

In an embodiment of the third aspect, the medicament is for inhibiting angiogenesis, neovascularization, inflammation and metastasis.

In a fourth aspect, the problem underlying the present invention is solved by the use of the nucleic acid according to the first aspect for the manufacture of a diagnostic means.

In an embodiment of the fourth aspect, the diagnostic means is for the diagnosis of a disease, whereby the disease is selected from the group comprising back-of-the-eye diseases like diabetic retinopathy and age-related macular degeneration; cancer of breast, ovaries, prostate, pancreas, thyroid, nasopharynx, colon, lung, and stomach; osteosarcoma; melanoma; glioma; medullo- and neuroblastoma; leukemia; WHIM syndrome; immunologic deficiency syndromes; pathologic neovascularization; inflammation; multiple sclerosis; rheumatoid arthritis/osteoarthritis and nephritis.

In an embodiment of the fourth aspect, the diagnostic means is for diagnosing angiogenesis, neovascularization, inflammation and/or metastasis.

In a fifth aspect, the problem underlying the present invention is solved by a complex comprising SDF-1 and a nucleic acid according to the first aspect, whereby preferably the complex is a crystalline complex.

In a sixth aspect, the problem underlying the present invention is solved by the use of the nucleic acid according to the first aspect for the detection of SDF-1.

In a seventh aspect, the problem underlying the present invention is solved by a method for the screening of an SDF-1 antagonist or an SDF-1 agonist comprising the following steps:
  providing a candidate SDF-1 antagonist and/or a candidate SDF-1 agonist,
  providing a nucleic acid according to the first aspect,
  providing a test system which provides a signal in the presence of an SDF-1 antagonist and/or an SDF-1 agonist, and
  determining whether the candidate SDF-1 antagonist is an SDF-1 antagonist and/or whether the candidate SDF-1 agonist is an SDF-1 agonist.

In an eighth aspect, the problem underlying the present invention is solved by a method for the screening of an SDF-1 agonist and/or an SDF-1 antagonist comprises the following steps:
  providing SDF-1 immobilised to a phase, preferably a solid phase,
  providing a nucleic acid according to the first aspect, preferably a nucleic acid according to the first aspect which is labelled,
  adding a candidate SDF-1 agonist and/or a candidate SDF-1 antagonist, and
  determining whether the candidate SDF-1 agonist is an SDF-1 agonist and/or whether the candidate SDF-1 antagonist is an SDF-1 antagonist.

In an embodiment of the eighth aspect, the determining is carried out such that it is assessed whether the nucleic acid is replaced by the candidate SDF-1 agonist or by a candidate SDF-1 antagonist.

In a ninth aspect, the problem underlying the present invention is solved by a kit for the detection of SDF-1, comprising a nucleic acid according to the first aspect.

In a tenth aspect, the problem underlying the present invention is solved by an SDF-1 antagonist obtainable by the method according to the seventh aspect or the eighth aspect.

BRIEF DESCRIPTION OF THE FIGURES

The present invention is further illustrated by the figures, examples and the sequence listing from which further features, embodiments and advantages may be taken.

FIG. 1 shows an alignment of sequences of related RNA ligands binding to human SDF-1 indicating the sequence motif ("Type A") that is in a preferred embodiment in its entirety essential for binding to human SDF-1. In the figure and in subsequent figures, terminal nucleotides that may hybridize to each other are indicated in boldface; nucleotides that comprise a motif that binds SDF-1 are delimited in a box; nt. is nucleotides; variable positions are indicated by background shading; and Comp. relates to clones that were tested as aptamers in a competition binding assay. In this figure, the clones were tested with 192-A10-001 as a reference, where = indicates equal binding affinity as 192-A10-001, < indicates weaker binding affinity than 192-A10-001 and << indicates much weaker binding affinity than 192-A10-001.

FIG. 2A shows derivatives of RNA ligand 192-A10-001 (human SDF-1 RNA ligand of sequence motif "Type A"). In the figure and in subsequent figures, i.a. is inactive, PD. provides the results of a pull-down assay where clones were tested as aptamers; and TAX provides the results of clones tested as spiegelmers in a cell culture chemotaxis assay. In this figure, in the competition assay <<< indicates very much weaker binding affinity than 192-A1 0-001.

FIG. 2B shows derivatives of RNA ligand 192-A10-001 (human SDF-1 RNA ligand of sequence motif "Type A"). In the figure, the results of the competition assay relate to 192-A10-001 or 192-A10-008. Clones were tested as aptamers with 192-A10-001, except * are clones 192-A10-020, -021, -022 and -023 which were tested with 192-A10-008 which has the same binding affinity to SDF-1 as does 192A10-001.

FIG. 3 shows an alignment of sequences of related RNA ligands binding to human SDF-1 indicating the sequence motif ("Type B") that is in a preferred embodiment in its entirety essential for binding to human SDF-1. For the competition assay, clones C2, G2 and F2 were tested as aptamers with 192-A10-001. All other clones were tested with 193-G2-012 which has the same binding affinity for SDF-1 as does 193-G2-001, see FIG. 4B. + is better binding affinity than 192-A10-001 and the other results indicate varying levels of reduced binding affinity as compared to 193-G2-001 or -012. $X_1$ is A or absent. $X_4$ is U or absent.

FIG. 4A shows derivatives of RNA ligands 193-C2-001 and 193-G2-001 (human SDF-1 RNA ligands of sequence motif "Type B"). The results of the competition assay are relative to 193-G2-001.

FIG. 4B shows derivatives of RNA ligands 193-C2-001 and 193-G2-001 (human SDF-1 RNA ligands of sequence motif "Type B"). The results of the competition assay are relative to 193-G2-001 or -012. Clones were tested as aptamers with 193-G2-001 except * are clones 193-G2-015, -016 and -017 which were tested with 193-G2-012 which has the same binding affinity for SDF-1 as does 193-G2-001.

FIG. 5 shows an alignment of sequences of related RNA ligands binding to human SDF-1 indicating the sequence motif ("Type C") that is in a preferred embodiment in its entirety essential for binding to human SDF-1. Competition assay results are relative to 192-A10-001. * is alternative hybridization.

FIG. 6 shows derivatives of RNA ligand 190-A3-001 (human SDF-1 RNA ligand of sequence motif "Type C"). Competition assay results are relative to 190-A3-001. * is alternative hybridization of the terminal nucleotides.

FIG. 7A shows derivatives of RNA ligand 190-D5-001 (human SDF-1 RNA ligand of sequence motif "Type C").

The competition assay results were obtained with 191-D5-001 and -007, which have the same binding affinity for SDF-1.

FIG. 7B shows derivatives of RNA ligand 190-D5-001 (human SDF-1 RNA ligand of sequence motif "Type C"). The competition assay results were obtained using as reference, 191-D5-007.

FIG. 8 shows derivatives of RNA ligand 197-B2 (human SDF-1 RNA ligand of sequence motif "Type C"). In the competition assay, 197-B2 and 191-D5-007, which have equivalent binding affinity for SDF-1, were used.

FIG. 9 shows further RNA ligands binding to human SDF-1.

Figure 10:
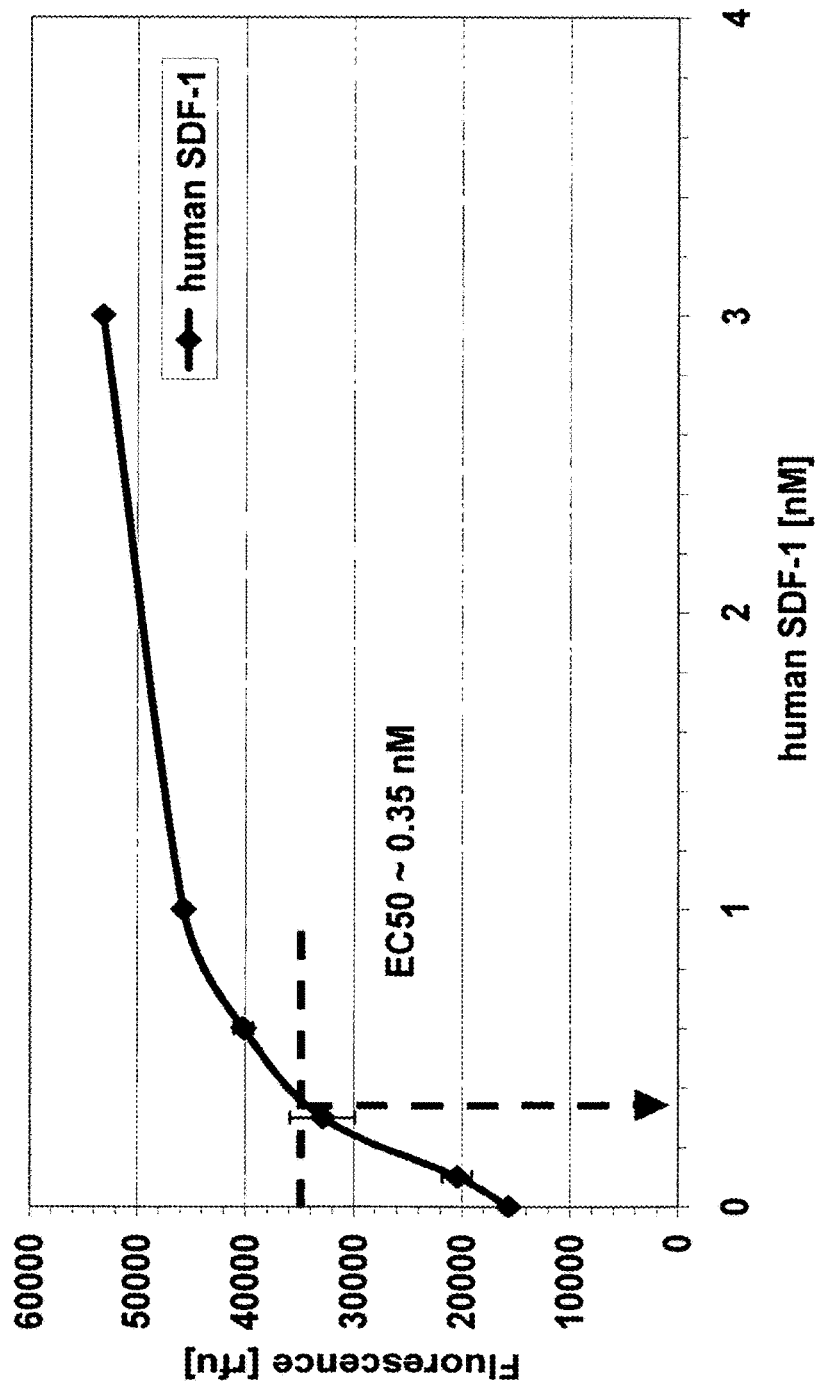

FIG. 10 shows the human SDF-1-induced chemotaxis of Jurkat human T cell leukemia cells whereas after 3 hours migration of Jurkat human T cell leukemia cells towards various human SDF-1 concentrations a dose-response curve for human SDF-1 was obtained, represented as fluorescence signal over concentration of human SDF-1.

Figure 11:
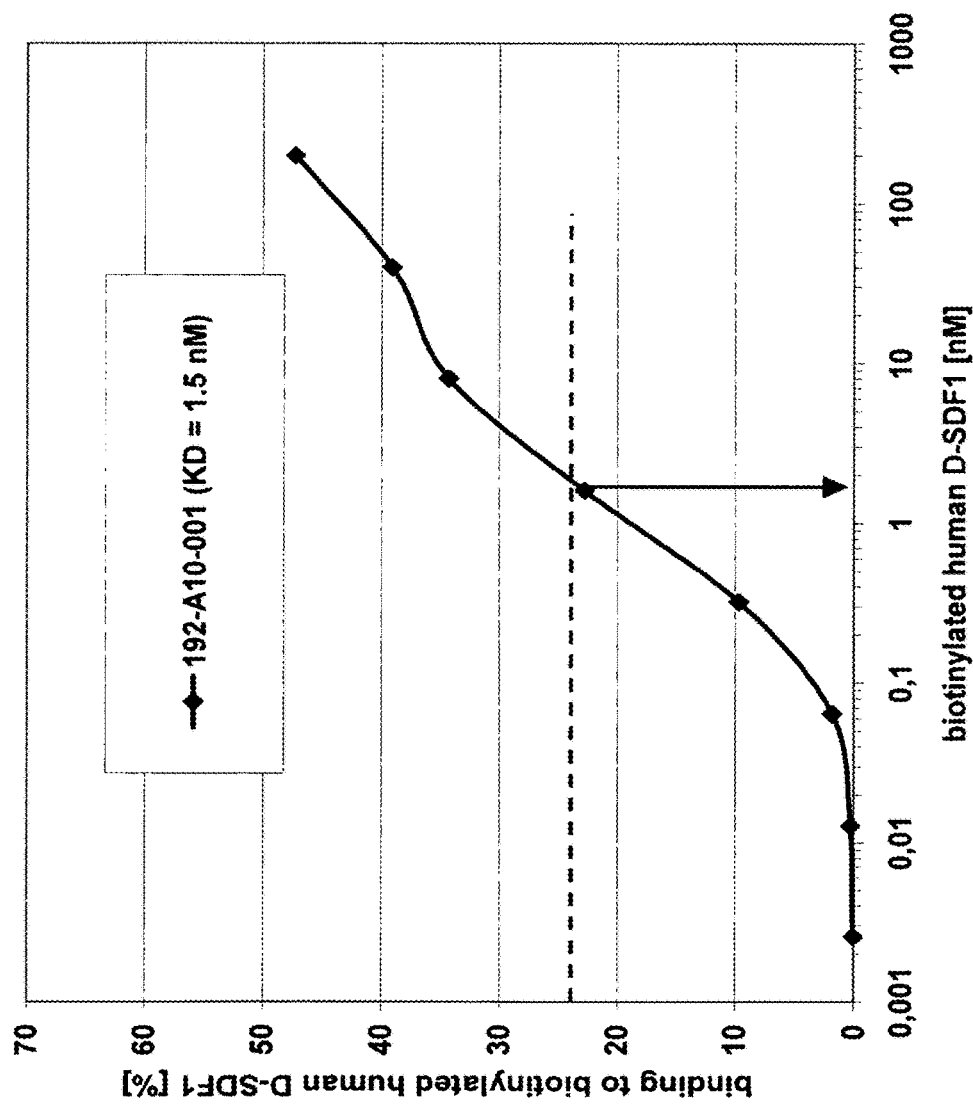

FIG. 11 shows the result of a binding analysis of the human SDF-1 binding aptamer 192-A10-001 to biotinylated human D-SDF-1 at 37° C., represented as binding of the aptamer over concentration of biotinylated human D-SDF-1.

Figure 12:
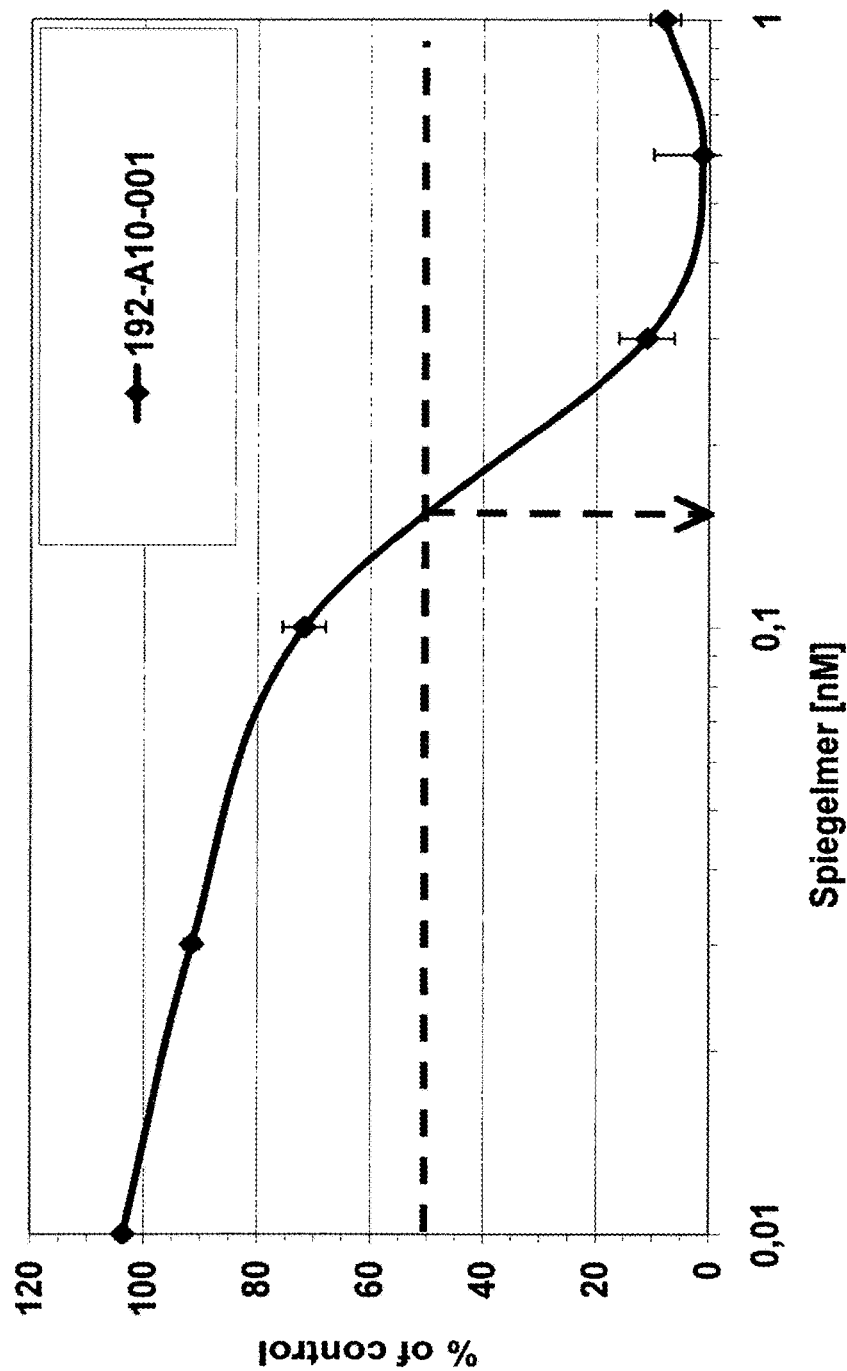

FIG. 12 shows the efficacy of human SDF-1 binding Spiegelmer 192-A10-001 in a chemotaxis assay; cells were allowed to migrate towards human 0.3 nM SDF-1 preincubated at 37° C. with various amounts of Spiegelmer 192-A10-001, represented as percentage of control over concentration of Spiegelmer 192-A10-001.

Figure 13:
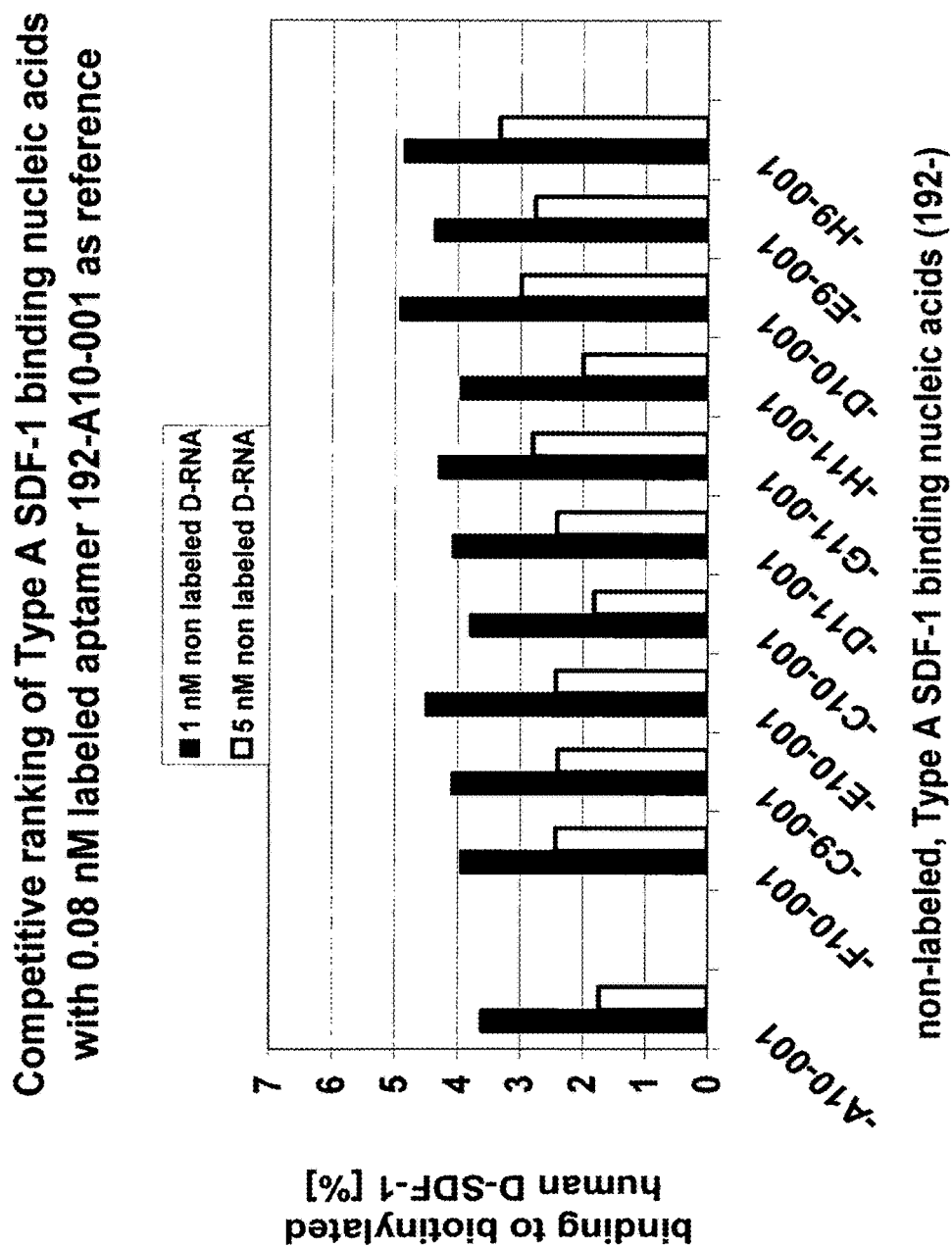

FIG. 13 shows the result of a competitive binding analysis of the human SDF-1 binding aptamers 192-A10-001, 192-F10-001, 192-C9-001, 192-E10-001, 192-C10-001, 192-D11-001, 192-G11-001, 192-H11-001, 192-D10-001, 192-E9-001 and 192-H9-001 to biotinylated human D-SDF-1 at 37° C., represented as binding of the labeled aptamer 192-A10-001 (used as reference that is displaced by the non-labeled aptamers) at 1 nM and 5 nM non-labeled aptamers 192-A10-001, 192-F10-001, 192-C9-001, 192-E10-001, 192-C10-001, 192-D11-001, 192-G11-001, 192-H11-001, 192-D10-001, 192-E9-001 and 192-H9-001.

Figure 14:
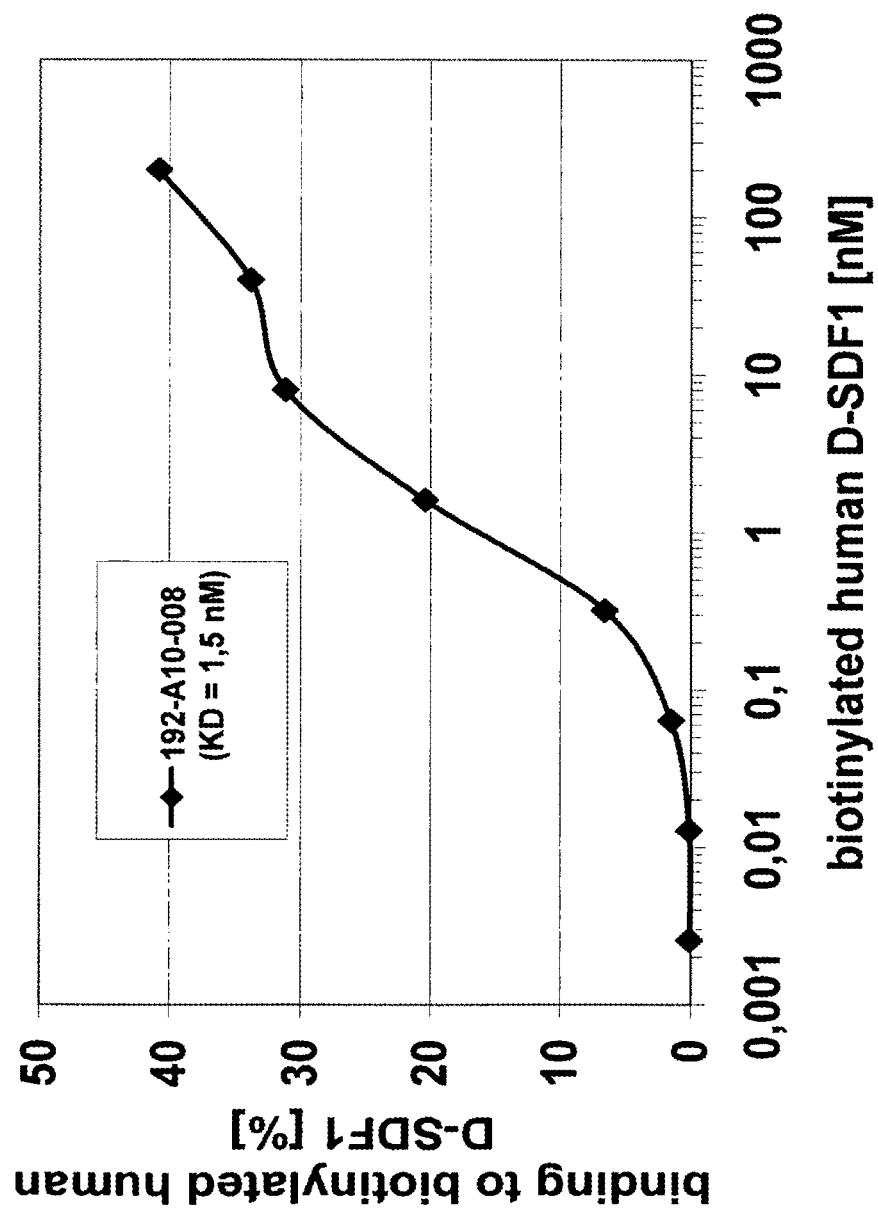

FIG. 14 shows the result of a binding analysis of the human SDF-1 binding aptamer 192-A10-008 to biotinylated human D-SDF-1 at 37° C., represented as binding of the aptamer over concentration of biotinylated human D-SDF-1.

Figure 15:
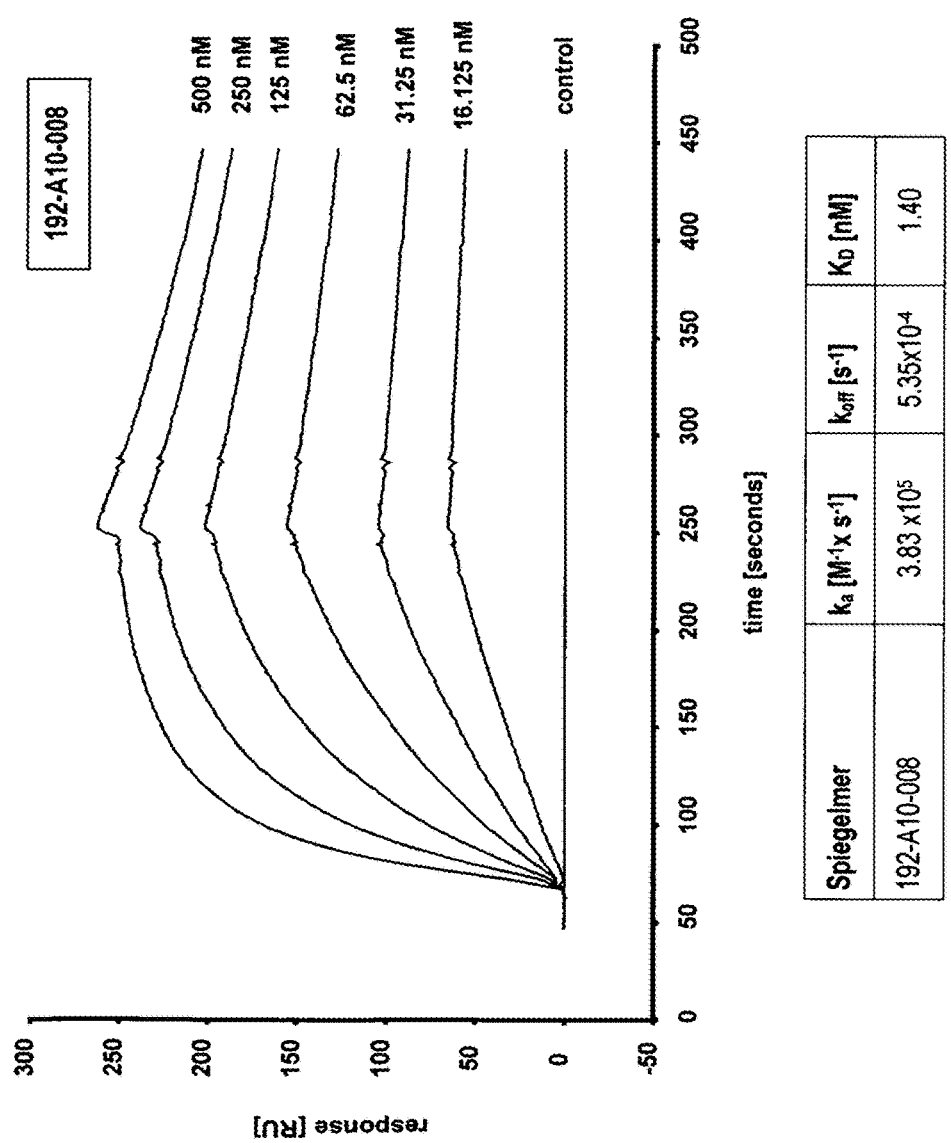

FIG. 15 shows a Biacore 2000 sensorgram indicating the $K_D$ value of the human SDF-1 binding Spiegelmer 192-A10-008 binding to human SDF-1 which was immobilized on a PioneerF1 sensor chip by amine coupling procedure, represented as response (RU) over time, additionally the on- and off-rates and the $K_D$ values of Spiegelmers 192-A10-008 and 192-A10-001 are listed.

Figure 16:
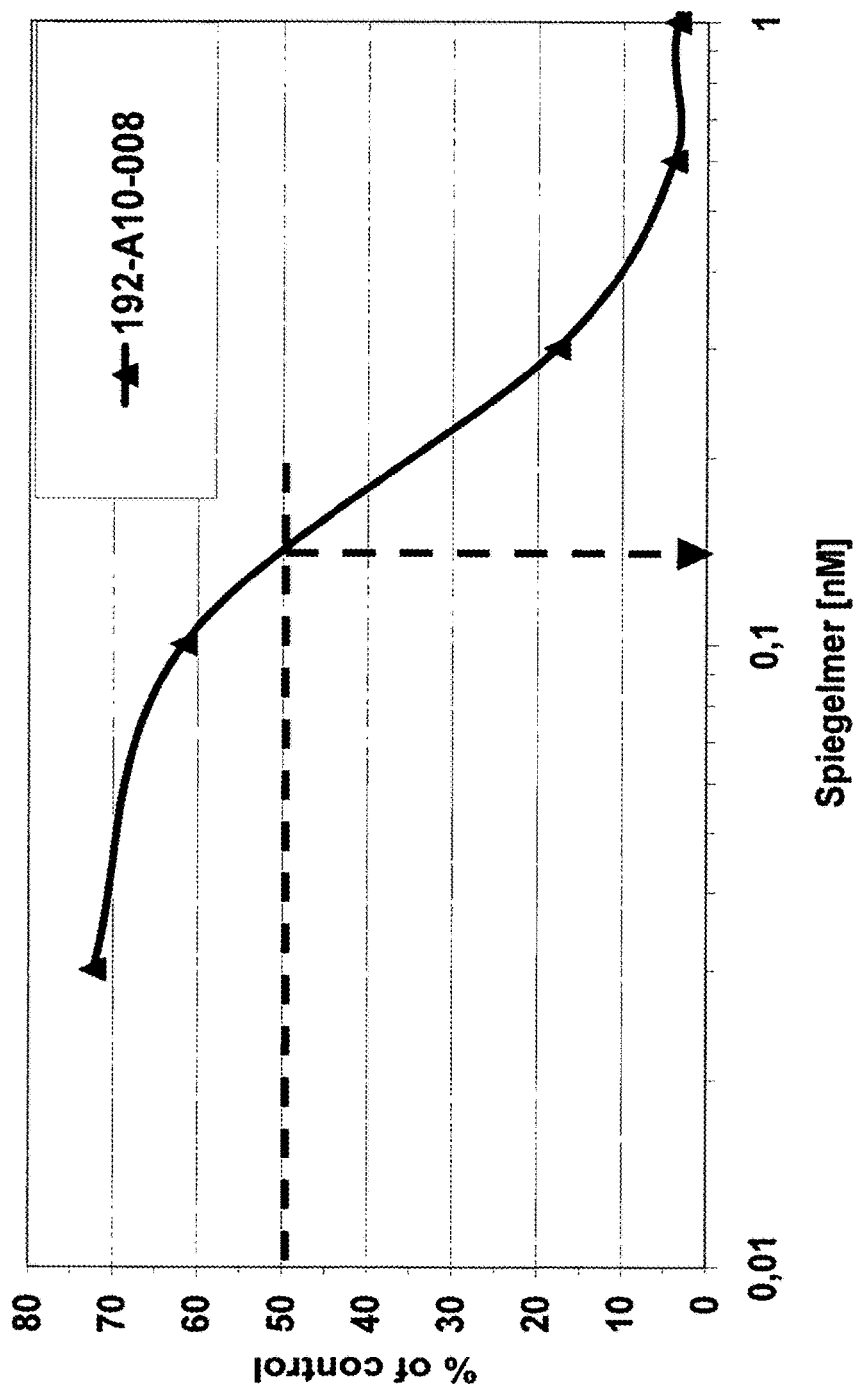

FIG. 16 shows the efficacy of SDF-1 binding Spiegelmer 192-A10-008 in a chemotaxis assay; cells were allowed to migrate towards 0.3 nM human SDF-1 preincubated at 37° C. with various amounts of Spiegelmer 192-A10-008, represented as percentage of control over concentration of Spiegelmer 192-A10-008.

Figure 17:
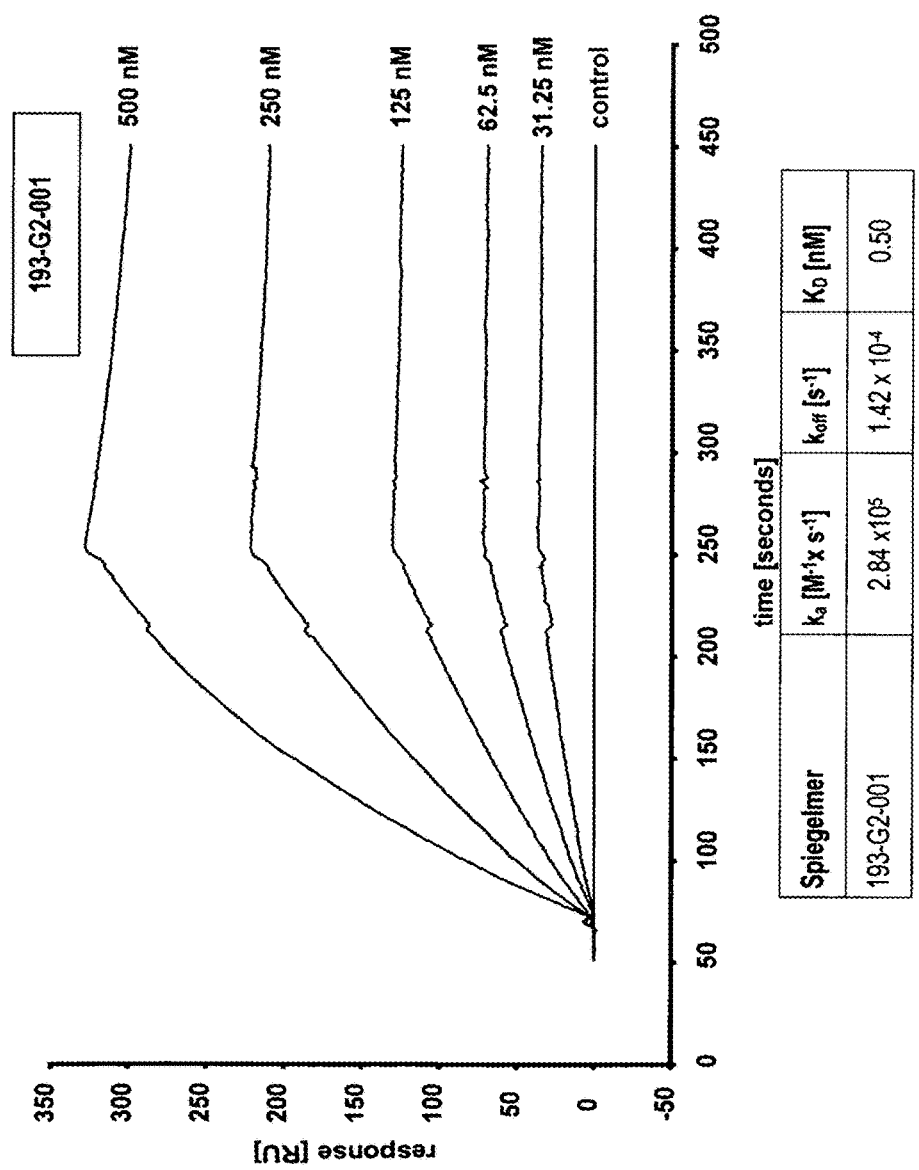

FIG. 17 shows a Biacore 2000 sensorgram indicating the $K_D$ value of Spiegelmer 193-G2-01 binding to human SDF-1 which was immobilized on a PioneerF1 sensor chip by amine coupling procedure, represented as response (RU) over time, additionally the on- and off-rates and the $K_D$ values of Spiegelmer 193-G2-001 are listed.

Figure 18:
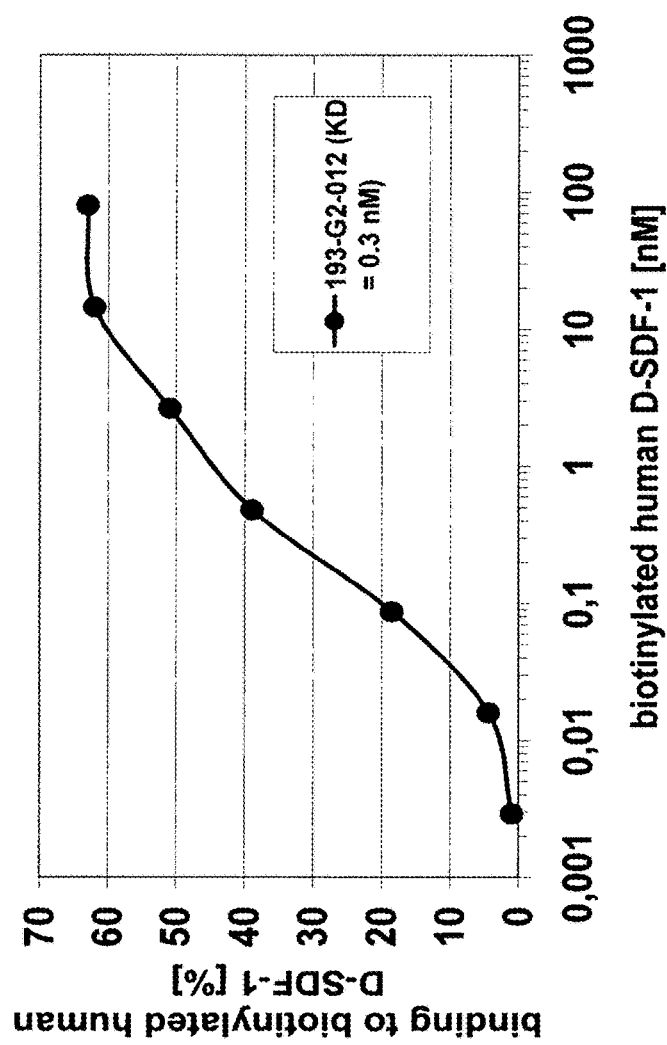

FIG. 18 shows the result of a binding analysis of the human anti-SDF-1 aptamer 193-G2-012 to biotinylated human D-SDF-1 at 37° C., represented as binding of the aptamer over concentration of biotinylated human D-SDF-1.

Figure 19:
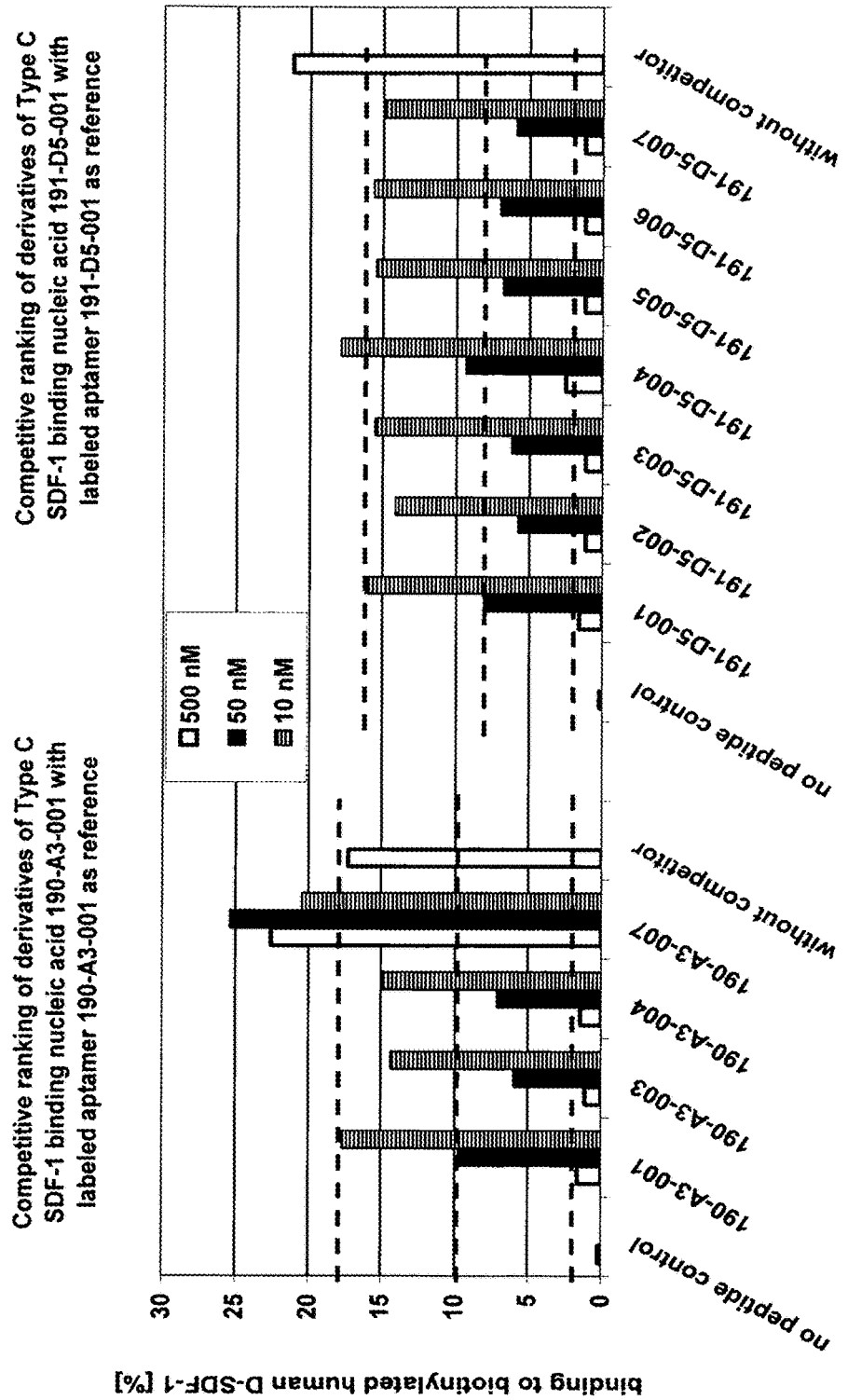

FIG. 19 shows the result of a competitive binding analysis of the human SDF-1 binding aptamers 190-A3-001, 190-A3-003, 190-A3-004, 190-A3-007, 191-D5-001, 191-D5-002, 191-D5-003, 191-D5-004, 191-D5-005, 191-D5-006 and 191-D5-007 to biotinylated human D-SDF-1 at 37° C., represented as binding of the labeled aptamer 190-A3-001 or 191-D5-001 (used as reference that is displaced by the non-labeled aptamers) at 500 nM, 50 nM and 10 nM non-labeled aptamers 190-A3-001, 190-A3-003, 190-A3-004, 190-A3-007, 191-D5-001, 191-D5-002, 191-D5-003, 191-D5-004, 191-D5-005, 191-D5-006 and 191-D5-007.

Figure 20:
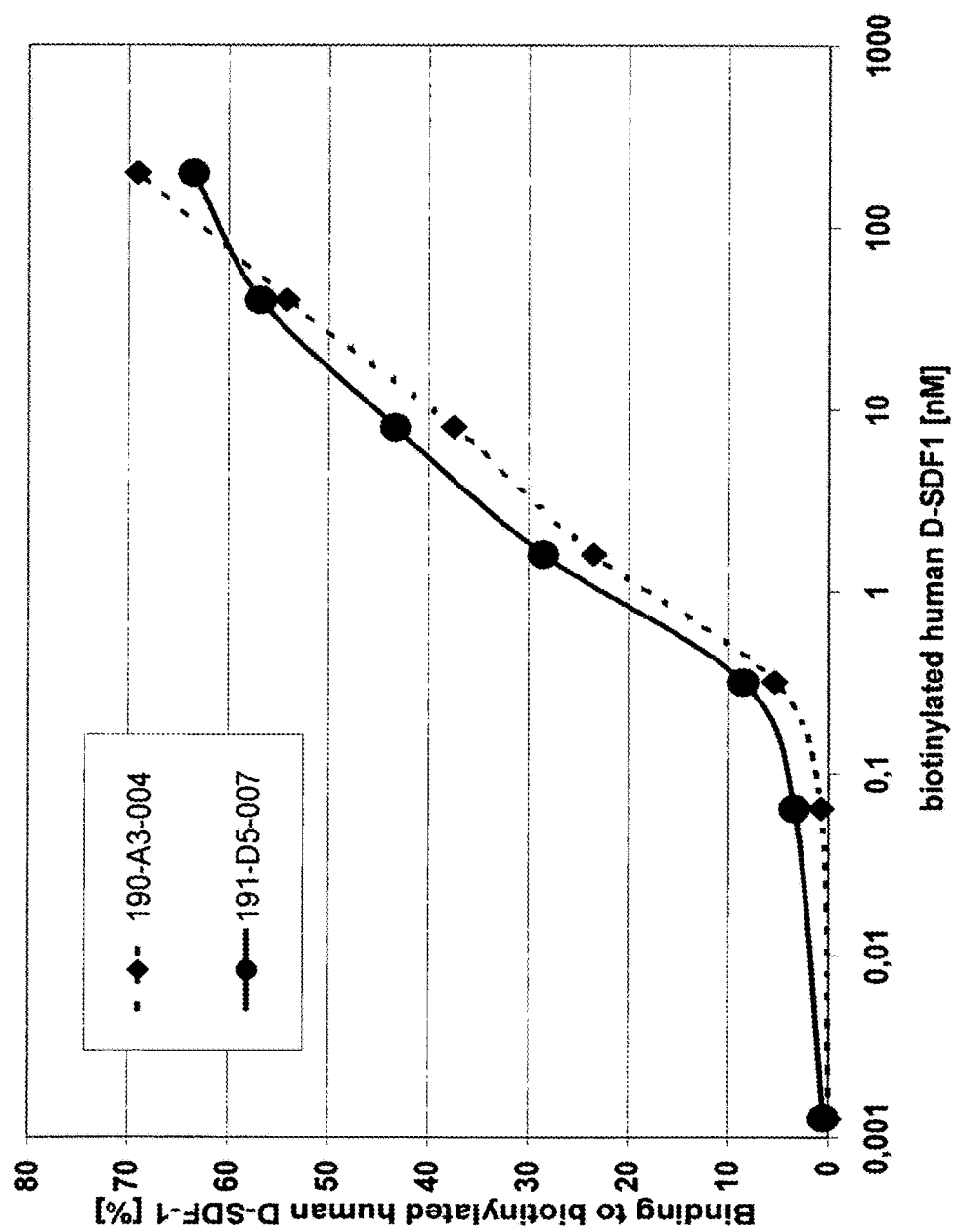

FIG. 20 shows the result of a binding analysis of the human SDF-1 binding aptamers 190-A3-004 and 191-D5-007 to biotinylated human D-SDF-1 37° C., represented as binding of the aptamer over concentration of biotinylated human D-SDF-1.

Figure 21:
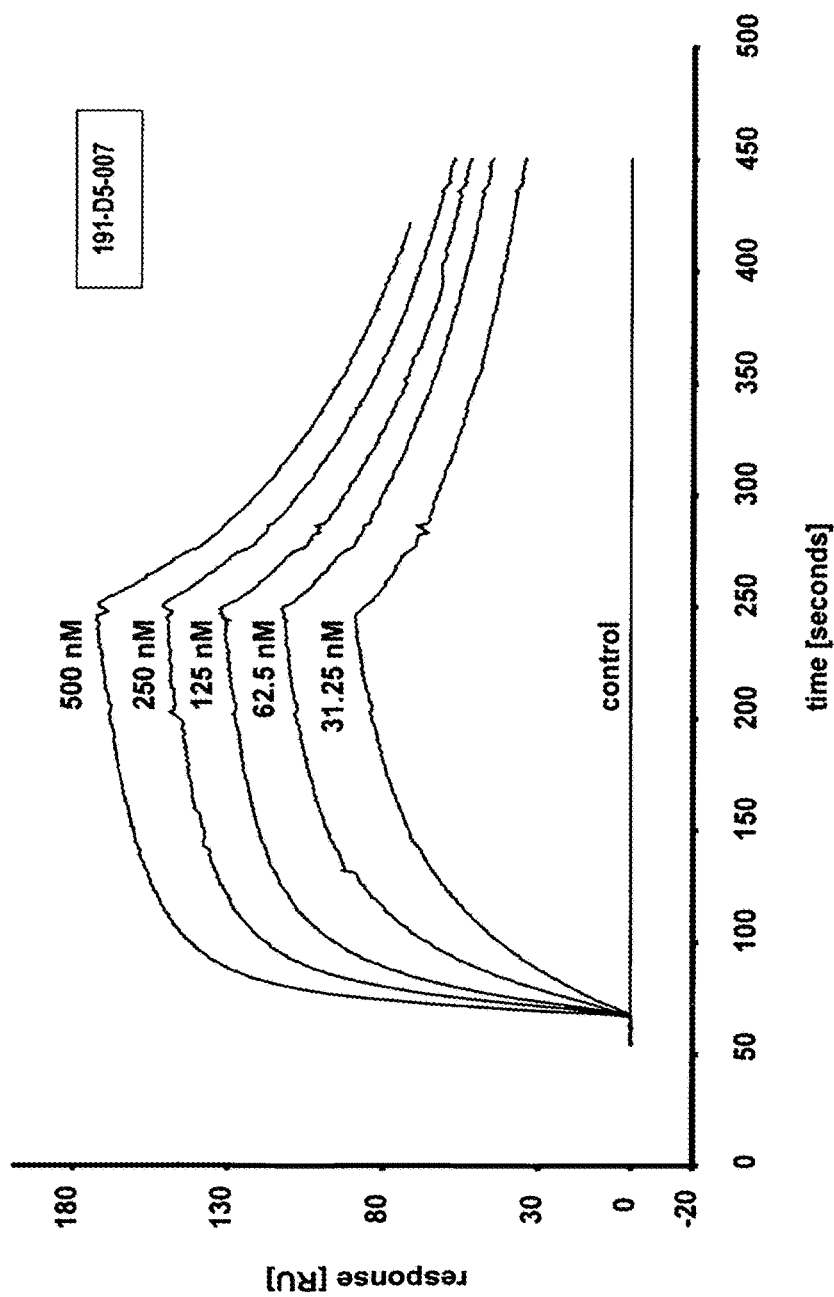

FIG. 21 shows a Biacore 2000 sensorgram indicating the $K_D$ value of Spiegelmer 191-D5-007 binding to human SDF-1 which was immobilized on a PioneerF1 sensor chip by amine coupling procedure, represented as response (RU) over time, additionally the on- and off-rates and the $K_D$ values of Spiegelmer 191-D5-007 are listed.

Figure 22:
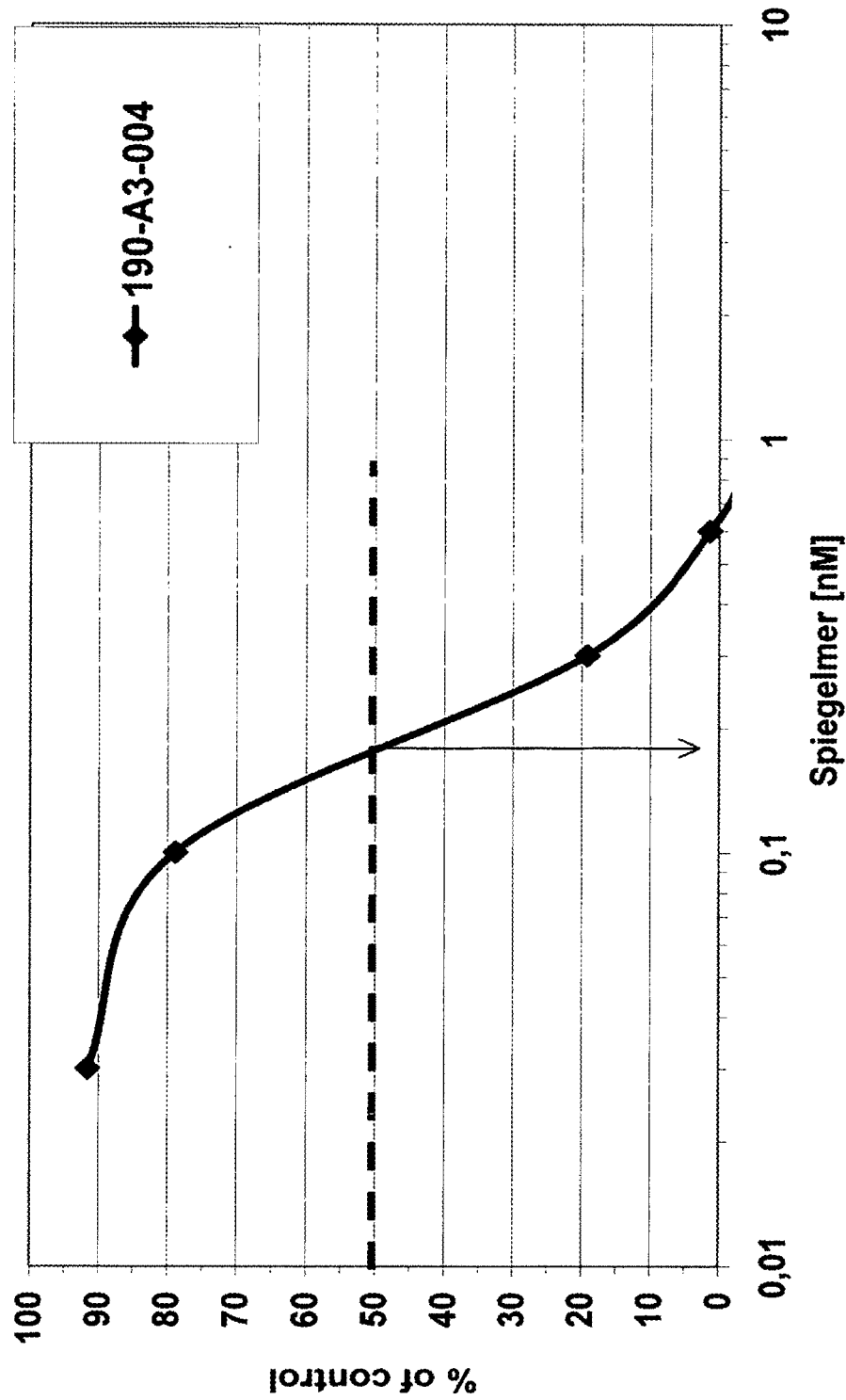

FIG. 22 shows the efficacy of SDF-1 binding Spiegelmer 190-A3-004 in a chemotaxis assay; cells were allowed to migrate towards 0.3 nM human SDF-1 preincubated at 37° C. with various amounts of Spiegelmer 190-A3-004, represented as percentage of control over concentration of Spiegelmer 190-A3-004.

Figure 23A:
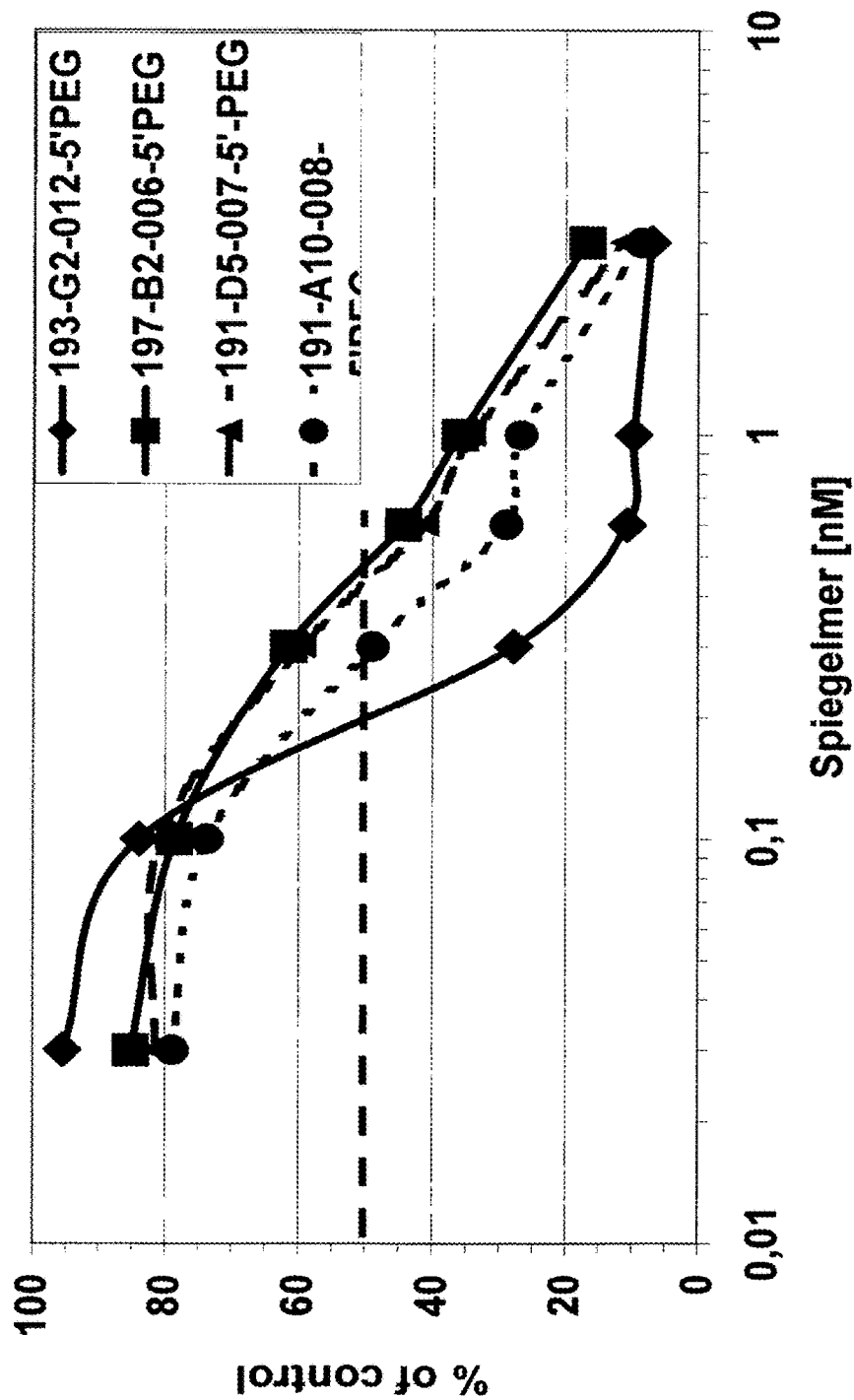

FIG. 23A shows the efficacy of SDF-1 binding Spiegelmers 193-G2-012-5'-PEG, 197-B2-006-5'-PEG, 191-D5-007-5'-PEG and 191-A10-008-5'-PEG in a chemotaxis assay; cells were allowed to migrate towards 0.3 nM human SDF-1 preincubated at 37° C. with various amounts of Spiegelmers 193-G2-012-5'-PEG, 197-B2-006-5'-PEG, 191-D5-007-5'-PEG and 191-A10-008-5'-PEG, represented as percentage of control over concentration of Spiegelmers 193-G2-012-5'-PEG, 197-B2-006-5'-PEG, 191-D5-007-5'-PEG and 191-A10-008-5'-PEG.

Figure 23B:
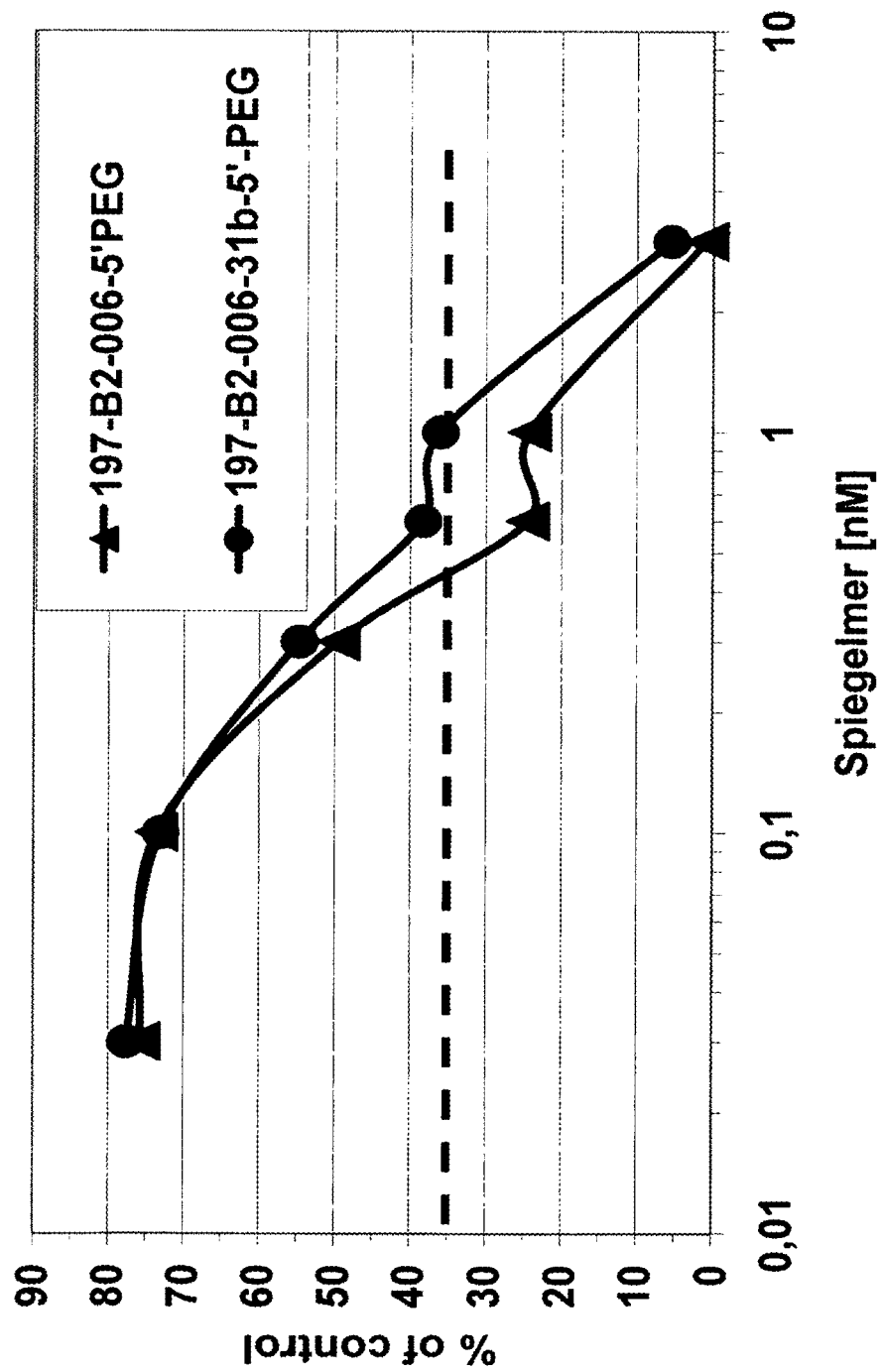

FIG. 23B shows the efficacy of SDF-1 binding Spiegelmers 197-B2-006-5'PEG and 197-B2-006-31b-5'-PEG in a chemotaxis assay; cells were allowed to migrate towards 0.3 nM human SDF-1 preincubated at 37° C. with various amounts of Spiegelmers 197-B2-006-5'PEG and 197-B2-006-31b-5'-PEG, represented as percentage of control over concentration of Spiegelmers 197-B2-006-5'PEG and 197-B2-006-31b-5'-PEG.

Figure 24:
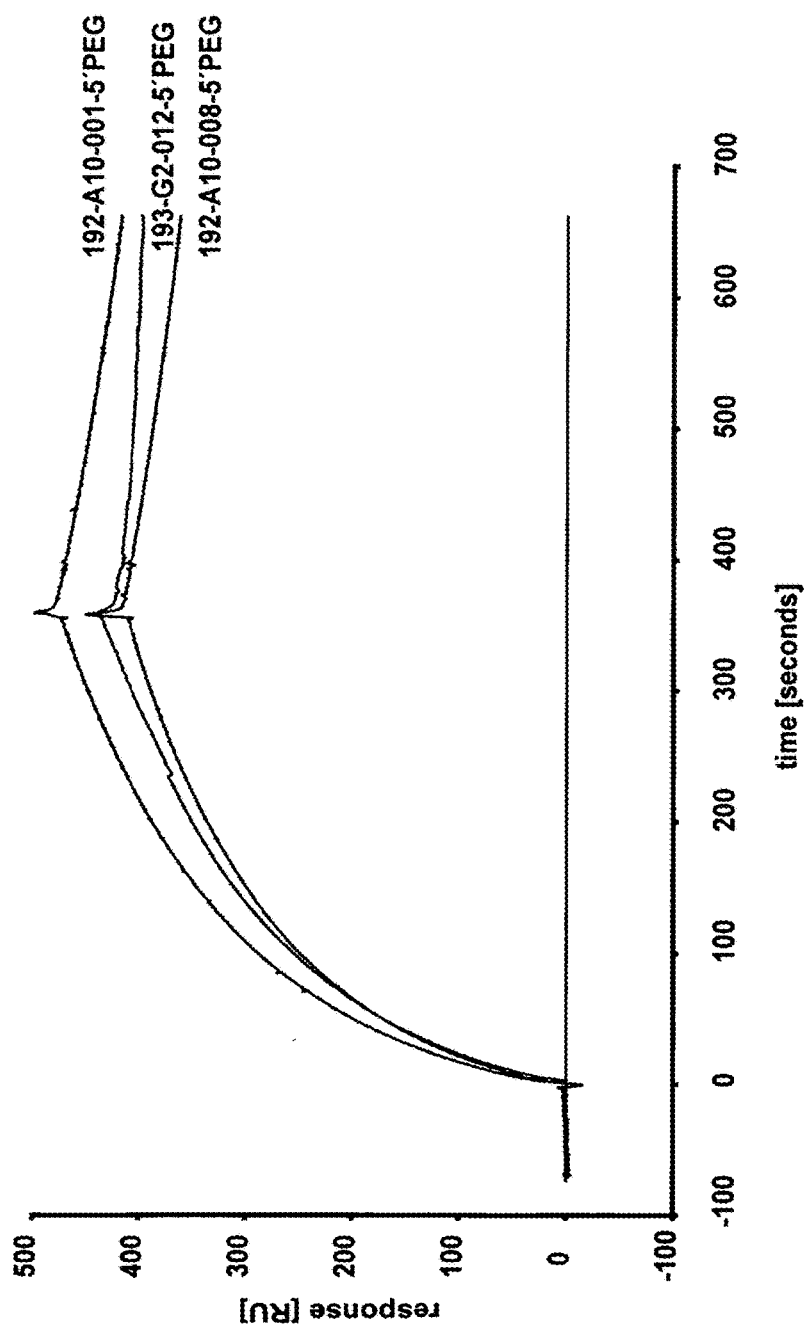

FIG. 24A shows a Biacore 2000 sensorgram indicating the $K_D$ values of Spiegelmers 193-G2-012-5'-PEG, 191-A10-008-5'-PEG and 191-A10-001-5'-PEG binding to human SDF-1 which was immobilized on a PioneerF1 sensor chip by amine coupling procedure, represented as response (RU) over time.

Figure 24B:
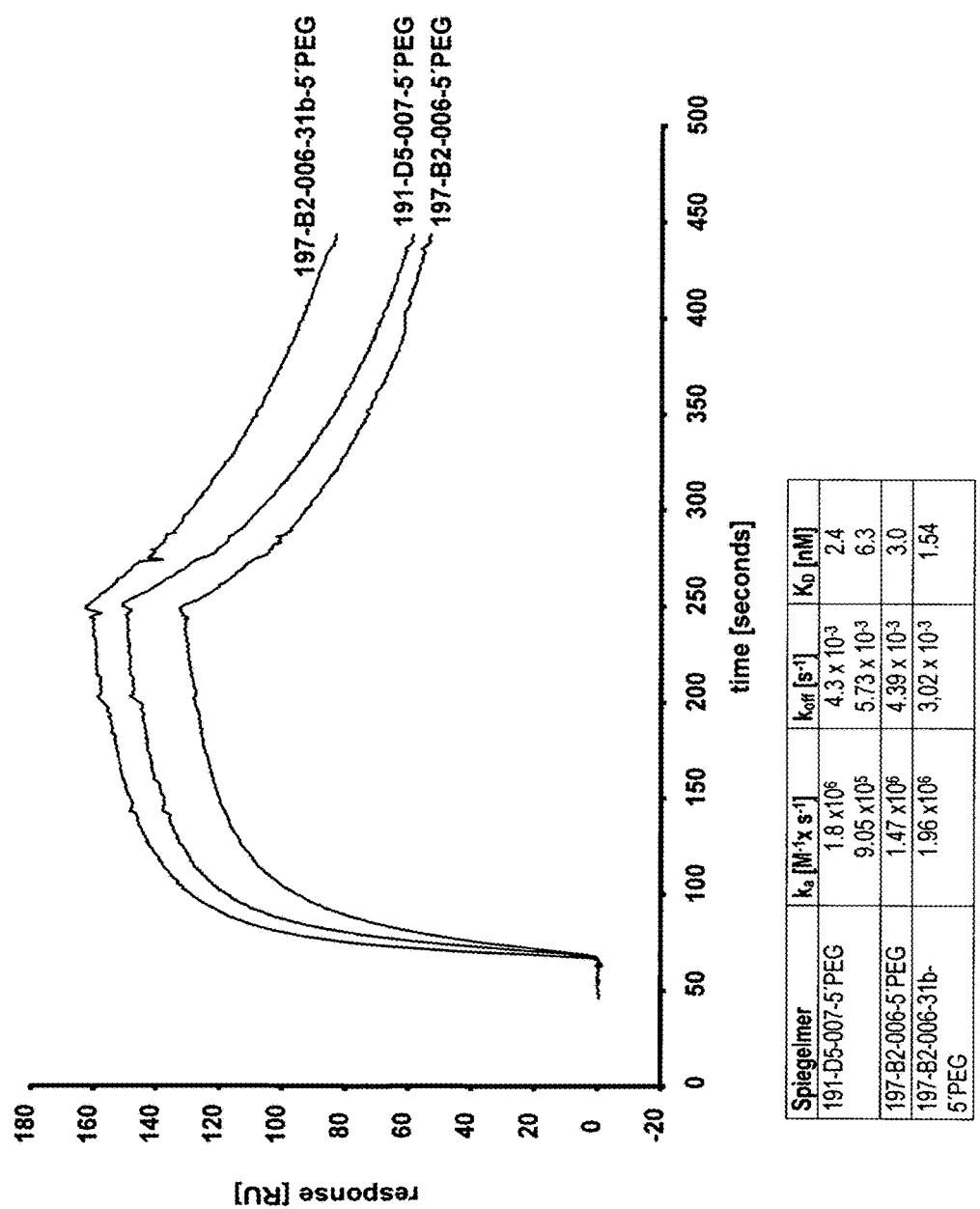

FIG. 24B shows a Biacore 2000 sensorgram indicating the $K_D$ values of Spiegelmers 197-B2-006-5'PEG, 197-B2-006-31b-5'-PEG and 191-D5-007-5'-PEG binding to human SDF-1 which was immobilized on a PioneerF1 sensor chip by amine coupling procedure, represented as response (RU) over time.

Figure 25A:
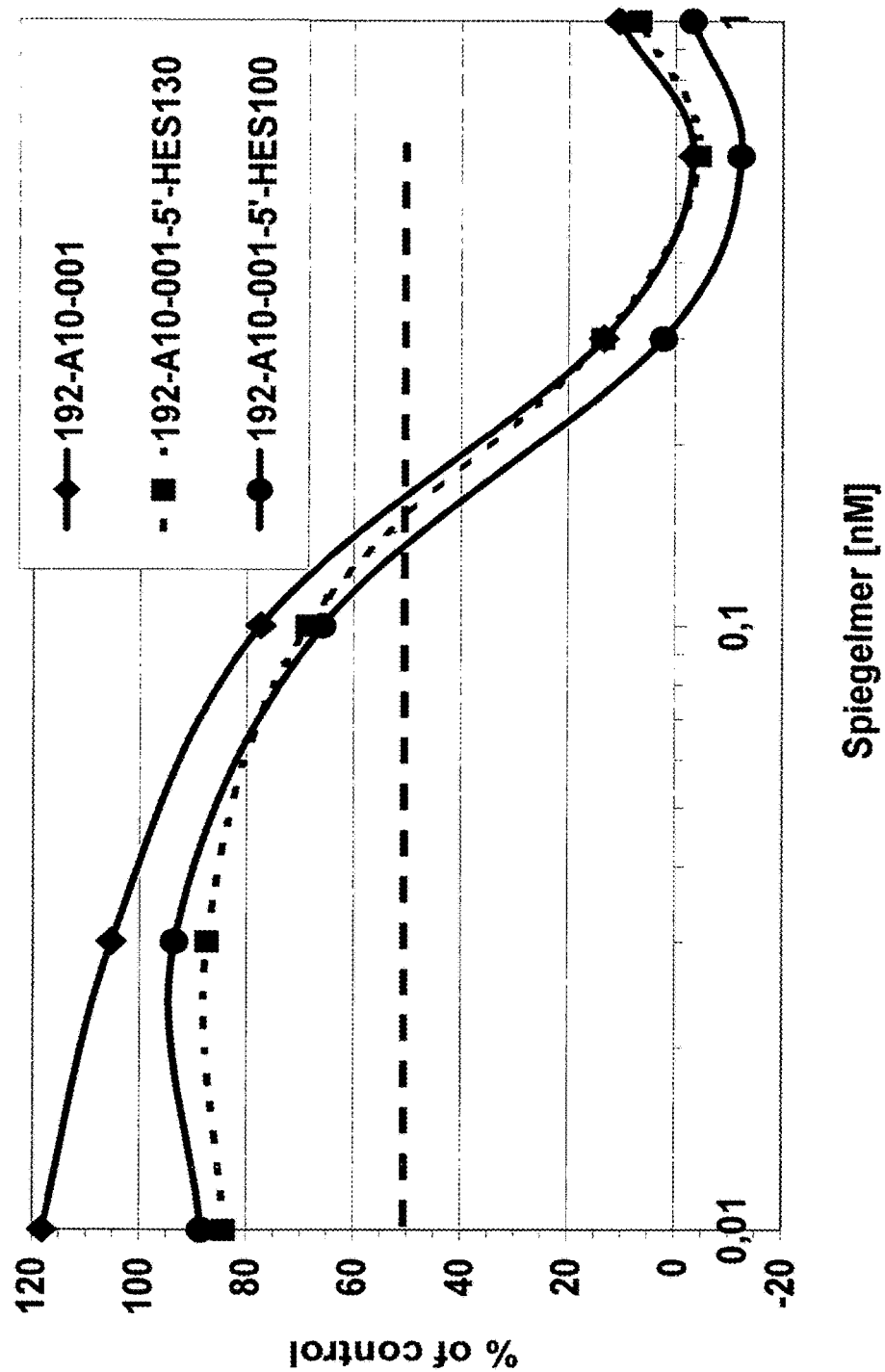

FIG. 25A shows the efficacy of SDF-1 binding Spiegelmers 192-A10-001, 192-A10-001-5'-HES130 and 192-A10-001-5'-HES100 in a chemotaxis assay; cells were allowed to migrate towards 0.3 nM human SDF-1 preincubated at 37° C. with various amounts of Spiegelmers 192-A10-001, 192-A10-001-5'-HES130 and 192-A10-001-5'-HES100, represented as percentage of control over concentration of Spiegelmers 192-A10-001, 192-A10-001-5'-HES130 and 192-A10-001-5'-HES100.

Figure 25B:
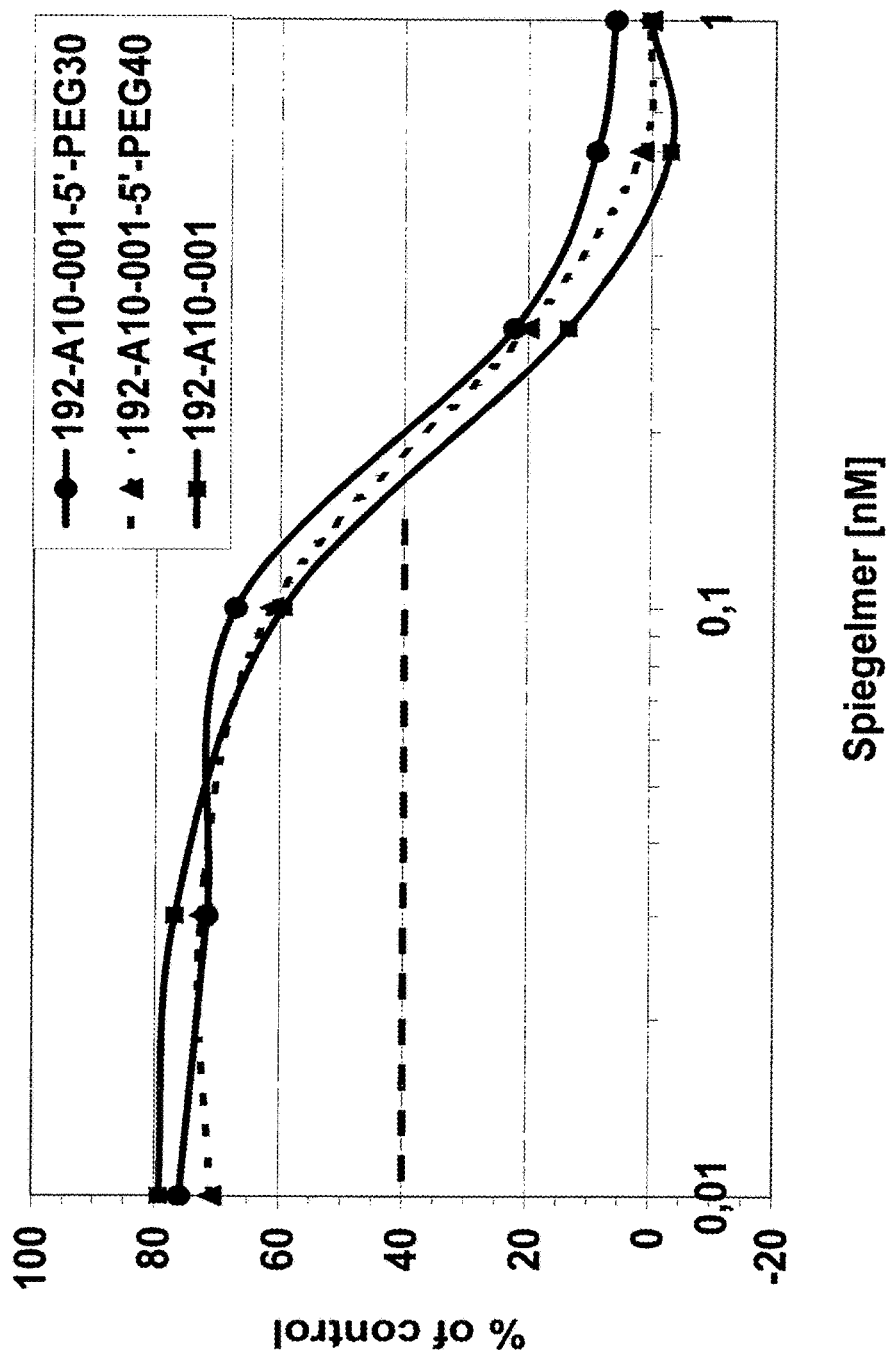

FIG. 25B shows the efficacy of SDF-1 binding Spiegelmers 192-A10-001, 192-A10-001-5'-PEG30 and 192-A10-001-5'-PEG40 in a chemotaxis assay; cells were allowed to migrate towards 0.3 nM human SDF-1 preincubated at 37° C. with various amounts of Spiegelmers 192-A10-001, 192-A10-001-5'-PEG30 and 192-A10-001-5'-PEG40, represented as percentage of control over concentration of Spiegelmers 192-A10-001, 192-A10-001-5'-PEG30 and 192-A10-001-5'-PEG40.

Figure 26:
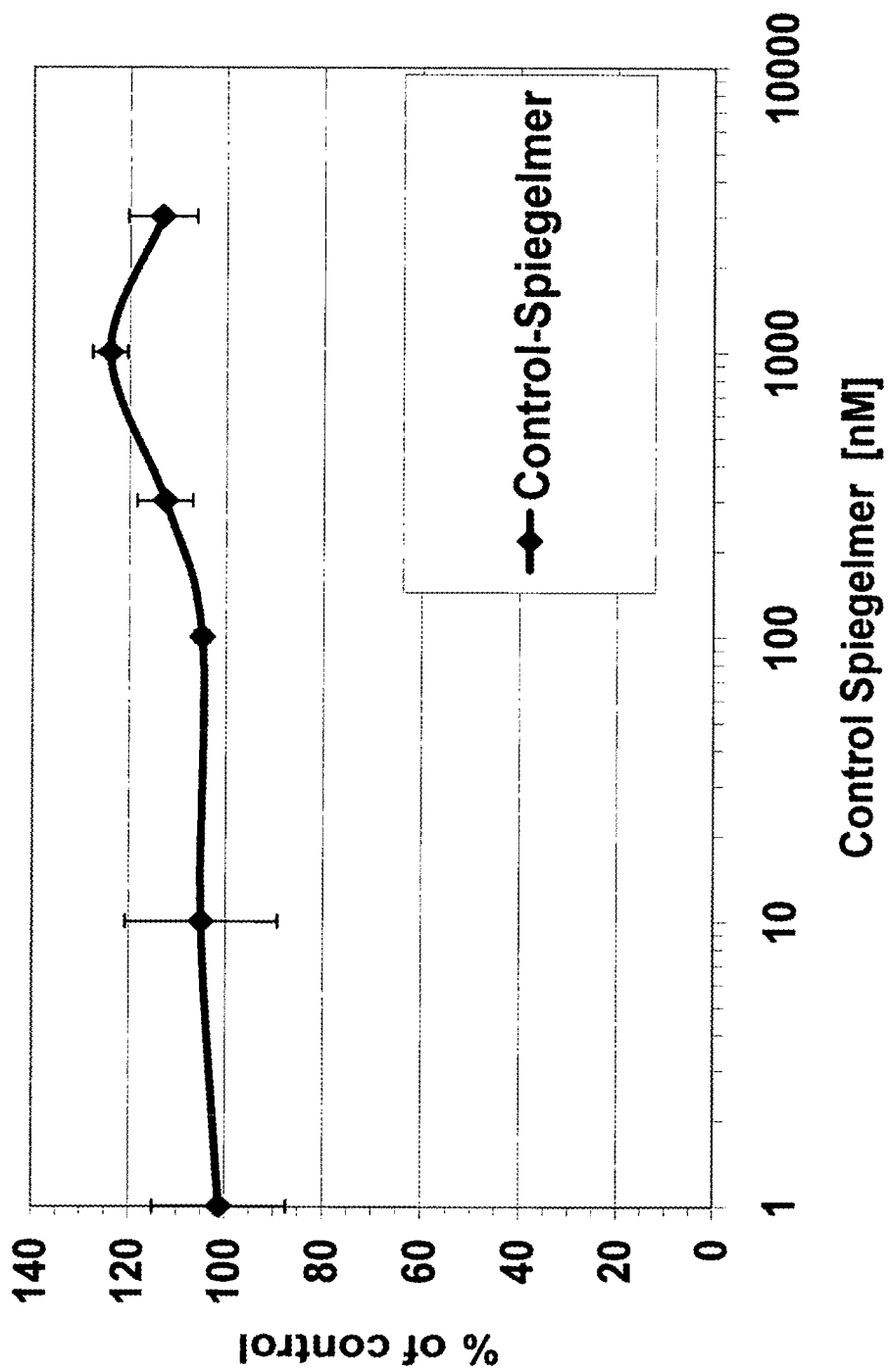

FIG. 26 shows the inefficacy of a control-Spiegelmer in a chemotaxis assay; cells were allowed to migrate towards 0.3 nM human or murine SDF-1 preincubated at 37° C. with various amounts of control-Spiegelmer, represented as percentage of control over concentration of control Spiegelmer.

Figure 27:
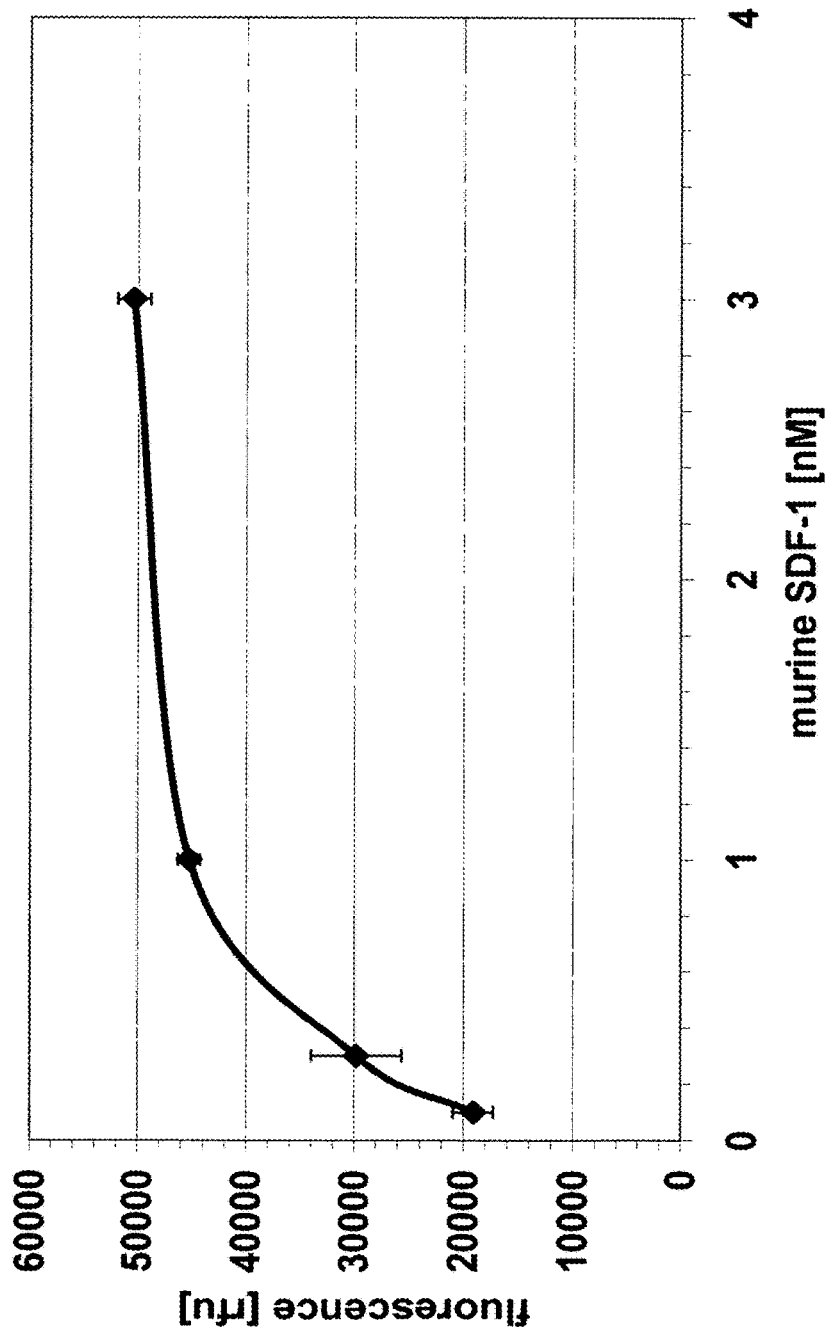

FIG. 27 shows the murine SDF-1-induced chemotaxis of Jurkat human T cell leukemia cells whereas after 3 hours migration of Jurkat human T cell leukemia cells towards various SDF-1 concentrations a dose-response curve for SDF-1 was obtained, represented as fluorescence signal.

Figure 28:
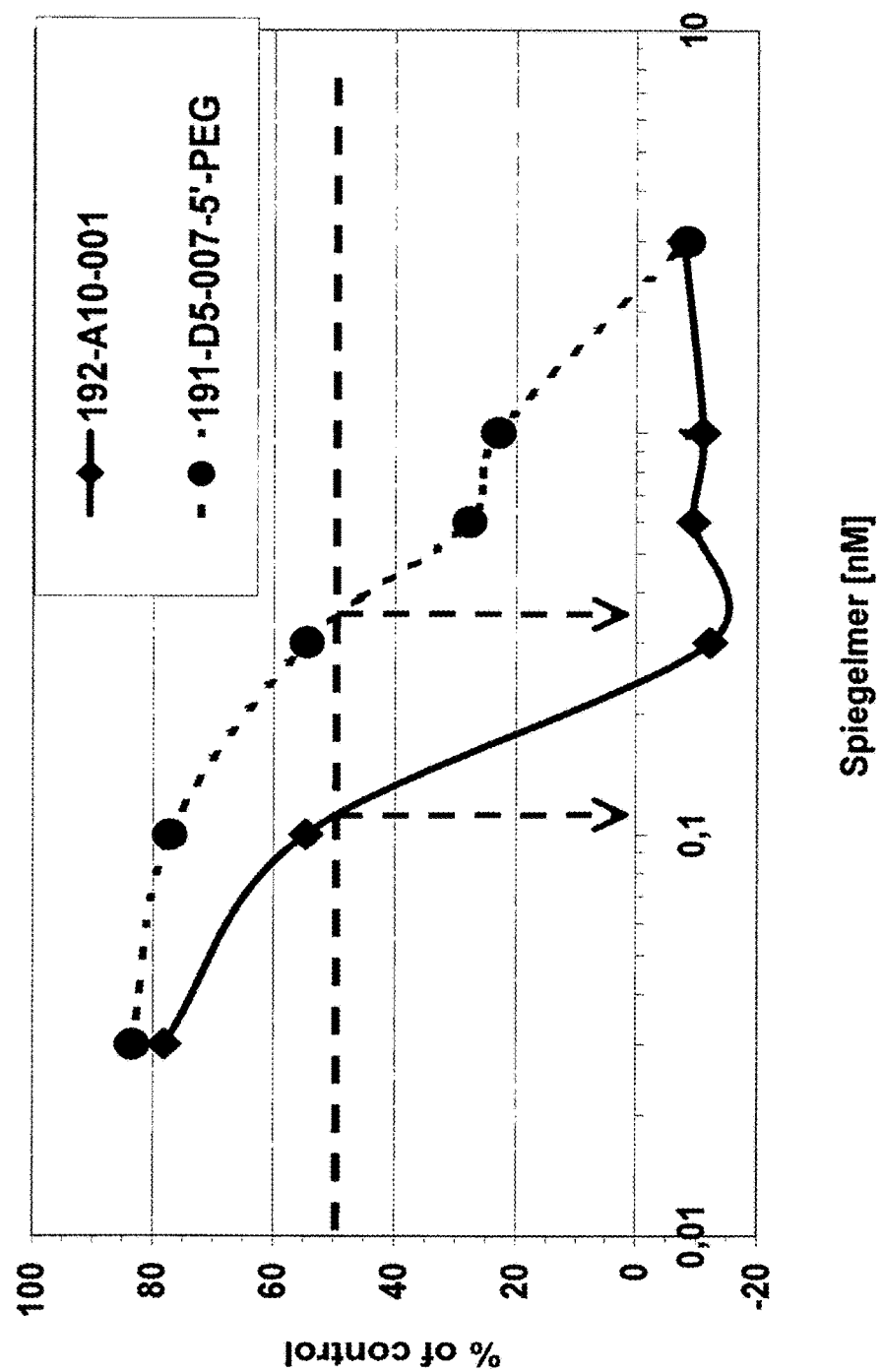

FIG. 28 shows the efficacy of SDF-1 binding Spiegelmers 192-A10-001 and 191-D5-007-5'PEG in a chemotaxis assay; cells were allowed to migrate towards 0.3 nM murine SDF-1 preincubated at 37° C. with various amounts of Spiegelmers 192-A10-001 and 191-D5-007-5'PEG represented as percentage of control over concentration of Spiegelmers 192-A10-001 and 191-D5-007-5'PEG.

Figure 29:
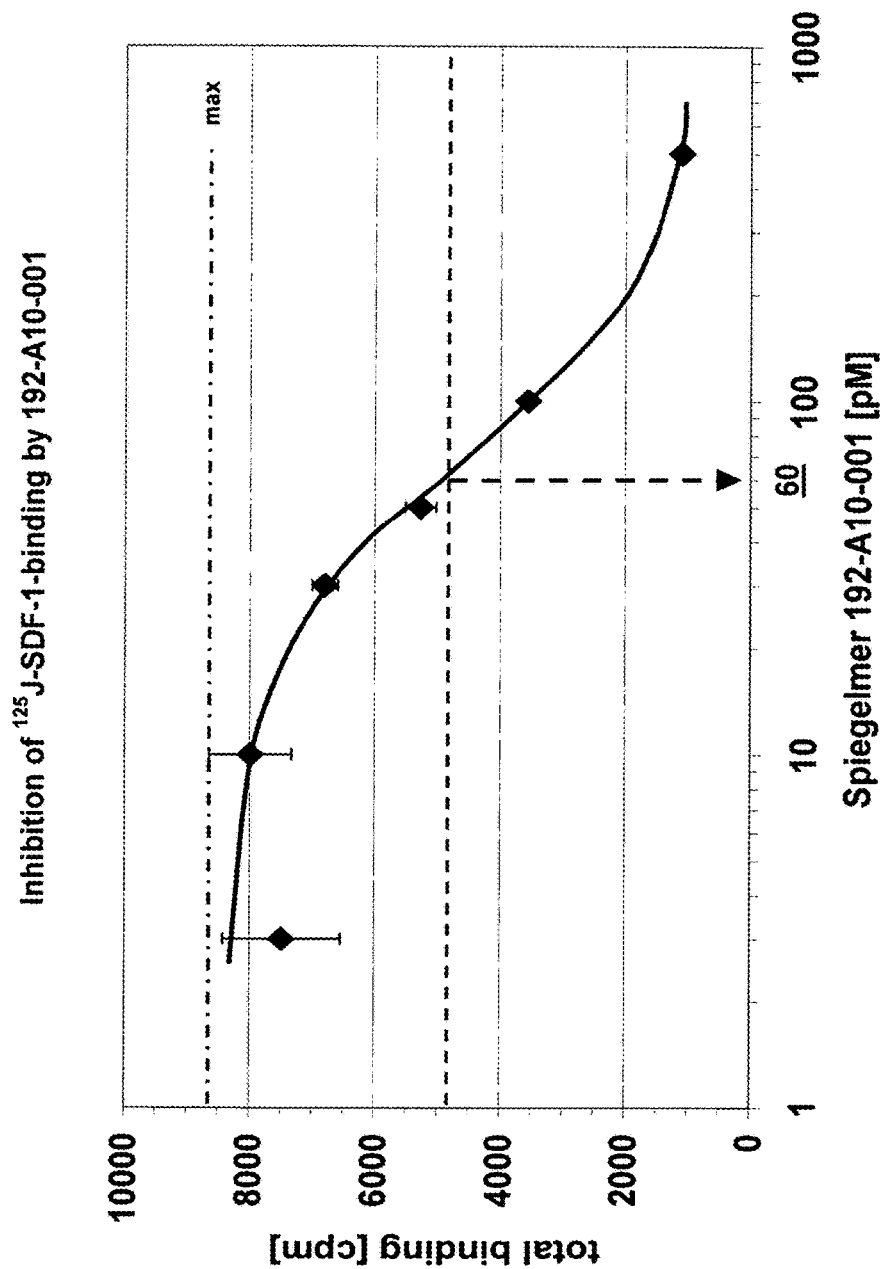

FIG. 29 shows the efficacy of SDF-1 binding Spiegelmer 192-A10-001 in a CXCR4-receptor binding assay using human [$^{125}$I]-SDF-1α that was preincubated at 37° C. with various amounts of Spiegelmers 192-A10-001, specifically bound [$^{125}$I]-SDF-1α was plotted over concentration of Spiegelmer 192-A10-001.

Figure 30:
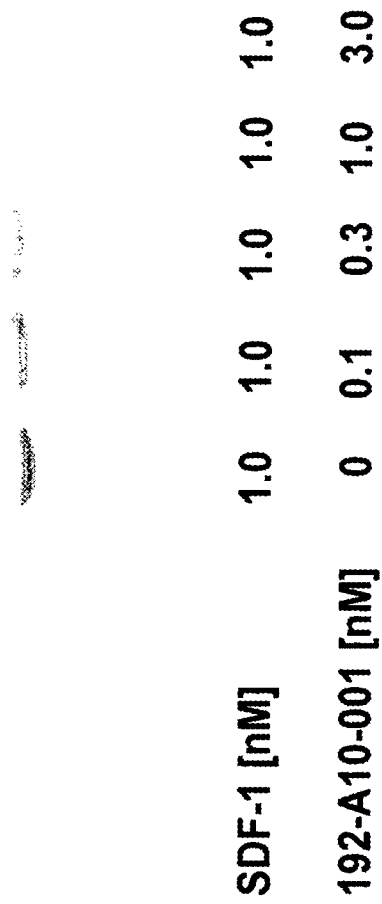

FIG. 30 shows the inhibition of MAP-kinase stimulation of CXCR4-expressing cells with 1 nM human SDF-1α by human SDF-1 binding Spiegelmer 192-A10-001.

Figure 31:
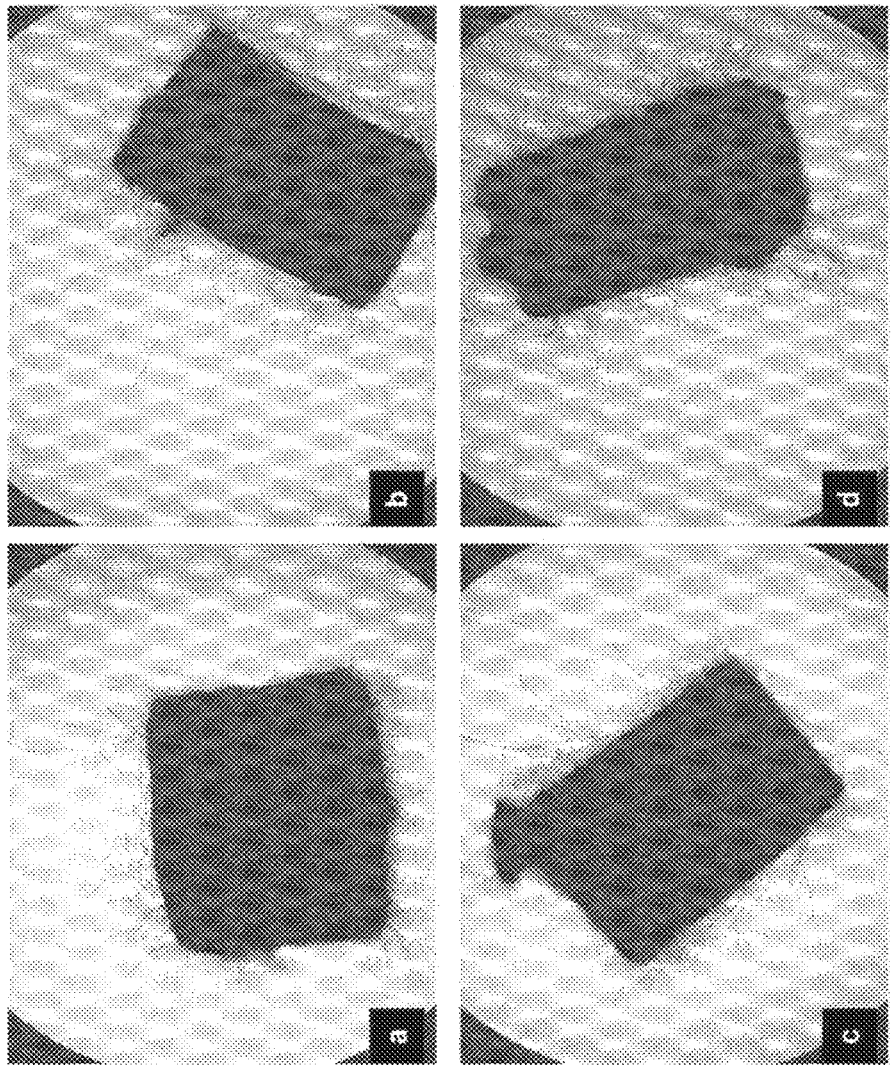

FIG. 31 shows the inhibition of SDF-1 induced sprouting by human SDF-1 binding Spiegelmer 193-G2-012-5'-PEG and by PEGylated Control Spiegelmer in aortic ring sprouting assay, whereby rings from rat aorta were embedded in collagen matrix and incubated for 6 days with SDF-1 with or without Spiegelmers (a: control; b: 10 nM SDF-1; c: 10 nM SDF-1+1 μM human SDF-1 binding Spiegelmer 193-G2-012-5'-PEG; d: 10 nM SDF-1+1 μM PEGylated Control Spiegelmer).

Figure 32:
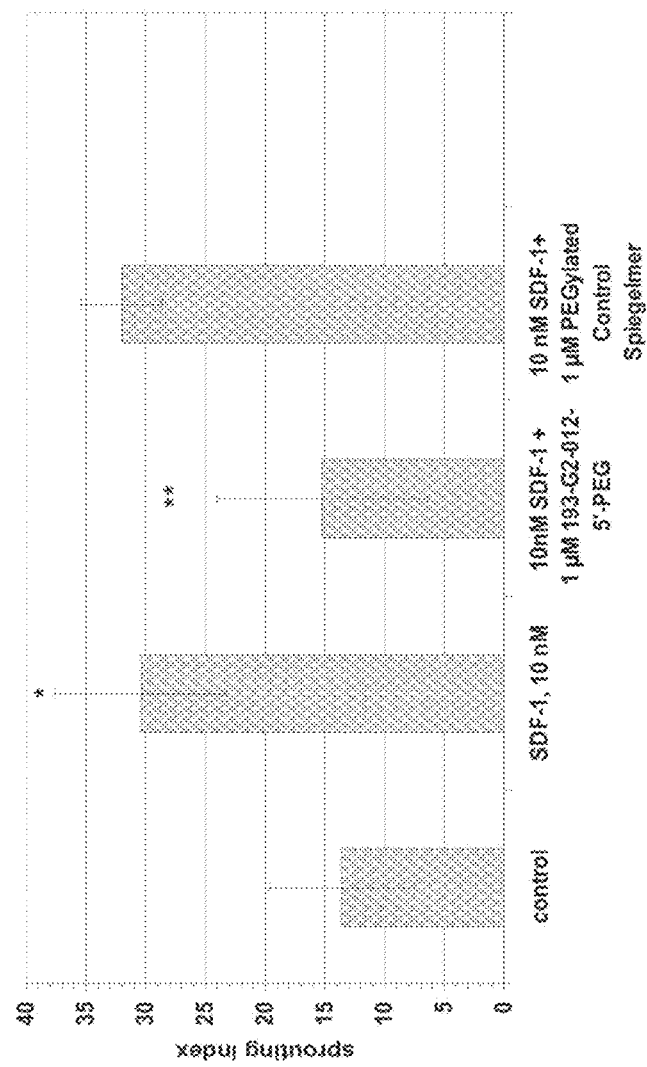

FIG. 32 shows the inhibition of SDF-1 induced sprouting by human SDF-1 binding Spiegelmer 193-G2-012-5'-PEG and by PEGylated Control Spiegelmer in aortic ring sprouting assay whereby sprouting indices are shown as mean+/−SD for 5 rings per condition (*: the value for SDF-1 is significantly different from control (Mann-Whitney test; p=0.009); **: the value for SDF-1+human SDF-1 binding Spiegelmer 193-G2-012-5'-PEG is significantly different from that for SDF-1 (Mann-Whitney test; p=0.028).

Figure 33:
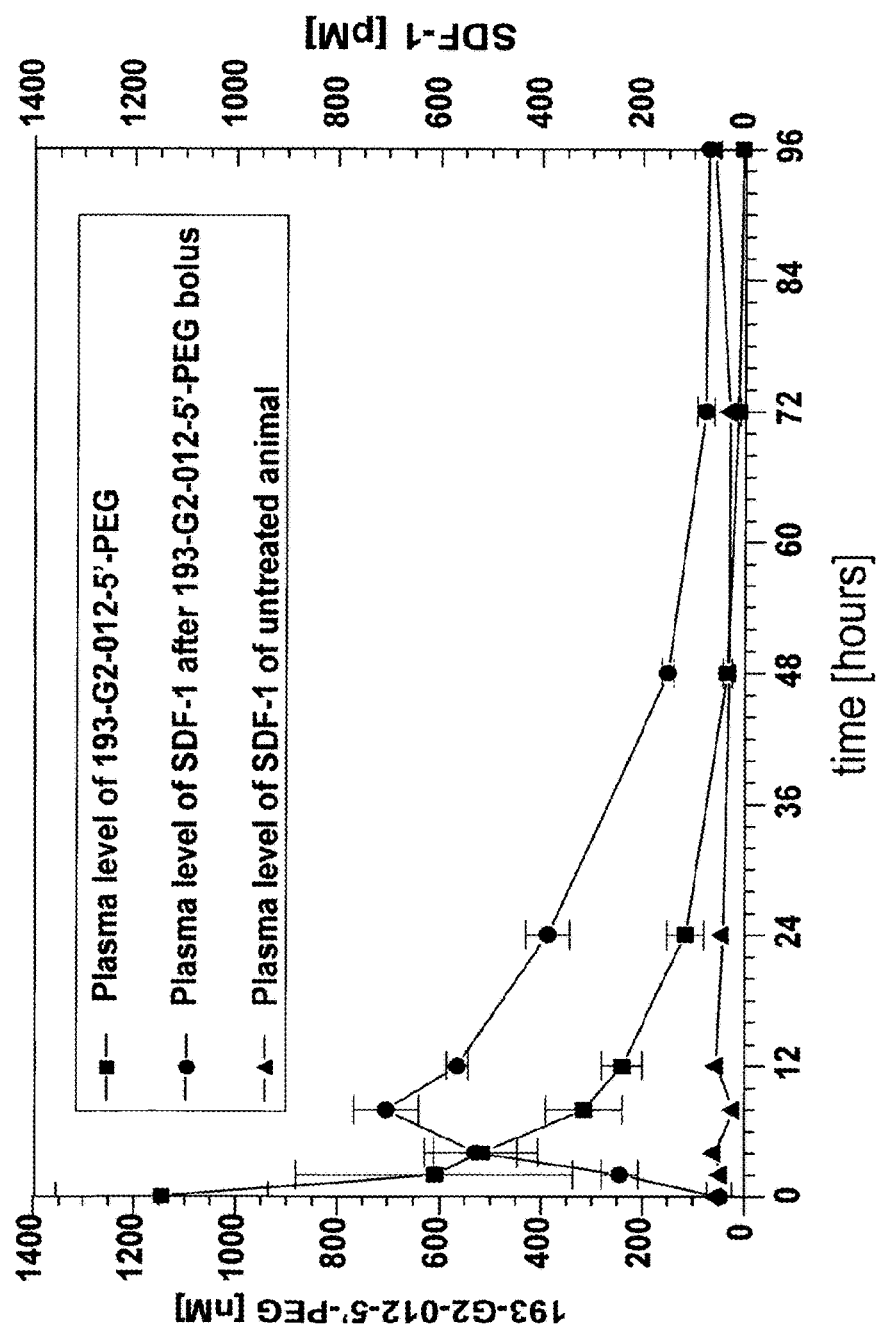

FIG. 33 shows the plasma level of human SDF-1 binding Spiegelmer 193-G2-012-5'-PEG and SDF-1 in rats after an intravenous bolus of human SDF-1 binding Spiegelmer 193-G2-012-5'-PEG in comparison with the SDF-1 plasma level of rat that was not treated with human SDF-1 binding Spiegelmer 193-G2-012-5'-PEG, whereby the plasma level of human SDF-1 binding Spiegelmer 193-G2-012-5'-PEG and SDF-1 were determined over a period of 96 hours.

DETAILED DESCRIPTION OF THE INVENTION

The present invention is based on the surprising finding that it is possible to generate nucleic acids binding specifically and with high affinity to SDF-1.

SDF-1 is a basic peptide having the amino acid sequence according to SEQ ID NO:1. The calculated pI of SDF-1 is 9.70. As used herein, the term SDF-1 refers to any SDF-1 including, but not limited to, mammalian SDF-1. Preferably, the mammalian SDF-1 is selected from the group comprising mice, rat, rabbit, hamster, monkey and human SDF-1. Most preferably, the SDF-1 is human SDF-1 (SEQ ID NO:1).

The finding that high affinity binding nucleic acids to SDF-1 could be identified, is insofar surprising as Eaton et al. (Eaton, Gold et al. 1997) observed that the generation of aptamers, i.e. D-nucleic acids binding to a target molecule, directed to a basic protein is in general very difficult because this kind of target produces a high but non-specific signal-to-noise ratio. This high signal-to-noise ratio results from the high non-specific affinity shown by nucleic acids for basic targets such as SDF-1.

The features of the nucleic acid according to the present invention as described herein can be realised in any aspect of the present invention where the nucleic acid is used, either alone or in any combination.

Without wishing to be bound by any theory, the present inventors assume that the observed specificity of the SDF-1 binding nucleic acids according to the present invention share some structural features and in particular one of the nucleotide sequences which are also referred to therein as core sequences which shall be discussed in more detail in the following, whereby reference is made to FIGS. 1 to 8 and to Example 1. However, it is to be understood that said Figures and Example 1 incorporate several of said structural features which do not have to be necessarily realized in each and any of the nucleic acids according to the present invention.

As outlined in more detail in the claims and Example 1, the various human SDF-1 binding nucleic acid molecules can be categorised based on said Boxes and some structural features and elements, respectively. The various categories thus defined are also referred to herein as types and more specifically as Type A, Type B and Type C.

In a preferred embodiment, the nucleic acid according to the present invention is a single nucleic acid molecule. In a further embodiment, the single nucleic acid molecule is present as a multitude of the single nucleic acid molecule. Preferably, the terms nucleic acid and nucleic acid molecule are used in an interchangeable manner herein if not indicated to the contrary.

It will be acknowledged by the ones skilled in the art that the nucleic acid molecule in accordance with the invention preferably consists of nucleotides which are covalently linked to each other, preferably through phosphodiester links or linkages.

The nucleic acids according to the present invention shall also comprise nucleic acids which are essentially homologous to the particular sequences disclosed herein. The term substantially homologous shall be understood such as the homology is at least 75%, preferably 85%, more preferably 90% and most preferably more that 95%, 96%, 97%, 98% or 99%.

The actual percentage of homologous nucleotides present in the nucleic acid according to the present invention will depend on the total number of nucleotides present in the nucleic acid. The percent modification can be based upon the total number of nucleotides present in the nucleic acid.

The homology can be determined as known to the person skilled in the art. More specifically, a sequence comparison algorithm then calculates the percent sequence identity for the test sequence(s) relative to the reference sequence, based on the designated program parameters. The test sequence is preferably the sequence or nucleic acid molecule which is said to be or to be tested whether it is homologous, and if so, to what extent, to another nucleic acid molecule, whereby such another nucleic acid molecule is also referred to as the reference sequence. In an embodiment, the reference sequence is a nucleic acid molecule as described herein, more preferably a nucleic acid molecule having a sequence according to any of SEQ ID NOs:5 to 144. Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al. (Altschul et al. 1990 and Altschul et al., 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al. (McGinnis et al., 2004).

The term, "inventive nucleic acid" or "nucleic acid" according to the present invention shall also comprise those nucleic acids comprising the nucleic acids sequences disclosed herein or part thereof, preferably to the extent that the nucleic acids or said parts are involved in the binding to SDF-1. Such a nucleic acid may be derived from the ones disclosed herein, e.g., by truncation. Truncation may be related to either or both of the ends of the nucleic acids as disclosed herein. Also, truncation may be related to the inner sequence of nucleotides, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the inventive nucleic acid(s), whereby the stretch can be as little as one nucleotide long. The binding of a nucleic acid according to the present invention can be determined by the ones skilled in the art using routine experiments or by using or adopting a method as described herein, preferably as described herein in the example part.

The nucleic acids according to the present invention may be either D-nucleic acids or L-nucleic acids. Preferably, the inventive nucleic acids are L-nucleic acids. In addition, it is possible that one or several parts of the nucleic acid are present as D-nucleic acids or at least one or several parts of the nucleic acids are L-nucleic acids. The term "part" of the nucleic acids shall mean as little as one nucleotide. Such nucleic acids are generally referred to herein as D- and L-nucleic acids, respectively. Therefore, in a particularly preferred embodiment, the nucleic acids according to the present invention consist of L-nucleotides and comprise at least one D-nucleotide. Such a D-nucleotide is preferably attached to a part different from the stretches defining the nucleic acids according to the present invention, preferably those parts thereof, where an interaction with other parts of the nucleic acid is involved. Preferably, such D-nucleotide is attached at a terminus of any of the stretches and of any nucleic acid according to the present invention, respectively. In a further preferred embodiment, such D-nucleotides may act as a spacer or a linker, preferably attaching modifications such as PEG and HES to the nucleic acids according to the present invention.

It is also within the present invention that each and any of the nucleic acid molecules described herein in their entirety in terms of their nucleic acid sequence(s) are limited to the particular nucleotide sequence(s). In other words, the terms "comprising" or "comprise(s)" shall be interpreted in such embodiment in the meaning of containing or consisting of.

It is also within the present invention that the nucleic acids according to the present invention are part of a longer nucleic acid whereby this longer nucleic acid comprises several parts whereby at least one such part is a nucleic acid, or a part thereof, according to the present invention. The other part(s) of these longer nucleic acids can be either one or several D-nucleic acid(s) or L-nucleic acid(s). Any combination may be used in connection with the present invention. These other part(s) of the longer nucleic acid can exhibit a function which is different from binding, preferably from binding to SDF-1. One possible function is to allow interaction with other molecules, whereby such other molecules preferably are different from SDF-1, such as, e.g., for immobilization, cross-linking, detection or amplification. In a further embodiment of the present invention, the nucleic acids according to the invention comprise, as individual or combined moieties, several of the nucleic acids of the present invention. Such nucleic acid comprising several of the nucleic acids of the present invention is also encompassed by the term longer nucleic acid.

L-nucleic acids as used herein are nucleic acids consisting of L-nucleotides, preferably consisting completely of L-nucleotides.

D-nucleic acids as used herein are nucleic acids consisting of D-nucleotides, preferably consisting completely of D-nucleotides.

The terms nucleic acid and nucleic acid molecule are used herein in an interchangeable manner if not explicitly indicated to the contrary.

Also, if not indicated to the contrary, any nucleotide sequence is set forth herein in 5'→3' direction.

Irrespective of whether the inventive nucleic acid consists of D-nucleotides, L-nucleotides or a combination of both with the combination being e.g. a random combination or a defined sequence of stretches consisting of at least one L-nucleotide and at least one D-nucleic acid, the nucleic acid may consist of desoxyribonucleotide(s), ribonucleotide(s) or combinations thereof.

Designing the inventive nucleic acids as L-nucleic acid is advantageous for several reasons. L-nucleic acids are enantiomers of naturally occurring nucleic acids. D-nucleic acids, however, are not very stable in aqueous solutions and particularly in biological systems or biological samples due to the widespread presence of nucleases. Naturally occurring nucleases, particularly nucleases from animal cells are not capable of degrading L-nucleic acids. Because of this, the biological half-life of the L-nucleic acid is significantly increased in such a system, including the animal and human body. Due to the lacking degradability of L-nucleic acid no nuclease degradation products are generated and thus no side effects arising therefrom are observed. This aspect delimits the L-nucleic acid from factually all other compounds which are used in the therapy of diseases and/or disorders involving the presence of SDF-1. L-nucleic acids which specifically bind to a target molecule through a mechanism different from Watson Crick base pairing, or aptamers which consists partially or completely of L-nucleotides, particularly with those parts of the aptamer being involved in the binding of the aptamer to the target molecule, are also called spiegelmers.

It is within the present invention that the first and the second stretch of nucleotides flanking the core nucleotide sequence can, in principle, hybridise with each other. Upon such hybridisation a double-stranded structure is formed. It will be acknowledged by the one skilled in the art that such hybridisation may or may not occur, particularly under in vitro and/or in vivo conditions. Also, in case of such hybridisation, it is not necessarily the case that the hybridisation occurs over the entire length of the two stretches where, at least based on the rules for base pairing, such hybridisation and thus formation of a double-stranded structure may occur. As preferably used herein, a double-stranded structure is a part of a molecule or a structure formed by two or more separate strands, whereby at least one, preferably two or more base pairs exist which are base paired preferably in accordance with the Watson-Crick base pairing rules. It will also be acknowledged by the one skilled in the art that other base pairing such as Hoogsten base pairing may exist in or form such double-stranded structure.

It is also within the present invention that the inventive nucleic acids, regardless whether they are present as D-nucleic acids, L-nucleic acids or D,L-nucleic acids or whether they are DNA or RNA, may be present as single-stranded or double-stranded nucleic acids. Typically, the inventive nucleic acids are single-stranded nucleic acids that exhibit defined secondary structures due to the primary sequence and may thus also form tertiary structures. The inventive nucleic acids, however, may also be double-stranded in the meaning that two strands which are complementary or partially complementary to each other are hybridised to each other. This confers stability to the nucleic acid which, in particular, will be advantageous if the nucleic acid is present in the naturally occurring D-form rather than the L-form.

The inventive nucleic acids may be modified. Such modifications may be related to the single nucleotide of the nucleic acid and are well known in the art. Examples for such modification are described by, among others, Venkatesan et al. (Venkatesan, Kim et al. 2003) and Kusser (Kusser 2000). Such modification can be an H atom, an F atom or an O—CH$_3$ group or NH$_2$-group at the 2' position of the individual nucleotide of which the nucleic acid consists. Also, the nucleic acid according to the present invention can comprise at least one LNA nucleotide. In an embodiment, the nucleic acid according to the present invention consists of LNA nucleotides.

In an embodiment, the nucleic acids according to the present invention may be a multipartite nucleic acid. A multipartite nucleic acid as used herein, is a nucleic acid which consists of at least two nucleic acid strands. These at least two nucleic acid strands form a functional unit whereby the functional unit is a ligand to a target molecule. The at least two nucleic acid strands may be derived from any of the inventive nucleic acids by either cleaving the nucleic acid to generate two strands or by synthesising one nucleic acid corresponding to a first part of the inventive, i.e. overall nucleic acid, and another nucleic acid corresponding to the second part of the overall nucleic acid. It is to be acknowledged that both the cleavage and the synthesis may be applied to generate a multipartite nucleic acid where there are more than two strands as exemplified above. In other words, the at least two nucleic acid strands are typically different from two strands being complementary and hybridising to each other, although a certain extent of complementarity between the various nucleic acid parts may exist.

Finally, it is also within the present invention that a fully closed, i.e. circular structure for the nucleic acids according to the present invention is realized, i.e. that the nucleic acids according to the present invention are closed, preferably through a covalent linkage, whereby more preferably such covalent linkage is made between the 5' end and the 3' end of the nucleic acid sequences as disclosed herein.

The present inventors have discovered that the nucleic acids according to the present invention exhibit a very favourable Kd value range.

A way to determine the binding constant is surface plasmon resonance measurement by the use of the so-called Biacore device (Biacore AB, Uppsala, Sweden), which is also known to the one skilled in the art. Affinity, as preferably used herein, was also measured by the use of "pull-down binding assay" as described in the examples. An appropriate measure in order to express the intensity of the binding between the nucleic acid and the target which is in the present case SDF-1, is the so-called Kd value which as such as well as the method for its determination are known to the one skilled in the art.

The nucleic acids according to the present invention are characterized by a certain Kd value. Preferably, the Kd value shown by the nucleic acids according to the present invention is below 1 µM. A Kd value of about 1 µM is said to be characteristic for a non-specific binding of a nucleic acid to a target. As will be acknowledged by the ones in the art, the Kd value of a group of compounds such as the nucleic acids according to the present invention are within a certain range. The above-mentioned Kd of about 1 µM is a preferred upper limit for the Kd value. The preferred lower limit for the Kd of target binding nucleic acids can be about 10 picomolar or higher. It is within the present invention that the Kd values of individual nucleic acids binding to SDF-1 are preferably within this range. Preferred ranges can be defined by choosing any first number within this range and any second number within this range. Preferred upper values are 250 nM and 100 nM, and preferred lower values are 50 nM, 10 nM, 1 nM, 100 pM and 10 pM.

The nucleic acid molecules according to the present invention may have any length provided that they are still able to bind to the target molecule. It will be acknowledged in the art that there are preferred lengths of the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 20 to 50 nucleotides and about 20 to 40 nucleotides.

It is within the present invention that the nucleic acids disclosed herein comprise a moiety which preferably is a high molecular weight moiety and/or which preferably allows to modify the characteristics of the nucleic acid in terms of, among others, residence time in the animal body, preferably the human body. A particularly preferred embodiment of such modification is PEGylation and HESylation of the nucleic acids according to the present invention. As used herein PEG stands for poly(ethylene glycole) and HES for hydroxyethyl starch. PEGylation as preferably used herein is the modification of a nucleic acid according to the present invention whereby such modification consists of a PEG moiety which is attached to a nucleic acid according to the present invention. HESylation as preferably used herein is the modification of a nucleic acid according to the present invention whereby such modification consists of a HES moiety which is attached to a nucleic acid according to the present invention. These modifications as well as the process of modifying a nucleic acid using such modifications, is described in European patent application EP 1 306 382, the disclosure of which is herewith incorporated in its entirety by reference.

Preferably, the molecular weight of a modification consisting of or comprising a high molecular weight moiety is about from 2,000 to 200,000 Da, preferably 40,000 to 120,000 Da, particularly in the case of PEG being such high molecular weight moiety, and is preferably about from 3,000 to 180,000 Da, more preferably from 60,000 to 140,000 Da, particularly in the case of HES being such high molecular weight moiety. The process of HES modification is, e.g., described in German patent application DE 1 2004 006 249.8 the disclosure of which is herewith incorporated in its entirety by reference.

It is within the present invention that either of PEG and HES may be used as either a linear or branched from as further described in the patent applications, WO2005074993 and PCT/EP02/11950. Such modification can, in principle, be made to the nucleic acid molecules of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule.

The modification, and preferably the PEG and/or HES moiety, can be attached to the nucleic acid molecule of the present invention either directly or through a linker. It is also within the present invention that the nucleic acid molecule according to the present invention comprises one or more modifications, preferably one or more PEG and/or HES moiety. In an embodiment, the individual linker molecule attaches more than one PEG moiety or HES moiety to a nucleic acid molecule according to the present invention. The linker used in connection with the present invention can itself be either linear or branched. This kind of linkers is known to the ones skilled in the art, and is further described in the patent applications, WO2005074993 and PCT/EP02/11950.

Without wishing to be bound by any theory, it seems that by modifying the nucleic acids according to the present invention with a high molecular weight moiety such as a polymer and more particularly the polymers disclosed herein, which are preferably physiologically acceptable, the excretion kinetic is changed. More particularly, it seems that due to the increased molecular weight of such modified inventive nucleic acids and due to the nucleic acids not being subject to metabolism particularly when in the L form, excretion from an animal body, preferably from a mammalian body, and more preferably from a human body, is decreased. As excretion typically occurs via the kidneys, the present inventors assume that the glomerular filtration rate of the thus modified nucleic acid is significantly reduced compared to the nucleic acids not having this kind of high molecular weight modification, which results in an increase in the residence time in the body. In connection therewith, it is particularly noteworthy that despite such high molecular weight modification, the specificity of the nucleic acid according to the present invention is not affected in a detrimental manner. Insofar the nucleic acids according to the present invention have surprising characteristics—which normally cannot be expected from pharmaceutically active compounds—a pharmaceutical formulation providing for a sustained release is not necessarily required to provide for a sustained release. Rather, the nucleic acids according to the present invention in their modified form comprising a high molecular weight moiety, can as such already be used as a sustained release formulation. Also, the modification(s) of the nucleic acid molecules as disclosed herein, and the thus the modified nucleic acid molecules and any composition comprising the same, provide for a distinct, preferably controlled pharmacokinetics and biodistribution. This also includes residence time in circulation and distribution to tissues. Such modifications are further described in the patent application PCT/EP02/11950.

However, it is also within the present invention that the nucleic acids disclosed herein do not comprise any modification and particularly no high molecular weight modification, such as PEGylation or HESylation. Such embodiment is particularly preferred when fast clearance of the nucleic acids from the body after administration is desired. Such fast clearance might be desired in case of in vivo imaging or specific therapeutic dosing requirements using the nucleic acids or medicaments comprising the same, according to the present invention.

The inventive nucleic acids, which are also referred to herein as the nucleic acids according to the present invention, and/or the antagonists according to the present invention may be used for the generation or manufacture of a medicament. Such medicament contains at least one of the inventive nucleic acids, optionally together with further pharmaceutically active compounds, whereby the inventive nucleic acid preferably acts as the pharmaceutically active compound itself. Such medicaments comprise in preferred embodiments at least a pharmaceutically acceptable carrier. Such carrier may be, e. g., water, buffer, PBS, glucose solution, sucrose solution, mannose solution, preferably a 5% sucrose balanced solution, starch, sugar, gelatin or any other acceptable carrier substance. Such carriers are generally known to the one skilled in the art. It will be acknowledged by the person skilled in the art that any embodiments, use and aspects of or related to the medicament of the present invention is also applicable to the pharmaceutical composition of the present invention and vice versa.

The indication, diseases and disorders for the treatment and/or prevention of which the nucleic acids, the pharmaceutical compositions and medicaments in accordance with or prepared in accordance with the present invention, result from the involvement, either direct or indirect, of SDF-1 in the respective pathogenic mechanism.

Of course, because the SDF-1 binding nucleic acids according to the present invention interact with or bind to human or murine SDF-1, a skilled person will generally understand that the SDF-1 binding nucleic acids according to the present invention can easily be used for the treatment, prevention and/or diagnosis of any disease as described herein of humans and animals.

Disease and/or disorders and/or diseased conditions for the treatment and/or prevention of which such medicament may be used include, but are not limited to back-of-the-eye diseases like retinopathy, diabetic retinopathy and age-related macular degeneration, both dry and wet form; cancer; cancer of breast, ovaries, prostate, pancreas, thyroid, nasopharynx, colon, lung, and stomach; osteosarcoma; melanoma; glioma; medullo- and neuroblastoma; leukemia; B cell chronic lymphocytic leukaemia; multiple myeloma; lymphoma; WHIM syndrome; immunologic deficiency syndromes; pathologic neovascularization; inflammation; multiple sclerosis; arthritis, rheumatoid arthritis, osteoarthritis and nephritis.

In a further embodiment, the medicament comprises a further pharmaceutically active agent. Such further pharmaceutically active compounds can be those known to the ones skilled in the art and are preferably selected from the group comprising chemokine or cytokine antagonists, corticosteroids, and the like. It will be understood by the one skilled in the art that given the various indications which can be addressed in accordance with the present invention by the nucleic acids according to the present invention, said further pharmaceutically active agent(s) may be any one which in principle is suitable for the treatment and/or prevention of such diseases. The nucleic acid molecules according to the present invention, particularly if present or used as a medicament, are preferably combined with VEGF-inhibitors such as Macugen (Pegatanib) from Pfizer Ophthalmics, Lucentis (Ranitizumab) from Novartis Ophthalmics, Avastin (Bevacizumab) from Roche (off-label use); or with photodynamic therapy such as Visudyne (Verteporfing) from Novartis Ophthalmics and intravitreally injectable cortisone derivative such as Retaane (Anecortave acetate) from Alcon Inc.

Alternatively, or additionally, such further pharmaceutically active agent is a further nucleic acid according to the present invention. Alternatively, the medicament comprises at least one more nucleic acid which binds to a target molecule different from SDF-1 or exhibits a function which is different from the one of the nucleic acids according to the present invention.

As will be acknowledged by the ones of the art, the inventive nucleic acids may factually be used in any disease where an antagonist to SDF-1 can be administered to a patient in need of such antagonist and such antagonist is suitable to eliminate the cause of the disease or the disorder or at least to reduce the effects from the disease or the disorder. Such effect includes, but is not limited to pathologic neovascularization, inflammation and metastasis. The applicability of the nucleic acids according to the present invention in connection with these and other diseases or disorders results, among others, from the involvement of SDF-1 as outlined in the introductory part of the present specification which is incorporated herein by reference so as to avoid any unnecessary repetition.

It is within the present invention that the medicament is alternatively or additionally used, in principle, for the prevention of any of the diseases disclosed in connection with the use of the medicament for the treatment of said diseases. Respective markers therefore, i.e. for the respective diseases, are known to the ones skilled in the art. Preferably, the respective marker is SDF-1. Alternatively and/or additionally, the respective marker is selected from the group of oxidative stress markers, comprising transmembrane reductase of ferricyanide (TMR), increased activity of the sorbitol pathway which includes after accumulation of sorbitol, increased cytosolic NADH/NAD ratio, depletion of NADPH and accumulation of fructose with the resulting non-enzymatic production of advanced glycation end products (AGES) and consequent activation of protein kinase C, nitrosative and oxidative stress-mediated downstream events such as MAP kinase activation; inflammatory markers, comprising ICAM-1, VCAM-1, RANTES, haptoglobin, or C-reactive protein; and pro-angiogenic markers like erythropoietin or VEGF. In view of this, said markers can be used to determine whether or not a subject or a patient can be treated with any of the nucleic acid molecules in accordance with the present invention. Therefore, in a further aspect, the present invention is related to such method, whereby the presence or absence and more specifically the concentration of the respective marker(s) is/are determined. Methods for the detection of said markers and optionally their quantification, as well as the range within which the respective marker shall be present or absent so as to decide whether or not the subject or patient is suffering from any of said diseases or is a risk to develop such diseases, and, accordingly, may thus be treated in accordance with the present invention, are known to the ones skilled in the art.

In one embodiment of the medicament of the present invention, such medicament is for use in combination with other treatments for any of the diseases disclosed herein, particularly those for which the medicament of the present invention is to be used.

"Combination therapy" (or "co-therapy") includes the administration of a medicament of the invention and at least a second agent as part of a specific treatment regimen intended to provide the beneficial effect from the co-action of these therapeutic agents, i.e. the medicament of the present invention and said second agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As outlined in general terms above, the medicament according to the present invention can be administered, in principle, in any form known to the ones skilled in the art. A preferred route of administration is systemic administration, more preferably by parenteral administration, preferably by injection. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficacy.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that are well known to the one of ordinary skill in the art.

Furthermore, preferred medicaments of the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

The medicament of the present invention will generally comprise an effective amount of the active component(s) of the therapy, including, but not limited to, a nucleic acid molecule of the present invention, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least one of the nucleic acids according to the present invention and preferably a pharmaceutically acceptable binder. Such binder can be any binder used and/or known in the art. More particularly such binder is any binder as discussed in connection with the manufacture of the medicament disclosed herein. In a further embodiment, the pharmaceutical composition comprises a further pharmaceutically active agent.

The preparation of a medicament and a pharmaceutical composition will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, a medicament will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the individual or the subject to be treated. Specific amounts of active compound required for administration depend on the judgment of the practitioner and are peculiar to each individual.

A minimal volume of a medicament required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatin capsule), the active drug component, i.e. a nucleic acid molecule of the present invention and/or any further pharmaceutically active agent, also referred to herein as therapeutic agent(s) or active compound(s) can be combined with an oral, non-toxic, pharmaceutically acceptable inert carrier such as ethanol, glycerol, water and the like. Moreover, when desired or necessary, suitable binders, lubricants, disintegrating agents, and colouring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or β-lactose, corn sweeteners, natural and synthetic gums such as acacia, tragacanth or sodium alginate, polyethylene glycol, waxes, and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol, and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The medicament of the invention can also be administered in such oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical composition or medicament may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

For solid compositions, excipients include pharmaceutical grades of mannitol, lactose, starch, magnesium stearate, sodium saccharin, talcum, cellulose, glucose, sucrose, magnesium carbonate, and the like. The active compound defined above, may be also formulated as suppositories, using for example, polyalkylene glycols, for example, propylene glycol, as the carrier. In some embodiments, suppositories are advantageously prepared from fatty emulsions or suspensions.

The medicaments and nucleic acid molecules, respectively, of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, what is well known to the ordinary skill in the art. For example, the nucleic acid molecules described herein can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic acid-associated complexes is provided in U.S. Pat. No. 6,011,020.

The medicaments and nucleic acid molecules, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethyl-aspanamidephenol, or polyethyleneoxidepolylysine substituted with palmitoyl residues. Furthermore, the medicaments and nucleic acid molecules, respectively, of the present invention may be coupled to a class of biodegradable polymers useful in achieving controlled release of a drug, for example, polylactic acid, polyepsilon capro lactone, polyhydroxy butyric acid, polyorthoesters, polyacetals, polydihydropyrans, polycyanoacrylates and crosslinked or amphipathic block copolymers of hydrogels.

If desired, the pharmaceutical composition and medicament, respectively, to be administered may also contain minor amounts of non-toxic auxiliary substances such as wetting or emulsifying agents, pH buffering agents, and other substances such as, for example, sodium acetate, and triethanolamine oleate.

The dosage regimen utilizing the nucleic acid molecules and medicaments, respectively, of the present invention is selected in accordance with a variety of factors including type, species, age, weight, sex and medical condition of the patient; the severity of the condition to be treated; the route of administration; the renal and hepatic function of the patient; and the particular nucleic acid or salt thereof employed. An ordinarily skilled physician or veterinarian can readily determine and prescribe the effective amount of the drug required to prevent, counter or arrest the progress of the condition.

Effective plasma levels of the nucleic acid according to the present invention preferably range from 500 fM to 500 µM in the treatment of any of the diseases disclosed herein.

The nucleic acid molecules and medicaments, respectively, of the present invention may preferably be administered in a single daily dose, every second or third day, weekly, every second week, in a single monthly dose or every third month.

It is within the present invention that the medicament as described herein constitutes the pharmaceutical composition disclosed herein.

In a further aspect the present invention is related to a method for the treatment of a subject who is in need of such treatment, whereby the method comprises the administration of a pharmaceutically active amount of at least one of the nucleic acids according to the present invention. In an embodiment, the subject suffers from a disease or is in risk to develop such disease, whereby the disease is any of those disclosed herein, particularly any of those diseases disclosed in connection with the use of any of the nucleic acids according to the present invention for the manufacture of a medicament.

As preferably used herein a diagnostic or diagnostic agent or diagnostic means is suitable to detect, either directly or indirectly SDF-1 as described herein in connection with the various disorders and diseases described herein. The diagnostic is suitable for the detection and/or follow-up of any of the disorders and diseases, respectively, described herein. Such detection is possible through the binding of the nucleic acids according to the present invention to SDF-1. Such binding can be either directly or indirectly be detected. The respective methods and means are known to the ones skilled in the art. Among others, the nucleic acids according to the present invention may comprise a label which allows the detection of the nucleic acids according to the present invention, preferably the nucleic acid bound to SDF-1. Such a label is preferably selected from the group comprising radioactive, enzymatic and fluorescent labels. In principle, all known assays developed for antibodies can be adopted for the nucleic acids according to the present invention whereas the target-binding antibody is substituted with a target-binding nucleic acid. In antibody assays using unlabeled target-binding antibodies, the detection is preferably done by a secondary antibody which is modified with radioactive, enzymatic and fluorescent labels and binds to the target-binding antibody at its $F_c$ fragment. In the case of a nucleic acid, preferably a nucleic acid according to the present invention, the nucleic acid is modified with such a label, whereby preferably such a label is selected from the group comprising biotin, Cy-3 and Cy-5, and such label is detected by an antibody directed against such label, e.g. an anti-biotin antibody, an anti-Cy3 antibody or an anti-Cy5 antibody, or—in the case that the label is biotin—the label is detected by streptavidin or avidin which naturally bind to biotin. Such antibody, streptavidin or avidin in turn is preferably modified with a respective label, e.g. a radioactive, enzymatic or fluorescent label (like a secondary antibody).

In a further embodiment, the nucleic acid molecules according to the invention are detected or analysed by a second detection means, wherein the said detection means is a molecular beacon. The methodology of molecular beacon is known to persons skilled in the art. In brief, nucleic acids probes which are also referred to as molecular beacons, are a reverse complement to the nucleic acid sample to be detected and hybridise because of this to a part of the nucleic acid sample to be detected. Upon binding to the nucleic acid sample, the fluorophoric groups of the molecular beacon are separated which results in a change of the fluorescence signal, preferably a change in intensity. This change correlates with the amount of nucleic acid sample present.

It will be understood by the one skilled in the art that due to the relationship outlined herein between SDF-1 and its corresponding receptor, the diseases and conditions which can be diagnosed using the nucleic acid molecules of the present invention, are, in principle, the very same as described herein in connection with the use of said nucleic acid molecules for the treatment and/or prevention of said disease.

Apart from that, further uses of the nucleic acid molecules according to the present invention reside in a decrease in hematopoiesis, a decrease in invasion or metastasis, a decrease in B cell development and chemotaxis, a decrease in T cell chemoattraction and an induction of growth arrest and apoptosis.

In connection with the detection of SDF-1, a preferred method comprises the following steps:
(a) providing a sample which is to be tested for the presence of SDF-1,
(b) providing a nucleic acid according to the present invention, and
(c) reacting the sample with the nucleic acid, preferably in a reaction vessel,
wherein step (a) can be performed prior to step (b), or step (b) can be preformed prior to step (a).

In a preferred embodiment a further step d) is provided, which consists in the detection of the reaction of the sample with the nucleic acid. Preferably, the nucleic acid of step b) is immobilised to a surface. The surface may be the surface of a reaction vessel such as a reaction tube, a well of a plate, or the surface of a device contained in such reaction vessel such as, for example, a bead. The immobilisation of the nucleic acid to the surface can be made by any means known to the ones skilled in the art including, but not limited to, non-covalent or covalent linkages. Preferably, the linkage is established via a covalent chemical bond between the surface and the nucleic acid. However, it is also within the present invention that the nucleic acid is indirectly immobilised to a surface, whereby such indirect immobilisation involves the use of a further component or a pair of interaction partners. Such further component is preferably a compound which specifically interacts with the nucleic acid to be immobilised which is also referred to as interaction partner, and thus mediates the attachment of the nucleic acid to the surface. The interaction partner is preferably selected from the group comprising nucleic acids, polypeptides, proteins and antibodies. Preferably, the interaction partner is an antibody, more preferably a monoclonal antibody. Alternatively, the interaction partner is a nucleic acid, preferably a functional nucleic acid. More preferably such functional nucleic acid is selected from the group comprising aptamers, spiegelmers, and nucleic acids which are at least partially complementary to the nucleic acid. In a further alternative embodiment, the binding of the nucleic acid to the surface is mediated by a multi-partite interaction partner. Such multi-partite interaction partner is preferably a pair of interaction partners or an interaction partner consisting of a first member and a second member, whereby the first member is comprised by or attached to the nucleic acid and the second member is attached to or comprised by the surface. The multi-partite interaction partner is preferably selected from the group of pairs of interaction partners comprising biotin and avidin, biotin and streptavidin, and biotin and neutravidin. Preferably, the first member of the pair of interaction partners is biotin.

A preferred result of such method is the formation of an immobilised complex of SDF-1 and the nucleic acid, whereby more preferably said complex is detected. It is within an embodiment that from the complex the SDF-1 is detected.

The method for the detection of SDF-1 also comprises that the sample is removed from the reaction vessel that has preferably been used to perform step c).

The method comprises in a further embodiment also the step of immobilising an interaction partner of SDF-1 on a surface, preferably a surface as defined above, whereby the interaction partner is defined as herein and preferably as above in connection with the respective method and more preferably comprises nucleic acids, polypeptides, proteins and antibodies in their various embodiments. In this embodiment, a particularly preferred detection means is a nucleic acid according to the present invention, whereby such nucleic acid may preferably be labelled or non-labelled. In case such nucleic acid is labelled, it can be directly or indirectly detected. Such detection may also involve the use of a second detection means that is, preferably, also selected from the group comprising nucleic acids, polypeptides, proteins and embodiments in the various embodiments described herein. Such detection means are preferably specific for the nucleic acid according to the present invention. In a more preferred embodiment, the second detection means is a molecular beacon. Either the nucleic acid or the second detection means or both may comprise in a preferred embodiment a detection label. The detection label is preferably selected from the group comprising biotin, a bromo-desoxyuridine label, a digoxigenin label, a fluorescence label, a UV label, a radiolabel, and a chelator molecule. Alternatively, the second detection means interacts with the detection label which is preferably contained by, comprised by or attached to the nucleic acid. Particularly preferred combinations are as follows:
the detection label is biotin and the second detection means is an antibody directed against biotin, or wherein
the detection label is biotin and the second detection means is an avidin or an avidin carrying molecule, or wherein
the detection label is biotin and the second detection means is a streptavidin or a streptavidin carrying molecule, or wherein
the detection label is biotin and the second detection means is a neutravidin or a neutravidin carrying molecule, or wherein the detection label is a bromo-desoxyuridine and the second detection means is an antibody directed against bromo-desoxyuridine, or wherein
the detection label is a digoxigenin and the second detection means is an antibody directed against digoxigenin, or wherein the detection label is a chelator and the second detection means is a radionuclide, whereby it is preferred that said detection label is attached to the nucleic acid. It is to be acknowledged that this kind of combination is also applicable to the embodiment where the nucleic acid is attached to the surface. In such embodiment, it is preferred that the detection label is attached to the interaction partner.

Finally, it is also within the present invention that the second detection means is detected using a third detection means, preferably the third detection means is an enzyme, more preferably showing an enzymatic reaction upon detection of the second detection means, or the third detection means is a means for detecting radiation, more preferably radiation emitted by a radio-nuclide. Preferably, the third detection means is specifically detecting and/or interacting with the second detection means.

Also in the embodiment with an interaction partner of SDF-1 being immobilised on a surface and the nucleic acid according to the present invention is preferably added to the complex formed between the interaction partner and the SDF-1, the sample can be removed from the reaction, more preferably from the reaction vessel where step c) and/or d) are preformed.

In an embodiment, the nucleic acid according to the present invention comprises a fluorescence moiety and whereby the fluorescence of the fluorescence moiety is different upon complex formation between the nucleic acid and SDF-1 and free SDF-1.

In a further embodiment, the nucleic acid is a derivative of the nucleic acid according to the present invention, whereby the derivative of the nucleic acid comprises at least one fluorescent derivative of adenosine replacing adenosine. In a preferred embodiment, the fluorescent derivative of adenosine is ethenoadenosine.

In a further embodiment, the complex consisting of the derivative of the nucleic acid according to the present invention and the SDF-1 is detected using fluorescence.

In an embodiment of the method, a signal is created in step (c) or step (d) and preferably the signal is correlated with the concentration of SDF-1 in the sample.

In a preferred aspect, the assays may be performed in 96-well plates, where components are immobilized in the reaction vessels as described above and the wells acting as reaction vessels.

The inventive nucleic acid may further be used as starting material for drug design. Basically there are two possible approaches. One approach is the screening of compound libraries whereas such compound libraries are preferably low molecular weight compound libraries. In an embodiment, the screening is a high throughput screening Preferably, high throughput screening is the fast, efficient, trial-and-error evaluation of compounds in a target-based assay.

In best case, the analysis is carried by a colorimetric measurement. Libraries as used in connection therewith are known to the one skilled in the art.

Alternatively, the nucleic acid according to the present invention may be used for rational design of drugs. Preferably, rational drug design is the design of a pharmaceutical lead structure. Starting from the 3-dimensional structure of the target which is typically identified by methods such as X-ray crystallography or nuclear magnetic resonance spectroscopy, computer programs are used to search through databases containing structures of many different chemical compounds. The selection is done by a computer, the identified compounds can subsequently be tested in the laboratory.

The rational design of drugs may start from any of the nucleic acids according to the present invention and involves a structure, preferably a three dimensional structure, which is similar to the structure of the inventive nucleic acids or identical to the binding mediating parts of the structure of the inventive nucleic acids. In any case such a structure still shows the same or a similar binding characteristic as the inventive nucleic acids. In either, a further step or as an alternative step in the rational design of drugs, the preferably three dimensional structure of those parts of the nucleic acid binding to the neurotransmitter are mimicked by chemical groups which are different from nucleotides and nucleic acids. By this mimicry, a compound different from the nucleic acids can be designed. Such a compound is preferably a small molecule or a peptide.

In case of screening of compound libraries, such as by using a competitive assay which is known to the one skilled in the arts, appropriate SDF-1 analogues, SDF-1 agonists or SDF-1 antagonists may be found. Such competitive assays may be set up as follows. The inventive nucleic acid, preferably a spiegelmer which is a target binding L-nucleic acid, is coupled to a solid phase. In order to identify SDF-1 analogues, labelled SDF-1 may be added to the assay. A potential analogue would compete with the SDF-1 molecules binding to the spiegelmer which would go along with a decrease in the signal obtained by the respective label. Screening for agonists or antagonists may involve the use of a cell culture assay as known to the ones skilled in the art.

The kit according to the present invention may comprise at least one or several of the inventive nucleic acids. Additionally, the kit may comprise at least one or several positive or negative controls. A positive control may, for example, be SDF-1, particularly the one against which the inventive nucleic acid is selected or to which it binds, preferably, in liquid form. A negative control may, e.g., be a peptide which is defined in terms of biophysical properties similar to SDF-1, but which is not recognized by the inventive nucleic acids. Furthermore, said kit may comprise one or several buffers. The various ingredients may be contained in the kit in dried or lyophilised form or solved in a liquid. The kit may comprise one or several containers which in turn may contain one or several ingredients of the kit. In a further embodiment, the kit comprises an instruction or instruction leaflet which provides to the user information on how to use the kit and its various ingredients.

As preferably used herein, the term treatment comprises in a preferred embodiment additionally or alternatively prevention and/or follow-up.

The pharmaceutical and bioanalytical determination of the nucleic acid according to the present invention is elementarily for the assessment of its pharmacokinetic and biodynamic profile in several humours, tissues and organs of the human and non-human body. For such purpose, any of the detection methods disclosed herein or known to a person skilled in the art may be used. In a further aspect of the present invention, a sandwich hybridisation assay for the detection of the nucleic acid according to the present invention is provided. Within the detection assay, a capture probe and a detection probe are used. The capture probe is complementary to the first part and the detection probe to the second part of the nucleic acid according to the present invention. Both capture and detection probe can be formed by DNA nucleotides, modified DNA nucleotides, modified RNA nucleotides, RNA nucleotides, LNA nucleotides and/or PNA nucleotides.

Hence, the capture probe comprises a sequence stretch complementary to the 5'-end of the nucleic acid according to the present invention and the detection probe comprise a sequence stretch complementary to the 3'-end of the nucleic acid according to the present invention. In this case, the capture probe is immobilised to a surface or matrix via its 5'-end whereby the capture probe can be immobilised directly at its 5' end or via a linker between of its 5' end and the surface or matrix. However, in principle, the linker can be linked to each nucleotide of the capture probe. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucicotidcs, L-DNA nucicotidcs, modified L-RNA nucicotidcs, modified L-DNA nucleotides and/or L-LNA nucleotides.

Alternatively, the capture probe comprises a sequence stretch complementary to the 3'-end of the nucleic acid according to the present invention and the detection probe comprise a sequence stretch complementary to the 5'-end of the nucleic acid according to the present invention. In this case, the capture probe is immobilised to a surface or matrix via its 3'-end whereby the capture probe can be immobilised directly at its 3'-end or via a linker between of its 3'-end and the surface or matrix. However, in principle, the linker can be linked to each nucleotide of the sequence stretch that is complementary to the nucleic acid according to the present invention. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

The number of nucleotides of the capture and detection probe that may hybridise to the nucleic acid according to the present invention is variable and can be dependent from the number of nucleotides of the capture and/or the detection probe and/or the nucleic acid according to the present invention itself. The total number of nucleotides of the capture and the detection probe that may hybridise to the nucleic acid according to the present invention should be maximal the number of nucleotides that are comprised by the nucleic acid according to the present invention. The minimal number of nucleotides (2 to 10 nucleotides) of the detection and capture probe should allow hybridisation to the 5'-end or 3'-end, respectively, of the nucleic acid according to the present invention. In order to realize high specificity and selectivity between the nucleic acid according to the present invention and other nucleic acids occurring in samples that are analyzed the total number of nucleotides of the capture and detection probe should be or maximal the number of nucleotides that are comprised by the nucleic acid according to the present invention.

Moreover, the detection probe preferably carries a marker molecule or label that can be detected as previously described herein. The label or marker molecule can, in principle, be linked to each nucleotide of the detection probe. Preferably, the label or marker is located at the 5'-end or 3'-end of the detection probe, whereby, between the nucleotides within the detection probe that are complementary to the nucleic acid according to the present invention and the label, a linker can be inserted. The linker can be formed by hydrophilic linkers of the ones skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

The detection of the nucleic acid according to the present invention can be carried out as follows:

The nucleic acid according to the present invention hybridises with one of its ends to the capture probe and with the other end to the detection probe. Afterwards unbound detection probe is removed by, e.g., one or several washing steps. The amount of bound detection probe which preferably carries a label or marker molecule, can be measured subsequently.

As preferably used herein, the terms disease and disorder shall be used in an interchangeable manner, if not indicated to the contrary.

As used herein, the term comprise is preferably not intended to limit the subject matter followed or described by such term. However, in an alternative embodiment the term comprises shall be understood in the meaning of containing and thus as limiting the subject matter followed or described by such term.

The various SEQ ID NOs, the chemical nature of the nucleic acid molecules according to the present invention and the target molecules SDF-1 as used herein, the actual sequence thereof and the internal reference number is summarized in the following table.

It has to be noticed that the nucleic acids were characterized on the aptamer, i.e. D-nucleic acid level (D-RNA) with the biotinylated human D-SDF-1 (SEQ. ID. 4) or on the Spiegelmer level, i.e. L-nucleic acid (L-RNA) with the natural configuration of SDF-1, the L-SDF-1 (human SDF-1α, SEQ ID NO:1). The different nucleic acids share one internal reference name but one SEQ ID NO for the D-RNA (Aptamer) molecule and one SEQ ID NO for the L-RNA (Spiegelmer) molecule, respectively.

TABLE 1 (A)

| Seq.-ID | RNA/Peptide | Sequence | Internal Reference |
| --- | --- | --- | --- |
| 1 | L-peptide | KPVSLSYRCPCRFFESHVARANVKHLKILNTPNCALQIVARL KNNNRQVCIDPKLKWIQEYLEKALNK | human/monkey/cat SDF-1α human/monkey/cat SDF-1 |
| 2 | L-peptide | KPVSLSYRCPCRFFESHVARANVKHLKILNTPNCALQIVARL KNNNRQVCIDPKLKWIQEYLEKALNKRFKM | human/monkey/cat SDF-1β |
| 3 | L-peptide | KPVSLSYRCPCRFFESHIARANVKHLKILNTPNCALQIVARL KNNNRQVCIDPKLKWIQEYLEKALNK | murine SDF-1α murine SDF-1 |
| 4 | D-peptide | KPVSLSYRCPCRFFESHVARANVKHLKILNTPNCALQIVARL KNNNRQVCIDPKLKWIQEYLEKALNKRFK-Biotin | biotinylated hu D-SDF-1 |
| 5 | L-RNA (SPIEGELMER) | GCUGUGAAAGCAACAUGUCAAUGAAAGGUAGCCGCAGC | 192-A10-001 |
| 6 | L-RNA (SPIEGELMER) | GCUGUGAAAGUAACAUGUCAAUGAAAGGUAACCACAGC | 192-G10 |
| 7 | L-RNA (SPIEGELMER) | GCUGUGAAAGUAACACGUCAAUGAAAGGUAACCGCAGC | 192-F10 |
| 8 | L-RNA (SPIEGELMER) | GCUGUGAAAGUAACACGUCAAUGAAAGGUAACCACAGC | 192-B11 |
| 9 | L-RNA (SPIEGELMER) | GCUGUAAAAGUAACAUGUCAAUGAAAGGUAACUACAGC | 192-C9 |

TABLE 1 (A)-continued

| Seq.-ID | RNA/Peptide | Sequence | Internal Reference |
|---|---|---|---|
| 10 | L-RNA (SPIEGELMER) | GCUGUAAAAGUAACAAGUCAAUGAAAGGUAACUACAGC | 192-E10 |
| 11 | L-RNA (SPIEGELMER) | GCUGUGAAAGUAACAAGUCAAUGAAAGGUAACCACAGC | 192-C10 |
| 12 | L-RNA (SPIEGELMER) | GCAGUGAAAGUAACAUGUCAAUGAAAGGUAACCACAGC | 192-D11 |
| 13 | L-RNA (SPIEGELMER) | GCUGUGAAAGUAACAUGUCAAUGAAAGGUAACCACUGC | 192-G11 |
| 14 | L-RNA (SPIEGELMER) | GCUAUGAAAGUAACAUGUCAAUGAAAGGUAACCAUAGC | 192-H11 |
| 15 | L-RNA (SPIEGELMER) | GCUGCGAAAGCGACAUGUCAAUGAAAGGUAGCCGCAGC | 192-D10 |
| 16 | L-RNA (SPIEGELMER) | GCUGUGAAAGCAACAUGUCAAUGAAAGGUAGCCACAGC | 192-E9 |
| 17 | L-RNA (SPIEGELMER) | GCUGUGAAAGUAACAUGUCAAUGAAAGGUAGCCGCAGC | 192-H9 |

TABLE 1 (B)

| Seq.-ID | RNA/Peptide | Sequence | Internal Reference |
|---|---|---|---|
| 18 | L-RNA (SPIEGELMER) | AGCGUGAAAGUAACACGUAAAAUGAAAGGUAACCACGCU | 191-A6 |
| 19 | L-RNA (SPIEGELMER) | AAAGYRACAHGUMAAX$_A$UGAAAGGUARC; X$_A$ = A or absent | Type A Formula-1 |
| 20 | L-RNA (SPIEGELMER) | AAAGYRACAHGUMAAUGAAAGGUARC | Type A Formula-2 |
| 21 | L-RNA (SPIEGELMER) | AAAGYRACAHGUMAAAUGAAAGGUARC | Type A Formula-3 |
| 22 | L-RNA (SPIEGELMER) | AAAGYAACAHGUCAAUGAAAGGUARC | Type A Formula-4 |
| 23 | L-RNA (SPIEGELMER | RSHRYR | Type A Formula-5-5' |
| 24 | L-RNA (SPIEGELMER | YRYDSY | Type A Formula-5-3' |
| 25 | L-RNA (SPIEGELMER) | CUGUGAAAGCAACAUGUCAAUGAAAGGUAGCCGCAG | 192-A10-002 |
| 26 | L-RNA (SPIEGELMER) | UGUGAAAGCAACAUGUCAAUGAAAGGUAGCCGCA | 192-A10-003 |
| 27 | L-RNA (SPIEGELMER) | GUGAAAGCAACAUGUCAAUGAAAGGUAGCCGC | 192-A10-004 |
| 28 | L-RNA (SPIEGELMER) | UGAAAGCAACAUGUCAAUGAAAGGUAGCCG | 192-A10-005 |
| 29 | L-RNA (SPIEGELMER) | GAAAGCAACAUGUCAAUGAAAGGUAGCC | 192-A10-006 |
| 30 | L-RNA (SPIEGELMER) | AAAGCAACAUGUCAAUGAAAGGUAGC | 192-A10-007 |
| 31 | L-RNA (SPIEGELMER) | GCGUGAAAGCAACAUGUCAAUGAAAGGUAGCCGCGC | 192-A10-008 |
| 32 | L-RNA (SPIEGELMER) | GCGCGAAAGCAACAUGUCAAUGAAAGGUAGCCGCGC | 192-A10-015 |
| 33 | L-RNA (SPIEGELMER) | GCGGAAAGCAACAUGUCAAUGAAAGGUAGCCCGC | 192-A10-014 |

TABLE 1 (B)-continued

| Seq.-ID | RNA/Peptide | Sequence | Internal Reference |
|---|---|---|---|
| 34 | L-RNA (SPIEGELMER) | CGUGAAAGCAACAUGUCAAUGAAAGGUAGCCGCG | 192-A10-016 |
| 35 | L-RNA (SPIEGELMER) | GCGCAAAGCAACAUGUCAAUGAAAGGUAGCGUGC | 192-A10-017 |
| 36 | L-RNA (SPIEGELMER) | GUGCAAAGCAACAUGUCAAUGAAAGGUAGCGCGC | 192-A10-018 |

TABLE 1 (C)

| Seq.-ID | RNA/Peptide | Sequence | Internal Reference |
|---|---|---|---|
| 37 | L-RNA (SPIEGELMER) | CGCGAAAGCAACAUGUCAAUGAAAGGUAGCCGUG | 192-A10-019 |
| 38 | L-RNA (SPIEGELMER) | GGGCAAAGCAACAUGUCAAUGAAAGGUAGCGCCC | 192-A10-020 |
| 39 | L-RNA (SPIEGELMER) | GGCCAAAGCAACAUGUCAAUGAAAGGUAGCGGCC | 192-A10-021 |
| 40 | L-RNA (SPIEGELMER) | GCCCAAAGCAACAUGUCAAUGAAAGGUAGCGGGC | 192-A10-022 |
| 41 | L-RNA (SPIEGELMER) | CCCCAAAGCAACAUGUCAAUGAAAGGUAGCGGGG | 192-A10-023 |
| 42 | L-RNA (SPIEGELMER) | $X_2$BBBS; X2 = S or absent | Type A Formula-6-5' |
| 43 | L-RNA (SPIEGELMER) | SBBV$X_3$; $X_3$ = S or absent | Type A Formula-6-3' |
| 44 | L-RNA (SPIEGELMER) | $X_1X_2$NNBV; $X_1$ = R or absent, $X_2$= S or absent | Type A Formula-7-5' |
| 45 | L-RNA (SPIEGELMER) | BNBN$X_3X_4$; $X_3$ = R or absent, $X_4$ = Y or absent | Type A Formula-7-3' |
| 46 | L-RNA (SPIEGELMER) | AGCGUGGUGUGAUCUAGAUGUAGUGGCUGAUCCUAGUCAGGUACGCU | 193-C2-001 |
| 47 | L-RNA (SPIEGELMER) | AGCGUGGUGUGAUCUAGAUGUAUUGGCUGAUCCUAGUCAGGUACGCU | 193-G2-001 |
| 48 | L-RNA (SPIEGELMER) | AGCGUGGUGUGAUCUAGAUGUAAUGGCUGAUCCUAGUCAGGUGCGCU | 193-F2-001 |
| 49 | L-RNA (SPIEGELMER) | GCGAGGUGUGAUCUAGAUGUAGUGGCUGAUCCUAGUCAGGUGCGC | 193-G1-002 |
| 50 | L-RNA (SPIEGELMER) | GCGUGGUGUGAUCUAGAUGUAGUGGCUGAUCCUAGUCAGGUGCGC | 193-D2-002 |
| 51 | L-RNA (SPIEGELMER) | GCAUGGUGUGAUCUAGAUGUAGUGGCUGAUCCUAGUCAGGUGCCC | 193-A1-002 |
| 52 | L-RNA (SPIEGELMER) | GCGUGGUGUGAUCUAGAUGUAAUGGCUGAUCCUAGUCAGGGACGC | 193-D3-002 |

TABLE 1 (D)

| Seq.-ID | RNA/Peptide | Sequence | Internal Reference |
|---|---|---|---|
| 53 | L-RNA (SPIEGELMER) | GCGUGGUGUGAUCUAGAUGUAGAGGCUGAUCCUAGUCAGGUACGC | 193-B3-002 |
| 54 | L-RNA (SPIEGELMER) | GCGUGGUGUGAUCUAGAUGUAAAGGCUGAUCCUAGUCAGGUACGC | 193-H3-002 |
| 55 | L-RNA (SPIEGELMER) | GCGUGGUGUGAUCUAGAUGUAGUGGCUGUUCCUAGUCAGGUAUGC | 193-E3-002 |

TABLE 1 (D)-continued

| Seq.-ID | RNA/Peptide | Sequence | Internal Reference |
|---|---|---|---|
| 56 | L-RNA (SPIEGELMER) | GCGUGGUGUGAUCUAGAUGUAGUGGCUGAUCCUAGUUAGGUACGC | 193-D1-002 |
| 57 | L-RNA (SPIEGELMER) | GUGUGAUCUAGAUGUADWGGCUGWUCCUAGUYAGG | Type B Formula-1 |
| 58 | L-RNA (SPIEGELMER) | GUGUGAUCUAGAUGUADUGGCUGAUCCUAGUCAGG | Type B Formula-2 |
| 59 | L-RNA (SPIEGELMER) | $X_1$GCRWG; $X_1$ = A or absent | Type B Formula-3-5' |
| 60 | L-RNA (SPIEGELMER) | KRYSC$X_4$; $X_4$ = U or absent | Type B Formula-3-3' |
| 61 | L-RNA (SPIEGELMER) | GCGUGGUGUGAUCUAGAUGUAGUGGCUGAUCCUAGUCAGGUACGC | 193-C2-002 |
| 62 | L-RNA (SPIEGELMER) | CGUGGUGUGAUCUAGAUGUAGUGGCUGAUCCUAGUCAGGUACG | 193-C2-003 |
| 63 | L-RNA (SPIEGELMER) | GUGGUGUGAUCUAGAUGUAGUGGCUGAUCCUAGUCAGGUAC | 193-C2-004 |
| 64 | L-RNA (SPIEGELMER) | UGGUGUGAUCUAGAUGUAGUGGCUGAUCCUAGUCAGGUA | 193-C2-005 |
| 65 | L-RNA (SPIEGELMER) | GGUGUGAUCUAGAUGUAGUGGCUGAUCCUAGUCAGGU | 193-C2-006 |
| 66 | L-RNA (SPIEGELMER) | GUGUGAUCUAGAUGUAGUGGCUGAUCCUAGUCAGG | 193-C2-007 |
| 67 | L-RNA (SPIEGELMER) | GCGUGGUGUGAUCUAGAUGUAUUGGCUGAUCCUAGUCAGGUACGC | 193-G2-012 |

TABLE 1 (E)

| Seq.-ID | RNA/Peptide | Sequence | Internal Reference |
|---|---|---|---|
| 68 | L-RNA (SPIEGELMER) | GCGCGGUGUGAUCUAGAUGUAUUGGCUGAUCCUAGUCAGGCGCGC | 193-G2-013 |
| 69 | L-RNA (SPIEGELMER) | GCGCGUGUGAUCUAGAUGUAUUGGCUGAUCCUAGUCAGGGCGC | 193-G2-014 |
| 70 | L-RNA (SPIEGELMER) | GGGCGUGUGAUCUAGAUGUAUUGGCUGAUCCUAGUCAGGGCCC | 193-G2-015 |
| 71 | L-RNA (SPIEGELMER) | GGCCGUGUGAUCUAGAUGUAUUGGCUGAUCCUAGUCAGGGGCC | 193-G2-016 |
| 72 | L-RNA (SPIEGELMER) | GCCCGUGUGAUCUAGAUGUAUUGGCUGAUCCUAGUCAGGGGGC | 193-G2-017 |
| 73 | L-RNA (SPIEGELMER) | $X_2$SSBS; $X_2$ = G or absent | Type B Formula-4-5' |
| 74 | L-RNA (SPIEGELMER) | BVSS$X_3$; $X_3$ = C or absent | Type B Formula-4-3' |
| 75 | L-RNA (SPIEGELMER) | $X_1$GCGUG; $X_1$ = A or absent | Type B Formula-5-5' |
| 76 | L-RNA (SPIEGELMER) | UACGC$X_4$; $X_4$ = U or absent | Type B Formula-5-3' |
| 77 | L-RNA (SPIEGELMER) | $X_1X_2$SVNS; $X_1$ = A or absent, $X_2$ = G or absent | Type B Formula-6-5' |
| 78 | L-RNA (SPIEGELMER) | BVBS$X_3X_4$; $X_3$ = C or absent, $X_4$ = U or absent | Type B Formula-6-3' |
| 79 | L-RNA (SPIEGELMER) | GUGCUGCGGGGGUUAGGGCUAGAAGUCGGCCUGCAGCAC | 197-B2 |

TABLE 1 (E)-continued

| Seq.-ID | RNA/Peptide | Sequence | Internal Reference |
|---|---|---|---|
| 80 | L-RNA (SPIEGELMER) | AGCGUGGCGAGGUUAGGGCUAGAAGUCGGUCGACACGCU | 191-D5-001 |
| 81 | L-RNA (SPIEGELMER) | GUGUUGCGGAGGUUAGGGCUAGAAGUCGGUCAGCAGCAC | 197-H1 |
| 82 | L-RNA (SPIEGELMER) | CGUGCGCUUGAGAUAGGGGUUAGGGCUUAAAGUCGGCUGAUUCUCACG | 190-A3-001 |
| 83 | L-RNA (SPIEGELMER) | AGCGUGAAGGGGUUAGGGCUCGAAGUCGGCUGACACGCU | 191-A5 |

TABLE 1 (F)

| Seq.-ID | RNA/Peptide | Sequence | Internal Reference |
|---|---|---|---|
| 84 | L-RNA (SPIEGELMER) | GUGCUGCGGGGGUUAGGGCUCGAAGUCGGCCCGCAGCAC | 197-H3 |
| 85 | L-RNA (SPIEGELMER) | GUGUUCCCGGGGUUAGGGCUUGAAGUCGGCCGGCAGCAC | 197-B1 |
| 86 | L-RNA (SPIEGELMER) | GUGUUGCAGGGGUUAGGGCUUGAAGUCGGCCUGCAGCAC | 197-E3 |
| 87 | L-RNA (SPIEGELMER) | GUGCUGCGGGGGUUAGGGCUCAAAGUCGGCCUGCAGCAC | 197-H2 |
| 88 | L-RNA (SPIEGELMER) | GUGCUGCCGGGGUUAGGGCUAA-AGUCGGCCGACAGCAC | 197-D1 |
| 89 | L-RNA (SPIEGELMER) | GUGCUGUGGGGGUCAGGGCUAGAAGUCGGCCUGCAGCAC | 197-D2 |
| 90 | L-RNA (SPIEGELMER) | GGUYAGGGCUHRX$_A$AGUCGG; X$_A$ = A or absent | Type C Formula-1 |
| 91 | L-RNA (SPIEGELMER) | GGUYAGGGCUHRAAGUCGG | Type C Formula-2 |
| 92 | L-RNA (SPIEGELMER) | GGUYAGGGCUHRAGUCGG | Type C Formula-3 |
| 93 | L-RNA (SPIEGELMER) | GGUUAGGGCUHGAAGUCGG | Type C Formula-4 |
| 94 | L-RNA (SPIEGELMER) | UGAGAUAGGGGUUAGGGCUUAAAGUCGGCUGAUUCUCA | 190-A3-003 |
| 95 | L-RNA (SPIEGELMER) | GAGAUAGGGGUUAGGGCUUAAAGUCGGCUGAUUCUC | 190-A3-004 |
| 96 | L-RNA (SPIEGELMER) | GGGGUUAGGGCUUAAAGUCGGCUGAUUCU | 190-A3-007 |
| 97 | L-RNA (SPIEGELMER) | GCGUGGCGAGGUUAGGGCUAGAAGUCGGUCGACACGC | 191-D5-002 |
| 98 | L-RNA (SPIEGELMER) | CGUGGCGAGGUUAGGGCUAGAAGUCGGUCGACACG | 191-D5-003 |
| 99 | L-RNA (SPIEGELMER) | CGGGCGAGGUUAGGGCUAGAAGUCGGUCGACCG | 191-D5-004 |
| 100 | L-RNA (SPIEGELMER) | CGGGCGAGGUUAGGGCUAGAAGUCGGUCGCCCG | 191-D5-005 |

TABLE 1 (G)

| Seq.-ID | RNA/Peptide | Sequence | Internal Reference |
|---|---|---|---|
| 101 | L-RNA (SPIEGELMER) | CGGCGAGGUUAGGGCUAGAAGUCGGUCGCCG | 191-D5-006 |

TABLE 1 (G)-continued

| Seq.-ID | RNA/Peptide | Sequence | Internal Reference |
|---|---|---|---|
| 102 | L-RNA (SPIEGELMER) | CGGGAGGUUAGGGCUAGAAGUCGGUCCCG | 191-D5-007 |
| 103 | L-RNA (SPIEGELMER) | GGGAGGUUAGGGCUAGAAGUCGGUCCC | 191-D5-010 |
| 104 | L-RNA (SPIEGELMER) | CCGCGGUUAGGGCUAGAAGUCGGGCGG | 191-D5-017 |
| 105 | L-RNA (SPIEGELMER) | CCCGGGUUAGGGCUAGAAGUCGGCGGG | 191-D5-029 |
| 106 | L-RNA (SPIEGELMER) | GGCGGGUUAGGGCUAGAAGUCGGCGCC | 191-D5-024 |
| 107 | L-RNA (SPIEGELMER) | CCCCGGGUUAGGGCUAGAAGUCGGCGGGG | 191-D5-017-29a |
| 108 | L-RNA (SPIEGELMER) | GCCGCGGUUAGGGCUAGAAGUCGGGCGGC | 191-D5-017-29b |
| 109 | L-RNA (SPIEGELMER) | CCCCGGGUUAGGGCUAGAAGUCGGCGGGG | 191-D5-019-29a |
| 110 | L-RNA (SPIEGELMER) | CGGCGGGUUAGGGCUAGAAGUCGGCGCCG | 191-D5-024-29a |
| 111 | L-RNA (SPIEGELMER) | GGGCGGGUUAGGGCUAGAAGUCGGCGCCC | 191-D5-024-29b |
| 112 | L-RNA (SPIEGELMER) | UGCUGCGGGGUUAGGGCUAGAAGUCGGCCUGCAGCA | 197-B2-001 |
| 113 | L-RNA (SPIEGELMER) | GCUGCGGGGUUAGGGCUAGAAGUCGGCCUGCAGC | 197-B2-002 |
| 114 | L-RNA (SPIEGELMER) | CUGCGGGGUUAGGGCUAGAAGUCGGCCUGCAG | 197-B2-003 |
| 115 | L-RNA (SPIEGELMER) | UGCGGGGUUAGGGCUAGAAGUCGGCCUGCA | 197-B2-004 |
| 116 | L-RNA (SPIEGELMER) | GCGGGGUUAGGGCUAGAAGUCGGCCUGC | 197-B2-005 |

TABLE 1 (H)

| Seq.-ID | RNA/Peptide | Sequence | Internal Reference |
|---|---|---|---|
| 117 | L-RNA (SPIEGELMER) | GCCGGGGUUAGGGCUAGAAGUCGGCCGGC | 197-B2-006 |
| 118 | L-RNA (SPIEGELMER) | GGCCGGGGUUAGGGCUAGAAGUCGGCCGGCC | 197-B2-006-31a |
| 119 | L-RNA (SPIEGELMER) | CGCCGGGGUUAGGGCUAGAAGUCGGCCGGCG | 197-B2-006-31b |
| 120 | L-RNA (SPIEGELMER) | RKSBUSNVGR | Type C Formula-5-5' |
| 121 | L-RNA (SPIEGELMER) | YNRCASSMY | Type C Formula-5-3' |
| 122 | L-RNA (SPIEGELMER) | RKSBUGSVGR | Type C Formula-6-5' |
| 123 | L-RNA (SPIEGELMER) | YCNRCASSMY | Type C Formula-6-3' |
| 124 | L-RNA (SPIEGELMER) | $X_S$SSSV; $X_s$ = S or absent | Type C Formula-7-5' |
| 125 | L-RNA (SPIEGELMER) | BSSSX$_S$; $X_s$ = S or absent | Type C Formula-7-3' |

TABLE 1 (H)-continued

| Seq.-ID | RNA/Peptide | Sequence | Internal Reference |
|---|---|---|---|
| 126 | L-RNA (SPIEGELMER) | SGGSV | Type C Formula-8-5' |
| 127 | L-RNA (SPIEGELMER) | YSCCS | Type C Formula-8-3' |
| 128 | L-RNA (SPIEGELMER) | GCSGG | Type C Formula-9-5' |
| 129 | L-RNA (SPIEGELMER) | CCKGC | Type C Formula-9-3' |
| 130 | L-RNA (SPIEGELMER) | SSSSR | Type C Formula-10-5' |
| 131 | L-RNA (SPIEGELMER) | YSBSS | Type C Formula-10-3' |

TABLE 1 (I)

| Seq.-ID | RNA/Peptide | Sequence | Internal Reference |
|---|---|---|---|
| 132 | L-RNA (SPIEGELMER) | 5'-40 kDa-PEG-GCGUGGUGUGAUCUAGAUGUAUUGGCUGAUCCUAGUCAGGUACGC | 193-G2-012-5'-PEG |
| 133 | L-RNA (SPIEGELMER) | 5'-40 kDa-PEG-GCGUGAAAGCAACAUGUCAAUGAAAGGUAGCCGCGC | 192-A10-008-5'-PEG |
| 134 | L-RNA (SPIEGELMER) | 5'-40 kDa-PEG-CGGGAGGUUAGGGCUAGAAGUCGGUCCCG | 191-D5-007-5'-PEG |
| 135 | L-RNA (SPIEGELMER) | 5'-40 kDa-PEG-GCCGGGGUUAGGGCUAGAAGUCGGCCGGC | 197-B2-006-5'-PEG |
| 136 | L-RNA (SPIEGELMER) | 5'-40 kDa-PEG-CGCCGGGGUUAGGGCUAGAAGUCGGCCGGCG | 197-B2-006-31b-5'PEG |
| 137 | L-RNA (SPIEGELMER) | 5'-40 kDa-PEG-GCUGUGAAAGCAACAUGUCAAUGAAAGGUAGCCGCAGC | 192-A10-001-5'-PEG 192-A10-001-5'-PEG40 |
| 138 | L-RNA (SPIEGELMER) | UAAGGAAACUCGGUCUGAUGCGGUAGCGCUGUGCAGAGCU | Control Spiegelmer |
| 139 | L-RNA (SPIEGELMER) | 5'-30 kDa-PEG-GCUGUGAAAGCAACAUGUCAAUGAAAGGUAGCCGCAGC | 192-A10-001-5'-PEG30 |
| 140 | L-RNA (SPIEGELMER) | 5'-100 kDa-HES-GCUGUGAAAGCAACAUGUCAAUGAAAGGUAGCCGCAGC | 192-A10-001-5'-HES100 |
| 141 | L-RNA (SPIEGELMER) | 5'-130 kDa-HES-GCUGUGAAAGCAACAUGUCAAUGAAAGGUAGCCGCAGC | 192-A10-001-5'-HES130 |
| 142 | L-RNA (SPIEGELMER) | CGUGGUCCGUUGUGUCAGGUCUAUUCGCCCCGGUGCAGGGCAUCCGCG | 194-A2-001 |
| 143 | L-RNA (SPIEGELMER) | GCAGUGUGACGCGGACGUGAUAGGACAGAGCUGAUCCCGCUCAGGUGAG | 196-B12-003 |
| 144 | L-RNA (SPIEGELMER) | CAACAGCAGUGUGACGCGGACGUGAUAGGACAGAGCUGAUCCCGCUCAG | 196-B12-004 |

TABLE 1 (J)

| Seq.-ID | RNA/Peptide | Sequence | Internal Reference |
|---|---|---|---|
| 145 | D-RNA (APTAMER) | GCUGUGAAAGCAACAUGUCAAUGAAAGGUAGCCGCAGC | 192-A10-001 |
| 146 | D-RNA (APTAMER) | GCUGUGAAAGUAACAUGUCAAUGAAAGGUAACCACAGC | 192-G10 |
| 147 | D-RNA (APTAMER) | GCUGUGAAAGUAACACGUCAAUGAAAGGUAACCGCAGC | 192-F10 |
| 148 | D-RNA (APTAMER) | GCUGUGAAAGUAACACGUCAAUGAAAGGUAACCACAGC | 192-B11 |

TABLE 1 (J)-continued

| Seq.-ID | RNA/Peptide | Sequence | Internal Reference |
|---|---|---|---|
| 149 | D-RNA (APTAMER) | GCUGUAAAAGUAACAUGUCAAUGAAAGGUAACUACAGC | 192-C9 |
| 150 | D-RNA (APTAMER) | GCUGUAAAAGUAACAAGUCAAUGAAAGGUAACUACAGC | 192-E10 |
| 151 | D-RNA (APTAMER) | GCUGUGAAAGUAACAAGUCAAUGAAAGGUAACCACAGC | 192-C10 |
| 152 | D-RNA (APTAMER) | GCAGUGAAAGUAACAUGUCAAUGAAAGGUAACCACAGC | 192-D11 |
| 153 | D-RNA (APTAMER) | GCUGUGAAAGUAACAUGUCAAUGAAAGGUAACCACUGC | 192-G11 |
| 154 | D-RNA (APTAMER) | GCUAUGAAAGUAACAUGUCAAUGAAAGGUAACCAUAGC | 192-H11 |
| 155 | D-RNA (APTAMER) | GCUGCGAAAGCGACAUGUCAAUGAAAGGUAGCCGCAGC | 192-D10 |
| 156 | D-RNA (APTAMER) | GCUGUGAAAGCAACAUGUCAAUGAAAGGUAGCCACAGC | 192-E9 |
| 157 | D-RNA (APTAMER) | GCUGUGAAAGUAACAUGUCAAUGAAAGGUAGCCGCAGC | 192-H9 |
| 158 | D-RNA (APTAMER) | AGCGUGAAAGUAACACGUAAAAUGAAAGGUAACCACGCU | 191-A6 |
| 159 | D-RNA (APTAMER) | CUGUGAAAGCAACAUGUCAAUGAAAGGUAGCCGCAG | 192-A10-002 |
| 160 | D-RNA (APTAMER) | UGUGAAAGCAACAUGUCAAUGAAAGGUAGCCGCA | 192-A10-003 |

TABLE 1 (K)

| Seq.-ID | RNA/Peptide | Sequence | Internal Reference |
|---|---|---|---|
| 161 | D-RNA (APTAMER) | GUGAAAGCAACAUGUCAAUGAAAGGUAGCCGC | 192-A10-004 |
| 162 | D-RNA (APTAMER) | UGAAAGCAACAUGUCAAUGAAAGGUAGCCG | 192-A10-005 |
| 163 | D-RNA (APTAMER) | GAAAGCAACAUGUCAAUGAAAGGUAGCC | 192-A10-006 |
| 164 | D-RNA (APTAMER) | AAAGCAACAUGUCAAUGAAAGGUAGC | 192-A10-007 |
| 165 | D-RNA (APTAMER) | GCGUGAAAGCAACAUGUCAAUGAAAGGUAGCCGCGC | 192-A10-008 |
| 166 | D-RNA (APTAMER) | GCGCGAAAGCAACAUGUCAAUGAAAGGUAGCCGCGC | 192-A10-015 |
| 167 | D-RNA (APTAMER) | GCGGAAAGCAACAUGUCAAUGAAAGGUAGCCCGC | 192-A10-014 |
| 168 | D-RNA (APTAMER) | CGUGAAAGCAACAUGUCAAUGAAAGGUAGCCGCG | 192-A10-016 |
| 169 | D-RNA (APTAMER) | GCGCAAAGCAACAUGUCAAUGAAAGGUAGCGUGC | 192-A10-017 |
| 170 | D-RNA (APTAMER) | GUGCAAAGCAACAUGUCAAUGAAAGGUAGCGCGC | 192-A10-018 |
| 171 | D-RNA (APTAMER) | CGCGAAAGCAACAUGUCAAUGAAAGGUAGCCGUG | 192-A10-019 |
| 172 | D-RNA (APTAMER) | GGGCAAAGCAACAUGUCAAUGAAAGGUAGCGCCC | 192-A10-020 |
| 173 | D-RNA (APTAMER) | GGCCAAAGCAACAUGUCAAUGAAAGGUAGCGGCC | 192-A10-021 |
| 174 | D-RNA (APTAMER) | GCCCAAAGCAACAUGUCAAUGAAAGGUAGCGGGC | 192-A10-022 |
| 175 | D-RNA (APTAMER) | CCCCAAAGCAACAUGUCAAUGAAAGGUAGCGGGG | 192-A10-023 |
| 176 | D-RNA (APTAMER) | AGCGUGGUGUGAUCUAGAUGUAGUGGCUGAUCCUAGUCAGGUACGCU | 193-C2-001 |

TABLE 1 (L)

| Seq.-ID | RNA/Peptide | Sequence | Internal Reference |
|---|---|---|---|
| 177 | D-RNA (APTAMER) | AGCGUGGUGUGAUCUAGAUGUAUUGGCUGAUCCUAGUCAGGUACGCU | 193-G2-001 |
| 178 | D-RNA (APTAMER) | AGCGUGGUGUGAUCUAGAUGUAAUGGCUGAUCCUAGUCAGGUGCGCU | 193-F2-001 |
| 179 | D-RNA (APTAMER) | GCGAGGUGUGAUCUAGAUGUAGUGGCUGAUCCUAGUCAGGUGCGC | 193-G1-002 |

TABLE 1 (L)-continued

| Seq.-ID | RNA/Peptide | Sequence | Internal Reference |
|---|---|---|---|
| 180 | D-RNA (APTAMER) | GCGUGGUGUGAUCUAGAUGUAGUGGCUGAUCCUAGUCAGGUGCGC | 193-D2-002 |
| 181 | D-RNA (APTAMER) | GCAUGGUGUGAUCUAGAUGUAGUGGCUGAUCCUAGUCAGGUGCCC | 193-A1-002 |
| 182 | D-RNA (APTAMER) | GCGUGGUGUGAUCUAGAUGUAAUGGCUGAUCCUAGUCAGGGACGC | 193-D3-002 |
| 183 | D-RNA (APTAMER) | GCGUGGUGUGAUCUAGAUGUAGAGGCUGAUCCUAGUCAGGUACGC | 193-B3-002 |
| 184 | D-RNA (APTAMER) | GCGUGGUGUGAUCUAGAUGUAAAGGCUGAUCCUAGUCAGGUACGC | 193-F13-002 |
| 185 | D-RNA (APTAMER) | GCGUGGUGUGAUCUAGAUGUAGUGGCUGUUCCUAGUCAGGUAUGC | 193-E3-002 |
| 186 | D-RNA (APTAMER) | GCGUGGUGUGAUCUAGAUGUAGUGGCUGAUCCUAGUUAGGUACGC | 193-D1-002 |
| 187 | D-RNA (APTAMER) | GCGUGGUGUGAUCUAGAUGUAGUGGCUGAUCCUAGUCAGGUACGC | 193-C2-002 |
| 188 | D-RNA (APTAMER) | CGUGGUGUGAUCUAGAUGUAGUGGCUGAUCCUAGUCAGGUACG | 193-C2-003 |
| 189 | D-RNA (APTAMER) | GUGGUGUGAUCUAGAUGUAGUGGCUGAUCCUAGUCAGGUAC | 193-C2-004 |
| 190 | D-RNA (APTAMER) | UGGUGUGAUCUAGAUGUAGUGGCUGAUCCUAGUCAGGUA | 193-C2-005 |
| 191 | D-RNA (APTAMER) | GGUGUGAUCUAGAUGUAGUGGCUGAUCCUAGUCAGGU | 193-C2-006 |

TABLE 1 (M)

| Seq.-ID | RNA/Peptide | Sequence | Internal Reference |
|---|---|---|---|
| 192 | D-RNA (APTAMER) | GUGUGAUCUAGAUGUAGUGGCUGAUCCUAGUCAGG | 193-C2-007 |
| 193 | D-RNA (APTAMER) | GCGUGGUGUGAUCUAGAUGUAUUGGCUGAUCCUAGUCAGGUACGC | 193-G2-012 |
| 194 | D-RNA (APTAMER) | GCGCGGUGUGAUCUAGAUGUAUUGGCUGAUCCUAGUCAGGCGCGC | 193-G2-013 |
| 195 | D-RNA (APTAMER) | GCGCGUGUGAUCUAGAUGUAUUGGCUGAUCCUAGUCAGGGCGC | 193-G2-014 |
| 196 | D-RNA (APTAMER) | GGGCGUGUGAUCUAGAUGUAUUGGCUGAUCCUAGUCAGGGCCC | 193-G2-015 |
| 197 | D-RNA (APTAMER) | GGCCGUGUGAUCUAGAUGUAUUGGCUGAUCCUAGUCAGGGGCC | 193-G2-016 |
| 198 | D-RNA (APTAMER) | GCCCGUGUGAUCUAGAUGUAUUGGCUGAUCCUAGUCAGGGGGC | 193-G2-017 |
| 199 | D-RNA (APTAMER) | GUGCUGCGGGGGUUAGGGCUAGAAGUCGGCCUGCAGCAC | 197-B2 |
| 200 | D-RNA (APTAMER) | AGCGUGGCGAGGUUAGGGCUAGAAGUCGGUCGACACGCU | 191-D5-001 |
| 201 | D-RNA (APTAMER) | GUGUUGCGGAGGUUAGGGCUAGAAGUCGGUCAGCAGCAC | 197-H1 |
| 202 | D-RNA (APTAMER) | CGUGCGCUUGAGAUAGGGGUUAGGGCUUAAAGUCGGCUGAUUCUCACG | 190-A3-001 |
| 203 | D-RNA (APTAMER) | AGCGUGAAGGGGUUAGGGCUCGAAGUCGGCUGACACGCU | 191-A5 |
| 204 | D-RNA (APTAMER) | GUGCUGCGGGGGUUAGGGCUCGAAGUCGGCCCGCAGCAC | 197-H3 |
| 205 | D-RNA (APTAMER) | GUGUUCCCGGGGUUAGGGCUUGAAGUCGGCCGGCAGCAC | 197-B1 |

TABLE 1 (N)

| Seq.-ID | RNA/Peptide | Sequence | Internal Reference |
|---|---|---|---|
| 206 | D-RNA (APTAMER) | GUGUUGCAGGGGUUAGGGCUUGAAGUCGGCCUGCAGCAC | 197-E3 |
| 207 | D-RNA (APTAMER) | GUGCUGCGGGGGUUAGGGCUCAAAGUCGGCCUGCAGCAC | 197-H2 |
| 208 | D-RNA (APTAMER) | GUGCUGCCGGGGUUAGGGCUAA-AGUCGGCCGACAGCAC | 197-D1 |
| 209 | D-RNA (APTAMER) | GUGCUGUGGGGGUCAGGGCUAGAAGUCGGCCUGCAGCAC | 197-D2 |
| 210 | D-RNA (APTAMER) | UGAGAUAGGGGUUAGGGCUUAAAGUCGGCUGAUUCUCA | 190-A3-003 |
| 211 | D-RNA (APTAMER) | GAGAUAGGGGUUAGGGCUUAAAGUCGGCUGAUUCUC | 190-A3-004 |
| 212 | D-RNA (APTAMER) | GGGGUUAGGGCUUAAAGUCGGCUGAUUCU | 190-A3-007 |
| 213 | D-RNA (APTAMER) | GCGUGGCGAGGUUAGGGCUAGAAGUCGGUCGACACGC | 191-D5-002 |
| 214 | D-RNA (APTAMER) | CGUGGCGAGGUUAGGGCUAGAAGUCGGUCGACACG | 191-D5-003 |
| 215 | D-RNA (APTAMER) | CGGGCGAGGUUAGGGCUAGAAGUCGGUCGACCG | 191-D5-004 |
| 216 | D-RNA (APTAMER) | CGGGCGAGGUUAGGGCUAGAAGUCGGUCGCCCG | 191-D5-005 |
| 217 | D-RNA (APTAMER) | CGGCGAGGUUAGGGCUAGAAGUCGGUCGCCG | 191-D5-006 |
| 218 | D-RNA (APTAMER) | CGGGAGGUUAGGGCUAGAAGUCGGUCCCG | 191-D5-007 |
| 219 | D-RNA (APTAMER) | GGGAGGUUAGGGCUAGAAGUCGGUCCC | 191-D5-010 |
| 220 | D-RNA (APTAMER) | CCGCGGUUAGGGCUAGAAGUCGGGCGG | 191-D5-017 |
| 221 | D-RNA (APTAMER) | CCCGGGUUAGGGCUAGAAGUCGGCGGG | 191-D5-029 |
| 222 | D-RNA (APTAMER) | GGCGGGUUAGGGCUAGAAGUCGGCGCC | 191-D5-024 |
| 223 | D-RNA (APTAMER) | CCCGCGGUUAGGGCUAGAAGUCGGGCGGG | 191-D5-017-29a |

TABLE 1 (O)

| Seq.-ID | RNA/Peptide | Sequence | Internal Reference |
|---|---|---|---|
| 224 | D-RNA (APTAMER) | GCCGGGGUUAGGGCUAGAAGUCGGCCGGC | 191-D5-017-29b |
| 225 | D-RNA (APTAMER) | CCCCGGGUUAGGGCUAGAAGUCGGCGGGG | 191-D5-019-29a |
| 226 | D-RNA (APTAMER) | CGGCGGGUUAGGGCUAGAAGUCGGCGCCG | 191-D5-024-29a |
| 227 | D-RNA (APTAMER) | GGGCGGGUUAGGGCUAGAAGUCGGCGCCC | 191-D5-024-29b |
| 228 | D-RNA (APTAMER) | UGCUGCGGGGGUUAGGGCUAGAAGUCGGCCUGCAGCA | 197-B2-001 |
| 229 | D-RNA (APTAMER) | GCUGCGGGGGUUAGGGCUAGAAGUCGGCCUGCAGC | 197-B2-002 |
| 230 | D-RNA (APTAMER) | CUGCGGGGGUUAGGGCUAGAAGUCGGCCUGCAG | 197-B2-003 |
| 231 | D-RNA (APTAMER) | UGCGGGGGUUAGGGCUAGAAGUCGGCCUGCA | 197-B2-004 |
| 232 | D-RNA (APTAMER) | GCGGGGGUUAGGGCUAGAAGUCGGCCUGC | 197-B2-005 |
| 233 | D-RNA (APTAMER) | GCCGGGGUUAGGGCUAGAAGUCGGCCGGC | 197-B2-006 |
| 234 | D-RNA (APTAMER) | GGCCGGGGUUAGGGCUAGAAGUCGGCCGGCC | 197-B2-006-31a |
| 235 | D-RNA (APTAMER) | CGCCGGGGUUAGGGCUAGAAGUCGGCCGGCG | 197-B2-006-31b |
| 236 | D-RNA (APTAMER) | CGUGGUCCGUUGUGUCAGGUCUAUUCGCCCCGGUGCAGGGCAUCCGCG | 194-A2-001 |
| 236 | D-RNA (APTAMER) | GCAGUGUGACGCGGACGUGAUAGGACAGAGCUGAUCCCGCUCAGGUGAG | 196-B12-003 |
| 238 | D-RNA (APTAMER) | CAACAGCAGUGUGACGCGGACGUGAUAGGACAGAGCUGAUCCCGCUCAG | 196-B12-004 |

TABLE 1 (P)

| Seq.-ID | RNA/Peptide | Sequence | Internal Reference |
|---|---|---|---|
| 239 | L-RNA (Spiegelmer) | 5'-PEG-UAAGGAAACUCGGUCUGAUGCGGUAGCGCUGUGCAGAGCU | PEGylated Control Spiegelmer |
| 240 | L-RNA (Spiegelmer) | GATCACACCACGC-(C18-PEG-spacer)-(C18-PEG-spacer)-1-NH$_2$-3' | 193-G2-012-5'-PEG capture probe |
| 241 | L-RNA (Spiegelmer) | 5'-NH$_2$-(C18-PEG-spacer)-(C18-PEG-spacer)-GCGUACCUGAC | 193-G2-012-5'-PEG detect probe |

Example 1: Nucleic Acids that Bind Human SDF-1

Using biotinylated human D-SDF-1 as a target, several nucleic acids that bind to human SDF-1 could be generated, the nucleotide sequences of which are depicted in FIGS. 1 through 9. The nucleic acids were characterized on the aptamer, i.e. D-nucleic acid level with biotinylated human D-SDF-1 or on the Spiegelmer level, i.e. L-nucleic acid with the natural configuration of SDF-1 (L-SDF-1).

Aptamers were analyzed with biotinylated human D-SDF-1 using competitive or direct pull-down binding assays with biotinylated human D-SDF-1 (Example 4). Spiegelmers were tested with the natural configuration of SDF-1 (L-SDF-1) by surface plasmon resonance measurement using a Biacore 2000 instrument (Example 6) and a cell culture in vitro chemotaxis assay (Example 5).

The nucleic acid molecules thus generated exhibit different sequence motifs, three main types are defined in FIGS. 1, 2A and 2B (Type A), FIGS. 3, 4A and 4B (Type B), and FIGS. 5, 6, 7A, 7B and 8 (Type C). For definition of nucleotide sequence motifs, the IUPAC abbreviations for ambiguous nucleotides is used:

| S | strong | G or C; |
|---|---|---|
| W | weak | A or U; |
| R | purine | G or A; |
| Y | pyrimidine | C or U; |
| K | keto | G or U; |
| M | imino | A or C; |
| B | not A | C or U or G; |
| D | not C | A or G or U; |
| H | not G | A or C or U; |
| V | not U | A or C or G; and |
| N | all | A or G or C or U |

If not indicated to the contrary, any nucleic acid sequence or sequence of stretches and boxes, respectively, is indicated in the 5'→3' direction.

1.1 Type A SDF-1-Binding Nucleic Acids

As depicted in FIG. 1, all sequences of SDF-1-binding nucleic acids of Type A comprise one core nucleotide sequence which is flanked by 5'-terminal and 3'-terminal stretches that can hybridize to each other. However, such hybridization is not necessarily given in the molecule.

The nucleic acids were characterized on the aptamer level using direct and competitive pull-down binding assays with biotinylated human D-SDF-1 in order to rank them with respect to their binding behaviour (Example 4). Selected sequences were synthesized as Spiegelmers (Example 3) and were tested using the natural configuration of SDF-1 (L-SDF) in a cell culture in vitro chemotaxis assay (Example 5) and by surface plasmon resonance measurement using a Biacore 2000 instrument (Example 6).

The sequences of the defined boxes or stretches may be different between the SDF-1-binding nucleic acids of Type A which influences the binding affinity to SDF-1. Based on binding analysis of the different SDF-1-binding nucleic acids summarized as Type A SDF-1-binding nucleic acids, the core nucleotide sequence and its nucleotide sequences as described in the following are individually and more preferably in their entirety essential for binding to SDF-1:

The core nucleotide sequence of all identified sequences of Type A SDF-1-binding nucleic acids share the sequence (SEQ ID NO: 19)
AAAGYRACAHGUMAAX$_A$UGAAAGGUARC (Type A Formula-1), whereby X$_A$ is either absent or is 'A'. If 'A' is absent, the sequence of the core nucleotide sequence can be summarized as Type A Formula-2

(SEQ ID NO: 20)
AAAGYRACAHGUMAA-UGAAAGGUARC.

Type A SDF-1-binding nucleic acid 191-A6 (core nucleotide sequence:

(SEQ ID NO: 18)
AAAGUAACACGUAAAAUGAAAGGUAAC)

carrying the additional nucleotide 'A' within the core nucleotide sequence and still binding to SDF-1 let conclude an alternative core nucleotide sequence (SEQ ID NO: 21)
AAGYRACAHGUMAAAUGAAAGGUARC, Type A Formula-3).

Exemplarily for all the other nucleic acids of Type A SDF-1-binding nucleic acids, the Type A SDF-1-binding nucleic acid 192-A10-001 was characterized for its binding affinity to human SDF-1. The equilibrium binding constant K$_D$ was determined using the pull-down binding assay (K$_D$=1.5 nM, FIG. 11) and by surface plasmon resonance measurement (K$_D$=1.0 nM, FIG. 15). The IC$_{50}$ (inhibitory concentration 50%) of 0.12 nM for 192-A10-001 was measured using a cell culture in vitro chemotaxis assay (FIG. 12). Consequently, all Type A SDF-1-binding nucleic acids as depicted in FIG. 1 were analyzed in a competitive pull-down binding assay vs. 192-A10-001 (FIG. 13; not all of Type A SDF-1-binding nucleic acids tested are shown in FIG. 13). The Type A SDF-1-binding nucleic acids 192-B11 and 192-C10 showed equal binding affinities with 192-A10-001 in these competition experiments. Weaker binding affinity was determined for Type A SDF-1-binding nucleic acids 192-G10, 192-F10, 192-C9, 192-E10, 192-D11, 192-G11, 192-H11 and 191-A6. The Type A SDF-1-binding nucleic acids 192-D10, 192-E9 and 192-H9 have much weaker binding affinity than 192-A10-001 (FIG. 13).

As mentioned above, the Type A SDF-1-binding nucleic acid 192-B11 and 192-C10 exhibit equal binding affinity to SDF-1 as 192-A10-001. However, they show slight differences in the nucleotide sequence of the core nucleotide sequence. Therefore the consensus sequence of the three molecules binding to SDF-1 with almost the same high affinity can be summarized by the nucleotide sequence (SEQ ID NO: 22)
AAAGYAACAHGUCAAUGAAAGGUARC (Type A Formula-4)

whereby the nucleotide sequence of the core nucleotide sequence of 192-A10-001 (nucleotide sequence:

(SEQ ID NO: 30)
AAAGCAACAUGUCAAUGAAAGGUAGC)

represents the nucleotide sequence with the best binding affinity of Type A SDF-1-binding nucleic acids.

Five or six out of the six nucleotides of the 5'-terminal stretch of Type A SDF-1-binding nucleic acids may hybridize to the respective five or six nucleotides out of the six nucleotides of the 3'-terminal stretch Type A SDF-1-binding nucleic acids to form a terminal helix. Although these nucleotides are variable at several positions, the different nucleotides allow for hybridization of five or six out of the six nucleotides of the 5'-terminal and 3'-terminal stretches each. The 5'-terminal and 3'-terminal stretches of Type A SDF-1-binding nucleic acids as shown in FIG. 1 can be summarized in a generic formula for the 5'-terminal stretch ('RSHRYR', Type A Formula-5-5') and for the 3'-terminal stretch ('YRYDSY', Type A Formula-5-3'). Truncated derivatives of Type A SDF-1-binding nucleic acid 192-A10-001 were analyzed in a competitive pull-down binding assay vs. the original molecule 192-A10-001 and 192-A10-008 (FIGS. 2A and 2B). These experiments showed that a reduction of the six terminal nucleotides (5'end: GCUGUG; 3'end: CGCAGC) of 192-A10-001 to five nucleotides (5'end: CUGUG; 3'end: CGCAG) of the derivative 192-A10-002 could be done without reduction of binding affinity. However, the truncation to four terminal nucleotides (5'end: UGUG; 3'end: CGCA; 192-A10-003) or less (192-A10-004/-005/-006/-007) led to reduced binding affinity to SDF-1 (FIG. 2A). The determined 5'-terminal and 3'-terminal stretches with a length of five and four nucleotides of the derivatives of Type A SDF-1-binding nucleic acid 192-A10-001 as shown in FIGS. 2A and 2B can be described in a generic formula for the 5'-terminal stretch ('X$_2$BBBS', Type A Formula-6-5') and of the 3'-terminal stretch ('SBBVX$_3$'; Type A Formula-6-3'), whereby X$_2$ is either absent or is 'S' and X$_3$ is either absent or is 'S'.

The nucleotide sequence of the 5'-terminal and 3'-terminal stretches has an influence on the binding affinity of Type A SDF-1-binding nucleic acids. This is not only shown by the nucleic acids 192-F10 and 192-E10, but also by derivatives of 192-A10-001 (FIG. 2B). The core nucleotide sequences of 192-F10 and 192-E10 are identical to 192-B11 and 192-C10, but comprise slight differences at the 3'-end of 5'-terminal stretch and at the 5'-end of 3'-terminal stretch resulting in reduced binding affinity.

The substitution of 5'-terminal and 3'-terminal nucleotides 'CUGUG' and 'CGCAG' of Type A SDF-1-binding nucleic acid 192-A10-002 by 'GCGCG' and 'CGCGC' (192-A10-015) resulted in a reduced binding affinity whereas substitutions by 'GCGUG' and 'CGCGC' (192-A10-008) resulted in same binding affinity as shown for 192-A10-002 (FIG. 2B, FIG. 15, FIG. 12, FIG. 16). Additionally, nine derivatives of Type A SDF-1-binding nucleic acid 192-A10-001 (192-A10-014/-015/-016/-017/-018/-019/-020/-021/-022/-023) bearing four 5'-terminal and 3'-terminal nucleotides, respectively, were tested as aptamers for their binding affinity vs. 192-A10-001 or its derivative 192-A10-008 (both have the identical binding affinity to SDF-1). All clones showed weaker, much weaker or very much weaker binding affinity to SDF-1 as 192-A10-001 (six nucleotides forming a terminal helix) or as 192-A10-008 with five terminal nucleotides, respectively (FIG. 2B). Consequently, the sequence and the number of nucleotides of the 5'- and 3'-terminal stretches are essential for an effective binding to SDF-1. As shown for Type A SDF-1-binding nucleic acids 192-A10-002 and 192-A10-08, the preferred combination of 5'-terminal and 3'-terminal stretches are 'CUGUG' and 'CGCAG' (5'- and 3'-terminal stretches of Type A SDF-1-binding nucleic acid 192-A10-002) and 'GCGUG' and 'CGCGC' (5'- and 3'-terminal stretches of Type A SDF-1-binding nucleic acid 192-A10-008).

However, combining the 5'- and 3'-terminal stretches of all tested Type A SDF-1-binding nucleic acids the generic formula for the 5'-terminal stretch of Type A SDF-1-binding nucleic acids is 'X$_1$X$_2$NNBV' (Type A Formula-7-5') and the generic formula for the 3'-terminal stretch of Type A SDF-1-binding nucleic acids is 'BNBNX$_3$X$_4$' (Type A Formula-7-3'), wherein X$_1$ is 'R' or absent, X$_2$ is 'S', X$_3$ is 'S' and X$_4$ is 'Y' or absent; or X$_1$ is absent, X$_2$ is 'S' or absent, X$_3$ is 'S' or absent and X$_4$ is absent.

1.2 Type B SDF-1-Binding Nucleic Acids

As depicted in FIG. 3, all sequences of SDF-1-binding nucleic acids of Type B comprise one core nucleotide sequence which is flanked by 5'- and 3'-terminal stretches that can hybridize to each other. However, such hybridization is not necessarily given in the molecule.

The nucleic acids were characterized on the aptamer level using direct and competitive pull-down binding assays with biotinylated human D-SDF-1 in order to rank them with respect to their binding behaviour (Example 4). Selected sequences were synthesized as Spiegelmers (Example 3) and were tested using the natural configuration of SDF-1 (L-SDF) in a cell culture in vitro chemotaxis assay (Example 5) and by surface plasmon resonance measurement using a Biacore 2000 instrument (Example 6).

The sequences of the defined boxes or stretches may be different between the SDF-1-binding nucleic acids of Type B which influences the binding affinity to SDF-1. Based on binding analysis of the different SDF-1-binding nucleic acids summarized as Type B SDF-1-binding nucleic acids, the core nucleotide sequence and its nucleotide sequences as described in the following are individually and more preferably in their entirety essential for binding to SDF-1:

The core nucleotide sequence of all identified sequences of Type B SDF-1-binding nucleic acids share the sequence (SEQ ID NO: 57)
GUGUGAUCUAGAUGUADWGGCUGWUCCUAGUYAGG
(Type B Formula-1).

The Type B SDF-1-binding nucleic acids 193-G2-001, 193-C2-001 and 193-F2-001 that differ in one position of the core nucleotide sequence were analyzed in a competitive pull-down binding assay vs. the Type A SDF-1-binding nucleic acid 192-A10-001 ($K_D$ of 1.5 nM determined in a pull-down binding assay [FIG. 11], $K_D$ of 1.0 nM determined by surface plasmon resonance measurement [FIG. 15], $IC_{50}$ of 0.12 nM; [FIG. 12]). Each of the three tested Type B SDF-1-binding nucleic acids showed superior binding to human SDF-1 in comparison to Type A SDF-1-binding nucleic acid 192-A10-001 whereby the binding affinity of 193-G2-001 is as good as 193-C2-001 and 193-F2-001 (FIG. 3). The data suggest that the difference in the nucleotide sequence of the core nucleotide sequence of Type B SDF-1-binding nucleic acids 193-G2-001, 193-C2-001 and 193-F2-001 has no influence on the binding affinity to SDF-1. Exemplarily, the Type B SDF-1-binding nucleic acid 193-G2-001 was characterized for its binding affinity to human SDF-1. The equilibrium binding constant $K_D$ was determined using the pull-down binding assay ($K_D$=0.3 nM) and by surface plasmon resonance measurement ($K_D$=0.5 nM, FIG. 17). The $IC_{50}$ (inhibitory concentration 50%) of 0.08 nM for 193-G2-001 was measured using a cell culture in vitro chemotaxis assay. In contrast, the Type B SDF-1-binding nucleic acids 193-B3-002, 193-H3-002, 193-E3-002 and 193-D1-002 that differ in the sequence of the core nucleotide sequence have worse binding properties (FIG. 3). As result Type B SDF-1-binding nucleic acids with improved binding affinity to SDF-1 share a core nucleotide sequence with the sequence (SEQ ID NO: 58)
GUGUGAUCUAGAUGUADUGGCUGAUCCUAGUCAGG
(Type B Formula-2).

Four, five or six nucleotides out of the six nucleotides of the 5'-terminal stretch of Type B SDF-1-binding nucleic acids may hybridize to the respective four, five or six out of the six nucleotides of the 3'-terminal stretch of Type B SDF-1-binding nucleic acids to form a terminal helix. Although the nucleotides are variable at several positions, the different nucleotides allow the hybridization for four, five or six nucleotides out of the six nucleotides of the 5'- and 3'-terminal stretches each. The 5'-terminal and 3'-terminal stretches of Type B SDF-1-binding nucleic acids as shown in FIG. 3 can be summarized in a generic formula for the 5'-terminal stretch (Type B Formula-3-5'; '$X_1$GCRWG' whereas $X_1$ is 'A' or absent) and of the 3'-terminal stretch (Type B Formula-3-3'; 'KRYSCX$_4$' whereas $X_4$ is 'U' or absent). Type B SDF-1-binding nucleic acids 193-G1-002, 193-D2-002, 193-A1-002 and 193-D3-002 have weaker binding affinities to SDF-1 although they share the identical core nucleotide sequence (Type B Formula-2) with 193-C2-001, 193-G2-001 and 193-F2-001 (FIG. 3). The unfavorable binding properties of Type B SDF-1-binding nucleic acids 193-G1-002, 193-D2-002, 193-A1-002 and 193-D3-002 may be due to the number of nucleotides and sequence of the 5'-terminal and 3'-terminal stretches.

Truncated derivatives of the Type B SDF-1-binding nucleic acids 193-G2-001 and 193-C2-001 were analyzed in a competitive pull-down binding assay vs. 193-G2-001 and 193-G2-012, respectively (FIGS. 4A and 4B). These experiments showed that a reduction of the six terminal nucleotides (5'end: AGCGUG; 3'end: UACGCU) of Type B SDF-1-binding nucleic acids 193-G2-001 and 193-C2-001 to five nucleotides (5'end: GCGUG; 3'end: UACGC) lead to molecules with similar binding affinity (193-C2-002 and 193-G2-012). The equilibrium dissociation constant $K_D$ was determined using the pull-down binding assay ($K_D$=0.3 nM, FIG. 18). A truncation to four (5'end: CGUG; 3'end: UACG; 193-C2-003) or less nucleotides (193-C2-004, 193-C2-005, 193-C2-006, 193-C2-007) resulted in a reduced binding affinity to SDF-1 which was measured by using the competition pull-down binding assay (FIG. 4A). The nucleotide sequence of the five terminal nucleotides at the 5'- and 3'-end, respectively, has an influence on the binding affinity of Type B SDF-1-binding nucleic acids. The substitution of 5'- and 3'-terminal nucleotides 'GCGUG' and 'UACGC' (193-C2-002, 193-G2-12) by 'GCGCG' and 'CGCGC' (193-G2-013) resulted in a reduced binding affinity. Additionally, the four different derivatives of Type B SDF-1-binding nucleic acid 193-C2-001 with a terminal helix with a length of four base-pairing nucleotides (193-G2-014/-015/-016/-017) were tested. All of them showed reduced binding affinity to SDF-1 (FIG. 4B). Therefore the sequence and the length of the 5'-terminal and 3'-terminal nucleotides are essential for an effective binding to SDF-1. The 5'-terminal and 3'-terminal stretches with a length of five and four nucleotides of the derivatives of Type B SDF-1-binding nucleic acids 193-C2-003 and 193-G2-012 as shown in FIGS. 4A and 4B can be described in a generic formula for the 5'-terminal stretch ('$X_2$SSBS', Type B Formula-4-5'), whereby $X_2$ is either absent or is 'G', and of the 3'-terminal stretch ('BVSSX$_3$', Type B Formula-4-3'), and whereby $X_3$ is either absent or is 'C'. As shown for Type B SDF-1-binding nucleic acids 193-G2-001 and 193-C2-01 and their derivatives 193-G2-012 and 193-C2-002, the preferred combination of 5'- and 3'-terminal stretches are '$X_1$GCGUG' (5'-terminal stretch; Type B Formula 5-5') and 'UACGCX$_4$' (3'-terminal stretch; Type B Formula 5-3'), whereas $X_1$ is either 'A' or absent and $X_4$ is 'U' or absent.

However, combining the 5'- and 3'-terminal stretches of all tested Type B SDF-1-binding nucleic acids the generic formula for the 5'-terminal stretch of Type B SDF-1-binding nucleic acids is '$X_1X_2$SVNS' (Type B Formula-6-5') and the generic formula for the 3'-terminal stretch Type B SDF-1-binding nucleic acids is 'BVBSX$_3$X$_4$' (Type B Formula-6-3'), wherein $X_1$ is 'A' or absent, $X_2$ is 'G', $X_3$ is 'C' and $X_4$ is U or absent; or $X_1$ is absent, $X_2$ is 'G' or absent, $X_3$ is 'C' or absent and $X_4$ is absent.

1.3 Type C SDF-1-Binding Nucleic Acids

As depicted in FIG. 5, all sequences of SDF-1-binding nucleic acids of Type C comprise one core nucleotide sequence which is flanked by 5'- and 3'-terminal stretches that can hybridize to each other. However, such hybridization is not necessarily given in the molecule.

The nucleic acids were characterized on the aptamer level using direct and competitive pull-down binding assays with biotinylated human D-SDF-1 in order to rank them with respect to their binding behaviour (Example 4). Selected sequences were synthesized as Spiegelmers (Example 3) and were tested using the natural configuration of SDF-1 (L-SDF) in a cell culture in vitro chemotaxis assay (Example 5) and by surface plasmon resonance measurement using a Biacore 2000 instrument (Example 6).

The sequences of the defined boxes or stretches may be different between the SDF-1-binding nucleic acids of Type C which influences the binding affinity to SDF-1. Based on binding analysis of the different SDF-1-binding nucleic acids summarized as Type C SDF-1-binding nucleic acids, the core nucleotide sequence and its nucleotide sequence as described in the following are individually and more preferably in their entirety essential for binding to SDF-1:

The core nucleotide sequence of all identified sequences of Type C SDF-1-binding nucleic acids share the sequence (SEQ ID NO: 90)

GGUYAGGGCUHRX$_A$AGUCGG (Type C Formula-1), whereby $X_A$ is either absent or is 'A'. With the exception of Type C SDF-1-binding nucleic acid 197-D1, the core nucleotide sequence of all identified sequences of Type C SDF-1-binding nucleic acids share the nucleotide sequence (SEQ ID NO: 91)

GGUYAGGGCUHRAAGUCGG (Type C Formula-2).

Type C SDF-1-binding nucleic acid 197-D1 (core nucleotide sequence:

(SEQ ID NO: 88)

GGUUAGGGCUAA-AGUCGG)

missing one nucleotide 'A' within the core nucleotide sequence and still binding to SDF-1 let conclude an alternative core nucleotide sequence (SEQ ID NO: 92)

(GGUYAGGGCUHR-AGUCGG, Type C Formula-3).

Initially, all Type C SDF-1-binding nucleic acids as depicted in FIG. 5 were analyzed in a competitive pull-down binding assay vs. Type A SDF-1-binding nucleic acid 192-A10-001 ($K_D$=1.5 nM determined by pull-down assay and by surface plasmon resonance measurements; $IC_{50}$=0.12 nM). The Type C SDF-1-binding nucleic acids 191-D5-001, 197-B2, 190-A3-001, 197-H1, 197-H3 and 197-E3 showed weaker binding affinities than 192-A10-001 in competition experiments. Much weaker binding affinity was determined for 191-A5, 197-B1, 197-D1, 197-H2 and 197-D2 (FIG. 5). The molecules or derivatives thereof were further characterized by further competitive pull-down binding assays, plasmon resonance measurements and an in vitro chemotaxis assay. The Type C SDF-1-binding nucleic acid 191-D5-001 was characterized for its binding affinity to human SDF-1 whereas the equilibrium binding constant $K_D$ was determined by surface plasmon resonance measurement ($K_D$=0.8 nM, FIG. 21). The $IC_{50}$ (inhibitory concentration 50%) of 0.2 nM for 191-D5-001 was measured using a cell culture in vitro chemotaxis assay. The binding affinity of Type C SDF-1-binding nucleic acid 197-B2 for human SDF-1 was determined by surface plasmon resonance measurement ($K_D$=0.9 nM), its $IC_{50}$ (inhibitory concentration 50%) of 0.2 nM was analyzed in a cell-culture in vitro chemotaxis assay. These data indicates that Type C SDF-1-binding nucleic acids 191-D5-001 and 197-B2 have the similar binding affinity to SDF-1 (FIGS. 5 and 8).

Type C SDF-1-binding nucleic acid 190-A3-001 (48 nt) comprises a 5'-terminal stretch of 17 nucleotides and a 3'-terminal stretch of 12 nucleotides whereby on the one hand the four nucleotides at the 5'-end of the 5'-terminal stretch and the four nucleotides at the 3'-end of the 3'-terminal stretch may hybridize to each other to form a terminal helix. Alternatively, the nucleotides 'UGAGA' in the 5'-terminal stretch may hybridize to the nucleotides 'UCUCA' in the 3'-terminal stretch to form a terminal helix. A reduction to eight nucleotides of the 5'-terminal stretch ('GAGAUAGG') and to nine nucleotides of the 3'-terminal stretch ('CUGAUUCUC') of molecule 190-A3-001 (whereby six out of the eight/nine nucleotides of the 5'-terminal and 3'-terminal stretch can hybridize to each other) does not have an influence on the binding affinity to SDF-1 (190-A3-004; FIG. 6 and FIG. 19). The equilibrium binding constant $K_D$ of 190-A3-004 was determined using the pull-down binding assay ($K_D$=4.6 nM, FIG. 20) and by surface plasmon resonance measurement ($K_D$=4.7 nM). The $IC_{50}$ (inhibitory concentration 50%) of 0.1 nM for 190-A3-004 was measured using a cell culture in vitro chemotaxis assay (FIG. 22). However, the truncation to two nucleotides at the 5'-terminal stretch leads to a very strong reduction of binding affinity (190-A3-007; FIG. 6 and FIG. 19).

The Type C SDF-1-binding nucleic acids 191-D5-001, 197-B2 and 197-H1 (core nucleotide sequence (SEQ ID NO: 79)

GGUUAGGGCUAGAAGUCGG),

197-H3/191-A5 (core nucleotide sequence:

(SEQ ID NO: 83)

GGUUAGGGCUCGAAGUCGG)

and 197-E3/197-B1 (core nucleotide sequence:

(SEQ ID NO: 85)

GGUUAGGGCUUGAAGUCGG)

share an almost identical core nucleotide sequence (Type C formula-4; nucleotide sequence:

(SEQ ID NO: 93)

GGUUAGGGCUHGAAGUCGG).

191-D5-001, 197-B2 and 197-H1 do not share a similar 5'- and 3'-terminal stretch (197-H3 and 197-E3 have the identical 5'- and 3'-terminal stretch as 197-B2). However, the respective ten (197-B2, 197-E3, 197-H3) or nine out of the ten (191-D5-001, 197-H1) nucleotides of the 5'-terminal stretch may hybridize to the respective ten (197-B2, 197-E3, 197-H3) or nine out of the ten (191-D5-001, 197-H1) nucleotides of the 3'-terminal stretch (FIG. 5). Thus, the 5'-terminal stretch of Type C SDF-1-binding nucleic acids 197-B2, 191-D5-001, 197-H1, 197-E3 and 197-H3 as mentioned above plus 191-A5, 197-B1, 197-H2, 197-D1 and 197-D2 comprise a common generic nucleotide sequence of 'RKSBUSNVGR' (Type C Formula-5-5') (SEQ ID NO:120). The 3'-terminal stretch of Type C SDF-1-binding nucleic acids 197-B2, 191-D5-001, 197-H1, 197-E3, and 197-H3 as mentioned above plus 191-A5, 197-B1, 197-H2, 197-D1 and 197-D2 comprise a common generic nucleotide sequence of 'YYNRCASSMY' (Type C Formula-5-3') (SEQ ID NO:121), whereby the 5' and the 3'-terminal stretches of Type C SDF-1-binding nucleic acids 197-B2, 191-D5-001, 197-H1, 197-E3 and 197-H3 are preferred. These preferred 5'-terminal and 3'-terminal stretches of Type C SDF-1-binding nucleic acids 197-B2, 191-D5-001, 197-H1, 197-E3 and 197-H3 can be summarized in the generic formula 'RKSBUGSVGR' (Type C Formula-6-5'; 5'-terminal stretch) (SEQ ID NO:122) and 'YCNRCASSMY' (Type C Formula-6-3'; 3'-terminal stretch) (SEQ ID NO:123).

Truncated derivatives of Type C SDF-1-binding nucleic acid 191-D5-001 were constructed and tested in a competitive pull-down binding assay vs. the original molecule 191-D5-001 (FIG. 7A, FIG. 7B and FIG. 19). At first the length of the 5'-terminal and 3'-terminal stretches were shortened from ten nucleotides (191-D5-001) each to seven nucleotides each (191-D5-004) as depicted in FIG. 7A whereby nine out of the ten (191-D5-001) or six out of the seven nucleotides (191-D5-004) of the 5'-terminal stretch and of the 3'-terminal stretch, respectively, can hybridize to each other. The reduction to seven nucleotides of the 5'- and 3'-terminal stretch, respectively (whereas six out of the seven nucleotides can hybridize to each other) led to reduced binding affinity to SDF-1 (191-D5-004). The terminal stretches of Type C SDF-1-binding nucleic acid 191-D5-004 were modified whereby the non-pairing nucleotide 'A' within the 3'-terminal stretch of 191-D5-004 was substituted by a 'C' (191-D5-005). This modification led to an improvement of binding. This derivative, Type C SDF-1-binding nucleic acid 191-D5-005, showed similar binding to SDF-1 as 191-D5-001. Further truncation of the 5'-terminal and 3'-terminal stretch to five nucleotides respectively led to a molecule with a length of total 29 nucleotides (191-D5-007). Because of the similarities of 191-D5-001 and of the Type C SDF-1-binding nucleic acids 197-B2, 191-D5-001, 197-H1, 191-A5, 197-H3, 197-B1, 197-E3, 197-D1, 197-H2 and 197-D2 and because of the data shown for 191-D5-007, it may assume that the 5'-terminal and 3'-terminal stretch can in principle be truncated down to five nucleotides whereby the nucleotide sequence 'CGGGA' for the 5'-terminal stretch and 'UCCCG' for the 3'-terminal stretch were successfully tested (Type C SDF-1-binding nucleic acid 191-D5-007). Type C SDF-1-binding nucleic acid 191-D5-007 surprisingly binds somewhat better to SDF-1 than 191-D5-001 (determined on aptamer level using the competition binding assay). The equilibrium binding constant $K_D$ of 191-D5-007 was determined using the pull-down binding assay ($K_D$=2.2 nM, FIG. 20) and by surface plasmon resonance measurement ($K_D$=0.8 nM, FIG. 21). The $IC_{50}$ (inhibitory concentration 50%) of 0.1 nM for 191-D5-007 was measured using a cell culture in vitro chemotaxis assay. A nucleic acid with further truncation of both terminal stretches to four nucleotides (191-D5-010, FIG. 7A) was tested.

Further derivatives of Type C SDF-1-binding nucleic acid 191-D5-001 (191-D5-017/-024/-029) bearing 5'-terminal and 3'-terminal stretches of four nucleotides also showed reduced binding affinity to SDF-1 in the competition pull-down binding assay vs. 191-D5-007 (FIG. 7B). Alternative 5'-terminal and 3'-terminal stretches with a length of five nucleotides were additionally tested (191-D5-017-29a, 191-D5-017-29b, 191-D5-019-29a, 191-D5-024-29a and 191-D5-024-29b). The generic formula of these derivatives for the 5'-terminal stretch is '$X_S$SSSV' (Type C Formula-7-5') (SEQ ID NO:124) and for the 3'-stretch is 'BSSS$X_S$' Type C Formula-7-3') (SEQ ID NO:125), whereby $X_S$ is absent or S. Two out of the five tested variants showed identical binding affinity to SDF-1 as 191-D5-007 (191-D5-024-29a and 191-D5-024-29b; FIG. 7B). The sequences of the 5'-terminal and 3'-terminal stretches of 191-D5-001-derivatives that show the best binding affinity to SDF-1 and comprise a 5'-terminal and 3'-terminal stretch of five nucleotides respectively (191-D5-007, 191-D5-024-29a and 191-D5-024-29b) can be summarized in a generic formula (5'-terminal stretch: SGGSR, Type C Formula-8-5' (SEQ ID NO:126); 3'-terminal stretch: YSCCS, Type C Formula-8-3') (SEQ ID NO:127).

Truncated derivatives of Type C SDF-1-binding nucleic acid 197-B2 were analyzed in a competitive pull-down binding assay vs. the original molecule 197-B2 and 191-D5-007 (FIG. 8). Using the competitive pull-down binding assay vs. 191-D5-007, it was shown that 197-B2 has the same binding affinity to SDF-1 as 191-D5-007. The 5'-terminal and 3'-terminal stretches were shortened without loss of binding affinity from ten nucleotides (197-B2) each to five nucleotides each (197-B2-005) whereby the nucleotides of the 5'-terminal stretch and of the 3'-terminal stretch can completely hybridize to each other. If the 5'-terminal ('GCGGG') and 3'-terminal ('CCUGC') stretch of 197-B2-005 was substituted by 'GCCGG' (5'-terminal stretch) and by 'CCGGC' (3'-terminal stretch) of 197-B2-006, the binding affinity to SDF-1 fully persisted. Because 197-B2 and 191-D5-001 (and their derivatives) share the identical core nucleotide sequence (SEQ ID NO: 79)
(GGUUAGGGCUAGAAGUCGG)

and several derivatives of 191-D5 with 5'-terminal and 3'-terminal stretches with a length of four nucleotides were tested, a further truncation of the 5'-terminal and 3'-terminal stretch was omitted. Two further derivatives were designed that comprise six nucleotides at the 5'-end and 3'-end (5'-terminal and 3'-terminal stretches), respectively. The binding affinity to SDF-1 of both molecules (197-B2-006-31a and 197-B2-006-31b) is the same as shown for 191-D5-007 and 197-B2-006 (FIG. 8). The sequences of the 5'-terminal and 3'-terminal stretches of 197-B2 derivatives that show the best binding affinity to SDF-1 and comprise a 5'-terminal and 3'-terminal stretch of five nucleotides can be summarized in a generic formula (5'-terminal stretch: GCSGG, Type C Formula-9-5' (SEQ ID NO:128); 3'-terminal stretch: CCKGC, Type C Formula-9-3' (SEQ ID NO:129).

Combining the preferred 5'-stretches and 3'-stretches of truncated derivatives of Type C SDF-1-binding nucleic acids 191-D5-001 (5'-terminal stretch: SGGSR, Type C Formula-8-5' (SEQ ID NO:126); 3'-terminal stretch: YSCCS, Type C Formula-8-3' (SEQ ID NO:127)) and 197-B2 (5'-terminal stretch: GCSGG, Type C Formula-9-5' (SEQ ID NO:128); 3'-terminal stretch: CCKGC, Type C Formula-9-3' (SEQ ID NO:129)) the common preferred generic formula for the 5'-terminal and the 3'-terminal stretch is SSSSR (5'-terminal stretch, Type C Formula-10-5' (SEQ ID NO:130)) and YSBSS (3'-terminal stretch: Type C Formula-10-3' (SEQ ID NO:131)).

1.4 Further SDF-1-Binding Nucleic Acids

Additionally, three further SDF-1-binding nucleic acids that do not share the SDF-1-binding motifs of 'Type A', 'Type B' and 'Type C' were identified. There were analyzed as aptamers using the pull-down binding assay (FIG. 9).

It is to be understood that any of the sequences shown in FIGS. 1 through 9 are nucleic acids according to the present invention, including those truncated forms thereof, but also including those extended forms thereof under the proviso, however, that the thus truncated and extended, respectively, nucleic acid molecules are still capable of binding to the target.

Example 2: 40 kda-PEG and other Modification of SDF-Binding Spiegelmers

In order to prolong the Spiegelmer's plasma residence time in vivo, the Spiegelmers 193-G2-012, 192-A10-008, 191-D5-007, 197-B2-006 and 197-B2-006-31b were covalently coupled to a 40 kDa polyethylene glycol (PEG) moiety at the 5'-end as described in Example 3 (PEGylated-clones: 193-G2-012-5'-PEG, 192-A10-008-5'PEG, 191-D5-007-5'PEG, 197-B2-006-5'PEG and 197-B2-006-31b-5'PEG).

The PEGylated Spiegelmer molecules were analyzed in a cell culture in vitro TAX-assay (Example 5) and by plasmon resonance measurements using a Biacore (Example 6). All 40 kDa-PEG-modified Spiegelmers are still able to inhibit SDF-1 induced chemotaxis and to bind to SDF-1 in low nanomolar range (FIG. 23A, 23B, 24A and FIG. 24B).

Additionally, SDF-binding Spiegelmer 192-A10-001 was modified with 40 kDa-PEG, 30 kDa-PEG, 100 kDa-HES or 130 kDa-HES (PEGylated-clones: 192-A10-001-5'PEG40, 192-A10-001-5'PEG30, 192-A10-001-5'HES100, 192-A10-001-5'HES130; coupling procedure in Example 3). As depicted in FIG. 25A and FIG. 25B neither a PEG moiety nor a HES moiety has an influence on Spiegelmers potency to inhibit SDF-1 induced chemotaxis.

Example 3: Synthesis and Derivatization of Aptamers and Spiegelmers 3.1 Small Scale Synthesis Aptamers and Spiegelmers were produced by solid phase synthesis with an ABI 394 synthesizer (Applied Biosystems, Foster City, Calif., USA) using 2'TBDMS RNA phosphoramidite chemistry (Damha and Ogilvie, 1993). rA(N-Bz)-, rC(Ac)-, rG(N-ibu)-, and rU-phosphoramidites in the D- and L-configuration were purchased from ChemGenes, Wilmington, Mass. Aptamers and Spiegelmers were purified by gel electrophoresis.

3.2 Large Scale Synthesis Plus Modification

The Spiegelmers were produced by solid phase synthesis with an ÄktaPilot100 synthesizer (Amersham Biosciences; General Electric Healthcare, Freiburg) using 2'TBDMS RNA phosphoramiditc chemistry (Damha and Ogilvie, 1993). L-rA(N-Bz)-, L-rC(Ac)-, L-rG(N-ibu)-, and L-rU-phosphoramidites were purchased from ChemGenes (Wilmington, Mass., USA). The 5'-amino-modifier was purchased from American International Chemicals Inc. (Framingham, Mass., USA). Synthesis of the Spiegelmers was started on L-riboG; L-riboC, L-riboA and L-riboU with modified CPG of pore size 1000 Å (Link Technology, Glasgow, UK). For coupling (15 min per cycle), 0.3 M benzylthiotetrazole (American International Chemicals Inc., Framingham, Mass., USA) in acetonitrile, and 3.5 equivalents of the respective 0.2 M phosphoramidite solution in acetonitrile were used. An oxidation capping cycle was used. Further standard solvents and reagents for oligonucleotide synthesis were purchased from Biosolve (Valkenswaard, NL). The Spiegelmers were synthesized DMT-ON; after deprotection, it was purified via preparative RP-HPLC (Wincott F. et al., 1995) using Source15RPC medium (Amersham). The 5'DMT group was removed with 80% acetic acid (90 min at RT). Subsequently, aqueous 2 M NaOAc solution was added and the Spiegelmer was desalted by tangential flow filtration using a 5 K regenerated cellulose membrane (Millipore, Bedford, Mass.).

3.3 PEGylation

In order to prolong the Spiegelmer's plasma residence time in vivo, the Spiegelmers were covalently coupled to a 40 kDa polyethylene glycol (PEG) moiety at the 5'-end.

For PEGylation (for technical details of the method for PEGylation see European patent application EP 1 306 382), the purified 5'-amino modified Spiegelmers were dissolved in a mixture of $H_2O$ (2.5 ml), DMF (5 ml), and buffer A (5 ml; prepared by mixing citric acid•$H_2O$ [7 g], boric acid [3.54 g], phosphoric acid [2.26 ml], and 1 M NaOH [343 ml] and adding water to a final volume of 11; pH=8.4 was adjusted with 1 M HCl).

The pH of the Spiegelmer solution was brought to 8.4 with 1 M NaOH. Then, 40 kDa PEG-NHS ester (Nektar Therapeutics, Huntsville, Ala.) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M) and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C: 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC. The PEGylated Spiegelmer was desalted by tangential flow filtration (5 K regenerated cellulose membrane, Millipore, Bedford Mass.).

3.4 HESylation

In order to prolong the Spiegelmer's plasma residence time in vivo, the Spiegelmers were covalently coupled to Hydroxyl Ethyl Starch (HES) of various molecular weights of >130 kDa and substitution degree >0.5. The 5'-end of the Spiegelmer is the preferred site for conjugation.

For HESylation (for technical details of the method for HESylation of nucleic acids see German Offenlegungsschrift DE 101 12 825 A1, and for D/L-nucleic acids PCT WO 02/080979 A2), the purified 5'-amino modified Spiegelmer was dissolved in sodium bicarbonate (0.3 M, 1 ml) and the pH is adjusted to 8.5.

In respect to the Spiegelmer, a 5-fold excess of the free HES acid (3.3 mmol, Supramol, Rosbach, Germany) and di(N-succinimidyl) carbonate (3.3 mmol) were added to N,N-dimethylformamide (1 ml) to yield a solution of the activated N-hydroxysuccinimide ester of HES. To dissolve all reactants the mixture was stirred briefly at 60° C., cooled to 25° C. and then stirred for 1.5 h at 25° C. The solution of Spiegelmer was added to the solution of activated HES, and the resulting mixture was stirred at 25° C. and pH 8.5. The reaction was monitored by analytical IEX-HPLC. Typically, the conjugation proceeded to >75% within 1 hr.

For IEX-HPLC purification via Source 15Q medium (GE, Freiburg, Germany), the reaction mixture was blended with a 10-fold quantity of buffer A (1 mM EDTA, 25 mM Tris, 10 mM NaClO4 in water/acetonitrile 9:1, pH 4). Excess HES elutes at 5% buffer A (1 mM EDTA, 25 mM Tris, 500 mM NaClO4 in water/acetonitrile 9:1, pH 4), whereas the HES-Spiegelmer conjugate elutes at 20-30% buffer B. Product fractions with a purity of >95% (as assessed by HPLC) were combined and desalted by tangential flow filtration (5 K regenerated cellulose membrane, Millipore, Bedford Mass.).

Example 4: Determination of Binding Constants (Pull-Down Binding Assay)

4.1 Direct Pull-Down Binding Assay

The affinity of aptamers to biotinylated human D-SDF-1 was measured in a pull-down binding assay format at 37° C. Aptamers were 5'-phosphate labeled by T4 polynucleotide kinase (Invitrogen, Karlsruhe, Germany) using [γ-$^{32}$P]-labeled ATP (Hartmann Analytic, Braunschweig, Germany). The specific radioactivity of labeled aptamers was 200,000-800,000 cpm/pmol. Aptamers were incubated after de- and renaturation at 10, 20, 30 or 40 pM concentration at 37° C. in selection buffer (20 mM Tris-HCl pH 7.4; 137 mM NaCl; 5 mM KCl; 1 mM $MgCl_2$; 1 mM $CaCl_2$; 0.1% [w/vol] Tween-20) together with varying amounts of biotinylated human D-SDF-1 for 4-12 hours in order to reach equilibrium at low concentrations. Selection buffer was supplemented with 10 μg/ml human serum albumin (Sigma-Aldrich, Steinheim, Germany), and 10 μg/ml yeast RNA (Ambion, Austin, USA) in order to prevent adsorption of binding partners with surfaces of used plastic ware or the immobilization matrix. The concentration range of biotinylated human D-SDF-1 was set from 8 pM to 100 nM; total reaction volume was 1 ml. Peptide and peptide-aptamer complexes were immobilized on 1.5 μl Streptavidin Ultralink Plus particles (Pierce Biotechnology, Rockford, USA) which had been preequilibrated with selection buffer and resuspended in a total volume of 6 μl. Particles were kept in suspension for 30 min at the respective temperature in a thermomixer. Immobilized radioactivity was quantified in a scintillation counter after detaching the supernatant and appropriate washing. The percentage of binding was plotted against the concentration of biotinylated human D-SDF-1 and dissociation constants were obtained by using software algorithms (GRAFIT; Erithacus Software; Surrey U.K.) assuming a 1:1 stoichiometry.

4.2 Competitive Pull-Down Binding Assay

In order to compare different D-SDF-1-binding aptamers, a competitive ranking assay was performed. For this purpose the most affine aptamer available was radioactively labeled (see above) and served as reference. After denaturation and renaturation it was incubated at 37° C. with biotinylated human D-SDF-1 in 1 ml selection buffer at conditions that resulted in around 5-10% binding to the peptide after immobilization and washing on NeutrAvidin agarose or Streptavidin Ultralink Plus (both from Pierce) without competition. An excess of de- and renatured non-labeled D-RNA aptamer variants was added to different concentrations (e.g. 2, 10, and 50 nM) with the labeled reference aptamer to parallel binding reactions. The aptamers to be tested competed with the reference aptamer for target binding, thus decreasing the binding signal in dependence of their binding characteristics. The aptamer that was found most active in this assay could then serve as a new reference for comparative analysis of further aptamer variants.

Example 5: Analysis of the Inhibition of SDF-1-Induced Chemotaxis by SDF-1-Binding Spiegelmers Jurkat human T cell leukemia cells (obtained from DSMZ, Braunschweig) were cultivated at 37° C. and 5% $CO_2$ in RPMI 1640 medium with Glutamax (Invitrogen, Karlsruhe, Germany) which contains 10% fetal bovine serum, 100 units/ml penicillin and 100 μg/ml streptomycin (Invitrogen, Karlsruhe, Germany). One day before the experiment, cells were seeded in a new flask with a density of $0.3 \times 10^6$/ml ($9 \times 10^6$/30 ml) in standard medium (Invitrogen, Karlsruhe, Germany).

For the experiment, cells were centrifuged (5 min at 300 g), resuspended, counted and washed once with 15 ml HBH (Hanks balanced salt solution containing 1 mg/ml bovine serum albumin and 20 mM HEPES; Invitrogen, Karlsruhe, Germany). Then the cells were resuspended at $3 \times 10^6$/ml or $1.33 \times 10^6$/ml, depending on the type of filter plate used. Cells were then allowed to migrate through the porous membranes of the filter plates for several hours towards a solution containing SDF-1 and various amounts of Spiegelmer. Either Transwell plates and inserts with porous Polycarbonate membrane, 5 μm pore size (Corning; 3421) or MultiScreen MIC plates (Millipore, MAMIC5S10) were used.

5.1 Protocol for Transwell Plates

The stimulation solutions (SDF-1+various concentrations of Spiegelmer) were made up in 600 μl HBH in the lower compartments of the Transwell plates and incubated for 20-30 min. All conditions were made up at least twice. The inserts were transferred to the wells containing the stimulation solutions and 100 μl of a cell suspension with $3 \times 10^6$/ml were added to the inserts ($3 \times 10^5$ cells/well). The cells were then allowed to migrate for 3 h at 37° C.

Thereafter, the inserts were removed and 60 μl resazurin (Sigma, Deisenhofen, Germany) working solution (440 μM in PBS; Biochrom, Berlin, Germany) were added to the wells (also to calibration wells). The plates were then incubated at 37° C. for 2.5 to 3 h. After incubation, 200 μl of each well were transferred to a black 96-well plate. Measurement of the fluorescence signals was done at 544 nm (excitation) and 590 nm (emission) in a Fluostar Optima multidetection plate reader (BMG, Offenburg, Germany).

5.2 Protocol for Millipore MultiScreen Plates

The stimulation solutions (SDF-1+various concentrations of Spiegelmer) were made up as 10× solutions in a 0.2 ml low profile 96-tube plate. HBH (135 μl) were pipetted into the lower compartments of the MultiScreen plate and 15 μl of the stimulation solutions were added. All conditions were made up as triplicates. After 20 to 30 min the filter plate was inserted into the plate containing the stimulation solutions and 75 μl of a cell suspension with $1.33 \times 10^6$/ml were added to the wells of the filter plate ($1 \times 10^5$ cells/well). The cells were then allowed to migrate for 3 h at 37° C.

Thereafter, the insert plate is removed and 20 μl resazurin working solution (440 μM in PBS) are added to the lower wells. The plates were then incubated at 37° C. for 2.5 to 3 h.

After incubation, 100 μl of each well were transferred to a black 96-well plate. Measurement of the fluorescence signals was performed as described above.

5.3 Evaluation

For evaluation, fluorescence values were corrected for background fluorescence (no cells in well). Then the differences between experimental conditions with and without SDF-1 were calculated. The value for the sample without Spiegelmer (SDF-1 only) was set at 100% and the values for the samples with Spiegelmer were calculated as a percent of this. For a dose response curve the percent values were plotted against Spiegelmer concentration and the $IC_{50}$ value (concentration of Spiegelmer at which 50% of the activity without Spiegelmer is present) was determined graphically from the resulting curve.

5.4 Results 5.4.1 Dose-Dependent Stimulation of Jurkat Cells by Human SDF-1

Human SDF-1 was found to stimulate migration of Jurkat cells in a dose dependent manner, with half-maximal stimulation at about 0.3 nM (FIG. 11).

5.4.2 Dose-Dependent Inhibition of Human SDF-1-Induced Chemotaxis by SDF-1-Binding Spiegelmers When cells were allowed to migrate towards a solution containing human SDF-1 plus increasing concentrations of SDF-1-binding Spiegelmers, dose-dependent inhibition was observed. The respective IC50s of the tested Spiegelmers are specified in Example 1. When an unspecific Control Spiegelmer was used instead of SDF-1-binding Spiegelmers, no inhibitory effect was observed up to 1 μM (FIG. 26).

5.4.3 Dose-Dependant Inhibition of Mouse SDF-1-Induced Chemotaxis by SDF-1-Binding Spiegelmers SDF-1 is well conserved across species: SDF-1 from mouse differs from human SDF-1a in one amino acid (isoleucine at position 18 instead of valine). Murine SDF-1 can stimulate chemotaxis of Jurkat cells (FIG. 27) and this action was found to be inhibited by Spiegelmers 192-A10-001 and 191-D5-007-5'-PEG with the same potency as in the case of human SDF-1 (FIG. 28).

Example 6: Binding Analysis by Surface Plasmon Resonance Measurement

The Biacore 2000 instrument (Biacore AB, Uppsala, Sweden) was used to analyze binding of Spiegelmers to human SDF-1α. When coupling of SDF-1α was to be achieved via amine groups, SDF-1α was dialyzed against water for 1-2 h (Millipore VSWP mixed cellulose esters; pore size, 0.025 µM) to remove interfering amines. CM4 sensor chips (Biacore AB, Uppsala, Sweden) were activated before protein coupling by a 35 µl injection of a 1:1 dilution of 0.4 M NHS and 0.1 M EDC at a flow of 5 µl/min. Chemokine was then injected in concentrations of 0.1-1.5 µg/ml at a flow of 2 µl/min until the instrument's response was in the range of 1000-2000 RU (relative units). Unreacted NHS esters were deactivated by injection of 35 µl ethanolamine hydrochloride solution (pH 8.5) at a flow of 5 µl/min. The sensor chip was primed twice with binding buffer and equilibrated at 10 µl/min for 1-2 hours until the baseline appeared stable. For all proteins, kinetic parameters and dissociation constants were evaluated by a series of Spiegelmer injections at concentrations of 1000, 500, 250, 125, 62.5, 31.25, and 0 nM in selection buffer (Tris-HCl, 20 mM; NaCl, 137 mM; KCl, 5 mM; $CaCl_2$, 1 mM; $MgCl_2$, 1 mM; Tween 20, 0.1% [w/v]; pH 7.4). In all experiments, the analysis was performed at 37° C. using the Kinject command defining an association time of 180 and a dissociation time of 360 seconds at a flow of 10 µl/min. Data analysis and calculation of dissociation constants ($K_D$) was done with the BIAevaluation 3.0 software (BIACORE AB, Uppsala, Sweden) using the Langmuir 1:1 stoichiometric fitting algorithm.

Example 7: Inhibition of [$^{125}$I]-SDF-1-Binding to CXCR4 Expressing Cells by SDF-1-Binding Spiegelmers

7.1 Method

A cDNA clone coding for human CXCR4-receptor (NM_003467.2) was purchased from OriGene Technologies (Rockville, Md.) and cloned into the pCR3.1-vector (Invitrogen, Karlsruhe, Germany). The resulting vector was transfected into CHO-K1 cells (DSMZ, Braunschweig, Germany) using Lipofectamine 2000 (Invitrogen) and stable expressing cell lines were selected by treatment with geneticin. Expression of receptors was verified by RT-PCR.

For binding assays CXCR4-expressing cells were seeded into polylysine-coated 24-well plates at a cell density of 1×10$^5$ cells/well and cultivated overnight at 37° C. and 5% $CO_2$ in CHO-Ultra medium (Cambrex, Verviers, Belgium) containing 50 units/ml penicillin, 50 µg/ml streptomycin and 0.5 mg/ml geneticin.

For the binding experiment, the medium was removed and the cells were washed once with Hanks balanced salt solution, additionally containing 20 mM HEPES, 1 mg/ml bovine serum albumin, 0.1 mg/ml bacitracin (HBB). Then the cells were incubated in 0.2 ml HBB for 1 h at room temperature together with 50 pM [$^{125}$I]-1 (PerkinElmer, Rodgau, Germany) and varying concentrations of Spiegelmer.

Non-specific binding was determined by adding unlabeled human SDF-1 (R & D Systems, Wiesbaden, Germany) to a final concentration of 0.5 µM to several wells.

After the incubation period, the supernatant was removed and the wells were washed 3 times with ice cold HBB. Thereafter, the cells were lysed with 0.1 ml 0.1 M NaOH. Lysates were transferred into scintillation vials and after addition of 4 ml Unisafe 1 Liquid scintillation cocktail (Zinsser, Frankfurt, Germany) were counted in a Beckman LS6500 scintillation counter.

Since the values for non-specific binding (binding in the presence of high amount of unlabeled SDF-1) were somewhat higher than the values for total binding in the presence of high concentrations (500 pM) of Spiegelmer, the difference between maximal binding ("max") and binding in the presence of 500 pM Spiegelmer was used for calculation of $IC_{50}$-values.

7.2 Results

Plotting bound [$^{125}$I]-SDF-1 against Spiegelmer concentration revealed that binding of SDF-1 could be blocked by Spiegelmer 192-A10-001 with an $IC_{50}$ of about 60 pM (FIG. 29).

Example 8: Inhibition of SDF-1-Induced MAP-Kinase Activation by SDF-1-Binding Spiegelmers

8.1 Method

CXCR4-expressing CHO cells were seeded in 6-well plates at a density of 0.5×10$^6$ cells/well and cultivated for about three hours at 37° C. and 5% $CO_2$ in CHO-Ultra medium (Cambrex, Verviers, Belgium) containing 50 units/ml penicillin, 50 µg/ml streptomycin and 0.5 mg/ml geneticin. After cell attachment, the medium was removed and replaced by Ham's F12 medium containing 50 units/ml penicillin, 50 µg/ml streptomycin. Cells were then incubated overnight at 37° C. and 5% $CO_2$. Three hours before stimulation, the medium was replaced once more with fresh Ham's F12 medium. Cells were stimulated with human (1 nM) SDF-1 and various amounts of Spiegelmer for 5 or 10 minutes. Thereafter, the medium was removed and the cells were quickly washed once with 1 ml ice cold phosphate buffered saline (PBS), followed by lysis with SDS sample buffer (Tris/HCl, pH 6.8, 62.5 mM; glycerol, 10%; SDS, 2%; bromophenolblue, 0.01%; beta-mercaptoethanol, 5%). One µl of a 0.5 u/µl Benzonase solution (Merck, Darmstadt, Germany) was added to each well and after incubation for 5 to 10 min at room temperature, lysates were transferred to Eppendorf tubes, incubated at 95° C. for 5 min and stored at −20° C. until further analysis.

About 25 µl of the lysates were separated on 10% denaturing SDS-polyacrylamide gels. Proteins were then transferred by electroblotting onto HybondECL nitrocellulose membranes (Amersham/GE Healthcare, Munich, Germany). After blotting, the membranes were stained with Ponceau-red (0.2% in 3% trichloroacetic acid) for control of protein loading and transfer and then blocked by incubation in TBS-T (Tris-buffered saline (20 mM Tris/HCl, pH 7.6, 137 mM NaCl) with 0.1% Tween 20) containing 10% nonfat dried milk at 2-8° C. overnight.

The membrane was then incubated with a rabbit anti-Phospho-MAP kinase antibody (1:1000 in 10% milk in TBS-T) for 2 h at room temperature. After washing three times for 5 min with TBS-T, the membrane was incubated with anti-rabbit-IgG-HRP conjugate (1:2000 in 10% milk in TBS-T) for 1 h at room temperature. Then the membrane was again washed three times for 5 min with TBS-T, followed by incubation for 1 min in LumiGlo$^R$ chemiluminescent reagent. Luminescence was detected by exposure to Hyperfilm™ECL chemiluminescence films (Amersham/GE Healthcare) for 30 seconds to 2 minutes. The antibodies and the luminescence detection reagent were components of the PhosphoPlus p44/42 MAP Kinase (Thr202/Tyr204) Antibody kit from Cell Signaling Technology (New England Biolabs, Frankfurt a.M., Germany)

8.2 Results

Stimulation of CXCR4-expressing cells with 1 nM human SDF-1 for 5 min led to a profound stimulation of MAP kinase, indicated by an increase in intensity of the band reflecting activated MAP kinase. This activation of MAP kinase could be dose dependently inhibited by Spiegelmer 191-A10-001 (FIG. 30).

Example 9: Functional Analysis of Human SDF-1-Binding Spiegelmer 193-G2-012-5'-PEG in an Aortic Ring Sprouting Assay To test whether human SDF-1-binding Spiegelmer 193-G2-012-5'-PEG is functional also in a standard angiogenesis organ culture assay, aortic ring sprouting assays were performed. This assay, in which the length and abundance of vessel-like extensions from the explants are evaluated, has become the most widely used organ culture model for angiogenesis (Auerbach et al. 2003). It has already been shown that SDF-1 induces sprouting in this type of assay (Salcedo et al. 1999).

Rat aortae were cut into rings, embedded in a collagen matrix and incubated with SDF-1 and SDF-1 plus human SDF-1-binding Spiegelmer 193-G2-012-5'-PEG or SDF plus a non-functional PEGylated Control Spiegelmer that does not bind SDF-1. After 6 to 7 days, sprouting (i.e. outgrowth of endothelial cells) was analysed by taking pictures and determining a sprouting index.

Method

Aortae from male rats were obtained from Bagheri Life sciences (Berlin, Germany). The aortae were prepared freshly and transported on ice in MCDB 131-Medium (Invitrogen, Karlsruhe, Germany) containing 50 units/ml penicillin, 50 µg/ml streptomycin (both Invitrogen, Karlsruhe, Germany) and 2.5 µg/ml fungizone (Cambrex, USA).

For an experiment, a single aorta was transferred to a cell culture dish together with the medium and residual connective tissue was removed. Then the aorta was cut with a scalpel into rings of about 1 to 2 mm length. The rings were washed intensively (at least five times) in Medium 199 (Invitrogen, Karlsruhe, Germany) and then placed in wells of a 24-well plate, containing 450 µl of collagen solution per well. This collagen solution was prepared by mixing 9 ml rat tail collagen (3 mg/ml in 0.1% acetic acid; Sigma, Deisenhofen, Germany) with 1.12 ml 10× Medium 199 (Invitrogen, Karlsruhe, Germany), 1.12 ml 10× collagen buffer (0.05 N NaOH, 200 mM HEPES, 260 mM $NaHCO_3$) and 0.6 ml 200 mM glutamine. The rings were oriented such that the trimmed edges were perpendicular to the bottom of the well. The collagen was allowed to solidify by incubating the plates for at least one hour at 37° C. Thereafter, 1 ml MCDB131-medium with additions (SDF-1 and Spiegelmers) was added per well. Rings were then incubated at 37° C. for six to seven days. As control for sprouting, the experiments were additionally done with VEGF (vascular endothelial growth factor).

Sprouting was documented by taking pictures with a digital camera. In some cases, rings were fixed by addition of 1 ml 10% paraformaldehyde and stored at 2-8° C. for further documentation. Pictures were analysed with the Scion Image image processing software. After calibration with the help of a picture taken from a stage micrometer, a line was drawn in a distance of 0.33 mm from one edge of a ring. A plot histogram along this line was generated by the software, histograms were printed and peaks (representing sprouts crossing the line) were counted. This number was taken as sprouting index. Four to 5 rings per condition were evaluated. Statistical analysis was performed with WinSTAT for Excel.

Results

It could be demonstrated that SDF-1 induces sprouting and that this effect could be blocked with human SDF-1-binding Spiegelmer 193-G2-012-5'-PEG. No blockage of SDF-1 induced sprouting was observed by the non-functional PEGylated Control Spiegelmer (FIGS. 31 and 32).

Example 10: Plasma Level of SDF-1 and Human SDF-1-Binding Spiegelmer 193-G2-012-5'-PEG Administered to Rats as Single Intravenous Bolus of Human SDF-1-Binding Spiegelmer 193-G2-012-5'-PEG To test whether the human SDF-1-binding Spiegelmer 193-G2-012-5'-PEG is functional in vivo, human SDF-1-binding Spiegelmer 193-G2-012-5'-PEG was administered into rats as an intravenous bolus and the plasma level of human SDF-1-binding Spiegelmer 193-G2-012-5'-PEG and of SDF-1 were determined. As control the SDF-1 plasma levels of untreated rats were determined.

Animals, Administration and Sample Collection

Human SDF-1-binding Spiegelmer 193-G2-012-5'-PEG was dissolved in PBS to a final concentration of 0.5 mg/ml and sterile filtered. Male Sprague Dawley rats (weight approximately 300 g) were administered with 1.0 mg/kg human SDF-1-binding Spiegelmer 193-G2-012-5'-PEG as single intravenous bolus. Blood samples were collected at several time points (as shown in FIG. 33) to follow the plasma clearance of human SDF-1-binding Spiegelmer 193-G2-012-5'-PEG.

Sandwich Hybridisation Assay for Quantification of Spiegelmer

The amount of human SDF-1-binding Spiegelmer 193-G2-012-5'-PEG in the samples was quantified by a sandwich hybridisation assay. The principle of the sandwich hybridisation assay is quite similar to a commonly used ELISA (enzyme-linked immunosorbent assay): immobilization and detection of the Spiegelmer. The detection is based on the hybridisation of a biotinylated detect probe to one end of the Spiegelmer. The remaining single-stranded end of the Spiegelmer mediates immobilization of the complex upon hybridisation to an immobilized capture probe. After unbound complexes have been removed, the detect probe hybridised to the Spiegelmer is finally detected by a streptavidin/alkaline phosphatase conjugate converting a chemiluminescence substrate. Such a sandwich hybridisation assay was also applied to detection and quantification of an RNA aptamer as described by Drolet et al. (Drolet et al., 2000).

Hybridisation Plate Preparation

The 193-G2-012 capture probe (SEQ ID NO:240) was immobilized to white DNA-BIND 96-well plates (Corning Costar, Wiesbaden, Germany) at 100 nM in 0.5 M sodium phosphate, 1 mM EDTA, pH 8.5 over night at 4° C. Wells were washed twice and blocked with 0.5% w/v BSA in 0.25 M sodium phosphate, 0.5 mM EDTA, pH 8.5 for 2 h at 25° C., washed again and stored at room temperature until use. Prior to hybridisation, plates were washed twice with wash buffer (3×SSC, 0.5% [w/v] sodium dodecyl sarcosinate, pH 7.0; in advance a 20× stock [3 M NaCl, 0.3 M Na$_3$Citrate] is prepared without sodium lauroylsarcosine and diluted accordingly).

Sample Preparation

All samples were assayed in duplicates. Plasma samples were thawed on ice, vortexed and spun down briefly in a cooled tabletop centrifuge. Tissue homogenates were thawed at RT and centrifuged 5 min at maximum speed and RT. Samples were diluted with hybridisation buffer (40 nM 193-G2-012 detection probe [SEQ ID NO:241] in wash buffer) at RT according to the following scheme:

| | | |
|---|---|---|
| 1:10 | 10 µl sample | +90 µl hybridisation buffer and |
| 1:100 | 20 µl 1:10 | +180 µl hybridisation buffer. |

All sample dilutions were assayed. Human SDF-1-binding Spiegelmer 193-G2-012-5'-PEG standard was serial diluted to a 12-point calibration curve spanning the 0.001-40 nM range. Calibration standard was identical to that of the in-study samples.

Hybridisation and Detection

Samples were heated for 5 min at 95° C. and cooled to room temperature. Spiegelmer/detection probe complexes were annealed to immobilized capture probes for 45 min at 25° C. at 500 rpm on a shaker. Unbound Spiegelmers were removed by washing twice with wash buffer and 1× TBST (20 mM Tris-Cl, 137 mM NaCl, 0.1% Tween 20, pH 7.5), respectively. Hybridized complexes were detected by streptavidin alkaline phosphatase diluted 1:5000 in 1× TBST for 1 h at 25° C. at 500 rpm on a shaker. To remove unbound conjugate, wells were washed again with 1× TBST. Wells were finally filled with 100 ml CSDP substrate (Applied Biosystems, Darmstadt, Germany) and incubated for 45 min at 25° C. Chemiluminescence was measured on a FLUOstar Optima microplate reader (BMG Labtechnologies, Offenburg, Germany).

Data Analysis

The following assayed sample dilutions were used for quantitative data analysis: rat EDTA plasma 1:100

The data obtained from the vehicle group (no Spiegelmer was administered) was subtracted as background signal.

ELISA for Quantification of Spiegelmer

The amount of SDF-1 present in the plasma samples was quantified with an in vitro enzyme-linked immunosorbent assay which employs an antibody specific for human SDF-1α coated on a 96-well plate (Human SDF-1α ELISA kit; RayBiotech, Norcross Ga., USA). The assay was performed according to the instructions of the vendor.

Results

As shown in FIG. 33, the regular plasma level of SDF-1 in untreated rats is in the low picomolar range (approximately 50 pM). By contrast, the plasma level of rats that were treated with human SDF-1-binding Spiegelmer 193-G2-012-5'-PEG looks different: within the first eight hours after administration of human SDF-1-binding Spiegelmer, 193-G2-012-5'-PEG the SDF-1 plasma level increased to approximately 700 pM. Between 12 and 72 hours the SDF-1 plasma level decreased down to approximately 50 pM again. This time course of SDF-1 plasma level can be directly correlated with the plasma level of human SDF-1-binding Spiegelmer 193-G2-012-5'-PEG. Because of renal elimination of human SDF-1-binding Spiegelmer 193-G2-012-5'-PEG, the plasma level of human SDF-1-binding Spiegelmer 193-G2-012-5'-PEG decreased from approximately 1100 nM to below 50 nM within 72 hours. However, human SDF-1-binding Spiegelmer 193-G2-012-5'-PEG (MW approximately 54000 Da) was not eliminated out of the body within an hour as can be seen for non-PEGylated Spiegelmers (approximately 15000 Da) or other molecules with a molecular mass below the filtration limit of the kidney like SDF-1. The endogenous SDF-1 was bound by human SDF-1-binding Spiegelmer 193-G2-012-5'-PEG, forming SDF-1-Spiegelmer-complexes whereby the elimination and/or degradation of SDF-1 was retarded what as consequence led to elevated SDF-1 plasma levels within the first eight hours. Due to proceeding elimination of human SDF-1-binding Spiegelmer 193-G2-012-5'-PEG over time—whereby the elimination rate is much slower than for much smaller molecules like SDF-1—the plasma level of the complexes formed by human SDF-1-binding Spiegelmer 193-G2-012-5'-PEG and SDF-1 decreased (FIG. 33).

REFERENCES

The complete bibliographic data of the documents recited herein are, if not indicated to the contrary, as follows, whereby the disclosure of said references is incorporated herein by reference.

Aiuti, A., I. J. Webb et al. (1997). "The chemokine SDF-1 is a chemoattractant for human CD34+ hematopoietic progenitor cells and provides a new mechanism to explain the mobilization of CD34+ progenitors to peripheral blood." J Exp Med 185(1): 111-20.

Altschul S F, Gish W, Miller W, Myers E W, Lipman D J (1990), Basic local alignment search tool. J Mol Biol. 215(3):403-10.

Altschul S F, Madden T L, Schaffer A A, Zhang J, Zhang Z, Miller W, Lipman D J (1997). Gapped BLAST and PSI-BLAST: a new generation of protein database search programs. Nucleic Acids Res. 25(17):3389-402.

Ambati, J., A. Anand et al. (2003). An animal model of age-related macular degeneration in senescent Ccl-2- or Ccr-2-deficient mice. Nat Med. 9: 1390-7.

Arya, S. K., C. C. Ginsberg et al. (1999). "In vitro phenotype of SDF1 gene mutant that delays the onset of human immunodeficiency virus disease in vivo." J Hum Virol 2(3): 133-8.

Auerbach et al. (2003) Angiogenesis assays: a critical overview. Clin. Chem. 49: 32-40.

Baggiolini, M. (1998). "Chemokines and leukocyte traffic." Nature 392(6676): 565-8.

Baggiolini, M., B. Dewald et al. (1994). "Interleukin-8 and related chemotactic cytokines—CXC and CC chemokines." Adv Immunol 55: 97-179.

Balabanian, K., B. Lagane et al. (2005). "WHIM syndromes with different genetic anomalies are accounted for by impaired CXCR4 desensitization to CXCL12." Blood 105(6): 2449-57.

Balabanian, K., J. Couderc et al. (2003). "Role of the chemokine stromal cell-derived factor 1 in autoantibody production and nephritis in murine lupus." J Immunol 170(6): 3392-400.

Balkwill, F. (2004). "Cancer and the chemokine network." Nat Rev Cancer 4(7): 540-50.

Bazan, J. F., K. B. Bacon et al. (1997). "A new class of membrane-bound chemokine with a CX3C motif." Nature 385(6617): 640-4.

Bertolini, F., C. Dell'Agnola et al. (2002). "CXCR4 neutralization, a novel therapeutic approach for non-Hodgkin's lymphoma." Cancer Res 62(11): 3106-12.

Bleul, C. C., J. L. Schultze et al. (1998). "B lymphocyte chemotaxis regulated in association with microanatomic localization, differentiation state, and B cell receptor engagement." J Exp Med 187(5): 753-62.

Bleul, C. C., M. Farzan et al. (1996). "The lymphocyte chemoattractant SDF-1 is a ligand for LESTR/fusin and blocks HIV-1 entry." Nature 382(6594): 829-33.

Brooks, H. L., Jr., S. Caballero, Jr. et al. (2004). "Vitreous levels of vascular endothelial growth factor and stromal-derived factor 1 in patients with diabetic retinopathy and cystoid macular edema before and after intraocular injection of triamcinolone." Arch Ophthalmol 122(12): 1801-7.

Buckley, C. D., N. Amft et al. (2000). "Persistent induction of the chemokine receptor CXCR4 by TGF-beta 1 on synovial T cells contributes to their accumulation within the rheumatoid synovium." J Immunol 165(6): 3423-9.

Burger, J. A., N. Tsukada et al. (2000). "Blood-derived nurse-like cells protect chronic lymphocytic leukemia B cells from spontaneous apoptosis through stromal cell-derived factor-1." Blood 96(8): 2655-63.

Butler, J. M., S. M. Guthrie et al. (2005). "SDF-1 is both necessary and sufficient to promote proliferative retinopathy." J Clin Invest 115(1): 86-93.

Cabioglu, N., A. Sahin et al. (2005). "Chemokine receptor CXCR4 expression in breast cancer as a potential predictive marker of isolated tumor cells in bone marrow." Clin Exp Metastasis 22(1): 39-46.

Corcione, A., L. Ottonello et al. (2000). "Stromal cell-derived factor-1 as a chemoattractant for follicular center lymphoma B cells." J Natl Cancer Inst 92(8): 628-35.

Crump, M. P., J. H. Gong et al. (1997). "Solution structure and basis for functional activity of stromal cell-derived factor-1; dissociation of CXCR4 activation from binding and inhibition of HIV-1." Embo J 16(23): 6996-7007.

D'Apuzzo, M., A. Rolink et al. (1997). "The chemokine SDF-1, stromal cell-derived factor 1, attracts early stage B cell precursors via the chemokine receptor CXCR4." Eur J Immunol 27(7): 1788-93.

De Klerck, B., L. Geboes et al. (2005). "Pro-inflammatory properties of stromal cell-derived factor-1 (CXCL12) in collagen-induced arthritis." Arthritis Res Ther 7(6): R1208-20.

Drolet D W, Nelson J, Tucker C E, Zack P M, Nixon K, Bolin R, Judkins M B, Farmer J A, Wolf J L, Gill S C, Bendele R A (2000). Pharmacokinetics and safety of an anti-vascular endothelial growth factor aptamer (NX1838) following injection into the vitreous humor of rhesus monkeys. Pharm. Res. 17:1503

Eaton, B. E., L. Gold et al. (1997). "Post-SELEX combinatorial optimization of aptamers." Bioorg Med Chem 5(6): 1087-96.

Fedyk, E. R., D. Jones et al. (2001). "Expression of stromal-derived factor-1 is decreased by IL-1 and TNF and in dermal wound healing." J Immunol 166(9): 5749-54.

Fong, D. S., L. P. Aiello et al. (2004). "Diabetic retinopathy." Diabetes Care 27(10): 2540-53.

Geminder, H., O. Sagi-Assif et al. (2001). "A possible role for CXCR4 and its ligand, the CXC chemokine stromal cell-derived factor-1, in the development of bone marrow metastases in neuroblastoma." J Immunol 167(8): 4747-57.

Godessart, N. (2005). "Chemokine receptors: attractive targets for drug discovery." Ann N Y Acad Sci 1051: 647-57.

Grassi, F., S. Cristino et al. (2004). "CXCL12 chemokine up-regulates bone resorption and MMP-9 release by human osteoclasts: CXCL12 levels are increased in synovial and bone tissue of rheumatoid arthritis patients." J Cell Physiol 199(2): 244-51.

Grunewald, M., I. Avraham et al. (2006). "VEGF-induced adult neovascularization: recruitment, retention, and role of accessory cells." Cell 124(1): 175-89.

Guleng, B., K. Tateishi et al. (2005). "Blockade of the stromal cell-derived factor-1/CXCR4 axis attenuates in vivo tumor growth by inhibiting angiogenesis in a vascular endothelial growth factor-independent manner." Cancer Res 65(13): 5864-71.

Gulino, A. V., D. Moratto et al. (2004). "Altered leukocyte response to CXCL12 in patients with warts hypogammaglobulinemia, infections, myelokathexis (WHIM) syndrome." Blood 104(2): 444-52.

Hartmann, T. N., M. Burger et al. (2004). "The role of adhesion molecules and chemokine receptor CXCR4 (CD184) in small cell lung cancer." J Biol Regul Homeost Agents 18(2): 126-30.

Hwang, J. H., H. K. Chung et al. (2003). "CXC chemokine receptor 4 expression and function in human anaplastic thyroid cancer cells." J Clin Endocrinol Metab 88(1): 408-16.

Jiang, W., P. Zhou et al. (1994). "Molecular cloning of TPAR1, a gene whose expression is repressed by the tumor promoter 12-O-tetradecanoylphorbol 13-acetate (TPA)." Exp Cell Res 215(2): 284-93.

Jose, P. J., D. A. Griffiths-Johnson et al. (1994). "Eotaxin: a potent eosinophil chemoattractant cytokine detected in a guinea pig model of allergic airways inflammation." J Exp Med 179(3): 881-7.

Juarez, J. and L. Bendall (2004). "SDF-1 and CXCR4 in normal and malignant hematopoiesis." Histol Histopathol 19(1): 299-309.

Kanbe, K., K. Takagishi et al. (2002). "Stimulation of matrix metalloprotease 3 release from human chondrocytes by the interaction of stromal cell-derived factor 1 and CXC chemokine receptor 4." Arthritis Rheum 46(1): 130-7.

Kang, H., G. Watkins et al. (2005). "Stromal cell derived factor-1: its influence on invasiveness and migration of breast cancer cells in vitro, and its association with prognosis and survival in human breast cancer." Breast Cancer Res 7(4): R402-10.

Kawai, T., U. Choi et al. (2005). "Enhanced function with decreased internalization of carboxy-terminus truncated CXCR4 responsible for WHIM syndrome." Exp Hematol 33(4): 460-8.

Koshiba, T., R. Hosotani et al. (2000). "Expression of stromal cell-derived factor 1 and CXCR4 ligand receptor system in pancreatic cancer: a possible role for tumor progression." Clin Cancer Res 6(9): 3530-5.

Krumbholz, M., D. Theil et al. (2006). "Chemokines in multiple sclerosis: CXCL12 and CXCL13 up-regulation is differentially linked to CNS immune cell recruitment." Brain 129: 200-211.

Kryczek, I., A. Lange et al. (2005). "CXCL12 and vascular endothelial growth factor synergistically induce neoangiogenesis in human ovarian cancers." Cancer Res 65(2): 465-72.

Kucia, M., R. Reca et al. (2005). "Trafficking of normal stem cells and metastasis of cancer stem cells involve similar mechanisms: pivotal role of the SDF-1-CXCR4 axis." Stem Cells 23(7): 879-94.

Kusser, W. (2000). "Chemically modified nucleic acid aptamers for in vitro selections: evolving evolution." J Biotechnol 74(1): 27-38.

Lapteva, N., A. G. Yang et al. (2005). "CXCR4 knockdown by small interfering RNA abrogates breast tumor growth in vivo." Cancer Gene Ther 12(1): 84-9.

M. J. Damha, K. K. Ogilvie, Methods in Molecular Biology, Vol. 20 Protocols for oligonucleotides and analogs, ed. S. Agrawal, p. 81-114, Humana Press Inc. 1993

Ma, Q., D. Jones et al. (1998). "Impaired B-lymphopoiesis, myelopoiesis, and derailed cerebellar neuron migration in CXCR4- and SDF-1-deficient mice." Proc Natl Acad Sci USA 95(16): 9448-53.

Marechal, V., F. Arenzana-Seisdedos et al. (1999). "Opposite effects of SDF-1 on human immunodeficiency virus type 1 replication." J Virol 73(5): 3608-15.

Matthys, P., S. Hatse et al. (2001). "AMD3100, a potent and specific antagonist of the stromal cell-derived factor-1 chemokine receptor CXCR4, inhibits autoimmune joint inflammation in IFN-gamma receptor-deficient mice." J Immunol 167(8): 4686-92.

McGinnis S, Madden T L (2004). BLAST: at the core of a powerful and diverse set of sequence analysis tools. Nucleic Acids Res. 32(Web Server issue):W20-5.

Meleth, A. D., E. Agron et al. (2005). "Serum inflammatory markers in diabetic retinopathy." Invest Ophthalmol Vis Sci 46(11): 4295-301.

Menu, E., K. Asosingh et al. (2006). "The involvement of stromal derived factor 1alpha in homing and progression of multiple myeloma in the 5TMM model." Haematologica.

Miller, M. D. and M. S. Krangel (1992). "Biology and biochemistry of the chemokines: a family of chemotactic and inflammatory cytokines." Crit Rev Immunol 12(1-2): 17-46.

Moser, B., M. Wolf et al. (2004). "Chemokines: multiple levels of leukocyte migration control." Trends Immunol 25(2): 75-84.

Muller, A., B. Homey et al. (2001). "Involvement of chemokine receptors in breast cancer metastasis." Nature 410(6824): 50-6.

Murdoch, C. (2000). "CXCR4: chemokine receptor extraordinaire." Immunol Rev 177: 175-84.

Murphy, P. M., M. Baggiolini et al. (2000). "International union of pharmacology. XXII. Nomenclature for chemokine receptors." Pharmacol Rev 52(1): 145-76.

Nagasawa, T., H. Kikutani et al. (1994). "Molecular cloning and structure of a pre-B-cell growth-stimulating factor." Proc Natl Acad Sci USA 91(6): 2305-9.

Nagasawa, T., S. Hirota et al. (1996). "Defects of B-cell lymphopoiesis and bone-marrow myelopoiesis in mice lacking the CXC chemokine PBSF/SDF-1." Nature 382 (6592): 635-8.

Needleman & Wunsch (1970), A general method applicable to the search for similarities in the amino acid sequence of two proteins. J Mol Biol. 48(3):443-53.

Oppenheim, J. J., C. O. Zachariae et al. (1991). "Properties of the novel proinflammatory supergene "intercrine" cytokine family." Annu Rev Immunol 9: 617-48.

Orimo, A., P. B. Gupta et al. (2005). "Stromal fibroblasts present in invasive human breast carcinomas promote tumor growth and angiogenesis through elevated SDF-1/CXCL12 secretion." Cell 121(3): 335-48.

Pearson & Lipman (1988), Improved tools for biological sequence comparison. Proc. Nat'l. Acad. Sci. USA 85: 2444

Perissinotto, E., G. Cavalloni et al. (2005). "Involvement of chemokine receptor 4/stromal cell-derived factor 1 system during osteosarcoma tumor progression." Clin Cancer Res 11(2 Pt 1): 490-7.

Phillips, R. J., M. D. Burdick et al. (2003). "The stromal derived factor-1/CXCL12-CXC chemokine receptor 4 biological axis in non-small cell lung cancer metastases." Am J Respir Crit Care Med 167(12): 1676-86.

Ponath, P. D., S. Qin et al. (1996). "Cloning of the human eosinophil chemoattractant, eotaxin. Expression, receptor binding, and functional properties suggest a mechanism for the selective recruitment of eosinophils." J Clin Invest 97(3): 604-12.

Rubin, J. B., A. L. Kung et al. (2003). "A small-molecule antagonist of CXCR4 inhibits intracranial growth of primary brain tumors." Proc Natl Acad Sci USA 100(23): 13513-8.

Salcedo et al. (1999) Vascular endothelial growth factor and basic fibroblast growth factor induce expression of CXCR4 on human endothelial cells. In vivo neovascularization induced by stromal-derived factor-1a. Am. J. Pathol. 154:1125-1135.

Salcedo, R. and J. J. Oppenheim (2003). "Role of chemokines in angiogenesis: CXCL12/SDF-1 and CXCR4 interaction, a key regulator of endothelial cell responses." Microcirculation 10(3-4): 359-70.

Salcedo, R., K. Wasserman et al. (1999). "Vascular endothelial growth factor and basic fibroblast growth factor induce expression of CXCR4 on human endothelial cells: In vivo neovascularization induced by stromal-derived factor-1alpha." Am J Pathol 154(4): 1125-35.

Salvucci, O., L. Yao et al. (2002). "Regulation of endothelial cell branching morphogenesis by endogenous chemokine stromal-derived factor-1." Blood 99(8): 2703-11.

Saur, D., B. Seidler et al. (2005). "CXCR4 expression increases liver and lung metastasis in a mouse model of pancreatic cancer." Gastroenterology 129(4): 1237-50.

Schall, T. J. and K. B. Bacon (1994). "Chemokines, leukocyte trafficking, and inflammation." Curr Opin Immunol 6(6): 865-73.

Scotton, C. J., J. L. Wilson et al. (2002). "Multiple actions of the chemokine CXCL12 on epithelial tumor cells in human ovarian cancer." Cancer Res 62(20): 5930-8.

Sengupta, N., S. Caballero et al. (2005). "Preventing stem cell incorporation into choroidal neovascularization by targeting homing and attachment factors." Invest Ophthalmol Vis Sci 46(1): 343-8.

Shirozu, M., T. Nakano et al. (1995). "Structure and chromosomal localization of the human stromal cell-derived factor 1 (SDF1) gene." Genomics 28(3): 495-500.

Smith & Waterman (1981), Adv. Appl. Math. 2: 482

Soriano, A., C. Martinez et al. (2002). "Plasma stromal cell-derived factor (SDF)-1 levels, SDF1-3'A genotype, and expression of CXCR4 on T lymphocytes: their impact on resistance to human immunodeficiency virus type 1 infection and its progression." J Infect Dis 186(7): 922-31.

Springer, T. A. (1995). "Traffic signals on endothelium for lymphocyte recirculation and leukocyte emigration." Annu Rev Physiol 57: 827-72.

Sun, Y. X., A. Schneider et al. (2005). "Skeletal localization and neutralization of the SDF-1(CXCL12)/CXCR4 axis blocks prostate cancer metastasis and growth in osseous sites in vivo." J Bone Miner Res 20(2): 318-29.

Takenaga, M., H. Tamamura et al. (2004). "A single treatment with microcapsules containing a CXCR4 antagonist suppresses pulmonary metastasis of murine melanoma." Biochem Biophys Res Commun 320(1): 226-32.

Tamamura, H., M. Fujisawa et al. (2004). "Identification of a CXCR4 antagonist, a T140 analog, as an anti-rheumatoid arthritis agent." FEBS Lett 569(1-3): 99-104.

Tashiro, K., H. Tada et al. (1993). "Signal sequence trap: a cloning strategy for secreted proteins and type I membrane proteins." Science 261(5121): 600-3.

Venkatesan, N., S. J. Kim et al. (2003). "Novel phosphoramidite building blocks in synthesis and applications toward modified oligonucleotides." Curr Med Chem 10(19): 1973-91.

Wang, J., E. Guan et al. (2001). "Role of tyrosine phosphorylation in ligand-independent sequestration of CXCR4 in human primary monocytes-macrophages." J Biol Chem 276(52): 49236-43.

Wang, N., Q. L. Wu et al. (2005). "Expression of chemokine receptor CXCR4 in nasopharyngeal carcinoma: pattern of expression and correlation with clinical outcome." J Transl Med 3: 26.

Wincott F, DiRenzo A, Shaffer C, Grimm S, Tracz D, Workman C, Sweedler D, Gonzalez C, Scaringe S, Usman N (1995). Synthesis, deprotection, analysis and purification of RNA and ribozymes. Nucleic Acids Res. 23(14): 2677-84

Yamaguchi, J., K. F. Kusano et al. (2003). "Stromal cell-derived factor-1 effects on ex vivo expanded endothelial progenitor cell recruitment for ischemic neovascularization." Circulation 107(9): 1322-8.

Yasumoto, K., K. Koizumi et al. (2006). "Role of the CXCL12/CXCR4 axis in peritoneal carcinomatosis of gastric cancer." Cancer Res 66(4): 2181-7.

Zeelenberg, I. S., L. Ruuls-Van Stalle et al. (2001). "Retention of CXCR4 in the endoplasmic reticulum blocks dissemination of a T cell hybridoma." J Clin Invest 108(2): 269-77.

Zeelenberg, I. S., L. Ruuls-Van Stalle et al. (2003). "The chemokine receptor CXCR4 is required for outgrowth of colon carcinoma micrometastases." Cancer Res 63(13): 3833-9.

Zhou, Y., P. H. Larsen et al. (2002). "CXCR4 is a major chemokine receptor on glioma cells and mediates their survival." J Biol Chem 277(51): 49481-7.

Zou, Y. R., A. H. Kottmann et al. (1998). "Function of the chemokine receptor CXCR4 in haematopoiesis and in cerebellar development." Nature 393(6685): 595-9.

The features of the present invention disclosed in the specification, the claims and/or the drawings may both separately and in any combination thereof be material for realizing the invention in various forms thereof.

All references cited herein are herein incorporated by reference in entirety.

---

The invention claimed is:

1. An L-nucleic acid molecule, or a homolog thereof, wherein the L-nucleic acid molecule comprises SEQ ID NO:117 and said homolog comprises homology to SEQ ID NO:117 of at least 85%, and wherein said L-nucleic acid molecule and said homolog bind SDF-1.

2. The L-nucleic acid molecule according to claim 1, wherein said SDF-1 comprises a human SDF-1.

3. The L-nucleic acid molecule according to claim 1, wherein the L-nucleic acid molecule is an antagonist of an SDF-1.

4. The L-nucleic acid according to claim 1, further comprising a modification.

5. The L-nucleic acid according to claim 4, wherein said modification comprises a hydroxyl ethyl starch (HES) moiety or a polyethylene glycol (PEG) moiety.

6. The L-nucleic acid according to claim 4, wherein said modification consists of a straight or a branched PEG moiety.

7. The L-nucleic acid according to claim 6, wherein said straight or said branched PEG moiety comprises a molecular weight from 2 to 180 kD.

8. The L-nucleic acid according to claim 5, wherein said HES moiety comprises a molecular weight from 10 to 130 kD.

9. A pharmaceutical composition comprising the L-nucleic acid according to claim 1 and a pharmaceutically acceptable excipient, a pharmaceutically active agent or combination thereof.

10. The L-nucleic acid molecule according to claim 4, wherein said modification is at the 5' end of the L-nucleic acid molecule or the homolog.

11. The L-nucleic acid molecule according to claim 4, wherein said modification is at the 3' end of the L-nucleic acid molecule or the homolog.

12. The L-nucleic acid molecule according to claim 6, wherein said straight or said branched PEG moiety comprises a molecular weight from 40 kD to 120 kD.

13. The L-nucleic acid molecule according to claim 1, further comprising a linker.

14. The L-nucleic acid molecule according to claim 4, wherein said modification comprises a biotin.

* * * * *

SEQUENCE LISTING

```
<160> NUMBER OF SEQ ID NOS: 241

<210> SEQ ID NO 1
<211> LENGTH: 68
<212> TYPE: PRT
<213> ORGANISM: Homo sapiens

<400> SEQUENCE: 1

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 2
<211> LENGTH: 72
<212> TYPE: PRT
<213> ORGANISM: Homo sapiens

<400> SEQUENCE: 2

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45
```

Val Cys Ile Asp Pro Lys Leu Lys Trp Ile Gln Glu Tyr Leu Glu Lys
    50                  55                  60

Ala Leu Asn Lys Arg Phe Lys Met
65                  70

<210> SEQ ID NO 3
<211> LENGTH: 68
<212> TYPE: PRT
<213> ORGANISM: Mus musculus

<400> SEQUENCE: 3

Lys Pro Val Ser Leu Ser Tyr Arg Cys Pro Cys Arg Phe Phe Glu Ser
1               5                   10                  15

His Ile Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 4
<211> LENGTH: 71
<212> TYPE: PRT
<213> ORGANISM: Homo sapiens
<220> FEATURE:
<221> NAME/KEY: misc_feature
<222> LOCATION: (1)..(71)
<223> OTHER INFORMATION: D-peptide
<220> FEATURE:
<221> NAME/KEY: misc_feature
<222> LOCATION: (71)..(71)
<223> OTHER INFORMATION: biotinylated

<400> SEQUENCE: 4

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys
65                  70

<210> SEQ ID NO 5
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA

<400> SEQUENCE: 5
gcugugaaag caacauguca augaaaggua gccgcagc                           38

```
<210> SEQ ID NO 6
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA

<400> SEQUENCE: 6
gcugugaaag uaacauguca augaaaggua accacagc                              38

<210> SEQ ID NO 7
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA

<400> SEQUENCE: 7
gcugugaaag uaacacguca augaaaggua accgcagc                              38

<210> SEQ ID NO 8
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: L-RNA
<222> LOCATION: (1)..(38)
<223> OTHER INFORMATION:
<220> FEATURE:
<221> NAME/KEY: misc_feature
<222> LOCATION: (1)..(38)
<223> OTHER INFORMATION: L-RNA

<400> SEQUENCE: 8
gcugugaaag uaacacguca augaaaggua accacagc                              38

<210> SEQ ID NO 9
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: L-RNA
<222> LOCATION: (1)..(38)
<223> OTHER INFORMATION:
<220> FEATURE:
<221> NAME/KEY: misc_feature
<222> LOCATION: (1)..(38)
<223> OTHER INFORMATION: L-RNA

<400> SEQUENCE: 9
gcuguaaaag uaacauguca augaaaggua acuacagc                              38

<210> SEQ ID NO 10
<211> LENGTH: 38
<212> TYPE: RNA
<213> ORGANISM: Artificial
<220> FEATURE:
<221> NAME/KEY: L-RNA
<222> LOCATION: (1)..(38)
```

```
<223> OTHER INFORMATION:
<220> FEATURE:
<221> NAME/KEY: misc_feature
<222> LOCATION: (1)..(38)
<223> OTHER INFORMATION: L-RNA

<400> SEQUENCE: 10
gcuguaaaag uaacaaguca augaaaggua acuacagc                              38

<210> SEQ ID NO 11
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: L-RNA
<222> LOCATION: (1)..(38)
<223> OTHER INFORMATION:

<400> SEQUENCE: 11
gcugugaaag uaacaaguca augaaaggua accacagc                              38

<210> SEQ ID NO 12
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA

<400> SEQUENCE: 12
gcagugaaag uaacauguca augaaaggua accacagc                              38

<210> SEQ ID NO 13
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: L-RNA
<222> LOCATION: (1)..(38)
<223> OTHER INFORMATION:

<400> SEQUENCE: 13
gcugugaaag uaacauguca augaaaggua accacugc                              38

<210> SEQ ID NO 14
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA

<400> SEQUENCE: 14 gcaugaaag uaacauguca augaaaggua accauagc                               38

<210> SEQ ID NO 15
<211> LENGTH: 38
<212> TYPE: RNA
<213> ORGANISM: Artificial Sequence
```

```
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA

<400> SEQUENCE: 15
gcugcgaaag cgacauguca augaaaggua gccgcagc                              38

<210> SEQ ID NO 16
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: L-RNA
<222> LOCATION: (1)..(38)
<223> OTHER INFORMATION:
<220> FEATURE:
<221> NAME/KEY: misc_feature
<222> LOCATION: (1)..(38)
<223> OTHER INFORMATION: L-RNA

<400> SEQUENCE: 16
gcugugaaag caacauguca augaaaggua gccacagc                              38

<210> SEQ ID NO 17
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA

<400> SEQUENCE: 17
gcugugaaag uaacauguca augaaaggua gccgcagc                              38

<210> SEQ ID NO 18
<211> LENGTH: 39
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA

<400> SEQUENCE: 18
agcgugaaag uaacacguaa aaugaaaggu aaccacgcu                             39

<210> SEQ ID NO 19
<211> LENGTH: 27
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(27)
<223> OTHER INFORMATION: L-RNA
<220> FEATURE:
<221> NAME/KEY: misc_feature
<222> LOCATION: (16)..(16)
<223> OTHER INFORMATION: A or absent
```

```
<400> SEQUENCE: 19
aaagyracah gumaaaugaa agguarc                                27

<210> SEQ ID NO 20
<211> LENGTH: 26
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(26)
<223> OTHER INFORMATION: L-RNA

<400> SEQUENCE: 20
aaagyracah gumaaugaaa gguarc                                 26

<210> SEQ ID NO 21
<211> LENGTH: 27
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(27)
<223> OTHER INFORMATION: L-RNA

<400> SEQUENCE: 21
aaagyracah gumaaaugaa agguarc                                27

<210> SEQ ID NO 22
<211> LENGTH: 26
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(26)
<223> OTHER INFORMATION: L-RNA

<400> SEQUENCE: 22
aaagyaacah gucaaugaaa gguarc                                 26

<210> SEQ ID NO 23
<211> LENGTH: 6
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA

<400> SEQUENCE: 23 rshryr                                                        6

<210> SEQ ID NO 24
<211> LENGTH: 6
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
```

-continued

<400> SEQUENCE: 24 yrydsy                                                                    6

<210> SEQ ID NO 25
<211> LENGTH: 36
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(36)
<223> OTHER INFORMATION: L-RNA

<400> SEQUENCE: 25
cugugaaagc aacaugucaa ugaaagguag ccgcag                                  36

<210> SEQ ID NO 26
<211> LENGTH: 34
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-RNA

<400> SEQUENCE: 26
ugugaaagca acaugucaau gaaagguagc cgca                                    34

<210> SEQ ID NO 27
<211> LENGTH: 32
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(32)
<223> OTHER INFORMATION: L-RNA

<400> SEQUENCE: 27
gugaaagcaa caugucaaug aaagguagcc gc                                      32

<210> SEQ ID NO 28
<211> LENGTH: 30
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(30)
<223> OTHER INFORMATION: L-RNA

<400> SEQUENCE: 28
ugaaagcaac augucaauga aagguagccg                                         30

<210> SEQ ID NO 29
<211> LENGTH: 28
<212> TYPE: RNA
<213> ORGANISM: Artificial sequence
<220> FEATURE:
<223> OTHER INFORMATION: synthetic
<220> FEATURE:
<221> NAME/KEY: L-RNA
<222> LOCATION: (1)..(28)

```
<223> OTHER INFORMATION:

<400> SEQUENCE: 29
gaaagcaaca ugucaaugaa agguagcc                                           28

<210> SEQ ID NO 30
<211> LENGTH: 26
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(26)
<223> OTHER INFORMATION: L-RNA

<400> SEQUENCE: 30
aaagcaacau gucaaugaaa gguagc                                             26

<210> SEQ ID NO 31
<211> LENGTH: 36
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(36)
<223> OTHER INFORMATION: L-RNA

<400> SEQUENCE: 31
gcgugaaagc aacaugucaa ugaaagguag ccgcgc                                  36

<210> SEQ ID NO 32
<211> LENGTH: 36
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(36)
<223> OTHER INFORMATION: L-RNA

<400> SEQUENCE: 32
gcgcgaaagc aacaugucaa ugaaagguag ccgcgc                                  36

<210> SEQ ID NO 33
<211> LENGTH: 34
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-RNA

<400> SEQUENCE: 33
gcggaaagca acaugucaau gaaagguagc ccgc                                    34

<210> SEQ ID NO 34
<211> LENGTH: 34
<212> TYPE: RNA
<213> ORGANISM: Artificial sequence
<220> FEATURE:
<223> OTHER INFORMATION: synthetic
<220> FEATURE:
<221> NAME/KEY: misc_feature
```

```
<222> LOCATION: (1)..(34)
<223> OTHER INFORMATION: L-RNA

<400> SEQUENCE: 34
cgugaaagca acaugucaau gaaaggguagc cgcg                               34

<210> SEQ ID NO 35
<211> LENGTH: 34
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-RNA

<400> SEQUENCE: 35
gcgcaaagca acaugucaau gaaaggguagc gugc                               34

<210> SEQ ID NO 36
<211> LENGTH: 34
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-RNA

<400> SEQUENCE: 36
gugcaaagca acaugucaau gaaaggguagc gcgc                               34

<210> SEQ ID NO 37
<211> LENGTH: 34
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-RNA

<400> SEQUENCE: 37
cgcgaaagca acaugucaau gaaaggguagc cgug                               34

<210> SEQ ID NO 38
<211> LENGTH: 34
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-RNA

<400> SEQUENCE: 38
gggcaaagca acaugucaau gaaaggguagc gccc                               34

<210> SEQ ID NO 39
<211> LENGTH: 34
<212> TYPE: RNA
<213> ORGANISM: Artificial sequence
<220> FEATURE:
<223> OTHER INFORMATION: synthetic
<220> FEATURE:
```

<221> NAME/KEY: misc_feature
<222> LOCATION: (1)..(34)
<223> OTHER INFORMATION: L-RNA

<400> SEQUENCE: 39
ggccaaagca acaugucaau gaaagguagc ggcc                              34

<210> SEQ ID NO 40
<211> LENGTH: 34
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-RNA

<400> SEQUENCE: 40
gcccaaagca acaugucaau gaaagguagc gggc                              34

<210> SEQ ID NO 41
<211> LENGTH: 34
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(34)
<223> OTHER INFORMATION: L-RNA

<400> SEQUENCE: 41
ccccaaagca acaugucaau gaaagguagc gggg                              34

<210> SEQ ID NO 42
<211> LENGTH: 5
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA
<220> FEATURE:
<221> NAME/KEY: misc_feature
<222> LOCATION: (1)..(1)
<223> OTHER INFORMATION: s or absent

<400> SEQUENCE: 42 sbbbs                                                              5

<210> SEQ ID NO 43
<211> LENGTH: 5
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA
<220> FEATURE:
<221> NAME/KEY: misc_feature
<222> LOCATION: (5)..(5)
<223> OTHER INFORMATION: s or absent

<400> SEQUENCE: 43 sbbvs                                                              5

```
<210> SEQ ID NO 44
<211> LENGTH: 6
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: nucleotide = a, g, c or u
<220> FEATURE:
<221> NAME/KEY: misc_feature
<222> LOCATION: (4)..(4)
<223> OTHER INFORMATION: nucleotide = a, g, c or u
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (1)..(1)
<223> OTHER INFORMATION: R or absent
<220> FEATURE:
<221> NAME/KEY: misc_feature
<222> LOCATION: (2)..(2)
<223> OTHER INFORMATION: s or absent

<400> SEQUENCE: 44 rsnnbv                                                                    6

<210> SEQ ID NO 45
<211> LENGTH: 6
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (2)..(2)
<223> OTHER INFORMATION: nucleotide = a, g, c or u
<220> FEATURE:
<221> NAME/KEY: misc_feature
<222> LOCATION: (4)..(4)
<223> OTHER INFORMATION: nucleotide = a, g, c or u
<220> FEATURE:
<221> NAME/KEY: misc_feature
<222> LOCATION: (5)..(5)
<223> OTHER INFORMATION: R or absent
<220> FEATURE:
<221> NAME/KEY: misc_feature
<222> LOCATION: (6)..(6)
<223> OTHER INFORMATION: y or absent

<400> SEQUENCE: 45 bnbnry                                                                    6

<210> SEQ ID NO 46
<211> LENGTH: 47
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(47)
<223> OTHER INFORMATION: L-RNA

<400> SEQUENCE: 46
```
agcguggugu gaucuagaug uaguggcuga uccuagucag guacgcu        47

<210> SEQ ID NO 47
<211> LENGTH: 47
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(47)
<223> OTHER INFORMATION: L-RNA

<400> SEQUENCE: 47
agcguggugu gaucuagaug uauuggcuga uccuagucag guacgcu        47

<210> SEQ ID NO 48
<211> LENGTH: 47
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(47)
<223> OTHER INFORMATION: L-RNA

<400> SEQUENCE: 48
agcguggugu gaucuagaug uaauggcuga uccuagucag gugcgcu        47

<210> SEQ ID NO 49
<211> LENGTH: 45
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-RNA

<400> SEQUENCE: 49
gcgaggugug aucuagaugu aguggcugau ccuagucagg ugcgc        45

<210> SEQ ID NO 50
<211> LENGTH: 45
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-RNA

<400> SEQUENCE: 50
gcguggugug aucuagaugu aguggcugau ccuagucagg ugcgc        45

<210> SEQ ID NO 51
<211> LENGTH: 45
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-RNA

<400> SEQUENCE: 51
gcauggugug aucuagaugu aguggcugau ccuagucagg ugccc       45

<210> SEQ ID NO 52
<211> LENGTH: 45
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-RNA

<400> SEQUENCE: 52
gcguggugug aucuagaugu aauggcugau ccuagucagg gacgc       45

<210> SEQ ID NO 53
<211> LENGTH: 45
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-RNA

<400> SEQUENCE: 53
gcguggugug aucuagaugu agaggcugau ccuagucagg uacgc       45

<210> SEQ ID NO 54
<211> LENGTH: 45
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-RNA

<400> SEQUENCE: 54
gcguggugug aucuagaugu aaaggcugau ccuagucagg uacgc       45

<210> SEQ ID NO 55
<211> LENGTH: 45
<212> TYPE: RNA
<213> ORGANISM: Artificial sequence
<220> FEATURE:
<223> OTHER INFORMATION: synthetic
<220> FEATURE:
<221> NAME/KEY: L-RNA
<222> LOCATION: (1)..(45)
<223> OTHER INFORMATION:
<220> FEATURE:
<221> NAME/KEY: misc_feature
<222> LOCATION: (1)..(45)
<223> OTHER INFORMATION: L-RNA

<400> SEQUENCE: 55
gcguggugug aucuagaugu aguggcuguu ccuagucagg uaugc       45

<210> SEQ ID NO 56
<211> LENGTH: 45
<212> TYPE: RNA
<213> ORGANISM: Artificial sequence
<220> FEATURE:
<223> OTHER INFORMATION: synthetic
<220> FEATURE:

```
<221> NAME/KEY: misc_feature
<222> LOCATION: (1)..(45)
<223> OTHER INFORMATION: L-RNA

<400> SEQUENCE: 56
gcguggugug aucuagaugu aguggcugau ccuaguuagg uacgc          45

<210> SEQ ID NO 57
<211> LENGTH: 35
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(35)
<223> OTHER INFORMATION: L-RNA

<400> SEQUENCE: 57
gugugaucua gauguadwgg cugwuccuag uyagg                     35

<210> SEQ ID NO 58
<211> LENGTH: 35
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(35)
<223> OTHER INFORMATION: L-RNA

<400> SEQUENCE: 58
gugugaucua gauguadugg cugauccuag ucagg                     35

<210> SEQ ID NO 59
<211> LENGTH: 6
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (1)..(1)
<223> OTHER INFORMATION: A or absent

<400> SEQUENCE: 59 agcrwg                                                      6

<210> SEQ ID NO 60
<211> LENGTH: 6
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (6)..(6)
<223> OTHER INFORMATION: U or absent

<400> SEQUENCE: 60 kryscu                                                      6
```

<210> SEQ ID NO 61
<211> LENGTH: 45
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-RNA

<400> SEQUENCE: 61
gcguggugug aucuagaugu aguggcugau ccuagucagg uacgc          45

<210> SEQ ID NO 62
<211> LENGTH: 43
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(43)
<223> OTHER INFORMATION: L-RNA

<400> SEQUENCE: 62
cgugguguga ucuagaugua guggcugauc cuagucaggu acg            43

<210> SEQ ID NO 63
<211> LENGTH: 41
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(41)
<223> OTHER INFORMATION: L-RNA

<400> SEQUENCE: 63
guggugugau cuagauguag uggcugaucc uagucaggua c              41

<210> SEQ ID NO 64
<211> LENGTH: 39
<212> TYPE: RNA
<213> ORGANISM: Artificial sequence
<220> FEATURE:
<223> OTHER INFORMATION: synthetic
<220> FEATURE:
<221> NAME/KEY: L-RNA
<222> LOCATION: (1)..(39)
<223> OTHER INFORMATION:
<220> FEATURE:
<221> NAME/KEY: misc_feature
<222> LOCATION: (1)..(39)
<223> OTHER INFORMATION: L-RNA

<400> SEQUENCE: 64
uggugugauc uagauguagu ggcugauccu agucaggua                 39

<210> SEQ ID NO 65
<211> LENGTH: 37
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(37)

```
<223> OTHER INFORMATION: L-RNA

<400> SEQUENCE: 65
ggugugaucu agauguagug gcugauccua gucaggu                                    37

<210> SEQ ID NO 66
<211> LENGTH: 35
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(35)
<223> OTHER INFORMATION: L-RNA

<400> SEQUENCE: 66
gugugaucua gauguagugg cugauccuag ucagg                                      35

<210> SEQ ID NO 67
<211> LENGTH: 45
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-RNA

<400> SEQUENCE: 67
gcguggugug aucuagaugu auuggcugau ccuagucagg uacgc                           45

<210> SEQ ID NO 68
<211> LENGTH: 45
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-RNA

<400> SEQUENCE: 68
gcgcggugug aucuagaugu auuggcugau ccuagucagg cgcgc                           45

<210> SEQ ID NO 69
<211> LENGTH: 43
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(43)
<223> OTHER INFORMATION: L-RNA

<400> SEQUENCE: 69
gcgcguguga ucuagaugua uuggcugauc cuagucaggg cgc                             43

<210> SEQ ID NO 70
<211> LENGTH: 43
<212> TYPE: RNA
<213> ORGANISM: Artificial sequence
<220> FEATURE:
<223> OTHER INFORMATION: synthetic
<220> FEATURE:
<221> NAME/KEY: misc_feature
```

```
<222> LOCATION: (1)..(43)
<223> OTHER INFORMATION: L-RNA

<400> SEQUENCE: 70
gggcguguga ucuagaugua uuggcugauc cuagucaggg ccc                           43

<210> SEQ ID NO 71
<211> LENGTH: 43
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(43)
<223> OTHER INFORMATION: L-RNA

<400> SEQUENCE: 71
ggccguguga ucuagaugua uuggcugauc cuagucaggg gcc                           43

<210> SEQ ID NO 72
<211> LENGTH: 43
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(43)
<223> OTHER INFORMATION: L-RNA

<400> SEQUENCE: 72
gcccguguga ucuagaugua uuggcugauc cuagucaggg ggc                           43

<210> SEQ ID NO 73
<211> LENGTH: 5
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA
<220> FEATURE:
<221> NAME/KEY: misc_feature
<222> LOCATION: (1)..(1)
<223> OTHER INFORMATION: G or absent

<400> SEQUENCE: 73 gssbs                                                                      5

<210> SEQ ID NO 74
<211> LENGTH: 5
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA
<220> FEATURE:
<221> NAME/KEY: misc_feature
<222> LOCATION: (5)..(5)
<223> OTHER INFORMATION: C or absent

<400> SEQUENCE: 74 bvssc                                                                      5
```

```
<210> SEQ ID NO 75
<211> LENGTH: 6
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (1)..(1)
<223> OTHER INFORMATION: A or absent

<400> SEQUENCE: 75 agcgug                                                                    6

<210> SEQ ID NO 76
<211> LENGTH: 6
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (6)..(6)
<223> OTHER INFORMATION: U or absent

<400> SEQUENCE: 76 uacgcu                                                                    6

<210> SEQ ID NO 77
<211> LENGTH: 6
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
<220> FEATURE:
<221> NAME/KEY: misc_feature
<222> LOCATION: (1)..(1)
<223> OTHER INFORMATION: A or absent
<220> FEATURE:
<221> NAME/KEY: misc_feature
<222> LOCATION: (2)..(2)
<223> OTHER INFORMATION: G or absent
<220> FEATURE:
<221> NAME/KEY: misc_feature
<222> LOCATION: (5)..(5)
<223> OTHER INFORMATION: nucleotide = a, g, c or u

<400> SEQUENCE: 77 agsvns                                                                    6

<210> SEQ ID NO 78
<211> LENGTH: 6
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(6)
<223> OTHER INFORMATION: L-RNA
```

```
<220> FEATURE:
<221> NAME/KEY: misc_feature
<222> LOCATION: (5)..(5)
<223> OTHER INFORMATION: C or absent
<220> FEATURE:
<221> NAME/KEY: misc_feature
<222> LOCATION: (6)..(6)
<223> OTHER INFORMATION: U or absent

<400> SEQUENCE: 78 bvbscu                                                                       6

<210> SEQ ID NO 79
<211> LENGTH: 39
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-RNA

<400> SEQUENCE: 79
gugcugcggg gguuagggcu agaagucggc cugcagcac                                  39

<210> SEQ ID NO 80
<211> LENGTH: 39
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-RNA

<400> SEQUENCE: 80
agcguggcga gguuagggcu agaagucggu cgacacgcu                                  39

<210> SEQ ID NO 81
<211> LENGTH: 39
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-RNA

<400> SEQUENCE: 81
guguugcgga gguuagggcu agaagucggu cagcagcac                                  39

<210> SEQ ID NO 82
<211> LENGTH: 48
<212> TYPE: RNA
<213> ORGANISM: Artificial sequence
<220> FEATURE:
<223> OTHER INFORMATION: synthetic
<220> FEATURE:
<221> NAME/KEY: L-RNA
<222> LOCATION: (1)..(48)
<223> OTHER INFORMATION:

<400> SEQUENCE: 82
cgugcgcuug agauaggggu uagggcuuaa agucggcuga uucucacg                        48

<210> SEQ ID NO 83
```

```
<211> LENGTH: 39
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-RNA

<400> SEQUENCE: 83
agcgugaagg gguuagggcu cgaagucggc ugacacgcu                    39

<210> SEQ ID NO 84
<211> LENGTH: 39
<212> TYPE: RNA
<213> ORGANISM: Artificial sequence
<220> FEATURE:
<223> OTHER INFORMATION: synthetic
<220> FEATURE:
<221> NAME/KEY: L-RNA
<222> LOCATION: (1)..(39)
<223> OTHER INFORMATION:

<400> SEQUENCE: 84
gugcugcggg gguuagggcu cgaagucggc ccgcagcac                    39

<210> SEQ ID NO 85
<211> LENGTH: 39
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-RNA

<400> SEQUENCE: 85
guguucccgg gguuagggcu ugaagucggc cggcagcac                    39

<210> SEQ ID NO 86
<211> LENGTH: 39
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-RNA

<400> SEQUENCE: 86
guguugcagg gguuagggcu ugaagucggc cugcagcac                    39

<210> SEQ ID NO 87
<211> LENGTH: 39
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-RNA

<400> SEQUENCE: 87
gugcugcggg gguuagggcu caaagucggc cugcagcac                    39
```

```
<210> SEQ ID NO 88
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA

<400> SEQUENCE: 88
gugcugccgg gguuagggcu aaagucggcc gacagcac                              38

<210> SEQ ID NO 89
<211> LENGTH: 39
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(39)
<223> OTHER INFORMATION: L-RNA

<400> SEQUENCE: 89
gugcuguggg ggucagggcu agaagucggc cugcagcac                             39

<210> SEQ ID NO 90
<211> LENGTH: 19
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(19)
<223> OTHER INFORMATION: L-RNA
<220> FEATURE:
<221> NAME/KEY: misc_feature
<222> LOCATION: (13)..(13)
<223> OTHER INFORMATION: A or absent
<220> FEATURE:
<221> NAME/KEY: misc_feature
<222> LOCATION: (13)..(13)
<223> OTHER INFORMATION: A or absent

<400> SEQUENCE: 90
gguyagggcu hraagucgg                                                   19

<210> SEQ ID NO 91
<211> LENGTH: 19
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(19)
<223> OTHER INFORMATION: L-RNA

<400> SEQUENCE: 91
gguyagggcu hraagucgg                                                   19

<210> SEQ ID NO 92
<211> LENGTH: 18
<212> TYPE: RNA
<213> ORGANISM: Artificial sequence
<220> FEATURE:
<223> OTHER INFORMATION: synthetic
<220> FEATURE:
```

```
<221> NAME/KEY: misc_feature
<222> LOCATION: (1)..(18)
<223> OTHER INFORMATION: L-RNA

<400> SEQUENCE: 92
gguyagggcu hragucgg                                                        18

<210> SEQ ID NO 93
<211> LENGTH: 19
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(19)
<223> OTHER INFORMATION: L-RNA

<400> SEQUENCE: 93
gguuagggcu hgaagucgg                                                       19

<210> SEQ ID NO 94
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA

<400> SEQUENCE: 94
ugagauaggg guuagggcuu aaagucggcu gauucuca                                  38

<210> SEQ ID NO 95
<211> LENGTH: 36
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(36)
<223> OTHER INFORMATION: L-RNA

<400> SEQUENCE: 95
gagauagggg uuagggcuua aagucggcug auucuc                                    36

<210> SEQ ID NO 96
<211> LENGTH: 29
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA

<400> SEQUENCE: 96 ggggguuaggg cuuaaagucg gcugauucu                                           29

<210> SEQ ID NO 97
<211> LENGTH: 37
<212> TYPE: RNA
<213> ORGANISM: Artificial sequence
<220> FEATURE:
<223> OTHER INFORMATION: synthetic
```

```
<220> FEATURE:
<221> NAME/KEY: misc_feature
<222> LOCATION: (1)..(37)
<223> OTHER INFORMATION: L-RNA

<400> SEQUENCE: 97
gcguggcgag guuagggcua gaagucgguc gacacgc                                37

<210> SEQ ID NO 98
<211> LENGTH: 35
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(35)
<223> OTHER INFORMATION: L-RNA

<400> SEQUENCE: 98
cguggcgagg uuagggcuag aagucggucg acacg                                  35

<210> SEQ ID NO 99
<211> LENGTH: 33
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(33)
<223> OTHER INFORMATION: L-RNA

<400> SEQUENCE: 99
cgggcgaggu uagggcuaga agucggucga ccg                                    33

<210> SEQ ID NO 100
<211> LENGTH: 32
<212> TYPE: RNA
<213> ORGANISM: artificial sequence
<220> FEATURE:
<223> OTHER INFORMATION: synthetic
<220> FEATURE:
<221> NAME/KEY: misc_feature
<222> LOCATION: (1)..(32)
<223> OTHER INFORMATION: L-RNA

<400> SEQUENCE: 100
gggcgagguu agggcuagaa gucggucgcc cg                                     32

<210> SEQ ID NO 101
<211> LENGTH: 31
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(31)
<223> OTHER INFORMATION: L-RNA

<400> SEQUENCE: 101
cggcgagguu agggcuagaa gucggucgcc g                                      31

<210> SEQ ID NO 102
<211> LENGTH: 29
<212> TYPE: RNA
<213> ORGANISM: Artificial sequence
<220> FEATURE:
```

```
<223> OTHER INFORMATION: synthetic
<220> FEATURE:
<221> NAME/KEY: misc_feature
<222> LOCATION: (1)..(29)
<223> OTHER INFORMATION: L-RNA

<400> SEQUENCE: 102
cgggagguua gggcuagaag ucggucccg                                    29

<210> SEQ ID NO 103
<211> LENGTH: 27
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(27)
<223> OTHER INFORMATION: L-RNA

<400> SEQUENCE: 103
gggagguuag ggcuagaagu cgguccc                                      27

<210> SEQ ID NO 104
<211> LENGTH: 27
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(27)
<223> OTHER INFORMATION: L-RNA

<400> SEQUENCE: 104
ccgcgguuag ggcuagaagu cgggcgg                                      27

<210> SEQ ID NO 105
<211> LENGTH: 27
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(27)
<223> OTHER INFORMATION: L-RNA

<400> SEQUENCE: 105
cccggguuag ggcuagaagu cggcggg                                      27

<210> SEQ ID NO 106
<211> LENGTH: 27
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(27)
<223> OTHER INFORMATION: L-RNA

<400> SEQUENCE: 106
ggcggguuag ggcuagaagu cggcgcc                                      27

<210> SEQ ID NO 107
<211> LENGTH: 29
<212> TYPE: RNA
<213> ORGANISM: Artificial sequence
```

```
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA

<400> SEQUENCE: 107
cccgcgguua gggcuagaag ucgggcggg                              29

<210> SEQ ID NO 108
<211> LENGTH: 29
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA

<400> SEQUENCE: 108
gccgcgguua gggcuagaag ucgggcggc                              29

<210> SEQ ID NO 109
<211> LENGTH: 29
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA

<400> SEQUENCE: 109
ccccggguua gggcuagaag ucggcgggg                              29

<210> SEQ ID NO 110
<211> LENGTH: 29
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA

<400> SEQUENCE: 110
cggcggguua gggcuagaag ucggcgccg                              29

<210> SEQ ID NO 111
<211> LENGTH: 29
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA

<400> SEQUENCE: 111
gggcggguua gggcuagaag ucggcgccc                              29

<210> SEQ ID NO 112
<211> LENGTH: 37
<212> TYPE: RNA
```

```
<213> ORGANISM: Artificial sequence
<220> FEATURE:
<223> OTHER INFORMATION: synthetic
<220> FEATURE:
<221> NAME/KEY: misc_feature
<222> LOCATION: (1)..(37)
<223> OTHER INFORMATION: L-RNA

<400> SEQUENCE: 112
ugcugcgggg guuagggcua gaagucggcc ugcagca                              37

<210> SEQ ID NO 113
<211> LENGTH: 35
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(35)
<223> OTHER INFORMATION: L-RNA

<400> SEQUENCE: 113
gcugcggggg uuagggcuag aagucggccu gcagc                               35

<210> SEQ ID NO 114
<211> LENGTH: 33
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(33)
<223> OTHER INFORMATION: L-RNA

<400> SEQUENCE: 114 cugcggggu uaggcuaga agucggccug cag                                   33

<210> SEQ ID NO 115
<211> LENGTH: 31
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(31)
<223> OTHER INFORMATION: L-RNA

<400> SEQUENCE: 115
ugcggggguu agggcuagaa gucggccugc a                                   31

<210> SEQ ID NO 116
<211> LENGTH: 29
<212> TYPE: RNA
<213> ORGANISM: Artificial sequence
<220> FEATURE:
<223> OTHER INFORMATION: synthetic
<220> FEATURE:
<221> NAME/KEY: L-RNA
<222> LOCATION: (1)..(29)
<223> OTHER INFORMATION:

<400> SEQUENCE: 116 gcgggggguua gggcuagaag ucggccugc                                     29

<210> SEQ ID NO 117
<211> LENGTH: 29
```

```
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(29)
<223> OTHER INFORMATION: L-RNA

<400> SEQUENCE: 117
gccgggguua gggcuagaag ucggccggc                              29

<210> SEQ ID NO 118
<211> LENGTH: 31
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(31)
<223> OTHER INFORMATION: L-RNA

<400> SEQUENCE: 118 ggccggguu agggcuagaa gucggccggc c                            31

<210> SEQ ID NO 119
<211> LENGTH: 31
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(31)
<223> OTHER INFORMATION: L-RNA

<400> SEQUENCE: 119 cgccggguu agggcuagaa gucggccggc g                            31

<210> SEQ ID NO 120
<211> LENGTH: 10
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: L-RNA
<220> FEATURE:
<221> NAME/KEY: misc_feature
<222> LOCATION: (7)..(7)
<223> OTHER INFORMATION: nucleotide = a, g, c or u

<400> SEQUENCE: 120 rksbusnvgr                                                   10

<210> SEQ ID NO 121
<211> LENGTH: 10
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: L-RNA
<220> FEATURE:
<221> NAME/KEY: misc_feature
<222> LOCATION: (3)..(3)
```

```
<223> OTHER INFORMATION: n is any nucleotide
<220> FEATURE:
<221> NAME/KEY: misc_feature
<222> LOCATION: (3)..(3)
<223> OTHER INFORMATION: nucleotide = a, g, c or u

<400> SEQUENCE: 121 yynrcassmy                                                              10

<210> SEQ ID NO 122
<211> LENGTH: 10
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: L-RNA

<400> SEQUENCE: 122 rksbugsvgr                                                              10

<210> SEQ ID NO 123
<211> LENGTH: 10
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(10)
<223> OTHER INFORMATION: L-RNA
<220> FEATURE:
<221> NAME/KEY: misc_feature
<222> LOCATION: (3)..(3)
<223> OTHER INFORMATION: n is any nucleotide
<220> FEATURE:
<221> NAME/KEY: misc_feature
<222> LOCATION: (3)..(3)
<223> OTHER INFORMATION: nucleotide = a, g, c or u

<400> SEQUENCE: 123 ycnrcassmy                                                              10

<210> SEQ ID NO 124
<211> LENGTH: 5
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA
<220> FEATURE:
<221> NAME/KEY: S or absent
<222> LOCATION: (1)..(1)
<223> OTHER INFORMATION:
<220> FEATURE:
<221> NAME/KEY: misc_feature
<222> LOCATION: (1)..(1)
<223> OTHER INFORMATION: S or absent

<400> SEQUENCE: 124 ssssv                                                                    5

<210> SEQ ID NO 125
<211> LENGTH: 5
<212> TYPE: RNA
<213> ORGANISM: Artificial sequence
```

```
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA
<220> FEATURE:
<221> NAME/KEY: misc_feature
<222> LOCATION: (5)..(5)
<223> OTHER INFORMATION: S or absent

<400> SEQUENCE: 125 bssss                                                                    5

<210> SEQ ID NO 126
<211> LENGTH: 5
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA

<400> SEQUENCE: 126 sggsv                                                                    5

<210> SEQ ID NO 127
<211> LENGTH: 5
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA

<400> SEQUENCE: 127 ysccs                                                                    5

<210> SEQ ID NO 128
<211> LENGTH: 5
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA

<400> SEQUENCE: 128 gcsgg                                                                    5

<210> SEQ ID NO 129
<211> LENGTH: 5
<212> TYPE: RNA
<213> ORGANISM: Artificial
<220> FEATURE:
<221> NAME/KEY: misc_feature
<222> LOCATION: (1)..(5)
<223> OTHER INFORMATION: L-RNA

<400> SEQUENCE: 129 cckgc                                                                    5

<210> SEQ ID NO 130
```

```
<211> LENGTH: 5
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA

<400> SEQUENCE: 130 ssssr                                                                       5

<210> SEQ ID NO 131
<211> LENGTH: 5
<212> TYPE: RNA
<213> ORGANISM: artificial sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: L-RNA

<400> SEQUENCE: 131 ysbss                                                                       5

<210> SEQ ID NO 132
<211> LENGTH: 45
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(45)
<223> OTHER INFORMATION: L-RNA
<220> FEATURE:
<221> NAME/KEY: misc_feature
<222> LOCATION: (1)..(1)
<223> OTHER INFORMATION: 40 kDa-PEG

<400> SEQUENCE: 132
gcguggugug aucuagaugu auuggcugau ccuagucagg uacgc            45

<210> SEQ ID NO 133
<211> LENGTH: 36
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(36)
<223> OTHER INFORMATION: L-RNA
<220> FEATURE:
<221> NAME/KEY: misc_feature
<222> LOCATION: (1)..(1)
<223> OTHER INFORMATION: 40 kDa-PEG

<400> SEQUENCE: 133
gcgugaaagc aacaugucaa ugaaagguag ccgcgc                      36

<210> SEQ ID NO 134
<211> LENGTH: 29
<212> TYPE: RNA
<213> ORGANISM: Artificial sequence
<220> FEATURE:
<223> OTHER INFORMATION: synthetic
<220> FEATURE:
<221> NAME/KEY: misc_feature
```

<222> LOCATION: (1)..(29)
<223> OTHER INFORMATION: L-RNA
<220> FEATURE:
<221> NAME/KEY: misc_feature
<222> LOCATION: (1)..(1)
<223> OTHER INFORMATION: 40 kDa-PEG

<400> SEQUENCE: 134
cgggagguua gggcuagaag ucggucccg                              29

<210> SEQ ID NO 135
<211> LENGTH: 29
<212> TYPE: RNA
<213> ORGANISM: Artificial
<220> FEATURE:
<221> NAME/KEY: misc_feature
<222> LOCATION: (1)..(29)
<223> OTHER INFORMATION: L-RNA
<220> FEATURE:
<221> NAME/KEY: 40 kDa-PEG
<222> LOCATION: (1)..(1)
<223> OTHER INFORMATION:
<220> FEATURE:
<221> NAME/KEY: misc_feature
<222> LOCATION: (1)..(1)
<223> OTHER INFORMATION: 40 kDa-PEG

<400> SEQUENCE: 135 gccggguua gggcuagaag ucggccggc                              29

<210> SEQ ID NO 136
<211> LENGTH: 31
<212> TYPE: RNA
<213> ORGANISM: Artificial sequence
<220> FEATURE:
<223> OTHER INFORMATION: synthetic
<220> FEATURE:
<221> NAME/KEY: L-RNA
<222> LOCATION: (1)..(31)
<223> OTHER INFORMATION:
<220> FEATURE:
<221> NAME/KEY: 40 kDa-PEG
<222> LOCATION: (1)..(1)
<223> OTHER INFORMATION:
<220> FEATURE:
<221> NAME/KEY: misc_feature
<222> LOCATION: (1)..(1)
<223> OTHER INFORMATION: 40 kDa-PEG

<400> SEQUENCE: 136 cgccggggu agggcuagaa gucggccggc g                           31

<210> SEQ ID NO 137
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA
<220> FEATURE:
<221> NAME/KEY: 40 kDa-PEG-
<222> LOCATION: (1)..(1)
<223> OTHER INFORMATION:
<220> FEATURE:
<221> NAME/KEY: misc_feature
<222> LOCATION: (1)..(1)
<223> OTHER INFORMATION: 40 kDa-PEG-

<400> SEQUENCE: 137
gcugugaaag caacauguca augaaaggua gccgcagc 38

<210> SEQ ID NO 138
<211> LENGTH: 40
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(40)
<223> OTHER INFORMATION: L-RNA

<400> SEQUENCE: 138
uaaggaaacu cggucugaug cgguagcgcu gugcagagcu 40

<210> SEQ ID NO 139
<211> LENGTH: 38
<212> TYPE: RNA
<213> ORGANISM: Artificial
<220> FEATURE:
<221> NAME/KEY: misc_feature
<222> LOCATION: (1)..(38)
<223> OTHER INFORMATION: L-RNA
<220> FEATURE:
<221> NAME/KEY: misc_feature
<222> LOCATION: (1)..(1)
<223> OTHER INFORMATION: 30 kDa-PEG

<400> SEQUENCE: 139
gcugugaaag caacauguca augaaaggua gccgcagc 38

<210> SEQ ID NO 140
<211> LENGTH: 38
<212> TYPE: RNA
<213> ORGANISM: Artificial
<220> FEATURE:
<221> NAME/KEY: misc_feature
<222> LOCATION: (1)..(38)
<223> OTHER INFORMATION: L-RNA
<220> FEATURE:
<221> NAME/KEY: misc_feature
<222> LOCATION: (1)..(1)
<223> OTHER INFORMATION: 100 kDa-HES

<400> SEQUENCE: 140
gcugugaaag caacauguca augaaaggua gccgcagc 38

<210> SEQ ID NO 141
<211> LENGTH: 38
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(38)
<223> OTHER INFORMATION: L-RNA
<220> FEATURE:
<221> NAME/KEY: misc_feature
<222> LOCATION: (1)..(1)
<223> OTHER INFORMATION: 130 kDa-HES

<400> SEQUENCE: 141
gcugugaaag caacauguca augaaaggua gccgcagc 38

<210> SEQ ID NO 142
<211> LENGTH: 48
<212> TYPE: RNA
<213> ORGANISM: Artificial sequence

```
<220> FEATURE:
<223> OTHER INFORMATION: synthetic
<220> FEATURE:
<221> NAME/KEY: misc_feature
<222> LOCATION: (1)..(48)
<223> OTHER INFORMATION: L-RNA

<400> SEQUENCE: 142
cgugguccgu ugugucaggu cuauucgccc cggugcaggg cauccgcg                    48

<210> SEQ ID NO 143
<211> LENGTH: 49
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(49)
<223> OTHER INFORMATION: L-RNA

<400> SEQUENCE: 143
gcagugugac gcggacguga uaggacagag cugaucccgc ucaggugag                   49

<210> SEQ ID NO 144
<211> LENGTH: 49
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(49)
<223> OTHER INFORMATION: L-RNA

<400> SEQUENCE: 144
caacagcagu gugacgcgga cgugauagga cagagcugau cccgcucag                   49

<210> SEQ ID NO 145
<211> LENGTH: 38
<212> TYPE: RNA
<213> ORGANISM: Artificial sequence
<220> FEATURE:
<223> OTHER INFORMATION: synthetic

<400> SEQUENCE: 145
gcugugaaag caacauguca augaaaggua gccgcagc                               38

<210> SEQ ID NO 146
<211> LENGTH: 38
<212> TYPE: RNA
<213> ORGANISM: Artificial sequence
<220> FEATURE:
<223> OTHER INFORMATION: synthetic

<400> SEQUENCE: 146
gcugugaaag uaacauguca augaaaggua accacagc                               38

<210> SEQ ID NO 147
<211> LENGTH: 38
<212> TYPE: RNA
<213> ORGANISM: Artificial sequence
<220> FEATURE:
<223> OTHER INFORMATION: synthetic

<400> SEQUENCE: 147
gcugugaaag uaacacguca augaaaggua accgcagc                               38
```

<210> SEQ ID NO 148
<211> LENGTH: 38
<212> TYPE: RNA
<213> ORGANISM: Artificial sequence
<220> FEATURE:
<223> OTHER INFORMATION: synthetic

<400> SEQUENCE: 148
gcugugaaag uaacacguca augaaaggua accacagc                                38

<210> SEQ ID NO 149
<211> LENGTH: 38
<212> TYPE: RNA
<213> ORGANISM: artificial sequence
<220> FEATURE:
<223> OTHER INFORMATION: synthetic

<400> SEQUENCE: 149
gcuguaaaag uaacauguca augaaaggua acuacagc                                38

<210> SEQ ID NO 150
<211> LENGTH: 38
<212> TYPE: RNA
<213> ORGANISM: artificial sequence
<220> FEATURE:
<223> OTHER INFORMATION: synthetic

<400> SEQUENCE: 150
gcuguaaaag uaacaaguca augaaaggua acuacagc                                38

<210> SEQ ID NO 151
<211> LENGTH: 38
<212> TYPE: RNA
<213> ORGANISM: artificial sequence
<220> FEATURE:
<223> OTHER INFORMATION: synthetic

<400> SEQUENCE: 151
gcugugaaag uaacaaguca augaaaggua accacagc                                38

<210> SEQ ID NO 152
<211> LENGTH: 38
<212> TYPE: RNA
<213> ORGANISM: artificial sequence
<220> FEATURE:
<223> OTHER INFORMATION: synthetic

<400> SEQUENCE: 152
gcagugaaag uaacauguca augaaaggua accacagc                                38

<210> SEQ ID NO 153
<211> LENGTH: 38
<212> TYPE: RNA
<213> ORGANISM: artificial sequence
<220> FEATURE:
<223> OTHER INFORMATION: synthetic

<400> SEQUENCE: 153
gcugugaaag uaacauguca augaaaggua accacugc                                38

<210> SEQ ID NO 154
<211> LENGTH: 38
<212> TYPE: RNA
<213> ORGANISM: artificial sequence
<220> FEATURE:
<223> OTHER INFORMATION: synthetic

<400> SEQUENCE: 154
gcuaugaaag uaacauguca augaaaggua accauagc                                   38

<210> SEQ ID NO 155
<211> LENGTH: 38
<212> TYPE: RNA
<213> ORGANISM: artificial sequence
<220> FEATURE:
<223> OTHER INFORMATION: synthetic

<400> SEQUENCE: 155
gcugcgaaag cgacauguca augaaaggua gccgcagc                                   38

<210> SEQ ID NO 156
<211> LENGTH: 38
<212> TYPE: RNA
<213> ORGANISM: artificial sequence
<220> FEATURE:
<223> OTHER INFORMATION: synthetic

<400> SEQUENCE: 156
gcugugaaag caacauguca augaaaggua gccacagc                                   38

<210> SEQ ID NO 157
<211> LENGTH: 38
<212> TYPE: RNA
<213> ORGANISM: artificial sequence
<220> FEATURE:
<223> OTHER INFORMATION: synthetic
<220> FEATURE:
<221> NAME/KEY: synthetic
<222> LOCATION: (1)..(38)
<223> OTHER INFORMATION:

<400> SEQUENCE: 157
gcugugaaag uaacauguca augaaaggua gccgcagc                                   38

<210> SEQ ID NO 158
<211> LENGTH: 39
<212> TYPE: RNA
<213> ORGANISM: artificial sequence
<220> FEATURE:
<223> OTHER INFORMATION: synthetic

<400> SEQUENCE: 158
agcgugaaag uaacacguaa aaugaaaggu aaccacgcu                                  39

<210> SEQ ID NO 159
<211> LENGTH: 36
<212> TYPE: RNA
<213> ORGANISM: artificial sequence
<220> FEATURE:
<223> OTHER INFORMATION: synthetic

<400> SEQUENCE: 159
cugugaaagc aacaugucaa ugaaagguag ccgcag                                     36

<210> SEQ ID NO 160
<211> LENGTH: 34
<212> TYPE: RNA
<213> ORGANISM: Artificial sequence
<220> FEATURE:
<223> OTHER INFORMATION: synthetic

<400> SEQUENCE: 160
ugugaaagca acaugucaau gaaagguagc cgca    34

<210> SEQ ID NO 161
<211> LENGTH: 32
<212> TYPE: RNA
<213> ORGANISM: Artificial sequence
<220> FEATURE:
<223> OTHER INFORMATION: synthetic

<400> SEQUENCE: 161
gugaaagcaa caugucaaug aaagguagcc gc    32

<210> SEQ ID NO 162
<211> LENGTH: 30
<212> TYPE: RNA
<213> ORGANISM: Artificial sequence
<220> FEATURE:
<223> OTHER INFORMATION: synthetic

<400> SEQUENCE: 162
ugaaagcaac augucaauga aagguagccg    30

<210> SEQ ID NO 163
<211> LENGTH: 28
<212> TYPE: RNA
<213> ORGANISM: Artificial sequence
<220> FEATURE:
<223> OTHER INFORMATION: synthetic

<400> SEQUENCE: 163
gaaagcaaca ugucaaugaa agguagcc    28

<210> SEQ ID NO 164
<211> LENGTH: 26
<212> TYPE: RNA
<213> ORGANISM: Artificial sequence
<220> FEATURE:
<223> OTHER INFORMATION: synthetic

<400> SEQUENCE: 164
aaagcaacau gucaaugaaa gguagc    26

<210> SEQ ID NO 165
<211> LENGTH: 36
<212> TYPE: RNA
<213> ORGANISM: Artificial sequence
<220> FEATURE:
<223> OTHER INFORMATION: synthetic

<400> SEQUENCE: 165
gcgugaaagc aacaugucaa ugaaagguag ccgcgc    36

<210> SEQ ID NO 166
<211> LENGTH: 36
<212> TYPE: RNA
<213> ORGANISM: Artificial sequence
<220> FEATURE:
<223> OTHER INFORMATION: synthetic

<400> SEQUENCE: 166
gcgcgaaagc aacaugucaa ugaaagguag ccgcgc    36

<210> SEQ ID NO 167
<211> LENGTH: 34
<212> TYPE: RNA
<213> ORGANISM: Artificial sequence

```
<220> FEATURE:
<223> OTHER INFORMATION: synthetic

<400> SEQUENCE: 167
gcggaaagca acaugucaau gaaaggguagc ccgc                              34

<210> SEQ ID NO 168
<211> LENGTH: 34
<212> TYPE: RNA
<213> ORGANISM: Artificial sequence
<220> FEATURE:
<223> OTHER INFORMATION: synthetic

<400> SEQUENCE: 168
cgugaaagca acaugucaau gaaaggguagc cgcg                              34

<210> SEQ ID NO 169
<211> LENGTH: 34
<212> TYPE: RNA
<213> ORGANISM: Artificial sequence
<220> FEATURE:
<223> OTHER INFORMATION: synthetic

<400> SEQUENCE: 169
gcgcaaagca acaugucaau gaaaggguagc gugc                              34

<210> SEQ ID NO 170
<211> LENGTH: 34
<212> TYPE: RNA
<213> ORGANISM: Artificial sequence
<220> FEATURE:
<223> OTHER INFORMATION: synthetic

<400> SEQUENCE: 170
gugcaaagca acaugucaau gaaaggguagc gcgc                              34

<210> SEQ ID NO 171
<211> LENGTH: 34
<212> TYPE: RNA
<213> ORGANISM: Artificial sequence
<220> FEATURE:
<223> OTHER INFORMATION: synthetic

<400> SEQUENCE: 171
cgcgaaagca acaugucaau gaaaggguagc cgug                              34

<210> SEQ ID NO 172
<211> LENGTH: 34
<212> TYPE: RNA
<213> ORGANISM: Artificial sequence
<220> FEATURE:
<223> OTHER INFORMATION: synthetic

<400> SEQUENCE: 172
gggcaaagca acaugucaau gaaaggguagc gccc                              34

<210> SEQ ID NO 173
<211> LENGTH: 34
<212> TYPE: RNA
<213> ORGANISM: Artificial sequence
<220> FEATURE:
<223> OTHER INFORMATION: synthetic

<400> SEQUENCE: 173
ggccaaagca acaugucaau gaaaggguagc ggcc                              34
```

```
<210> SEQ ID NO 174
<211> LENGTH: 34
<212> TYPE: RNA
<213> ORGANISM: Artificial sequence
<220> FEATURE:
<223> OTHER INFORMATION: synthetic

<400> SEQUENCE: 174
gcccaaagca acaugucaau gaaagguagc gggc                              34

<210> SEQ ID NO 175
<211> LENGTH: 34
<212> TYPE: RNA
<213> ORGANISM: Artificial sequence
<220> FEATURE:
<223> OTHER INFORMATION: synthetic

<400> SEQUENCE: 175
ccccaaagca acaugucaau gaaagguagc gggg                              34

<210> SEQ ID NO 176
<211> LENGTH: 47
<212> TYPE: RNA
<213> ORGANISM: Artificial sequence
<220> FEATURE:
<223> OTHER INFORMATION: synthetic

<400> SEQUENCE: 176
agcguggugu gaucuagaug uaguggcuga uccuagucag guacgcu                47

<210> SEQ ID NO 177
<211> LENGTH: 47
<212> TYPE: RNA
<213> ORGANISM: Artificial sequence
<220> FEATURE:
<223> OTHER INFORMATION: synthetic

<400> SEQUENCE: 177
agcguggugu gaucuagaug uauuggcuga uccuagucag guacgcu                47

<210> SEQ ID NO 178
<211> LENGTH: 47
<212> TYPE: RNA
<213> ORGANISM: Artificial sequence
<220> FEATURE:
<223> OTHER INFORMATION: synthetic

<400> SEQUENCE: 178
agcguggugu gaucuagaug uaauggcuga uccuagucag gugcgcu                47

<210> SEQ ID NO 179
<211> LENGTH: 45
<212> TYPE: RNA
<213> ORGANISM: Artificial sequence
<220> FEATURE:
<223> OTHER INFORMATION: synthetic

<400> SEQUENCE: 179
gcgaggugug aucuagaugu aguggcugau ccuagucagg ugcgc                  45

<210> SEQ ID NO 180
<211> LENGTH: 45
<212> TYPE: RNA
<213> ORGANISM: Artificial sequence
<220> FEATURE:
<223> OTHER INFORMATION: synthetic
```

<400> SEQUENCE: 180
gcguggugug aucuagaugu aguggcugau ccuagucagg ugcgc    45

<210> SEQ ID NO 181
<211> LENGTH: 45
<212> TYPE: RNA
<213> ORGANISM: Artificial sequence
<220> FEATURE:
<223> OTHER INFORMATION: synthetic

<400> SEQUENCE: 181
gcauggugug aucuagaugu aguggcugau ccuagucagg ugccc    45

<210> SEQ ID NO 182
<211> LENGTH: 45
<212> TYPE: RNA
<213> ORGANISM: Artificial sequence
<220> FEATURE:
<223> OTHER INFORMATION: synthetic

<400> SEQUENCE: 182
gcguggugug aucuagaugu aauggcugau ccuagucagg gacgc    45

<210> SEQ ID NO 183
<211> LENGTH: 45
<212> TYPE: RNA
<213> ORGANISM: Artificial sequence
<220> FEATURE:
<223> OTHER INFORMATION: synthetic

<400> SEQUENCE: 183
gcguggugug aucuagaugu agaggcugau ccuagucagg uacgc    45

<210> SEQ ID NO 184
<211> LENGTH: 45
<212> TYPE: RNA
<213> ORGANISM: Artificial sequence
<220> FEATURE:
<223> OTHER INFORMATION: synthetic

<400> SEQUENCE: 184
gcguggugug aucuagaugu aaaggcugau ccuagucagg uacgc    45

<210> SEQ ID NO 185
<211> LENGTH: 45
<212> TYPE: RNA
<213> ORGANISM: Artificial sequence
<220> FEATURE:
<223> OTHER INFORMATION: synthetic

<400> SEQUENCE: 185
gcguggugug aucuagaugu aguggcuguu ccuagucagg uaugc    45

<210> SEQ ID NO 186
<211> LENGTH: 45
<212> TYPE: RNA
<213> ORGANISM: Artificial sequence
<220> FEATURE:
<223> OTHER INFORMATION: synthetic

<400> SEQUENCE: 186
gcguggugug aucuagaugu aguggcugau ccuaguuagg uacgc    45

<210> SEQ ID NO 187

```
<211> LENGTH: 45
<212> TYPE: RNA
<213> ORGANISM: Artificial sequence
<220> FEATURE:
<223> OTHER INFORMATION: synthetic

<400> SEQUENCE: 187
gcguggugug aucuagaugu aguggcugau ccuagucagg uacgc            45

<210> SEQ ID NO 188
<211> LENGTH: 43
<212> TYPE: RNA
<213> ORGANISM: Artificial sequence
<220> FEATURE:
<223> OTHER INFORMATION: synthetic

<400> SEQUENCE: 188
cgugguguga ucuagaugua guggcugauc cuagucaggu acg              43

<210> SEQ ID NO 189
<211> LENGTH: 41
<212> TYPE: RNA
<213> ORGANISM: Artificial sequence
<220> FEATURE:
<223> OTHER INFORMATION: synthetic

<400> SEQUENCE: 189 gugguguggau cuagauguag uggcugaucc uagucaggua c               41

<210> SEQ ID NO 190
<211> LENGTH: 39
<212> TYPE: RNA
<213> ORGANISM: Artificial sequence
<220> FEATURE:
<223> OTHER INFORMATION: synthetic

<400> SEQUENCE: 190
uggugugauc uagauguagu ggcugauccu agucaggua                   39

<210> SEQ ID NO 191
<211> LENGTH: 37
<212> TYPE: RNA
<213> ORGANISM: Artificial sequence
<220> FEATURE:
<223> OTHER INFORMATION: synthetic

<400> SEQUENCE: 191
ggugugaucu agauguagug gcugauccua gucaggu                     37

<210> SEQ ID NO 192
<211> LENGTH: 35
<212> TYPE: RNA
<213> ORGANISM: Artificial sequence
<220> FEATURE:
<223> OTHER INFORMATION: synthetic

<400> SEQUENCE: 192
gugugaucua gauguagugg cugauccuag ucagg                       35

<210> SEQ ID NO 193
<211> LENGTH: 45
<212> TYPE: RNA
<213> ORGANISM: Artificial sequence
<220> FEATURE:
<223> OTHER INFORMATION: synthetic

<400> SEQUENCE: 193
```
gcguggugug aucuagaugu auuggcugau ccuagucagg uacgc                    45

<210> SEQ ID NO 194
<211> LENGTH: 45
<212> TYPE: RNA
<213> ORGANISM: Artificial sequence
<220> FEATURE:
<223> OTHER INFORMATION: synthetic

<400> SEQUENCE: 194
gcgcggugug aucuagaugu auuggcugau ccuagucagg cgcgc                    45

<210> SEQ ID NO 195
<211> LENGTH: 43
<212> TYPE: RNA
<213> ORGANISM: Artificial sequence
<220> FEATURE:
<223> OTHER INFORMATION: synthetic

<400> SEQUENCE: 195
gcgcguguga ucuagaugua uuggcugauc cuagucaggg cgc                      43

<210> SEQ ID NO 196
<211> LENGTH: 43
<212> TYPE: RNA
<213> ORGANISM: Artificial sequence
<220> FEATURE:
<223> OTHER INFORMATION: synthetic

<400> SEQUENCE: 196
gggcguguga ucuagaugua uuggcugauc cuagucaggg ccc                      43

<210> SEQ ID NO 197
<211> LENGTH: 43
<212> TYPE: RNA
<213> ORGANISM: Artificial sequence
<220> FEATURE:
<223> OTHER INFORMATION: synthetic

<400> SEQUENCE: 197
ggccguguga ucuagaugua uuggcugauc cuagucaggg gcc                      43

<210> SEQ ID NO 198
<211> LENGTH: 43
<212> TYPE: RNA
<213> ORGANISM: Artificial sequence
<220> FEATURE:
<223> OTHER INFORMATION: synthetic

<400> SEQUENCE: 198
gcccguguga ucuagaugua uuggcugauc cuagucaggg ggc                      43

<210> SEQ ID NO 199
<211> LENGTH: 39
<212> TYPE: RNA
<213> ORGANISM: Artificial sequence
<220> FEATURE:
<223> OTHER INFORMATION: synthetic

<400> SEQUENCE: 199
gugcugcggg gguuagggcu agaagucggc cugcagcac                           39

<210> SEQ ID NO 200
<211> LENGTH: 39
<212> TYPE: RNA

```
<213> ORGANISM: Artificial sequence
<220> FEATURE:
<223> OTHER INFORMATION: synthetic

<400> SEQUENCE: 200
agcguggcga gguuagggcu agaagucggu cgacacgcu                    39

<210> SEQ ID NO 201
<211> LENGTH: 39
<212> TYPE: RNA
<213> ORGANISM: Artificial sequence
<220> FEATURE:
<223> OTHER INFORMATION: synthetic

<400> SEQUENCE: 201
guguugcgga gguuagggcu agaagucggu cagcagcac                    39

<210> SEQ ID NO 202
<211> LENGTH: 48
<212> TYPE: RNA
<213> ORGANISM: Artificial sequence
<220> FEATURE:
<223> OTHER INFORMATION: synthetic

<400> SEQUENCE: 202
cgugcgcuug agauaggggu uagggcuuaa agucggcuga uucucacg          48

<210> SEQ ID NO 203
<211> LENGTH: 39
<212> TYPE: RNA
<213> ORGANISM: Artificial sequence
<220> FEATURE:
<223> OTHER INFORMATION: synthetic

<400> SEQUENCE: 203
agcgugaagg gguuagggcu cgaagucggc ugacacgcu                    39

<210> SEQ ID NO 204
<211> LENGTH: 39
<212> TYPE: RNA
<213> ORGANISM: Artificial sequence
<220> FEATURE:
<223> OTHER INFORMATION: synthetic

<400> SEQUENCE: 204
gugcugcggg gguuagggcu cgaagucggc ccgcagcac                    39

<210> SEQ ID NO 205
<211> LENGTH: 39
<212> TYPE: RNA
<213> ORGANISM: Artificial sequence
<220> FEATURE:
<223> OTHER INFORMATION: synthetic

<400> SEQUENCE: 205
guguucccgg gguuagggcu ugaagucggc cggcagcac                    39

<210> SEQ ID NO 206
<211> LENGTH: 39
<212> TYPE: RNA
<213> ORGANISM: Artificial sequence
<220> FEATURE:
<223> OTHER INFORMATION: synthetic

<400> SEQUENCE: 206
guguugcagg gguuagggcu ugaagucggc cugcagcac                    39
```

<210> SEQ ID NO 207
<211> LENGTH: 39
<212> TYPE: RNA
<213> ORGANISM: Artificial sequence
<220> FEATURE:
<223> OTHER INFORMATION: synthetic

<400> SEQUENCE: 207
gugcugcggg gguuagggcu caaagucggc cugcagcac                    39

<210> SEQ ID NO 208
<211> LENGTH: 38
<212> TYPE: RNA
<213> ORGANISM: Artificial sequence
<220> FEATURE:
<223> OTHER INFORMATION: synthetic

<400> SEQUENCE: 208
gugcugccgg gguuagggcu aaagucggcc gacagcac                     38

<210> SEQ ID NO 209
<211> LENGTH: 39
<212> TYPE: RNA
<213> ORGANISM: Artificial sequence
<220> FEATURE:
<223> OTHER INFORMATION: synthetic

<400> SEQUENCE: 209
gugcuguggg ggucagggcu agaagucggc cugcagcac                    39

<210> SEQ ID NO 210
<211> LENGTH: 38
<212> TYPE: RNA
<213> ORGANISM: Artificial sequence
<220> FEATURE:
<223> OTHER INFORMATION: synthetic

<400> SEQUENCE: 210
ugagauaggg guuagggcuu aaagucggcu gauucuca                     38

<210> SEQ ID NO 211
<211> LENGTH: 36
<212> TYPE: RNA
<213> ORGANISM: Artificial sequence
<220> FEATURE:
<223> OTHER INFORMATION: synthetic

<400> SEQUENCE: 211
gagauagggg uuagggcuua aagucggcug auucuc                       36

<210> SEQ ID NO 212
<211> LENGTH: 29
<212> TYPE: RNA
<213> ORGANISM: Artificial sequence
<220> FEATURE:
<223> OTHER INFORMATION: synthetic

<400> SEQUENCE: 212
ggggguuagg cuuaaagucg gcugauucu                               29

<210> SEQ ID NO 213
<211> LENGTH: 37
<212> TYPE: RNA
<213> ORGANISM: Artificial sequence
<220> FEATURE:

-continued

<223> OTHER INFORMATION: synthetic

<400> SEQUENCE: 213
gcguggcgag guuagggcua gaagucgguc gacacgc                                37

<210> SEQ ID NO 214
<211> LENGTH: 35
<212> TYPE: RNA
<213> ORGANISM: Artificial sequence
<220> FEATURE:
<223> OTHER INFORMATION: synthetic

<400> SEQUENCE: 214
cguggcgagg uuagggcuag aagucggucg acacg                                 35

<210> SEQ ID NO 215
<211> LENGTH: 33
<212> TYPE: RNA
<213> ORGANISM: Artificial sequence
<220> FEATURE:
<223> OTHER INFORMATION: synthetic

<400> SEQUENCE: 215
cgggcgaggu uagggcuaga agucggucga ccg                                   33

<210> SEQ ID NO 216
<211> LENGTH: 33
<212> TYPE: RNA
<213> ORGANISM: Artificial sequence
<220> FEATURE:
<223> OTHER INFORMATION: synthetic

<400> SEQUENCE: 216
cgggcgaggu uagggcuaga agucggucgc ccg                                   33

<210> SEQ ID NO 217
<211> LENGTH: 31
<212> TYPE: RNA
<213> ORGANISM: Artificial sequence
<220> FEATURE:
<223> OTHER INFORMATION: synthetic

<400> SEQUENCE: 217
cggcgagguu agggcuagaa gucggucgcc g                                     31

<210> SEQ ID NO 218
<211> LENGTH: 29
<212> TYPE: RNA
<213> ORGANISM: Artificial sequence
<220> FEATURE:
<223> OTHER INFORMATION: synthetic

<400> SEQUENCE: 218
cgggagguua gggcuagaag ucggucccg                                        29

<210> SEQ ID NO 219
<211> LENGTH: 27
<212> TYPE: RNA
<213> ORGANISM: Artificial sequence
<220> FEATURE:
<223> OTHER INFORMATION: synthetic

<400> SEQUENCE: 219
gggagguuag ggcuagaagu cgguccc                                          27

```
<210> SEQ ID NO 220
<211> LENGTH: 27
<212> TYPE: RNA
<213> ORGANISM: Artificial sequence
<220> FEATURE:
<223> OTHER INFORMATION: synthetic

<400> SEQUENCE: 220
ccgcgguuag ggcuagaagu cgggcgg                                          27

<210> SEQ ID NO 221
<211> LENGTH: 27
<212> TYPE: RNA
<213> ORGANISM: Artificial sequence
<220> FEATURE:
<223> OTHER INFORMATION: synthetic

<400> SEQUENCE: 221
cccggguuag ggcuagaagu cggcggg                                          27

<210> SEQ ID NO 222
<211> LENGTH: 27
<212> TYPE: RNA
<213> ORGANISM: Artificial sequence
<220> FEATURE:
<223> OTHER INFORMATION: synthetic

<400> SEQUENCE: 222
ggcggguuag ggcuagaagu cggcgcc                                          27

<210> SEQ ID NO 223
<211> LENGTH: 29
<212> TYPE: RNA
<213> ORGANISM: Artificial sequence
<220> FEATURE:
<223> OTHER INFORMATION: synthetic

<400> SEQUENCE: 223
cccgcgguua gggcuagaag ucgggcggg                                        29

<210> SEQ ID NO 224
<211> LENGTH: 29
<212> TYPE: RNA
<213> ORGANISM: Artificial sequence
<220> FEATURE:
<223> OTHER INFORMATION: synthetic

<400> SEQUENCE: 224
gccgcgguua gggcuagaag ucgggcggc                                        29

<210> SEQ ID NO 225
<211> LENGTH: 29
<212> TYPE: RNA
<213> ORGANISM: Artificial sequence
<220> FEATURE:
<223> OTHER INFORMATION: synthetic

<400> SEQUENCE: 225
ccccggguua gggcuagaag ucggcgggg                                        29

<210> SEQ ID NO 226
<211> LENGTH: 29
<212> TYPE: RNA
<213> ORGANISM: Artificial sequence
<220> FEATURE:
<223> OTHER INFORMATION: synthetic
```

```
<400> SEQUENCE: 226
cggcggguua gggcuagaag ucggcgccg                                          29

<210> SEQ ID NO 227
<211> LENGTH: 29
<212> TYPE: RNA
<213> ORGANISM: Artificial sequence
<220> FEATURE:
<223> OTHER INFORMATION: synthetic

<400> SEQUENCE: 227
gggcggguua gggcuagaag ucggcgccc                                          29

<210> SEQ ID NO 228
<211> LENGTH: 37
<212> TYPE: RNA
<213> ORGANISM: Artificial sequence
<220> FEATURE:
<223> OTHER INFORMATION: synthetic

<400> SEQUENCE: 228
ugcugcgggg guuagggcua gaagucggcc ugcagca                                 37

<210> SEQ ID NO 229
<211> LENGTH: 35
<212> TYPE: RNA
<213> ORGANISM: Artificial sequence
<220> FEATURE:
<223> OTHER INFORMATION: synthetic

<400> SEQUENCE: 229
gcugcggggg uuagggcuag aagucggccu gcagc                                   35

<210> SEQ ID NO 230
<211> LENGTH: 33
<212> TYPE: RNA
<213> ORGANISM: Artificial sequence
<220> FEATURE:
<223> OTHER INFORMATION: synthetic

<400> SEQUENCE: 230 cugcggggu uagggcuaga agucggccug cag                                      33

<210> SEQ ID NO 231
<211> LENGTH: 31
<212> TYPE: RNA
<213> ORGANISM: Artificial sequence
<220> FEATURE:
<223> OTHER INFORMATION: synthetic

<400> SEQUENCE: 231
ugcggggguu agggcuagaa gucggccugc a                                       31

<210> SEQ ID NO 232
<211> LENGTH: 29
<212> TYPE: RNA
<213> ORGANISM: Artificial sequence
<220> FEATURE:
<223> OTHER INFORMATION: synthetic

<400> SEQUENCE: 232
gcggggguua gggcuagaag ucggccugc                                          29
```

```
<210> SEQ ID NO 233
<211> LENGTH: 29
<212> TYPE: RNA
<213> ORGANISM: Artificial sequence
<220> FEATURE:
<223> OTHER INFORMATION: synthetic

<400> SEQUENCE: 233
gccgggguua gggcuagaag ucggccggc                               29

<210> SEQ ID NO 234
<211> LENGTH: 31
<212> TYPE: RNA
<213> ORGANISM: Artificial sequence
<220> FEATURE:
<223> OTHER INFORMATION: synthetic

<400> SEQUENCE: 234
ggccgggguu agggcuagaa gucggccggc c                            31

<210> SEQ ID NO 235
<211> LENGTH: 31
<212> TYPE: RNA
<213> ORGANISM: Artificial sequence
<220> FEATURE:
<223> OTHER INFORMATION: synthetic

<400> SEQUENCE: 235
cgccgggguu agggcuagaa gucggccggc g                            31

<210> SEQ ID NO 236
<211> LENGTH: 48
<212> TYPE: RNA
<213> ORGANISM: Artificial sequence
<220> FEATURE:
<223> OTHER INFORMATION: synthetic

<400> SEQUENCE: 236
cgugguccgu ugugucaggu cuauucgccc cggugcaggg cauccgcg          48

<210> SEQ ID NO 237
<211> LENGTH: 49
<212> TYPE: RNA
<213> ORGANISM: Artificial sequence
<220> FEATURE:
<223> OTHER INFORMATION: synthetic

<400> SEQUENCE: 237
gcagugugac gcggacguga uaggacagag cugaucccgc ucaggugag         49

<210> SEQ ID NO 238
<211> LENGTH: 49
<212> TYPE: RNA
<213> ORGANISM: Artificial sequence
<220> FEATURE:
<223> OTHER INFORMATION: synthetic

<400> SEQUENCE: 238
caacagcagu gugacgcgga cgugauagga cagagcugau cccgcucag         49

<210> SEQ ID NO 239
<211> LENGTH: 40
<212> TYPE: RNA
<213> ORGANISM: Artificial sequence
<220> FEATURE:
<223> OTHER INFORMATION: synthetic
```

```
<220> FEATURE:
<221> NAME/KEY: misc_feature
<222> LOCATION: (1)..(40)
<223> OTHER INFORMATION: L-RNA
<220> FEATURE:
<221> NAME/KEY: misc_feature
<222> LOCATION: (1)..(1)
<223> OTHER INFORMATION: pegylated

<400> SEQUENCE: 239
uaaggaaacu cggucugaug cgguagcgcu gugcagagcu                              40

<210> SEQ ID NO 240
<211> LENGTH: 13
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(13)
<223> OTHER INFORMATION: L-RNA
<220> FEATURE:
<221> NAME/KEY: misc_feature
<222> LOCATION: (3)..(3)
<223> OTHER INFORMATION: u represents a t
<220> FEATURE:
<221> NAME/KEY: misc_feature
<222> LOCATION: (13)..(13)
<223> OTHER INFORMATION: attached to -(C18-PEG-spacer)-(C18-PEG-spacer)-
      1-NH2

<400> SEQUENCE: 240
gaucacacca cgc                                                          13

<210> SEQ ID NO 241
<211> LENGTH: 11
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(11)
<223> OTHER INFORMATION: L-RNA
<220> FEATURE:
<221> NAME/KEY: misc_feature
<222> LOCATION: (1)..(1)
<223> OTHER INFORMATION: attached to 5'-NH2-(C18-PEG-spacer)-(C18-PEG-
      spacer)-

<400> SEQUENCE: 241
gcguaccuga c                                                            11
```